(12) United States Patent
Faure

(10) Patent No.: US 9,193,774 B2
(45) Date of Patent: Nov. 24, 2015

(54) TRACEABILITY OF CELLULAR CYCLE ANOMALIES TARGETING ONCOLOGY AND NEURODEGENERATION

(76) Inventor: Laurence Faure, Paris (FR)

( * ) Notice: Subject to any disclaimer, the term of this patent is extended or adjusted under 35 U.S.C. 154(b) by 149 days.

(21) Appl. No.: 13/226,024

(22) Filed: Sep. 6, 2011

(65) Prior Publication Data

US 2013/0059792 A1 Mar. 7, 2013

Related U.S. Application Data

(60) Division of application No. 12/047,173, filed on Mar. 12, 2008, now Pat. No. 8,039,439, which is a continuation-in-part of application No. 11/908,103, filed as application No. PCT/FR2006/000510 on Mar. 7, 2006.

(30) Foreign Application Priority Data

Mar. 7, 2005 (FR) ...................................... 05 02257
Mar. 7, 2005 (FR) ...................................... 05 02258

(51) Int. Cl.
 *C12N 15/11* (2006.01)
 *A61K 48/00* (2006.01)
 *C07H 21/02* (2006.01)
 *C07H 21/04* (2006.01)
 *C07K 14/47* (2006.01)

(52) U.S. Cl.
 CPC ...................................... *C07K 14/47* (2013.01)

(58) Field of Classification Search
 USPC ............................................ 536/24.5; 514/44
 See application file for complete search history.

*Primary Examiner* — Terra Cotta Gibbs
(74) *Attorney, Agent, or Firm* — Henry J. Cittone; Cittone & Chinta LLP

(57) ABSTRACT

The present invention relates to the field of medicine and biology. It concerns a novel test for screening and for therapeutic follow-up in oncology. More particularly, it relates to diagnostic and/or therapeutic tests in oncology and on neurodegenerative diseases. It is a diagnostic test and a prognostic test for various cancers (breast cancer, bladder cancer, ovarian cancer, lung cancer, skin cancer, prostate cancer, colon cancer, liver cancer, glioblastoma, sarcoma, leukemia, etc.) and therapeutics solutions for specific neurodegenerative diseases. More particularly, the invention concerns the use of the LIV21 protein, LIV21 gene and of derivatives thereof as diagnostic and prognostic markers for cancers. The invention therefore concerns the detection of the LIV21 protein with a kit comprising LIV21-specific antibodies.

7 Claims, 86 Drawing Sheets

Up and Down Regulation of Proteins in Breast Cancer Cells

| | |
|---|---|
| 9097.5745643761 | 1340.3700633872 |
| 1178.1798867437 | 1379.0945955514 |
| 4628.6947049742 | 808.7878593298 |
| 3966.8497491287 | |
| 2406.1689412878 | 7445.2469663112 |
| 4319.0513938078 | 563.5600363604 |
| 982.3446853998 | 589.5926505684 |
| 6375.0431967305 | 361.0378467224 |
| 733.7540527608 | 462.7875641390 |
| 9804.7313643143 | |
| 1606.8017771118  1713.1417917105 | 295.0166028140 |
| 1669.8508901315 | 1461.8496984999 |
| 460.3771315815 | 1192.6109791420 |
| 1320.5297537971 | 435.3133984343 |
| 829.6077480012 | 376.5193988089 |
| 39.7198135388 | 423.9751957415 |
| 592.5875946486 | 306.0705242995 |
| 1904.7630135375 | 1774.4067859282 |
| 607.6492273556 | 273.5552102134 |
| 2798.0938636018 | 2541.2168875996 |
| 1885.6918138030  720.4989497003 | 277.9822801583 |
| 2317.0947499905 | 373.4533426579 |
| 533.2032303253 | 476.3703631634 |

BAND 3 : 49K

| Index | Centroid mass | Lower limit | Upper limit | Charge (z) | Height | Relative intensity | Area |
|---|---|---|---|---|---|---|---|
| 1 | 706.240123 | 706.01 | 706.37 | 1 | 222 | 7.11 | 351.17 |
| 2 | 707.284945 | 706.95 | 707.54 | 1 | 169 | 5.43 | 722.25 |
| 3 | 708.408118 | 708.27 | 708.67 | 0 | 204 | 6.54 | 304.71 |
| 4 | 709.196393 | 708.99 | 709.25 | 1 | 202 | 6.49 | 301.58 |
| 5 | 709.336808 | 709.25 | 709.40 | 1 | 195 | 6.27 | 63.33 |
| 6 | 709.440179 | 709.40 | 709.54 | 0 | 172 | 5.51 | 102.84 |
| 7 | 710.196836 | 710.05 | 710.31 | 1 | 243 | 7.80 | 484.75 |
| 8 | 710.384454 | 710.31 | 710.67 | 1 | 221 | 7.11 | 325.11 |
| 9 | 711.273828 | 710.89 | 711.59 | 1 | 280 | 8.99 | 891.32 |
| 10 | 711.648614 | 711.59 | 711.73 | 1 | 170 | 5.45 | 80.35 |
| 11 | 712.026202 | 711.84 | 712.06 | 0 | 161 | 6.18 | 64.99 |
| 12 | 712.244995 | 712.06 | 712.32 | 1 | 281 | 9.03 | 261.94 |
| 13 | 712.416201 | 712.32 | 712.54 | 0 | 279 | 8.96 | 291.12 |
| 14 | 712.631162 | 712.54 | 712.79 | 1 | 167 | 5.36 | 78.60 |
| 15 | 713.214345 | 713.05 | 713.30 | 1 | 320 | 10.28 | 449.54 |
| 16 | 713.402850 | 713.30 | 713.60 | 0 | 296 | 9.51 | 394.62 |
| 17 | 713.646192 | 713.60 | 713.71 | 1 | 167 | 5.34 | 54.49 |
| 18 | 714.245349 | 714.04 | 714.51 | 1 | 458 | 14.71 | 1225.47 |
| 19 | 714.603349 | 714.51 | 714.80 | 1 | 241 | 7.74 | 314.84 |
| 20 | 714.992707 | 714.80 | 715.06 | 1 | 186 | 5.98 | 130.23 |
| 21 | 715.227419 | 715.06 | 715.32 | 1 | 387 | 12.43 | 607.16 |
| 22 | 715.416815 | 715.32 | 715.68 | 0 | 322 | 10.35 | 704.09 |
| 23 | 715.861706 | 715.79 | 715.94 | 1 | 158 | 5.08 | 43.79 |
| 24 | 716.276476 | 715.94 | 716.76 | 0 | 413 | 13.26 | 1427.72 |
| 25 | 717.238224 | 716.93 | 717.33 | 1 | 345 | 11.08 | 717.31 |
| 26 | 717.427262 | 717.33 | 717.55 | 1 | 317 | 10.17 | 404.37 |
| 27 | 717.687798 | 717.55 | 717.77 | 1 | 182 | 5.83 | 135.50 |
| 28 | 718.241932 | 717.92 | 718.32 | 1 | 420 | 13.49 | 704.52 |
| 29 | 718.404433 | 718.32 | 718.73 | 1 | 329 | 10.57 | 659.45 |
| 30 | 718.786164 | 718.73 | 718.84 | 1 | 157 | 5.04 | 38.18 |
| 31 | 718.904279 | 718.84 | 718.95 | 0 | 158 | 5.07 | 25.25 |
| 32 | 719.016460 | 718.95 | 719.09 | 0 | 164 | 5.26 | 56.29 |
| 33 | 719.242767 | 719.09 | 719.43 | 1 | 361 | 11.58 | 636.34 |
| 34 | 719.479858 | 719.43 | 719.66 | 1 | 268 | 8.61 | 290.12 |
| 35 | 719.833163 | 719.79 | 719.94 | 1 | 154 | 4.94 | 29.48 |
| 36 | 720.249938 | 719.94 | 720.34 | 1 | 302 | 9.70 | 668.11 |
| 37 | 720.414316 | 720.34 | 720.60 | 0 | 299 | 9.59 | 423.62 |
| 38 | 720.711033 | 720.60 | 720.90 | 1 | 213 | 6.85 | 191.03 |
| 39 | 720.977762 | 720.90 | 721.04 | 0 | 163 | 5.24 | 67.13 |
| 40 | 721.131765 | 721.04 | 721.19 | 0 | 238 | 7.65 | 150.16 |
| 41 | 721.267350 | 721.19 | 721.37 | 1 | 270 | 8.68 | 105.03 |
| 42 | 721.469735 | 721.37 | 721.59 | 1 | 228 | 7.33 | 173.66 |
| 43 | 721.678563 | 721.59 | 721.76 | 1 | 180 | 5.79 | 59.88 |
| 44 | 721.855499 | 721.76 | 721.93 | 0 | 173 | 5.56 | 39.94 |
| 45 | 721.972145 | 721.93 | 722.04 | 1 | 160 | 5.13 | 16.92 |
| 46 | 722.243653 | 722.04 | 722.29 | 1 | 271 | 8.69 | 187.18 |
| 47 | 722.433917 | 722.29 | 722.73 | 1 | 299 | 9.61 | 607.15 |
| 48 | 722.808917 | 722.73 | 722.85 | 1 | 168 | 5.39 | 76.74 |
| 49 | 722.914855 | 722.85 | 723.03 | 1 | 155 | 4.96 | 46.50 |
| 50 | 723.286105 | 723.03 | 723.36 | 1 | 334 | 10.72 | 488.00 |
| 51 | 723.411737 | 723.36 | 723.58 | 1 | 276 | 8.85 | 300.67 |
| 52 | 723.680597 | 723.58 | 723.77 | 0 | 191 | 6.13 | 128.61 |
| 53 | 723.898253 | 723.77 | 723.99 | 1 | 180 | 5.79 | 87.39 |
| 54 | 724.292504 | 723.99 | 724.43 | 1 | 452 | 14.52 | 922.32 |

Figure 7D

| | | | | | | | |
|---|---|---|---|---|---|---|---|
| 55 | 724.498683 | 724.43 | 724.72 | 1 | 422 | 13.56 | 557.70 |
| 56 | 724.773459 | 724.72 | 724.87 | 1 | 163 | 5.24 | 64.66 |
| 57 | 724.999215 | 724.87 | 725.09 | 1 | 167 | 5.35 | 98.70 |
| 58 | 725.363735 | 725.09 | 725.72 | 1 | 472 | 15.14 | 1132.85 |
| 59 | 725.854091 | 725.72 | 725.94 | 1 | 194 | 6.24 | 87.10 |
| 60 | 725.982959 | 725.94 | 726.05 | 0 | 158 | 5.07 | 64.90 |
| 61 | 726.380960 | 726.05 | 726.72 | 1 | 613 | 19.68 | 1619.99 |
| 62 | 727.334979 | 726.97 | 727.64 | 1 | 483 | 15.49 | 1360.99 |
| 63 | 727.712657 | 727.68 | 727.82 | 1 | 171 | 5.49 | 69.56 |
| 64 | 728.251101 | 727.82 | 728.42 | 1 | 407 | 13.05 | 1005.90 |
| 65 | 728.489371 | 728.42 | 728.56 | 0 | 255 | 8.19 | 33.33 |
| 66 | 728.608680 | 728.56 | 728.75 | 1 | 248 | 7.97 | 254.60 |
| 67 | 728.892673 | 728.90 | 729.08 | 0 | 183 | 5.86 | 97.75 |
| 68 | 729.256048 | 729.08 | 729.38 | 1 | 417 | 13.37 | 858.90 |
| 69 | 729.420751 | 729.38 | 729.64 | 1 | 328 | 10.52 | 390.58 |
| 70 | 729.716986 | 729.64 | 729.78 | 1 | 192 | 6.15 | 39.27 |
| 71 | 729.825875 | 729.78 | 729.93 | 0 | 163 | 5.22 | 113.67 |
| 72 | 730.232908 | 729.93 | 730.30 | 1 | 352 | 11.31 | 656.21 |
| 73 | 730.388592 | 730.30 | 730.63 | 1 | 326 | 10.46 | 602.01 |
| 74 | 731.254940 | 730.97 | 731.38 | 1 | 342 | 10.97 | 718.40 |
| 75 | 731.428485 | 731.38 | 731.56 | 0 | 294 | 9.44 | 278.14 |
| 76 | 731.662254 | 731.56 | 731.78 | 1 | 199 | 6.38 | 159.42 |
| 77 | 731.858944 | 731.78 | 731.93 | 0 | 160 | 5.13 | 64.09 |
| 78 | 732.025193 | 731.93 | 732.12 | 1 | 165 | 5.31 | 83.35 |
| 79 | 732.312035 | 732.12 | 732.56 | 1 | 289 | 9.29 | 600.97 |
| 80 | 732.614839 | 732.56 | 732.78 | 1 | 203 | 6.52 | 215.95 |
| 81 | 732.895355 | 732.78 | 732.93 | 1 | 205 | 6.58 | 152.57 |
| 82 | 733.004671 | 732.93 | 733.08 | 1 | 212 | 6.80 | 76.31 |
| 83 | 733.223382 | 733.08 | 733.38 | 0 | 393 | 12.61 | 625.55 |
| 84 | 733.485131 | 733.38 | 733.75 | 1 | 279 | 8.97 | 307.09 |
| 85 | 733.782414 | 733.75 | 733.93 | 1 | 165 | 5.30 | 76.02 |
| 86 | 734.290627 | 733.93 | 734.34 | 1 | 309 | 9.91 | 566.16 |
| 87 | 734.443964 | 734.34 | 734.60 | 1 | 383 | 12.28 | 531.31 |
| 88 | 734.704787 | 734.60 | 734.82 | 0 | 168 | 5.39 | 49.07 |
| 89 | 734.871908 | 734.82 | 734.97 | 1 | 184 | 5.91 | 109.88 |
| 90 | 735.239510 | 734.97 | 735.34 | 1 | 339 | 10.89 | 732.00 |
| 91 | 735.450605 | 735.34 | 735.68 | 1 | 296 | 9.49 | 340.47 |
| 92 | 735.773080 | 735.71 | 735.90 | 1 | 155 | 4.96 | 91.86 |
| 93 | 736.390356 | 736.05 | 736.76 | 1 | 401 | 12.88 | 1252.57 |
| 94 | 736.903258 | 736.76 | 737.05 | 0 | 175 | 5.61 | 160.24 |
| 95 | 737.189216 | 737.05 | 737.24 | 0 | 272 | 8.72 | 253.84 |
| 96 | 737.339889 | 737.24 | 737.42 | 0 | 279 | 8.96 | 96.18 |
| 97 | 737.504272 | 737.42 | 737.61 | 1 | 321 | 10.30 | 213.86 |
| 98 | 737.718029 | 737.61 | 737.83 | 1 | 202 | 6.47 | 164.03 |
| 99 | 738.311317 | 737.91 | 738.39 | 1 | 277 | 8.88 | 495.04 |
| 100 | 738.444890 | 738.39 | 738.65 | 1 | 265 | 8.52 | 244.81 |
| 101 | 738.706255 | 738.65 | 738.84 | 1 | 190 | 6.11 | 98.51 |
| 102 | 738.914798 | 738.84 | 738.95 | 0 | 164 | 5.26 | 42.84 |
| 103 | 739.002024 | 738.95 | 739.06 | 1 | 157 | 5.03 | 37.99 |
| 104 | 739.313552 | 739.06 | 739.66 | 1 | 304 | 9.77 | 789.10 |
| 105 | 740.107292 | 739.96 | 740.14 | 1 | 242 | 7.77 | 275.09 |
| 106 | 740.260341 | 740.14 | 740.40 | 1 | 296 | 9.49 | 165.79 |
| 107 | 740.491072 | 740.40 | 740.63 | 0 | 318 | 10.21 | 353.02 |
| 108 | 740.709885 | 740.63 | 740.86 | 0 | 166 | 5.32 | 92.52 |
| 109 | 740.974679 | 740.86 | 741.07 | 1 | 176 | 5.66 | 149.58 |
| 110 | 741.324387 | 741.07 | 741.41 | 1 | 300 | 9.62 | 572.49 |

Figure 7E

| | | | | | | | |
|---|---|---|---|---|---|---|---|
| 111 | 741.918427 | 741.74 | 742.08 | 1 | 158 | 5.06 | 182.19 |
| 112 | 742.274393 | 742.08 | 742.45 | 1 | 372 | 11.94 | 901.40 |
| 113 | 742.521578 | 742.45 | 742.75 | 0 | 286 | 9.18 | 317.27 |
| 114 | 743.357953 | 743.08 | 743.54 | 1 | 366 | 11.76 | 851.72 |
| 115 | 743.585670 | 743.54 | 743.65 | 0 | 187 | 6.00 | 67.89 |
| 116 | 743.776421 | 743.65 | 743.98 | 1 | 191 | 6.12 | 128.04 |
| 117 | 744.282385 | 743.98 | 744.54 | 1 | 285 | 9.16 | 640.05 |
| 118 | 744.792754 | 744.69 | 744.92 | 1 | 196 | 6.28 | 124.85 |
| 119 | 744.979602 | 744.92 | 745.07 | 0 | 175 | 5.61 | 88.96 |
| 120 | 745.254436 | 745.07 | 745.33 | 0 | 367 | 11.76 | 509.97 |
| 121 | 745.414463 | 745.33 | 745.63 | 0 | 328 | 10.54 | 638.72 |
| 122 | 745.928762 | 745.62 | 746.00 | 1 | 156 | 5.02 | 41.60 |
| 123 | 746.318301 | 746.00 | 746.68 | 1 | 358 | 11.50 | 1001.72 |
| 124 | 746.765060 | 746.68 | 746.83 | 1 | 159 | 5.10 | 36.42 |
| 125 | 747.018545 | 746.84 | 747.09 | 0 | 172 | 5.51 | 79.16 |
| 126 | 747.249692 | 747.09 | 747.35 | 1 | 379 | 12.18 | 451.49 |
| 127 | 747.451590 | 747.35 | 747.61 | 1 | 345 | 11.08 | 370.99 |
| 128 | 747.668702 | 747.61 | 747.72 | 1 | 202 | 6.49 | 44.74 |
| 129 | 747.799416 | 747.72 | 747.95 | 0 | 175 | 5.63 | 16.78 |
| 130 | 748.292764 | 747.99 | 748.36 | 1 | 273 | 8.76 | 471.45 |
| 131 | 748.485145 | 748.36 | 748.77 | 1 | 472 | 15.15 | 761.38 |
| 132 | 748.855125 | 748.77 | 748.92 | 1 | 161 | 5.16 | 30.10 |
| 133 | 749.269650 | 749.11 | 749.34 | 1 | 316 | 10.13 | 152.62 |
| 134 | 749.447690 | 749.34 | 749.71 | 1 | 355 | 11.36 | 706.52 |
| 135 | 749.812161 | 749.71 | 749.90 | 1 | 182 | 5.84 | 106.31 |
| 136 | 749.956131 | 749.90 | 750.05 | 1 | 158 | 5.07 | 73.93 |
| 137 | 750.307179 | 750.05 | 750.35 | 1 | 308 | 9.90 | 627.40 |
| 138 | 750.476061 | 750.35 | 750.65 | 1 | 368 | 11.82 | 705.23 |
| 139 | 750.772452 | 750.65 | 750.87 | 1 | 183 | 5.88 | 103.46 |
| 140 | 751.017492 | 750.87 | 751.06 | 1 | 195 | 6.26 | 111.97 |
| 141 | 751.218425 | 751.06 | 751.36 | 0 | 315 | 10.11 | 416.87 |
| 142 | 751.544476 | 751.51 | 751.77 | 1 | 231 | 7.42 | 317.46 |
| 143 | 751.893058 | 751.77 | 751.96 | 1 | 178 | 5.71 | 97.32 |
| 144 | 752.274297 | 751.96 | 752.34 | 1 | 277 | 8.87 | 406.37 |
| 145 | 752.439006 | 752.34 | 752.49 | 0 | 320 | 10.27 | 115.44 |
| 146 | 752.549697 | 752.49 | 752.75 | 0 | 311 | 9.98 | 302.19 |
| 147 | 752.880066 | 752.75 | 752.98 | 1 | 173 | 5.55 | 63.76 |
| 148 | 753.295570 | 752.98 | 753.46 | 1 | 359 | 11.52 | 843.49 |
| 149 | 753.942189 | 753.69 | 753.99 | 0 | 194 | 6.21 | 184.85 |
| 150 | 754.036743 | 753.99 | 754.10 | 0 | 184 | 5.90 | 13.46 |
| 151 | 754.294220 | 754.10 | 754.33 | 1 | 345 | 11.08 | 269.48 |
| 152 | 754.377839 | 754.33 | 754.69 | 0 | 323 | 10.35 | 317.89 |
| 153 | 754.756388 | 754.69 | 754.86 | 0 | 214 | 6.86 | 302.24 |
| 154 | 755.160973 | 754.86 | 755.19 | 0 | 254 | 8.15 | 379.17 |
| 155 | 755.365852 | 755.19 | 755.72 | 1 | 309 | 9.93 | 867.93 |
| 156 | 756.056130 | 755.91 | 756.14 | 0 | 192 | 6.16 | 133.13 |
| 157 | 756.245813 | 756.14 | 756.36 | 1 | 333 | 10.69 | 382.83 |
| 158 | 756.431239 | 756.36 | 756.59 | 0 | 307 | 9.84 | 278.23 |
| 159 | 756.625601 | 756.59 | 756.70 | 1 | 189 | 6.05 | 110.35 |
| 160 | 756.842360 | 756.70 | 756.96 | 0 | 160 | 5.15 | 155.90 |
| 161 | 757.314019 | 756.96 | 757.60 | 1 | 362 | 11.61 | 856.57 |
| 162 | 757.703370 | 757.60 | 757.83 | 1 | 162 | 5.19 | 116.53 |
| 163 | 758.003334 | 757.83 | 758.09 | 1 | 181 | 5.80 | 177.48 |
| 164 | 758.276514 | 758.09 | 758.32 | 1 | 314 | 10.09 | 350.45 |
| 165 | 758.429123 | 758.32 | 758.74 | 1 | 321 | 10.29 | 637.43 |
| 166 | 758.890217 | 758.74 | 759.04 | 1 | 189 | 6.05 | 145.49 |

Figure 7F

| | | | | | | | |
|---|---|---|---|---|---|---|---|
| 167 | 759.118753 | 759.04 | 759.19 | 0 | 162 | 5.21 | 37.66 |
| 168 | 759.280531 | 759.19 | 759.42 | 1 | 354 | 11.37 | 392.53 |
| 169 | 759.464666 | 759.42 | 759.57 | 1 | 219 | 7.03 | 106.74 |
| 170 | 759.618445 | 759.57 | 759.72 | 0 | 182 | 5.84 | 97.89 |
| 171 | 760.282678 | 759.98 | 760.36 | 1 | 272 | 8.74 | 496.03 |
| 172 | 760.474949 | 760.36 | 760.81 | 1 | 272 | 8.73 | 551.99 |
| 173 | 760.838301 | 760.81 | 761.04 | 0 | 185 | 5.94 | 137.59 |
| 174 | 761.356685 | 761.04 | 761.61 | 0 | 286 | 9.18 | 670.90 |
| 175 | 761.943285 | 761.76 | 762.06 | 1 | 154 | 4.94 | 128.61 |
| 176 | 762.321953 | 762.06 | 762.36 | 1 | 215 | 6.89 | 334.62 |
| 177 | 762.505786 | 762.48 | 762.59 | 1 | 224 | 7.20 | 127.09 |
| 178 | 762.683035 | 762.59 | 762.74 | 1 | 186 | 5.96 | 62.33 |
| 179 | 762.989995 | 762.85 | 763.08 | 1 | 205 | 6.59 | 154.05 |
| 180 | 763.268290 | 763.08 | 763.35 | 1 | 293 | 9.42 | 274.43 |
| 181 | 763.452460 | 763.35 | 763.57 | 1 | 352 | 11.29 | 440.22 |
| 182 | 763.718544 | 763.57 | 763.91 | 1 | 190 | 6.09 | 138.78 |
| 183 | 764.293027 | 763.95 | 764.33 | 1 | 221 | 7.11 | 304.33 |
| 184 | 764.442860 | 764.33 | 764.71 | 1 | 253 | 8.12 | 450.30 |
| 185 | 764.825140 | 764.71 | 765.01 | 1 | 158 | 5.09 | 172.21 |
| 186 | 765.394706 | 765.28 | 765.65 | 1 | 270 | 8.68 | 499.08 |
| 187 | 765.761125 | 765.65 | 765.88 | 0 | 167 | 5.37 | 121.86 |
| 188 | 766.277754 | 765.88 | 766.37 | 1 | 295 | 9.48 | 549.19 |
| 189 | 766.475869 | 766.37 | 766.72 | 0 | 303 | 9.72 | 418.25 |
| 190 | 767.091275 | 766.94 | 767.17 | 0 | 187 | 5.99 | 140.30 |
| 191 | 767.323917 | 767.17 | 767.40 | 1 | 308 | 9.88 | 325.30 |
| 192 | 767.458948 | 767.40 | 767.78 | 1 | 263 | 8.44 | 445.83 |
| 193 | 767.850550 | 767.78 | 768.04 | 0 | 166 | 5.33 | 114.11 |
| 194 | 768.341064 | 768.04 | 768.39 | 1 | 322 | 10.35 | 545.34 |
| 195 | 768.593614 | 768.39 | 768.77 | 1 | 879 | 28.21 | 1421.11 |
| 196 | 769.047123 | 768.92 | 769.11 | 1 | 174 | 5.57 | 184.24 |
| 197 | 769.255983 | 769.11 | 769.33 | 1 | 380 | 12.20 | 349.41 |
| 198 | 769.512150 | 769.33 | 769.78 | 1 | 476 | 15.28 | 960.12 |
| 199 | 769.946629 | 769.83 | 770.06 | 1 | 169 | 5.41 | 93.24 |
| 200 | 770.251585 | 770.06 | 770.32 | 1 | 358 | 11.50 | 550.61 |
| 201 | 770.388509 | 770.32 | 770.55 | 1 | 322 | 10.32 | 75.22 |
| 202 | 770.794760 | 770.70 | 770.93 | 0 | 160 | 5.15 | 130.23 |
| 203 | 771.277489 | 770.93 | 771.31 | 0 | 318 | 10.19 | 445.54 |
| 204 | 771.399903 | 771.31 | 771.69 | 1 | 382 | 12.26 | 705.80 |
| 205 | 772.073025 | 771.96 | 772.11 | 1 | 204 | 6.53 | 138.65 |
| 206 | 772.253962 | 772.15 | 772.34 | 1 | 317 | 10.16 | 213.00 |
| 207 | 772.478867 | 772.34 | 772.64 | 0 | 300 | 9.64 | 372.23 |
| 208 | 772.693896 | 772.64 | 772.91 | 0 | 184 | 5.89 | 123.05 |
| 209 | 773.041197 | 772.91 | 773.14 | 1 | 181 | 5.80 | 103.27 |
| 210 | 773.326901 | 773.14 | 773.52 | 1 | 289 | 9.27 | 662.19 |
| 211 | 773.557094 | 773.52 | 773.67 | 1 | 194 | 6.22 | 116.67 |
| 212 | 773.788200 | 773.67 | 773.90 | 1 | 158 | 5.08 | 95.04 |
| 213 | 773.989153 | 773.90 | 774.09 | 1 | 174 | 5.58 | 70.98 |
| 214 | 774.291768 | 774.09 | 774.39 | 1 | 294 | 9.45 | 393.81 |
| 215 | 774.480082 | 774.39 | 774.62 | 1 | 303 | 9.73 | 278.47 |
| 216 | 774.717291 | 774.62 | 774.93 | 1 | 192 | 6.17 | 228.46 |
| 217 | 775.089464 | 774.93 | 775.16 | 0 | 184 | 5.92 | 161.94 |
| 218 | 775.303408 | 775.16 | 775.39 | 1 | 263 | 8.43 | 186.61 |
| 219 | 775.460739 | 775.39 | 775.69 | 1 | 257 | 8.23 | 212.62 |
| 220 | 775.861478 | 775.77 | 775.92 | 1 | 167 | 5.35 | 90.10 |
| 221 | 776.240204 | 775.96 | 776.30 | 1 | 262 | 8.40 | 329.44 |
| 222 | 776.479938 | 776.30 | 776.65 | 1 | 321 | 10.31 | 558.94 |

Figure 7G

| | | | | | | | |
|---|---|---|---|---|---|---|---|
| 223 | 776.697287 | 776.65 | 776.76 | 0 | 156 | 5.01 | 44.22 |
| 224 | 777.301839 | 776.99 | 777.64 | 1 | 350 | 11.22 | 1083.36 |
| 225 | 777.685990 | 777.64 | 777.76 | 1 | 156 | 5.00 | 43.98 |
| 226 | 778.196307 | 778.06 | 778.29 | 1 | 225 | 7.24 | 209.82 |
| 227 | 778.419426 | 778.29 | 778.59 | 1 | 288 | 9.25 | 402.94 |
| 228 | 778.673906 | 778.59 | 778.86 | 1 | 160 | 5.12 | 65.33 |
| 229 | 779.042732 | 778.90 | 779.09 | 0 | 165 | 5.28 | 109.12 |
| 230 | 779.283629 | 779.09 | 779.36 | 1 | 275 | 8.84 | 328.96 |
| 231 | 779.420764 | 779.36 | 779.78 | 1 | 315 | 10.10 | 574.44 |
| 232 | 779.648841 | 779.78 | 779.93 | 1 | 159 | 5.11 | 111.35 |
| 233 | 780.281324 | 779.93 | 780.35 | 1 | 301 | 9.68 | 629.64 |
| 234 | 780.422692 | 780.35 | 780.62 | 1 | 254 | 8.14 | 335.00 |
| 235 | 780.839130 | 780.77 | 781.04 | 1 | 170 | 5.44 | 93.52 |
| 236 | 781.326232 | 781.04 | 781.69 | 1 | 324 | 10.39 | 620.84 |
| 237 | 781.930042 | 781.84 | 782.11 | 1 | 159 | 5.09 | 130.46 |
| 238 | 782.363293 | 782.11 | 782.42 | 1 | 293 | 9.39 | 646.10 |
| 239 | 782.464168 | 782.42 | 782.84 | 0 | 285 | 9.13 | 446.78 |
| 240 | 782.876883 | 782.84 | 782.95 | 0 | 157 | 5.04 | 41.64 |
| 241 | 783.015801 | 782.95 | 783.11 | 1 | 185 | 5.93 | 118.53 |
| 242 | 783.318044 | 783.11 | 783.49 | 1 | 293 | 9.42 | 782.30 |
| 243 | 783.674275 | 783.61 | 783.84 | 0 | 166 | 6.00 | 119.86 |
| 244 | 784.406949 | 784.03 | 784.60 | 1 | 313 | 10.05 | 921.37 |
| 245 | 784.933274 | 784.87 | 785.10 | 1 | 178 | 5.71 | 85.91 |
| 246 | 785.263721 | 785.10 | 785.33 | 0 | 277 | 8.89 | 267.44 |
| 247 | 785.468285 | 785.33 | 785.52 | 1 | 253 | 8.11 | 67.61 |
| 248 | 785.598390 | 785.52 | 785.83 | 0 | 242 | 7.76 | 276.76 |
| 249 | 786.065541 | 785.83 | 786.14 | 1 | 178 | 5.70 | 205.68 |
| 250 | 786.242874 | 786.14 | 786.37 | 1 | 266 | 8.55 | 196.64 |
| 251 | 786.457126 | 786.37 | 786.64 | 1 | 271 | 8.70 | 273.14 |
| 252 | 787.265903 | 787.10 | 787.33 | 1 | 329 | 10.57 | 439.41 |
| 253 | 787.412894 | 787.33 | 787.60 | 1 | 319 | 10.22 | 392.05 |
| 254 | 787.697039 | 787.60 | 787.79 | 1 | 182 | 6.83 | 61.33 |
| 255 | 787.849090 | 787.79 | 788.02 | 0 | 186 | 5.98 | 100.56 |
| 256 | 788.214779 | 788.02 | 788.25 | 0 | 275 | 8.84 | 248.90 |
| 257 | 788.347375 | 788.25 | 788.44 | 1 | 308 | 9.88 | 60.19 |
| 258 | 788.494169 | 788.44 | 788.67 | 0 | 281 | 9.02 | 303.67 |
| 259 | 788.776006 | 788.67 | 788.87 | 1 | 194 | 6.22 | 112.30 |
| 260 | 789.333463 | 789.02 | 789.56 | 1 | 312 | 10.01 | 523.37 |
| 261 | 789.772896 | 789.71 | 789.94 | 1 | 169 | 5.43 | 123.85 |
| 262 | 790.191655 | 789.94 | 790.25 | 1 | 237 | 7.60 | 278.71 |
| 263 | 790.420207 | 790.25 | 790.71 | 1 | 277 | 8.90 | 619.98 |
| 264 | 790.940421 | 790.83 | 791.10 | 0 | 160 | 5.12 | 138.21 |
| 265 | 791.278406 | 791.10 | 791.37 | 1 | 290 | 9.32 | 460.95 |
| 266 | 791.451596 | 791.37 | 791.56 | 0 | 280 | 8.97 | 107.59 |
| 267 | 791.610835 | 791.56 | 791.83 | 1 | 191 | 6.12 | 193.41 |
| 268 | 791.952876 | 791.83 | 792.10 | 1 | 154 | 4.93 | 66.47 |
| 269 | 792.293260 | 792.10 | 792.37 | 0 | 272 | 8.72 | 367.61 |
| 270 | 792.442396 | 792.37 | 792.60 | 1 | 299 | 9.60 | 436.27 |
| 271 | 792.719051 | 792.60 | 792.83 | 1 | 157 | 5.05 | 85.15 |
| 272 | 793.017052 | 792.83 | 793.07 | 1 | 217 | 6.96 | 144.82 |
| 273 | 793.145350 | 793.07 | 793.18 | 0 | 225 | 7.23 | 37.23 |
| 274 | 793.382841 | 793.18 | 793.68 | 1 | 325 | 10.44 | 642.33 |
| 275 | 793.762032 | 793.68 | 793.91 | 1 | 157 | 5.04 | 45.79 |
| 276 | 794.308867 | 793.99 | 794.38 | 0 | 247 | 7.93 | 416.21 |
| 277 | 794.470628 | 794.38 | 794.72 | 1 | 284 | 9.13 | 336.05 |
| 278 | 794.960286 | 794.72 | 795.11 | 1 | 164 | 5.27 | 166.36 |

Figure 7H

| | | | | | | | |
|---|---|---|---|---|---|---|---|
| 279 | 795.357249 | 795.11 | 795.69 | 1 | 308 | 9.88 | 629.92 |
| 280 | 795.862459 | 795.81 | 796.04 | 1 | 166 | 5.34 | 71.89 |
| 281 | 796.171606 | 796.04 | 796.23 | 1 | 241 | 7.72 | 278.47 |
| 282 | 796.457935 | 796.23 | 796.62 | 1 | 350 | 11.22 | 716.50 |
| 283 | 796.690194 | 796.62 | 796.69 | 0 | 198 | 6.37 | 243.57 |
| 284 | 797.261770 | 797.08 | 797.35 | 1 | 306 | 9.87 | 411.55 |
| 285 | 797.468269 | 797.35 | 797.74 | 1 | 314 | 10.07 | 585.04 |
| 286 | 797.859362 | 797.74 | 798.01 | 0 | 193 | 6.18 | 226.55 |
| 287 | 798.311084 | 798.01 | 798.43 | 1 | 313 | 10.04 | 599.82 |
| 288 | 798.511867 | 798.43 | 798.74 | 1 | 270 | 8.67 | 247.19 |
| 289 | 799.301947 | 798.90 | 799.46 | 1 | 327 | 10.50 | 893.96 |
| 290 | 799.521198 | 799.46 | 799.63 | 1 | 207 | 6.66 | 92.52 |
| 291 | 799.708113 | 799.63 | 799.83 | 0 | 189 | 6.06 | 116.44 |
| 292 | 800.099598 | 799.98 | 800.14 | 0 | 166 | 5.34 | 53.39 |
| 293 | 800.404746 | 800.33 | 800.60 | 1 | 290 | 9.32 | 764.57 |
| 294 | 801.260901 | 801.07 | 801.34 | 0 | 219 | 7.04 | 332.43 |
| 295 | 801.431053 | 801.34 | 801.84 | 1 | 290 | 9.30 | 635.20 |
| 296 | 802.365040 | 801.96 | 802.54 | 1 | 288 | 9.23 | 627.52 |
| 297 | 802.622081 | 802.54 | 802.81 | 0 | 208 | 6.67 | 222.60 |
| 298 | 803.008252 | 802.81 | 803.12 | 0 | 185 | 5.93 | 175.63 |
| 299 | 803.316931 | 803.12 | 803.43 | 0 | 250 | 8.02 | 366.52 |
| 300 | 803.510050 | 803.43 | 803.63 | 1 | 252 | 8.08 | 243.29 |
| 301 | 803.841205 | 803.74 | 803.94 | 0 | 192 | 6.18 | 134.86 |
| 302 | 804.367144 | 804.09 | 804.63 | 1 | 264 | 8.47 | 877.87 |
| 303 | 805.298904 | 804.99 | 805.57 | 1 | 304 | 9.77 | 661.87 |
| 304 | 805.644987 | 805.57 | 805.76 | 1 | 170 | 5.46 | 149.53 |
| 305 | 806.254244 | 805.96 | 806.35 | 1 | 323 | 10.35 | 494.13 |
| 306 | 806.457986 | 806.35 | 806.56 | 0 | 287 | 9.21 | 342.85 |
| 307 | 806.687460 | 806.56 | 806.76 | 1 | 162 | 6.19 | 90.76 |
| 308 | 806.874312 | 806.78 | 806.97 | 0 | 157 | 5.04 | 86.63 |
| 309 | 807.052930 | 806.97 | 807.09 | 0 | 162 | 5.21 | 39.76 |
| 310 | 807.270471 | 807.09 | 807.63 | 1 | 307 | 9.86 | 810.02 |
| 311 | 808.266585 | 808.06 | 808.37 | 1 | 302 | 9.69 | 328.72 |
| 312 | 808.444072 | 808.37 | 808.80 | 0 | 273 | 8.76 | 520.52 |
| 313 | 808.963870 | 808.80 | 809.11 | 0 | 176 | 5.64 | 196.17 |
| 314 | 809.350137 | 809.11 | 809.70 | 1 | 303 | 9.72 | 763.38 |
| 315 | 810.282727 | 810.01 | 810.36 | 1 | 305 | 9.80 | 406.06 |
| 316 | 810.435154 | 810.36 | 810.67 | 0 | 263 | 8.11 | 299.44 |
| 317 | 810.739679 | 810.67 | 810.83 | 0 | 169 | 5.44 | 75.55 |
| 318 | 810.911202 | 810.83 | 811.02 | 1 | 170 | 5.47 | 85.49 |
| 319 | 811.385985 | 811.02 | 811.68 | 1 | 309 | 9.91 | 850.15 |
| 320 | 811.827365 | 811.68 | 812.00 | 1 | 163 | 5.23 | 86.82 |
| 321 | 812.061315 | 812.00 | 812.11 | 1 | 165 | 5.28 | 42.17 |
| 322 | 812.429828 | 812.11 | 812.76 | 1 | 322 | 10.35 | 877.34 |
| 323 | 812.975911 | 812.76 | 813.05 | 1 | 177 | 5.67 | 164.14 |
| 324 | 813.266134 | 813.05 | 813.32 | 0 | 284 | 9.11 | 275.24 |
| 325 | 813.410699 | 813.32 | 813.64 | 1 | 309 | 9.91 | 259.45 |
| 326 | 813.680295 | 813.64 | 813.87 | 0 | 176 | 5.65 | 127.09 |
| 327 | 814.291089 | 814.03 | 814.38 | 1 | 319 | 10.23 | 556.27 |
| 328 | 814.526820 | 814.38 | 814.85 | 0 | 316 | 10.15 | 553.28 |
| 329 | 814.966395 | 814.85 | 815.00 | 0 | 177 | 5.67 | 94.28 |
| 330 | 815.232849 | 815.00 | 815.32 | 0 | 219 | 7.02 | 156.14 |
| 331 | 815.456800 | 815.40 | 815.75 | 1 | 233 | 7.47 | 332.15 |
| 332 | 816.294919 | 816.06 | 816.37 | 0 | 270 | 8.66 | 403.42 |
| 333 | 816.448362 | 816.37 | 816.73 | 0 | 296 | 9.49 | 496.65 |
| 334 | 817.355632 | 816.88 | 817.76 | 1 | 279 | 8.96 | 1159.90 |

Figure 7I

| | | | | | | | |
|---|---|---|---|---|---|---|---|
| 335 | 818.345015 | 817.94 | 818.41 | 0 | 291 | 9.34 | 459.47 |
| 336 | 818.456948 | 818.41 | 818.64 | 1 | 298 | 9.56 | 283.64 |
| 337 | 818.779322 | 818.64 | 818.96 | 0 | 186 | 5.98 | 258.93 |
| 338 | 819.273131 | 819.15 | 819.31 | 1 | 267 | 8.56 | 244.24 |
| 339 | 819.417369 | 819.31 | 819.55 | 1 | 281 | 9.01 | 314.84 |
| 340 | 819.647542 | 819.55 | 819.86 | 1 | 165 | 5.29 | 156.85 |
| 341 | 820.274277 | 820.13 | 820.37 | 1 | 311 | 9.97 | 279.18 |
| 342 | 820.457501 | 820.37 | 820.57 | 0 | 196 | 6.28 | 39.56 |
| 343 | 820.656561 | 820.57 | 820.76 | 1 | 203 | 6.53 | 173.78 |
| 344 | 820.891073 | 820.76 | 821.04 | 1 | 197 | 6.32 | 148.58 |
| 345 | 821.341127 | 821.04 | 821.59 | 1 | 356 | 11.44 | 929.17 |
| 346 | 821.671113 | 821.59 | 821.74 | 1 | 188 | 6.02 | 47.83 |
| 347 | 821.791306 | 821.74 | 821.90 | 1 | 158 | 5.07 | 116.77 |
| 348 | 822.311493 | 822.10 | 822.61 | 1 | 337 | 10.80 | 636.91 |
| 349 | 822.671694 | 822.61 | 822.80 | 1 | 229 | 7.34 | 130.80 |
| 350 | 823.332136 | 823.04 | 823.43 | 1 | 268 | 8.60 | 602.58 |
| 351 | 823.516683 | 823.43 | 823.78 | 1 | 250 | 8.03 | 312.70 |
| 352 | 824.274992 | 823.94 | 824.34 | 1 | 282 | 9.05 | 466.79 |
| 353 | 824.386835 | 824.34 | 824.45 | 0 | 277 | 8.91 | 60.35 |
| 354 | 824.535896 | 824.45 | 824.61 | 1 | 315 | 10.11 | 593.64 |
| 355 | 825.239212 | 825.00 | 825.40 | 1 | 284 | 9.13 | 611.38 |
| 356 | 825.469907 | 825.40 | 825.79 | 1 | 285 | 9.15 | 445.45 |
| 357 | 826.091426 | 825.91 | 826.16 | 0 | 200 | 6.42 | 199.84 |
| 358 | 826.327679 | 826.18 | 826.62 | 1 | 309 | 9.92 | 576.01 |
| 359 | 827.371285 | 827.05 | 827.80 | 1 | 299 | 9.61 | 866.88 |
| 360 | 828.379461 | 828.19 | 828.67 | 1 | 522 | 16.76 | 974.67 |
| 361 | 828.863897 | 828.82 | 828.94 | 0 | 156 | 5.01 | 36.32 |
| 362 | 829.356844 | 829.10 | 829.81 | 1 | 362 | 11.61 | 935.73 |
| 363 | 830.160392 | 829.93 | 830.24 | 1 | 208 | 6.68 | 194.89 |
| 364 | 830.431676 | 830.24 | 830.72 | 1 | 365 | 11.73 | 742.22 |
| 365 | 831.239131 | 830.95 | 831.31 | 1 | 238 | 7.64 | 396.57 |
| 366 | 831.383839 | 831.31 | 831.66 | 1 | 285 | 9.15 | 479.16 |
| 367 | 832.064016 | 831.90 | 832.10 | 1 | 163 | 5.24 | 111.35 |
| 368 | 832.262974 | 832.10 | 832.34 | 1 | 249 | 7.99 | 201.07 |
| 369 | 832.440029 | 832.34 | 832.69 | 0 | 244 | 7.82 | 298.34 |
| 370 | 833.008510 | 832.89 | 833.09 | 1 | 163 | 5.24 | 139.50 |
| 371 | 833.291464 | 833.09 | 833.68 | 1 | 320 | 10.27 | 657.92 |
| 372 | 833.810002 | 833.68 | 834.00 | 0 | 159 | 5.12 | 98.18 |
| 373 | 834.286465 | 834.12 | 834.35 | 1 | 256 | 8.22 | 361.10 |
| 374 | 834.457941 | 834.35 | 834.71 | 1 | 218 | 7.00 | 467.98 |
| 375 | 835.074142 | 834.95 | 835.14 | 0 | 161 | 5.18 | 113.63 |
| 376 | 835.321418 | 835.14 | 835.42 | 1 | 292 | 9.37 | 327.11 |
| 377 | 835.482237 | 835.42 | 835.66 | 1 | 262 | 8.40 | 230.21 |
| 378 | 836.297816 | 836.13 | 836.41 | 1 | 274 | 8.79 | 467.70 |
| 379 | 836.474873 | 836.41 | 836.69 | 1 | 293 | 9.39 | 357.96 |
| 380 | 836.962693 | 836.85 | 837.04 | 0 | 177 | 5.67 | 148.58 |
| 381 | 837.408285 | 837.04 | 837.76 | 1 | 291 | 9.34 | 872.87 |
| 382 | 838.335501 | 838.11 | 838.43 | 0 | 263 | 8.43 | 437.80 |
| 383 | 838.538837 | 838.43 | 838.75 | 1 | 283 | 9.09 | 331.01 |
| 384 | 838.814979 | 838.75 | 838.91 | 0 | 171 | 5.48 | 69.29 |
| 385 | 839.313235 | 838.91 | 839.62 | 1 | 252 | 8.09 | 742.03 |
| 386 | 839.717634 | 839.62 | 839.82 | 1 | 156 | 5.01 | 78.45 |
| 387 | 840.423004 | 840.02 | 840.69 | 1 | 268 | 8.59 | 811.59 |
| 388 | 840.783747 | 840.69 | 840.89 | 1 | 190 | 6.09 | 92.71 |
| 389 | 841.087243 | 840.89 | 841.17 | 1 | 244 | 7.82 | 199.55 |
| 390 | 841.293215 | 841.17 | 841.41 | 0 | 285 | 9.15 | 234.44 |

Figure 7J

| | | | | | | | |
|---|---|---|---|---|---|---|---|
| 391 | 841.502497 | 841.41 | 841.73 | 1 | 281 | 9.01 | 442.45 |
| 392 | 842.112948 | 842.00 | 842.20 | 1 | 193 | 6.19 | 130.65 |
| 393 | 842.510038 | 842.20 | 842.84 | 1 | 3116 | 100.00 | 5283.32 |
| 394 | 842.952195 | 842.84 | 843.04 | 0 | 159 | 5.10 | 65.75 |
| 395 | 843.510316 | 843.04 | 843.91 | 1 | 1528 | 49.03 | 2973.12 |
| 396 | 844.509589 | 844.07 | 844.67 | 1 | 503 | 16.14 | 1082.44 |
| 397 | 844.638430 | 844.67 | 844.99 | 0 | 172 | 5.52 | 202.78 |
| 398 | 845.084452 | 844.99 | 845.19 | 0 | 168 | 5.40 | 150.19 |
| 399 | 845.306449 | 845.19 | 845.35 | 1 | 263 | 8.43 | 156.33 |
| 400 | 845.455321 | 845.35 | 845.74 | 1 | 318 | 10.21 | 676.28 |
| 401 | 846.267063 | 846.10 | 846.38 | 1 | 302 | 9.66 | 372.13 |
| 402 | 846.429119 | 846.38 | 846.66 | 1 | 226 | 7.25 | 186.38 |
| 403 | 847.262175 | 847.02 | 847.46 | 1 | 294 | 9.43 | 629.86 |
| 404 | 847.519779 | 847.46 | 847.74 | 1 | 213 | 6.85 | 357.87 |
| 405 | 848.494956 | 848.41 | 848.69 | 0 | 319 | 10.23 | 499.03 |
| 406 | 848.816010 | 848.69 | 848.93 | 0 | 156 | 5.02 | 94.71 |
| 407 | 849.295140 | 848.93 | 849.41 | 1 | 230 | 7.39 | 366.24 |
| 408 | 849.498147 | 849.41 | 849.73 | 1 | 237 | 7.60 | 181.91 |
| 409 | 850.260380 | 850.01 | 850.41 | 1 | 237 | 7.61 | 378.12 |
| 410 | 850.536708 | 850.41 | 850.81 | 1 | 352 | 11.29 | 574.25 |
| 411 | 851.038682 | 850.97 | 851.09 | 0 | 154 | 4.95 | 30.66 |
| 412 | 851.264301 | 851.09 | 851.41 | 1 | 322 | 10.34 | 332.62 |
| 413 | 851.497642 | 851.41 | 851.65 | 1 | 243 | 7.79 | 298.96 |
| 414 | 851.774873 | 851.65 | 851.93 | 0 | 177 | 5.69 | 171.49 |
| 415 | 852.341321 | 852.05 | 852.49 | 1 | 252 | 8.07 | 710.94 |
| 416 | 852.562613 | 852.49 | 852.77 | 0 | 235 | 7.56 | 254.27 |
| 417 | 853.263742 | 853.09 | 853.41 | 0 | 230 | 7.38 | 274.43 |
| 418 | 853.500117 | 853.41 | 853.61 | 0 | 265 | 8.50 | 141.59 |
| 419 | 853.657431 | 853.61 | 853.77 | 0 | 189 | 6.07 | 153.14 |
| 420 | 854.411336 | 854.09 | 854.69 | 0 | 250 | 8.02 | 659.11 |
| 421 | 855.391401 | 855.09 | 855.65 | 1 | 235 | 7.53 | 548.00 |
| 422 | 855.699055 | 855.65 | 855.77 | 0 | 159 | 5.12 | 64.66 |
| 423 | 855.861561 | 855.77 | 855.97 | 1 | 156 | 5.01 | 119.77 |
| 424 | 856.457540 | 855.97 | 856.65 | 1 | 407 | 13.07 | 1233.74 |
| 425 | 856.874065 | 856.77 | 856.97 | 1 | 163 | 5.23 | 74.79 |
| 426 | 857.334493 | 857.25 | 857.37 | 1 | 281 | 9.03 | 113.44 |
| 427 | 857.501577 | 857.37 | 857.69 | 1 | 339 | 10.87 | 543.58 |
| 428 | 857.740866 | 857.69 | 857.81 | 1 | 155 | 4.97 | 29.95 |
| 429 | 858.034625 | 857.81 | 858.13 | 0 | 185 | 5.93 | 106.41 |
| 430 | 858.282324 | 858.13 | 858.42 | 1 | 274 | 8.80 | 274.00 |
| 431 | 858.510956 | 858.42 | 858.74 | 1 | 208 | 6.68 | 318.17 |
| 432 | 859.289371 | 859.10 | 859.38 | 1 | 198 | 6.37 | 266.89 |
| 433 | 859.458516 | 859.38 | 859.78 | 0 | 267 | 8.57 | 445.64 |
| 434 | 860.085237 | 859.94 | 860.18 | 1 | 156 | 4.99 | 145.39 |
| 435 | 860.348121 | 860.18 | 860.58 | 1 | 227 | 7.27 | 303.72 |
| 436 | 861.060410 | 860.90 | 861.15 | 1 | 173 | 5.55 | 132.17 |
| 437 | 861.344247 | 861.15 | 861.55 | 1 | 287 | 9.21 | 519.19 |
| 438 | 861.636895 | 861.55 | 861.75 | 0 | 171 | 5.48 | 164.17 |
| 439 | 862.200336 | 861.91 | 862.27 | 1 | 229 | 7.34 | 358.39 |
| 440 | 862.328369 | 862.27 | 862.67 | 1 | 280 | 9.00 | 502.64 |
| 441 | 863.335946 | 863.12 | 863.40 | 1 | 212 | 6.80 | 282.56 |
| 442 | 863.491520 | 863.40 | 863.56 | 1 | 225 | 7.22 | 116.46 |
| 443 | 864.469898 | 864.08 | 864.81 | 1 | 393 | 12.62 | 1045.84 |
| 444 | 865.457790 | 865.05 | 865.81 | 1 | 347 | 11.15 | 951.47 |
| 445 | 866.416744 | 866.06 | 866.70 | 1 | 279 | 8.95 | 923.61 |
| 446 | 867.083304 | 866.98 | 867.18 | 0 | 169 | 5.43 | 93.85 |

Figure 7K

| | | | | | | | |
|---|---|---|---|---|---|---|---|
| 447 | 867.459584 | 867.18 | 867.63 | 1 | 344 | 11.05 | 631.35 |
| 448 | 867.697999 | 867.63 | 867.87 | 0 | 161 | 5.18 | 61.57 |
| 449 | 868.526203 | 868.03 | 868.72 | 1 | 413 | 13.24 | 1328.78 |
| 450 | 869.477947 | 868.96 | 869.73 | 1 | 333 | 10.68 | 1064.24 |
| 451 | 870.532057 | 870.09 | 870.70 | 1 | 679 | 21.80 | 1325.55 |
| 452 | 871.006884 | 870.90 | 871.10 | 0 | 176 | 5.64 | 79.16 |
| 453 | 871.259317 | 871.10 | 871.34 | 1 | 180 | 5.78 | 180.29 |
| 454 | 871.518616 | 871.34 | 871.75 | 1 | 413 | 13.26 | 609.61 |
| 455 | 872.324841 | 872.15 | 872.39 | 1 | 229 | 7.35 | 163.98 |
| 456 | 872.498825 | 872.39 | 872.68 | 1 | 241 | 7.74 | 422.82 |
| 457 | 873.211280 | 873.08 | 873.28 | 1 | 260 | 8.34 | 267.96 |
| 458 | 873.361297 | 873.28 | 873.41 | 0 | 227 | 7.29 | 24.25 |
| 459 | 873.484731 | 873.41 | 873.61 | 1 | 231 | 7.40 | 384.68 |
| 460 | 874.301956 | 874.09 | 874.42 | 1 | 279 | 8.95 | 425.48 |
| 461 | 874.503418 | 874.42 | 874.70 | 1 | 195 | 6.27 | 233.11 |
| 462 | 874.789541 | 874.70 | 874.86 | 0 | 164 | 5.25 | 98.75 |
| 463 | 875.373387 | 875.07 | 875.88 | 1 | 247 | 7.94 | 666.55 |
| 464 | 876.319169 | 876.04 | 876.40 | 0 | 215 | 6.91 | 381.12 |
| 465 | 876.498879 | 876.40 | 876.81 | 1 | 241 | 7.73 | 377.69 |
| 466 | 877.012418 | 876.93 | 877.13 | 0 | 188 | 6.02 | 135.26 |
| 467 | 877.213221 | 877.13 | 877.30 | 0 | 180 | 5.79 | 63.54 |
| 468 | 877.447796 | 877.30 | 877.70 | 1 | 213 | 6.84 | 236.25 |
| 469 | 878.285771 | 877.90 | 878.48 | 1 | 276 | 8.86 | 638.29 |
| 470 | 878.622489 | 878.43 | 878.82 | 0 | 247 | 7.92 | 492.56 |
| 471 | 879.258691 | 879.08 | 879.37 | 1 | 225 | 7.24 | 247.42 |
| 472 | 879.477408 | 879.37 | 879.73 | 1 | 228 | 7.32 | 369.83 |
| 473 | 880.014365 | 879.83 | 880.10 | 0 | 160 | 5.14 | 76.55 |
| 474 | 880.462927 | 880.10 | 880.62 | 1 | 316 | 10.16 | 648.09 |
| 475 | 881.412589 | 881.03 | 881.68 | 0 | 224 | 7.18 | 765.23 |
| 476 | 882.215429 | 882.09 | 882.41 | 1 | 223 | 7.16 | 410.69 |
| 477 | 882.553209 | 882.41 | 882.70 | 1 | 885 | 28.40 | 1194.99 |
| 478 | 882.752052 | 882.70 | 882.86 | 0 | 170 | 5.47 | 122.46 |
| 479 | 883.296313 | 882.98 | 883.39 | 1 | 231 | 7.40 | 378.65 |
| 480 | 883.556854 | 883.39 | 884.00 | 1 | 509 | 16.35 | 906.63 |
| 481 | 884.310197 | 884.12 | 884.45 | 1 | 193 | 6.21 | 302.00 |
| 482 | 884.560009 | 884.45 | 884.69 | 1 | 245 | 7.86 | 193.22 |
| 483 | 885.281369 | 885.10 | 885.35 | 0 | 217 | 6.97 | 211.76 |
| 484 | 885.419698 | 885.35 | 885.55 | 1 | 218 | 7.00 | 97.70 |
| 485 | 885.802294 | 885.55 | 885.71 | 0 | 160 | 5.13 | 96.68 |
| 486 | 886.238422 | 886.12 | 886.36 | 1 | 213 | 6.84 | 306.33 |
| 487 | 886.482788 | 886.36 | 886.77 | 1 | 254 | 8.16 | 546.46 |
| 488 | 887.233567 | 886.98 | 887.34 | 1 | 218 | 7.01 | 305.00 |
| 489 | 887.466132 | 887.34 | 887.75 | 1 | 240 | 7.69 | 606.68 |
| 490 | 888.396885 | 888.20 | 888.49 | 1 | 232 | 7.45 | 294.78 |
| 491 | 888.530286 | 888.49 | 888.65 | 0 | 220 | 7.05 | 229.78 |
| 492 | 889.240087 | 889.10 | 889.30 | 1 | 194 | 6.21 | 157.14 |
| 493 | 889.454739 | 889.30 | 889.55 | 1 | 225 | 7.21 | 206.30 |
| 494 | 890.222409 | 890.06 | 890.32 | 1 | 186 | 5.95 | 229.45 |
| 495 | 890.480773 | 890.32 | 890.85 | 1 | 252 | 8.08 | 523.14 |
| 496 | 891.339664 | 891.06 | 891.39 | 0 | 213 | 6.84 | 321.36 |
| 497 | 891.489927 | 891.39 | 891.71 | 1 | 255 | 8.19 | 374.18 |
| 498 | 892.249261 | 892.00 | 892.33 | 0 | 181 | 5.82 | 237.53 |
| 499 | 892.467736 | 892.33 | 892.57 | 1 | 230 | 7.38 | 146.72 |
| 500 | 892.624402 | 892.57 | 892.94 | 0 | 184 | 5.92 | 182.19 |
| 501 | 893.502142 | 893.39 | 893.76 | 1 | 215 | 6.89 | 339.80 |
| 502 | 894.210367 | 893.80 | 894.29 | 1 | 207 | 6.64 | 275.24 |

Figure 7L

| | | | | | | | |
|---|---|---|---|---|---|---|---|
| 503 | 894.456869 | 894.29 | 894.74 | 1 | 226 | 7.33 | 427.76 |
| 504 | 895.318284 | 895.07 | 895.40 | 1 | 240 | 7.70 | 296.63 |
| 505 | 895.497710 | 895.40 | 895.64 | 1 | 263 | 8.45 | 400.23 |
| 506 | 896.298864 | 896.05 | 896.38 | 1 | 199 | 6.39 | 228.55 |
| 507 | 896.516825 | 896.38 | 896.71 | 1 | 210 | 6.75 | 346.79 |
| 508 | 897.235833 | 897.00 | 897.28 | 1 | 200 | 6.42 | 181.43 |
| 509 | 897.447675 | 897.28 | 897.53 | 0 | 185 | 5.94 | 56.29 |
| 510 | 897.583523 | 897.53 | 897.73 | 1 | 186 | 5.98 | 206.44 |
| 511 | 898.379971 | 898.10 | 898.66 | 1 | 226 | 7.24 | 566.35 |
| 512 | 899.364998 | 899.13 | 899.46 | 1 | 237 | 7.60 | 393.86 |
| 513 | 899.526377 | 899.46 | 899.71 | 0 | 206 | 6.62 | 230.69 |
| 514 | 899.836746 | 899.71 | 900.12 | 0 | 195 | 6.25 | 306.09 |
| 515 | 900.254533 | 900.12 | 900.36 | 1 | 161 | 5.18 | 205.58 |
| 516 | 900.496362 | 900.36 | 900.69 | 1 | 218 | 6.99 | 230.31 |
| 517 | 901.218704 | 900.94 | 901.31 | 1 | 208 | 6.66 | 219.28 |
| 518 | 901.454266 | 901.31 | 901.72 | 0 | 236 | 7.58 | 348.65 |
| 519 | 902.296084 | 902.01 | 902.34 | 1 | 175 | 5.63 | 193.70 |
| 520 | 902.414882 | 902.34 | 902.46 | 1 | 185 | 5.95 | 21.30 |
| 521 | 902.618034 | 902.46 | 902.75 | 0 | 165 | 5.31 | 109.07 |
| 522 | 903.283815 | 902.99 | 903.41 | 0 | 207 | 6.64 | 299.91 |
| 523 | 903.485099 | 903.41 | 903.78 | 1 | 191 | 6.14 | 183.09 |
| 524 | 904.457777 | 904.35 | 904.58 | 1 | 226 | 7.25 | 191.18 |
| 525 | 904.641093 | 904.58 | 904.89 | 0 | 169 | 5.43 | 217.95 |
| 526 | 905.248516 | 904.89 | 905.38 | 0 | 258 | 8.26 | 506.64 |
| 527 | 905.487819 | 905.38 | 905.79 | 1 | 247 | 7.91 | 291.97 |
| 528 | 906.294053 | 906.12 | 906.33 | 1 | 222 | 7.12 | 243.05 |
| 529 | 906.461339 | 906.33 | 906.74 | 1 | 293 | 9.39 | 514.29 |
| 530 | 907.252149 | 907.03 | 907.36 | 1 | 449 | 14.42 | 584.02 |
| 531 | 907.473091 | 907.36 | 907.73 | 1 | 271 | 8.69 | 463.94 |
| 532 | 908.257712 | 907.94 | 908.39 | 1 | 351 | 11.27 | 643.09 |
| 533 | 908.512842 | 908.39 | 908.72 | 1 | 221 | 7.10 | 336.66 |
| 534 | 909.227627 | 909.14 | 909.30 | 1 | 236 | 7.57 | 184.05 |
| 535 | 909.342764 | 909.30 | 909.43 | 0 | 225 | 7.22 | 42.22 |
| 536 | 909.493310 | 909.43 | 909.80 | 1 | 225 | 7.22 | 394.67 |
| 537 | 910.335573 | 910.17 | 910.46 | 1 | 232 | 7.44 | 366.71 |
| 538 | 910.531161 | 910.46 | 910.87 | 1 | 233 | 7.49 | 332.24 |
| 539 | 911.411026 | 911.04 | 911.70 | 1 | 213 | 6.83 | 672.19 |
| 540 | 911.805737 | 911.70 | 911.90 | 0 | 160 | 5.12 | 92.90 |
| 541 | 911.971612 | 911.90 | 912.07 | 0 | 173 | 5.56 | 74.98 |
| 542 | 912.256294 | 912.07 | 912.36 | 0 | 213 | 6.83 | 215.62 |
| 543 | 912.457560 | 912.36 | 912.77 | 1 | 285 | 9.15 | 401.04 |
| 544 | 913.330580 | 913.19 | 913.39 | 1 | 190 | 6.11 | 228.74 |
| 545 | 913.494971 | 913.39 | 913.61 | 1 | 180 | 5.77 | 366.21 |
| 546 | 914.335918 | 913.93 | 914.39 | 0 | 197 | 6.31 | 371.13 |
| 547 | 914.451350 | 914.39 | 914.76 | 1 | 204 | 6.54 | 424.43 |
| 548 | 915.392345 | 914.97 | 915.80 | 1 | 264 | 8.49 | 877.87 |
| 549 | 916.424417 | 916.17 | 916.79 | 1 | 249 | 7.98 | 545.62 |
| 550 | 917.295117 | 917.12 | 917.37 | 1 | 245 | 7.85 | 237.82 |
| 551 | 917.458568 | 917.37 | 917.68 | 0 | 239 | 7.68 | 248.84 |
| 552 | 917.691861 | 917.68 | 917.79 | 0 | 176 | 5.63 | 64.61 |
| 553 | 918.390410 | 918.08 | 918.78 | 1 | 205 | 6.59 | 520.09 |
| 554 | 919.372369 | 919.20 | 919.46 | 1 | 226 | 7.26 | 252.37 |
| 555 | 919.500863 | 919.46 | 919.70 | 0 | 208 | 6.67 | 164.22 |
| 556 | 920.354766 | 919.99 | 920.44 | 1 | 221 | 7.11 | 282.89 |
| 557 | 920.613945 | 920.44 | 920.82 | 0 | 216 | 6.94 | 220.32 |
| 558 | 921.429505 | 921.11 | 921.65 | 1 | 198 | 6.36 | 498.74 |

Figure 7M

| | | | | | | | |
|---|---|---|---|---|---|---|---|
| 559 | 922.193094 | 922.06 | 922.23 | 1 | 178 | 5.71 | 138.50 |
| 560 | 922.503285 | 922.23 | 922.81 | 1 | 285 | 9.14 | 640.19 |
| 561 | 923.285729 | 923.10 | 923.36 | 1 | 213 | 6.84 | 277.23 |
| 562 | 923.458224 | 923.36 | 923.65 | 1 | 235 | 7.54 | 227.31 |
| 563 | 924.169416 | 924.06 | 924.23 | 0 | 194 | 6.23 | 182.76 |
| 564 | 924.431121 | 924.23 | 924.48 | 1 | 236 | 7.56 | 61.52 |
| 565 | 924.558691 | 924.48 | 924.73 | 0 | 230 | 7.37 | 191.42 |
| 566 | 925.497479 | 925.31 | 925.60 | 1 | 190 | 6.09 | 135.60 |
| 567 | 925.710285 | 925.60 | 925.89 | 0 | 157 | 5.05 | 59.34 |
| 568 | 925.986730 | 925.89 | 926.19 | 0 | 160 | 5.14 | 118.10 |
| 569 | 926.353954 | 926.19 | 926.39 | 1 | 198 | 6.34 | 82.68 |
| 570 | 926.451411 | 926.39 | 926.77 | 0 | 196 | 6.28 | 260.55 |
| 571 | 927.467163 | 927.14 | 927.81 | 1 | 234 | 7.50 | 703.47 |
| 572 | 928.310899 | 927.81 | 928.35 | 1 | 211 | 6.76 | 384.83 |
| 573 | 928.431762 | 928.35 | 928.73 | 1 | 203 | 6.52 | 301.81 |
| 574 | 929.247045 | 929.02 | 929.44 | 1 | 227 | 7.27 | 515.20 |
| 575 | 929.497380 | 929.44 | 929.77 | 1 | 196 | 6.29 | 267.65 |
| 576 | 930.462166 | 930.11 | 930.69 | 1 | 202 | 6.49 | 606.29 |
| 577 | 931.314340 | 931.19 | 931.40 | 1 | 201 | 6.47 | 162.98 |
| 578 | 931.524783 | 931.40 | 931.90 | 1 | 200 | 6.43 | 293.11 |
| 579 | 932.601147 | 932.41 | 932.66 | 1 | 323 | 10.35 | 371.32 |
| 580 | 933.276334 | 933.16 | 933.37 | 0 | 218 | 6.99 | 236.01 |
| 581 | 933.526666 | 933.37 | 933.79 | 1 | 231 | 7.41 | 374.22 |
| 582 | 934.427651 | 934.16 | 934.92 | 1 | 221 | 7.10 | 576.68 |
| 583 | 935.447017 | 935.08 | 935.84 | 1 | 305 | 9.80 | 942.77 |
| 584 | 936.313446 | 935.96 | 936.38 | 1 | 226 | 7.26 | 362.02 |
| 585 | 936.479063 | 936.38 | 936.68 | 1 | 268 | 8.60 | 337.68 |
| 586 | 937.210226 | 936.97 | 937.26 | 1 | 182 | 5.86 | 225.89 |
| 587 | 937.492719 | 937.26 | 937.93 | 1 | 291 | 9.34 | 831.54 |
| 588 | 938.416607 | 938.14 | 938.96 | 1 | 224 | 7.19 | 645.16 |
| 589 | 939.245956 | 938.96 | 939.32 | 0 | 161 | 5.16 | 164.89 |
| 590 | 939.472701 | 939.32 | 939.78 | 1 | 182 | 5.85 | 397.43 |
| 591 | 940.332651 | 940.12 | 940.41 | 0 | 223 | 7.14 | 297.92 |
| 592 | 940.523818 | 940.41 | 940.87 | 1 | 234 | 7.50 | 492.14 |
| 593 | 941.265175 | 941.08 | 941.33 | 0 | 180 | 5.78 | 182.66 |
| 594 | 941.463358 | 941.33 | 941.75 | 1 | 224 | 7.19 | 371.51 |
| 595 | 942.370183 | 942.09 | 942.72 | 1 | 214 | 6.87 | 501.12 |
| 596 | 943.274577 | 943.06 | 943.31 | 0 | 159 | 5.09 | 89.72 |
| 597 | 943.420011 | 943.31 | 943.62 | 1 | 231 | 7.42 | 155.42 |
| 598 | 944.478838 | 944.19 | 944.70 | 1 | 222 | 7.11 | 383.07 |
| 599 | 945.157087 | 944.99 | 945.20 | 0 | 156 | 5.01 | 118.48 |
| 600 | 945.389259 | 945.20 | 945.46 | 0 | 180 | 5.77 | 70.46 |
| 601 | 945.541445 | 945.46 | 945.98 | 1 | 246 | 7.89 | 377.89 |
| 602 | 946.441744 | 946.17 | 946.72 | 1 | 210 | 6.75 | 458.71 |
| 603 | 947.531462 | 947.31 | 947.82 | 1 | 209 | 6.70 | 289.98 |
| 604 | 948.255956 | 947.98 | 948.36 | 0 | 164 | 5.27 | 255.51 |
| 605 | 948.513137 | 948.36 | 948.62 | 1 | 194 | 6.23 | 128.71 |
| 606 | 948.672504 | 948.62 | 948.79 | 0 | 160 | 5.14 | 103.08 |
| 607 | 949.275082 | 949.12 | 949.33 | 1 | 189 | 6.09 | 87.05 |
| 608 | 949.503506 | 949.33 | 949.93 | 1 | 492 | 15.79 | 860.01 |
| 609 | 950.284051 | 950.14 | 950.39 | 1 | 225 | 7.22 | 254.84 |
| 610 | 950.517418 | 950.39 | 950.81 | 1 | 361 | 11.57 | 620.27 |
| 611 | 951.366848 | 951.23 | 951.45 | 1 | 248 | 7.96 | 256.41 |
| 612 | 951.514288 | 951.45 | 951.74 | 1 | 296 | 9.50 | 368.33 |
| 613 | 952.498072 | 952.16 | 952.88 | 1 | 218 | 7.00 | 798.23 |
| 614 | 953.458677 | 953.14 | 953.73 | 0 | 235 | 7.54 | 541.06 |

Figure 7N

| | | | | | | | |
|---|---|---|---|---|---|---|---|
| 615 | 955.635222 | 955.29 | 955.63 | 1 | 198 | 6.36 | 171.87 |
| 616 | 956.044603 | 955.89 | 956.18 | 0 | 157 | 5.04 | 97.42 |
| 617 | 956.432818 | 956.18 | 956.65 | 1 | 237 | 7.60 | 392.43 |
| 618 | 957.270158 | 957.16 | 957.37 | 0 | 170 | 5.44 | 96.56 |
| 619 | 957.494755 | 957.37 | 957.88 | 1 | 195 | 6.27 | 341.70 |
| 620 | 958.453510 | 958.34 | 958.51 | 0 | 180 | 5.78 | 134.22 |
| 621 | 958.690171 | 958.51 | 958.72 | 1 | 197 | 6.31 | 174.25 |
| 622 | 959.259921 | 958.98 | 959.32 | 0 | 154 | 4.93 | 163.24 |
| 623 | 959.500067 | 959.32 | 959.95 | 1 | 201 | 6.45 | 453.46 |
| 624 | 960.423828 | 960.08 | 960.93 | 1 | 226 | 7.26 | 901.83 |
| 625 | 961.250318 | 960.93 | 961.36 | 1 | 170 | 5.44 | 423.05 |
| 626 | 961.501838 | 961.36 | 961.74 | 1 | 225 | 7.21 | 373.84 |
| 627 | 962.356599 | 962.25 | 962.42 | 1 | 163 | 5.23 | 99.27 |
| 628 | 962.625113 | 962.42 | 962.71 | 1 | 210 | 6.73 | 294.92 |
| 629 | 963.518392 | 963.18 | 963.82 | 1 | 754 | 24.19 | 1442.46 |
| 630 | 964.498964 | 964.20 | 964.93 | 1 | 631 | 20.24 | 1403.47 |
| 631 | 965.512532 | 965.35 | 965.73 | 1 | 334 | 10.73 | 674.62 |
| 632 | 965.946268 | 965.73 | 966.12 | 0 | 155 | 4.99 | 170.64 |
| 633 | 966.498465 | 966.12 | 966.76 | 1 | 245 | 7.85 | 768.47 |
| 634 | 967.477010 | 967.35 | 967.85 | 1 | 207 | 6.65 | 209.53 |
| 635 | 968.260125 | 967.85 | 968.37 | 0 | 196 | 6.30 | 394.34 |
| 636 | 968.473905 | 968.37 | 968.54 | 1 | 163 | 5.22 | 36.75 |
| 637 | 968.600352 | 968.54 | 968.84 | 0 | 161 | 5.15 | 168.98 |
| 638 | 969.431446 | 969.10 | 969.74 | 1 | 236 | 7.59 | 648.84 |
| 639 | 970.151071 | 970.04 | 970.25 | 0 | 182 | 5.85 | 175.82 |
| 640 | 970.444564 | 970.25 | 970.68 | 1 | 186 | 5.96 | 271.43 |
| 641 | 971.309582 | 971.10 | 971.36 | 0 | 155 | 4.96 | 228.03 |
| 642 | 971.486796 | 971.36 | 971.66 | 0 | 225 | 7.23 | 286.46 |
| 643 | 972.453280 | 972.04 | 972.90 | 1 | 197 | 6.32 | 754.92 |
| 644 | 973.320582 | 973.11 | 973.41 | 0 | 227 | 7.30 | 327.77 |
| 645 | 973.501823 | 973.41 | 974.01 | 1 | 238 | 7.62 | 476.45 |
| 646 | 974.584313 | 974.35 | 974.65 | 1 | 178 | 5.72 | 132.22 |
| 647 | 975.508760 | 975.29 | 975.76 | 1 | 265 | 8.52 | 574.77 |
| 648 | 976.532156 | 976.36 | 976.66 | 1 | 232 | 7.46 | 261.61 |
| 649 | 977.227907 | 976.87 | 977.34 | 0 | 166 | 5.32 | 267.66 |
| 650 | 977.497751 | 977.34 | 977.77 | 1 | 188 | 6.05 | 373.46 |
| 651 | 978.447709 | 978.33 | 978.71 | 1 | 162 | 5.21 | 336.71 |
| 652 | 979.352312 | 979.27 | 979.40 | 1 | 157 | 5.04 | 19.97 |
| 653 | 979.545518 | 979.40 | 979.87 | 1 | 250 | 8.02 | 525.66 |
| 654 | 980.323689 | 980.00 | 980.43 | 1 | 160 | 5.13 | 254.74 |
| 655 | 980.564630 | 980.43 | 980.94 | 1 | 206 | 6.66 | 460.61 |
| 656 | 981.524704 | 981.29 | 981.76 | 1 | 191 | 6.14 | 276.24 |
| 657 | 982.120087 | 982.02 | 982.23 | 0 | 163 | 5.24 | 138.74 |
| 658 | 982.385244 | 982.23 | 982.49 | 1 | 198 | 6.37 | 267.11 |
| 659 | 982.595419 | 982.49 | 982.92 | 1 | 239 | 7.68 | 473.36 |
| 660 | 983.312900 | 983.18 | 983.43 | 1 | 180 | 5.77 | 206.25 |
| 661 | 983.579123 | 983.43 | 983.91 | 1 | 253 | 8.13 | 399.14 |
| 662 | 984.553716 | 984.29 | 984.94 | 1 | 210 | 6.75 | 388.44 |
| 663 | 985.433259 | 985.07 | 985.67 | 1 | 211 | 6.76 | 564.64 |
| 664 | 986.472131 | 986.36 | 986.79 | 1 | 167 | 5.37 | 300.39 |
| 665 | 987.394181 | 987.22 | 987.60 | 0 | 201 | 6.45 | 354.26 |
| 666 | 988.648045 | 988.33 | 988.77 | 1 | 170 | 5.47 | 300.91 |
| 667 | 989.502607 | 989.02 | 989.80 | 1 | 212 | 6.79 | 653.94 |
| 668 | 990.242640 | 990.14 | 990.40 | 0 | 168 | 5.38 | 189.85 |
| 669 | 990.550805 | 990.40 | 990.79 | 1 | 181 | 5.82 | 255.65 |
| 670 | 991.460607 | 991.01 | 991.83 | 0 | 197 | 6.34 | 728.01 |

Figure 7O

| 671 | 992.478204 | 992.08 | 992.73 | 1 | 188 | 6.03 | 471.36 |
|---|---|---|---|---|---|---|---|
| 672 | 993.461543 | 993.08 | 993.72 | 1 | 224 | 7.18 | 645.47 |
| 673 | 994.327323 | 994.20 | 994.37 | 1 | 170 | 5.45 | 96.42 |
| 674 | 994.631357 | 994.37 | 994.89 | 1 | 197 | 6.31 | 397.43 |
| 675 | 995.323172 | 995.11 | 995.36 | 1 | 154 | 4.93 | 103.74 |
| 676 | 995.546682 | 995.36 | 995.75 | 1 | 187 | 5.99 | 260.04 |
| 677 | 996.534676 | 996.14 | 996.79 | 1 | 312 | 10.02 | 870.88 |
| 678 | 997.537596 | 997.09 | 997.96 | 1 | 273 | 8.77 | 943.72 |
| 679 | 998.496968 | 998.35 | 998.82 | 1 | 181 | 5.81 | 380.60 |
| 680 | 999.520686 | 999.13 | 999.91 | 1 | 186 | 5.96 | 570.25 |
| 681 | 1000.606363 | 1000.17 | 1000.77 | 1 | 216 | 6.90 | 544.15 |
| 682 | 1001.408110 | 1000.95 | 1001.51 | 1 | 200 | 6.43 | 464.94 |
| 683 | 1001.578133 | 1001.51 | 1001.73 | 0 | 183 | 5.86 | 104.79 |
| 684 | 1002.502628 | 1002.38 | 1002.72 | 1 | 160 | 5.14 | 265.82 |
| 685 | 1003.333033 | 1003.16 | 1003.42 | 0 | 170 | 5.45 | 126.52 |
| 686 | 1003.526956 | 1003.42 | 1003.85 | 1 | 187 | 6.02 | 340.33 |
| 687 | 1004.478847 | 1004.02 | 1004.81 | 1 | 259 | 8.30 | 649.08 |
| 688 | 1004.962822 | 1004.81 | 1005.20 | 0 | 181 | 5.81 | 199.21 |
| 689 | 1005.507458 | 1005.20 | 1005.60 | 1 | 216 | 6.95 | 498.06 |
| 690 | 1006.572932 | 1006.28 | 1006.67 | 1 | 191 | 6.12 | 265.17 |
| 691 | 1007.274589 | 1007.11 | 1007.32 | 0 | 192 | 6.16 | 178.91 |
| 692 | 1007.554156 | 1007.32 | 1007.85 | 1 | 234 | 7.52 | 551.42 |
| 693 | 1008.552478 | 1008.28 | 1008.76 | 1 | 271 | 8.69 | 483.48 |
| 694 | 1009.442071 | 1009.02 | 1009.50 | 0 | 210 | 6.74 | 326.92 |
| 695 | 1009.571134 | 1009.50 | 1009.80 | 1 | 215 | 6.88 | 259.78 |
| 696 | 1010.465230 | 1010.24 | 1010.54 | 0 | 175 | 5.61 | 142.21 |
| 697 | 1010.600577 | 1010.54 | 1010.81 | 1 | 185 | 5.94 | 245.85 |
| 698 | 1011.293818 | 1011.02 | 1011.41 | 0 | 195 | 6.27 | 224.13 |
| 699 | 1011.527327 | 1011.41 | 1011.72 | 0 | 192 | 6.18 | 201.97 |
| 700 | 1014.450806 | 1014.16 | 1014.81 | 1 | 183 | 5.87 | 427.57 |
| 701 | 1015.497732 | 1015.29 | 1015.77 | 1 | 195 | 6.27 | 420.06 |
| 702 | 1016.410890 | 1016.25 | 1016.47 | 0 | 166 | 5.33 | 146.24 |
| 703 | 1016.593621 | 1016.47 | 1016.95 | 1 | 193 | 6.20 | 268.49 |
| 704 | 1017.679960 | 1017.22 | 1017.96 | 1 | 1074 | 34.48 | 1879.87 |
| 705 | 1018.591625 | 1018.22 | 1018.88 | 1 | 549 | 17.63 | 1025.11 |
| 706 | 1019.317145 | 1019.18 | 1019.36 | 0 | 168 | 5.39 | 58.67 |
| 707 | 1019.569161 | 1019.36 | 1019.88 | 1 | 466 | 14.97 | 916.52 |
| 708 | 1020.681248 | 1020.36 | 1020.84 | 1 | 238 | 7.63 | 550.71 |
| 709 | 1021.573974 | 1021.37 | 1021.89 | 1 | 238 | 7.63 | 494.66 |
| 710 | 1022.558864 | 1022.33 | 1022.99 | 1 | 249 | 7.99 | 617.56 |
| 711 | 1023.277874 | 1022.99 | 1023.38 | 0 | 156 | 4.99 | 247.80 |
| 712 | 1023.561959 | 1023.38 | 1023.60 | 1 | 190 | 6.10 | 153.95 |
| 713 | 1023.675087 | 1023.60 | 1024.04 | 0 | 184 | 5.91 | 265.89 |
| 714 | 1024.582557 | 1024.35 | 1024.87 | 1 | 186 | 5.95 | 428.43 |
| 715 | 1025.449944 | 1025.27 | 1025.76 | 1 | 191 | 6.14 | 374.51 |
| 716 | 1026.675377 | 1026.06 | 1026.72 | 1 | 258 | 8.28 | 497.18 |
| 717 | 1027.513332 | 1027.24 | 1027.81 | 1 | 198 | 6.37 | 574.29 |
| 718 | 1028.471515 | 1028.12 | 1028.95 | 1 | 196 | 6.29 | 626.59 |
| 719 | 1029.459695 | 1029.39 | 1029.83 | 1 | 161 | 5.17 | 259.93 |
| 720 | 1030.365902 | 1030.01 | 1030.49 | 0 | 184 | 5.91 | 354.87 |
| 721 | 1030.578438 | 1030.49 | 1030.89 | 1 | 184 | 5.91 | 273.24 |
| 722 | 1031.678487 | 1031.33 | 1031.77 | 1 | 253 | 8.12 | 456.19 |
| 723 | 1032.074860 | 1031.99 | 1032.21 | 0 | 155 | 4.98 | 82.25 |
| 724 | 1032.569462 | 1032.21 | 1032.87 | 1 | 297 | 9.54 | 647.85 |
| 725 | 1033.592029 | 1033.44 | 1033.84 | 1 | 248 | 7.96 | 448.63 |
| 726 | 1034.363123 | 1034.19 | 1034.54 | 1 | 165 | 5.31 | 263.30 |

Figure 7P

| | | | | | | | |
|---|---|---|---|---|---|---|---|
| 727 | 1034.620323 | 1034.54 | 1034.98 | 1 | 155 | 4.97 | 221.99 |
| 728 | 1035.265224 | 1034.88 | 1035.33 | 1 | 165 | 5.30 | 210.91 |
| 729 | 1035.541437 | 1035.33 | 1035.86 | 0 | 225 | 7.21 | 407.98 |
| 730 | 1036.674253 | 1036.30 | 1036.96 | 1 | 221 | 7.08 | 454.81 |
| 731 | 1037.362024 | 1037.01 | 1037.45 | 0 | 163 | 5.23 | 249.09 |
| 732 | 1037.655463 | 1037.45 | 1037.80 | 1 | 254 | 8.15 | 263.27 |
| 733 | 1038.548783 | 1038.33 | 1038.91 | 1 | 248 | 7.96 | 669.19 |
| 734 | 1039.607002 | 1039.35 | 1039.79 | 1 | 222 | 7.14 | 317.93 |
| 735 | 1040.517469 | 1040.19 | 1040.86 | 1 | 396 | 12.71 | 878.06 |
| 736 | 1041.526466 | 1041.38 | 1041.73 | 1 | 328 | 10.52 | 463.42 |
| 737 | 1042.404278 | 1042.22 | 1042.48 | 0 | 183 | 5.86 | 143.40 |
| 738 | 1042.570461 | 1042.48 | 1042.79 | 1 | 212 | 6.80 | 351.74 |
| 739 | 1043.546195 | 1043.37 | 1043.81 | 1 | 199 | 6.39 | 436.27 |
| 740 | 1044.511919 | 1044.17 | 1044.83 | 1 | 273 | 8.76 | 762.52 |
| 741 | 1045.554147 | 1045.09 | 1045.80 | 1 | 371 | 11.89 | 761.43 |
| 742 | 1046.665625 | 1046.47 | 1046.69 | 1 | 243 | 7.81 | 246.43 |
| 743 | 1047.425065 | 1047.13 | 1047.53 | 0 | 199 | 6.38 | 325.35 |
| 744 | 1047.586611 | 1047.53 | 1047.80 | 1 | 212 | 6.80 | 221.80 |
| 745 | 1048.597484 | 1048.37 | 1048.82 | 1 | 325 | 10.43 | 504.02 |
| 746 | 1049.576462 | 1048.99 | 1049.93 | 1 | 284 | 9.12 | 835.03 |
| 747 | 1050.546363 | 1050.37 | 1050.81 | 1 | 215 | 6.91 | 429.04 |
| 748 | 1051.691114 | 1051.17 | 1051.97 | 1 | 531 | 17.05 | 1010.76 |
| 749 | 1052.680322 | 1052.32 | 1053.03 | 1 | 446 | 14.31 | 800.74 |
| 750 | 1053.622314 | 1053.36 | 1053.88 | 1 | 259 | 8.31 | 559.35 |
| 751 | 1054.520293 | 1054.15 | 1054.63 | 1 | 226 | 7.25 | 390.06 |
| 752 | 1054.703656 | 1054.63 | 1055.08 | 0 | 176 | 5.64 | 161.70 |
| 753 | 1055.532931 | 1055.39 | 1055.88 | 1 | 258 | 8.29 | 344.46 |
| 754 | 1056.552454 | 1056.10 | 1056.77 | 1 | 215 | 6.89 | 539.40 |
| 755 | 1057.523464 | 1057.17 | 1057.93 | 1 | 203 | 6.53 | 352.02 |
| 756 | 1058.454906 | 1058.15 | 1058.73 | 1 | 195 | 6.25 | 442.93 |
| 757 | 1059.563768 | 1059.18 | 1059.84 | 1 | 204 | 6.55 | 565.12 |
| 758 | 1060.566737 | 1060.34 | 1060.83 | 1 | 192 | 6.16 | 339.42 |
| 759 | 1061.570322 | 1061.49 | 1061.76 | 1 | 167 | 5.37 | 205.68 |
| 760 | 1062.511005 | 1062.30 | 1062.88 | 1 | 203 | 6.52 | 429.09 |
| 761 | 1063.561107 | 1063.24 | 1063.82 | 1 | 193 | 6.18 | 377.03 |
| 762 | 1064.688468 | 1064.40 | 1064.84 | 1 | 177 | 5.67 | 346.03 |
| 763 | 1065.707742 | 1065.51 | 1065.92 | 1 | 161 | 5.18 | 313.65 |
| 764 | 1066.580954 | 1066.36 | 1066.90 | 1 | 230 | 7.37 | 376.65 |
| 765 | 1067.538276 | 1067.39 | 1067.71 | 1 | 155 | 4.98 | 198.31 |
| 766 | 1068.522650 | 1068.20 | 1068.69 | 1 | 185 | 5.94 | 460.14 |
| 767 | 1069.597087 | 1069.45 | 1069.90 | 1 | 208 | 6.67 | 362.20 |
| 768 | 1070.568265 | 1070.35 | 1070.89 | 1 | 207 | 6.66 | 447.11 |
| 769 | 1071.505629 | 1071.42 | 1071.56 | 0 | 202 | 6.48 | 86.81 |
| 770 | 1071.644237 | 1071.56 | 1071.83 | 0 | 208 | 6.66 | 219.47 |
| 771 | 1072.620730 | 1072.45 | 1072.90 | 1 | 168 | 5.38 | 271.29 |
| 772 | 1073.561764 | 1073.40 | 1073.89 | 1 | 177 | 5.69 | 292.40 |
| 773 | 1074.418938 | 1074.16 | 1074.62 | 0 | 162 | 5.20 | 370.37 |
| 774 | 1074.598256 | 1074.62 | 1074.83 | 1 | 188 | 6.03 | 283.65 |
| 775 | 1075.557730 | 1075.33 | 1075.96 | 1 | 206 | 6.62 | 375.56 |
| 776 | 1076.570464 | 1076.40 | 1076.94 | 1 | 215 | 6.91 | 478.73 |
| 777 | 1077.530618 | 1077.35 | 1077.71 | 1 | 190 | 6.10 | 319.83 |
| 778 | 1078.558598 | 1078.25 | 1078.70 | 1 | 231 | 7.43 | 310.09 |
| 779 | 1079.544116 | 1079.37 | 1079.96 | 1 | 187 | 6.01 | 356.63 |
| 780 | 1080.546577 | 1080.27 | 1080.95 | 1 | 332 | 10.65 | 825.76 |
| 781 | 1081.549723 | 1081.31 | 1081.94 | 1 | 304 | 9.74 | 525.08 |
| 782 | 1082.573351 | 1082.34 | 1082.84 | 1 | 202 | 6.49 | 323.49 |

Figure 7Q

| | | | | | | | |
|---|---|---|---|---|---|---|---|
| 783 | 1083.557924 | 1083.33 | 1083.79 | 0 | 228 | 7.32 | 341.42 |
| 784 | 1084.319577 | 1084.06 | 1084.42 | 0 | 176 | 5.65 | 162.89 |
| 785 | 1084.641412 | 1084.55 | 1084.73 | 1 | 156 | 5.01 | 94.09 |
| 786 | 1085.075650 | 1084.91 | 1085.32 | 0 | 156 | 5.01 | 218.80 |
| 787 | 1085.592151 | 1085.32 | 1085.86 | 1 | 182 | 5.83 | 386.14 |
| 788 | 1086.532288 | 1086.09 | 1086.90 | 1 | 213 | 6.82 | 603.06 |
| 789 | 1087.528966 | 1087.26 | 1087.85 | 1 | 255 | 8.19 | 568.68 |
| 790 | 1088.560487 | 1088.25 | 1088.89 | 1 | 277 | 8.87 | 831.70 |
| 791 | 1089.550826 | 1089.38 | 1089.84 | 1 | 261 | 8.39 | 467.51 |
| 792 | 1090.532464 | 1090.20 | 1090.86 | 1 | 215 | 6.88 | 690.32 |
| 793 | 1091.535621 | 1091.42 | 1091.69 | 1 | 206 | 6.60 | 197.83 |
| 794 | 1092.488623 | 1092.14 | 1093.00 | 1 | 199 | 6.39 | 410.07 |
| 795 | 1093.537929 | 1093.41 | 1093.64 | 1 | 180 | 5.76 | 107.55 |
| 796 | 1093.710146 | 1093.64 | 1093.86 | 0 | 159 | 5.09 | 200.02 |
| 797 | 1094.576256 | 1094.22 | 1094.86 | 1 | 329 | 10.58 | 716.79 |
| 798 | 1095.670560 | 1095.31 | 1095.95 | 1 | 374 | 12.02 | 759.67 |
| 799 | 1096.665016 | 1096.31 | 1096.94 | 1 | 284 | 9.13 | 678.46 |
| 800 | 1097.582061 | 1097.44 | 1097.94 | 1 | 257 | 8.23 | 368.95 |
| 801 | 1098.571325 | 1098.17 | 1098.78 | 1 | 232 | 7.43 | 442.50 |
| 802 | 1099.488682 | 1099.30 | 1099.87 | 1 | 188 | 6.05 | 273.87 |
| 803 | 1100.575340 | 1100.12 | 1100.98 | 1 | 184 | 5.91 | 403.08 |
| 804 | 1101.686508 | 1101.39 | 1101.94 | 1 | 179 | 5.75 | 275.38 |
| 805 | 1102.428738 | 1102.21 | 1102.58 | 0 | 157 | 5.04 | 216.33 |
| 806 | 1102.680281 | 1102.58 | 1102.80 | 1 | 164 | 5.27 | 91.06 |
| 807 | 1103.582217 | 1103.03 | 1103.80 | 1 | 194 | 6.21 | 654.64 |
| 808 | 1104.583288 | 1104.44 | 1104.81 | 1 | 210 | 6.73 | 276.43 |
| 809 | 1105.659815 | 1105.17 | 1105.85 | 1 | 202 | 6.48 | 627.73 |
| 810 | 1106.566625 | 1106.26 | 1106.76 | 1 | 200 | 6.43 | 383.07 |
| 811 | 1107.542909 | 1107.40 | 1107.67 | 1 | 225 | 7.22 | 223.37 |
| 812 | 1108.616204 | 1108.31 | 1108.81 | 1 | 199 | 6.37 | 441.17 |
| 813 | 1109.593831 | 1109.45 | 1109.82 | 1 | 242 | 7.77 | 361.21 |
| 814 | 1110.491992 | 1110.23 | 1110.59 | 1 | 160 | 5.14 | 157.37 |
| 815 | 1110.668787 | 1110.59 | 1111.00 | 1 | 167 | 5.34 | 306.28 |
| 816 | 1111.628968 | 1111.28 | 1111.69 | 1 | 167 | 5.37 | 365.48 |
| 817 | 1112.574752 | 1112.33 | 1112.62 | 1 | 235 | 7.54 | 448.73 |
| 818 | 1113.579510 | 1113.29 | 1113.84 | 1 | 210 | 6.74 | 476.78 |
| 819 | 1114.587270 | 1114.43 | 1114.69 | 1 | 208 | 6.67 | 351.91 |
| 820 | 1115.589156 | 1115.39 | 1115.80 | 1 | 187 | 5.99 | 321.74 |
| 821 | 1116.587823 | 1116.44 | 1116.72 | 1 | 172 | 5.51 | 121.85 |
| 822 | 1117.564099 | 1117.45 | 1117.95 | 1 | 176 | 5.65 | 335.46 |
| 823 | 1118.581547 | 1118.23 | 1118.78 | 1 | 222 | 7.14 | 369.72 |
| 824 | 1119.591195 | 1119.24 | 1119.83 | 1 | 162 | 5.20 | 311.32 |
| 825 | 1120.573681 | 1120.06 | 1120.93 | 1 | 199 | 6.38 | 591.03 |
| 826 | 1121.577928 | 1121.16 | 1121.94 | 1 | 214 | 6.86 | 730.10 |
| 827 | 1122.641450 | 1122.49 | 1122.95 | 1 | 189 | 6.08 | 413.35 |
| 828 | 1123.537566 | 1123.36 | 1123.78 | 1 | 182 | 5.84 | 277.86 |
| 829 | 1124.583119 | 1124.28 | 1124.83 | 1 | 229 | 7.34 | 432.94 |
| 830 | 1125.620946 | 1125.02 | 1125.84 | 1 | 247 | 7.92 | 761.83 |
| 831 | 1126.800704 | 1126.26 | 1126.85 | 1 | 176 | 5.66 | 311.94 |
| 832 | 1127.617041 | 1127.18 | 1127.87 | 1 | 204 | 6.56 | 563.17 |
| 833 | 1128.609300 | 1128.33 | 1128.86 | 1 | 204 | 6.55 | 323.21 |
| 834 | 1129.631301 | 1129.25 | 1129.80 | 1 | 176 | 5.65 | 352.69 |
| 835 | 1130.563899 | 1130.30 | 1130.86 | 1 | 200 | 6.42 | 360.53 |
| 836 | 1131.623928 | 1131.23 | 1131.87 | 1 | 212 | 6.80 | 505.92 |
| 837 | 1132.577732 | 1132.24 | 1132.84 | 1 | 267 | 8.58 | 611.66 |
| 838 | 1133.636608 | 1133.39 | 1133.99 | 1 | 218 | 6.99 | 395.24 |

Figure 7R

| | | | | | | | |
|---|---|---|---|---|---|---|---|
| 839 | 1134.659497 | 1134.54 | 1135.01 | 1 | 203 | 6.51 | 367.00 |
| 840 | 1135.562159 | 1135.33 | 1135.84 | 1 | 701 | 22.51 | 1279.10 |
| 841 | 1136.555087 | 1136.34 | 1136.90 | 1 | 506 | 16.24 | 935.49 |
| 842 | 1137.572148 | 1137.27 | 1138.06 | 1 | 341 | 10.95 | 739.61 |
| 843 | 1138.567410 | 1138.05 | 1139.07 | 1 | 224 | 7.18 | 662.72 |
| 844 | 1139.629320 | 1139.21 | 1139.90 | 1 | 184 | 5.92 | 447.59 |
| 845 | 1140.592494 | 1140.13 | 1141.01 | 1 | 222 | 7.12 | 458.85 |
| 846 | 1141.550005 | 1141.43 | 1141.89 | 1 | 271 | 8.71 | 541.44 |
| 847 | 1142.612340 | 1142.35 | 1142.86 | 1 | 254 | 8.14 | 490.09 |
| 848 | 1143.377516 | 1143.28 | 1143.42 | 0 | 157 | 5.05 | 68.56 |
| 849 | 1143.567433 | 1143.42 | 1143.79 | 1 | 178 | 5.73 | 303.29 |
| 850 | 1144.575718 | 1144.25 | 1144.89 | 1 | 174 | 5.58 | 640.76 |
| 851 | 1145.644963 | 1145.27 | 1146.87 | 1 | 238 | 7.65 | 516.05 |
| 852 | 1146.432190 | 1146.24 | 1146.48 | 0 | 158 | 5.08 | 164.89 |
| 853 | 1146.594127 | 1146.48 | 1146.85 | 1 | 211 | 6.76 | 266.92 |
| 854 | 1147.302724 | 1147.17 | 1147.40 | 0 | 157 | 5.04 | 155.57 |
| 855 | 1147.590605 | 1147.40 | 1147.96 | 1 | 207 | 6.63 | 516.24 |
| 856 | 1148.650352 | 1148.38 | 1148.84 | 1 | 194 | 6.23 | 384.49 |
| 857 | 1149.618379 | 1149.40 | 1149.96 | 1 | 298 | 9.56 | 698.24 |
| 858 | 1150.410377 | 1150.10 | 1150.51 | 0 | 159 | 5.09 | 266.20 |
| 859 | 1150.630783 | 1150.51 | 1150.89 | 1 | 279 | 8.97 | 341.32 |
| 860 | 1151.548768 | 1151.26 | 1151.81 | 1 | 664 | 21.32 | 1347.18 |
| 861 | 1152.564425 | 1152.37 | 1153.07 | 1 | 481 | 15.43 | 1055.73 |
| 862 | 1153.579868 | 1153.35 | 1153.95 | 1 | 305 | 9.78 | 621.41 |
| 863 | 1154.632470 | 1154.28 | 1154.93 | 1 | 176 | 5.66 | 478.30 |
| 864 | 1155.604006 | 1155.30 | 1156.00 | 1 | 212 | 6.80 | 611.28 |
| 865 | 1156.699077 | 1156.42 | 1157.07 | 1 | 182 | 5.85 | 435.89 |
| 866 | 1157.611267 | 1157.07 | 1157.91 | 1 | 293 | 9.39 | 817.39 |
| 867 | 1158.584386 | 1158.38 | 1158.80 | 1 | 244 | 7.82 | 364.43 |
| 868 | 1159.591432 | 1158.96 | 1159.87 | 1 | 177 | 5.68 | 610.76 |
| 869 | 1160.602865 | 1160.43 | 1160.90 | 1 | 173 | 5.55 | 336.05 |
| 870 | 1161.582280 | 1161.41 | 1162.06 | 0 | 203 | 6.50 | 373.65 |
| 871 | 1162.616984 | 1162.39 | 1162.81 | 1 | 179 | 5.73 | 279.37 |
| 872 | 1163.571424 | 1163.23 | 1163.70 | 1 | 191 | 6.12 | 260.50 |
| 873 | 1164.555897 | 1164.40 | 1164.72 | 1 | 310 | 9.94 | 436.22 |
| 874 | 1165.715075 | 1165.38 | 1165.99 | 0 | 567 | 18.21 | 1149.30 |
| 875 | 1166.118324 | 1165.99 | 1166.27 | 0 | 163 | 5.23 | 110.02 |
| 876 | 1166.691994 | 1166.41 | 1166.88 | 1 | 352 | 11.29 | 618.61 |
| 877 | 1167.605966 | 1167.39 | 1168.00 | 1 | 721 | 23.15 | 1327.31 |
| 878 | 1168.609408 | 1168.37 | 1169.03 | 1 | 558 | 17.92 | 1094.86 |
| 879 | 1169.623691 | 1169.36 | 1169.78 | 1 | 368 | 11.82 | 521.76 |
| 880 | 1170.646327 | 1170.29 | 1170.86 | 1 | 242 | 7.76 | 562.74 |
| 881 | 1171.595402 | 1171.09 | 1171.84 | 1 | 212 | 6.79 | 651.57 |
| 882 | 1172.678387 | 1172.21 | 1172.78 | 1 | 167 | 5.35 | 333.05 |
| 883 | 1173.606801 | 1173.48 | 1174.00 | 1 | 187 | 6.02 | 326.39 |
| 884 | 1174.546865 | 1174.18 | 1174.70 | 1 | 202 | 6.50 | 273.43 |
| 885 | 1175.598822 | 1175.26 | 1175.87 | 1 | 195 | 6.27 | 325.59 |
| 886 | 1176.645707 | 1176.53 | 1176.95 | 1 | 176 | 5.66 | 218.66 |
| 887 | 1177.597421 | 1177.42 | 1177.75 | 0 | 182 | 5.86 | 172.11 |
| 888 | 1178.628561 | 1178.46 | 1178.79 | 1 | 176 | 5.66 | 197.69 |
| 889 | 1179.654826 | 1179.31 | 1179.92 | 1 | 192 | 6.15 | 608.76 |
| 890 | 1180.577429 | 1180.34 | 1180.72 | 1 | 209 | 6.71 | 245.81 |
| 891 | 1181.632838 | 1181.33 | 1181.80 | 1 | 205 | 6.59 | 335.90 |
| 892 | 1182.625402 | 1182.27 | 1182.88 | 1 | 257 | 8.24 | 610.71 |
| 893 | 1183.607299 | 1183.21 | 1183.87 | 1 | 250 | 8.04 | 595.83 |
| 894 | 1184.612404 | 1184.30 | 1184.91 | 1 | 231 | 7.43 | 387.54 |

Figure 7S

| | | | | | | | |
|---|---|---|---|---|---|---|---|
| 895 | 1185.619963 | 1185.43 | 1185.85 | 1 | 236 | 7.56 | 476.45 |
| 896 | 1186.570342 | 1186.32 | 1186.89 | 1 | 179 | 5.75 | 368.54 |
| 897 | 1187.617302 | 1187.41 | 1187.93 | 0 | 198 | 6.37 | 319.65 |
| 898 | 1188.646105 | 1188.12 | 1189.01 | 1 | 176 | 5.65 | 416.35 |
| 899 | 1189.616607 | 1189.25 | 1190.00 | 1 | 235 | 7.55 | 666.05 |
| 900 | 1190.594660 | 1190.34 | 1191.09 | 1 | 209 | 6.71 | 443.02 |
| 901 | 1191.599224 | 1191.38 | 1191.89 | 1 | 272 | 8.74 | 486.76 |
| 902 | 1192.659534 | 1192.51 | 1192.89 | 1 | 255 | 8.18 | 285.60 |
| 903 | 1193.575848 | 1193.17 | 1193.79 | 1 | 194 | 6.21 | 303.72 |
| 904 | 1194.605585 | 1194.26 | 1194.92 | 1 | 267 | 8.57 | 465.89 |
| 905 | 1195.820895 | 1195.21 | 1195.92 | 1 | 221 | 7.09 | 583.41 |
| 906 | 1196.578193 | 1196.20 | 1196.91 | 1 | 245 | 7.87 | 598.35 |
| 907 | 1197.835129 | 1197.39 | 1197.95 | 1 | 213 | 6.83 | 461.28 |
| 908 | 1198.809160 | 1198.24 | 1198.76 | 1 | 217 | 6.96 | 408.98 |
| 909 | 1199.612206 | 1199.47 | 1199.80 | 1 | 169 | 5.43 | 117.82 |
| 910 | 1200.832637 | 1200.42 | 1200.89 | 1 | 182 | 5.84 | 316.55 |
| 911 | 1201.442731 | 1201.27 | 1201.51 | 0 | 157 | 5.02 | 97.56 |
| 912 | 1201.626473 | 1201.51 | 1201.84 | 1 | 216 | 6.92 | 185.33 |
| 913 | 1202.608303 | 1202.18 | 1202.75 | 1 | 204 | 6.55 | 474.92 |
| 914 | 1203.633789 | 1203.36 | 1203.84 | 1 | 183 | 5.87 | 380.67 |
| 915 | 1204.630887 | 1204.36 | 1204.93 | 1 | 307 | 9.85 | 580.51 |
| 916 | 1205.623534 | 1205.26 | 1205.88 | 1 | 237 | 7.61 | 529.85 |
| 917 | 1206.589829 | 1206.22 | 1206.93 | 1 | 653 | 20.97 | 1367.21 |
| 918 | 1207.594155 | 1207.41 | 1207.93 | 1 | 405 | 12.99 | 768.89 |
| 919 | 1208.671318 | 1208.40 | 1209.02 | 1 | 421 | 13.53 | 666.27 |
| 920 | 1209.670271 | 1209.31 | 1209.93 | 1 | 301 | 9.66 | 665.10 |
| 921 | 1210.685249 | 1210.31 | 1210.88 | 1 | 232 | 7.45 | 387.92 |
| 922 | 1211.624855 | 1211.41 | 1211.79 | 1 | 171 | 5.48 | 209.01 |
| 923 | 1212.625524 | 1212.41 | 1212.88 | 1 | 219 | 7.04 | 454.72 |
| 924 | 1213.617636 | 1213.22 | 1213.89 | 1 | 201 | 6.45 | 514.53 |
| 925 | 1214.559701 | 1214.46 | 1214.79 | 0 | 209 | 6.70 | 203.73 |
| 926 | 1215.524684 | 1215.41 | 1215.60 | 1 | 170 | 5.46 | 105.79 |
| 927 | 1216.626208 | 1216.37 | 1216.89 | 1 | 364 | 11.67 | 561.31 |
| 928 | 1217.160483 | 1216.89 | 1217.28 | 1 | 165 | 5.29 | 225.03 |
| 929 | 1217.368080 | 1217.28 | 1217.47 | 0 | 155 | 4.99 | 43.12 |
| 930 | 1217.639480 | 1217.47 | 1217.85 | 1 | 353 | 11.33 | 464.23 |
| 931 | 1218.141691 | 1217.99 | 1218.28 | 1 | 184 | 5.92 | 92.66 |
| 932 | 1218.628708 | 1218.42 | 1218.95 | 1 | 376 | 12.06 | 620.17 |
| 933 | 1219.646663 | 1219.43 | 1219.86 | 1 | 288 | 9.23 | 403.32 |
| 934 | 1220.628455 | 1220.10 | 1220.98 | 1 | 236 | 7.57 | 640.05 |
| 935 | 1221.640792 | 1221.44 | 1221.82 | 1 | 234 | 7.51 | 303.81 |
| 936 | 1222.620100 | 1222.30 | 1222.97 | 1 | 198 | 6.34 | 477.21 |
| 937 | 1223.625307 | 1223.26 | 1223.88 | 1 | 256 | 8.21 | 614.14 |
| 938 | 1224.743462 | 1224.21 | 1225.12 | 1 | 164 | 5.27 | 548.62 |
| 939 | 1225.659630 | 1225.32 | 1225.94 | 1 | 230 | 7.37 | 372.85 |
| 940 | 1226.659188 | 1226.42 | 1226.95 | 1 | 249 | 7.99 | 438.60 |
| 941 | 1227.863420 | 1227.33 | 1228.00 | 1 | 229 | 7.36 | 568.45 |
| 942 | 1228.853140 | 1228.43 | 1228.82 | 1 | 227 | 7.29 | 302.19 |
| 943 | 1229.668785 | 1229.25 | 1229.97 | 1 | 194 | 6.23 | 501.36 |
| 944 | 1230.594953 | 1230.31 | 1231.12 | 0 | 242 | 7.76 | 683.46 |
| 945 | 1231.622998 | 1231.92 | 1232.08 | 1 | 189 | 6.06 | 379.45 |
| 946 | 1232.610213 | 1232.37 | 1232.85 | 1 | 251 | 8.05 | 372.23 |
| 947 | 1233.606543 | 1233.33 | 1234.25 | 1 | 2219 | 71.21 | 4347.07 |
| 948 | 1234.613228 | 1234.25 | 1235.02 | 1 | 1532 | 49.18 | 3108.81 |
| 949 | 1235.604313 | 1235.36 | 1236.98 | 1 | 748 | 24.02 | 1301.35 |
| 950 | 1236.644952 | 1236.37 | 1236.99 | 1 | 315 | 10.10 | 604.72 |

Figure 7T

| | | | | | | | |
|---|---|---|---|---|---|---|---|
| 951 | 1237.637026 | 1237.43 | 1237.96 | 1 | 359 | 11.52 | 575.63 |
| 952 | 1238.647289 | 1238.34 | 1238.82 | 1 | 387 | 12.42 | 762.29 |
| 953 | 1239.655933 | 1239.45 | 1239.96 | 1 | 264 | 8.48 | 388.49 |
| 954 | 1240.634731 | 1240.27 | 1240.94 | 1 | 649 | 20.82 | 1312.52 |
| 955 | 1241.631214 | 1241.38 | 1241.91 | 1 | 464 | 14.89 | 781.21 |
| 956 | 1242.623922 | 1242.44 | 1242.92 | 1 | 286 | 9.17 | 446.20 |
| 957 | 1243.693960 | 1243.50 | 1244.08 | 1 | 212 | 6.81 | 436.98 |
| 958 | 1244.619281 | 1244.42 | 1245.00 | 1 | 205 | 6.58 | 434.32 |
| 959 | 1245.637246 | 1245.46 | 1245.82 | 1 | 204 | 6.55 | 260.56 |
| 960 | 1246.642430 | 1246.46 | 1246.89 | 1 | 200 | 6.42 | 354.64 |
| 961 | 1247.650640 | 1247.32 | 1247.96 | 0 | 206 | 6.60 | 427.76 |
| 962 | 1248.627918 | 1248.24 | 1248.97 | 1 | 181 | 5.81 | 468.36 |
| 963 | 1249.662038 | 1249.40 | 1249.93 | 1 | 220 | 7.07 | 331.48 |
| 964 | 1250.667419 | 1250.37 | 1250.90 | 1 | 180 | 5.79 | 364.15 |
| 965 | 1251.700861 | 1251.46 | 1252.02 | 1 | 570 | 18.31 | 1005.71 |
| 966 | 1252.689665 | 1252.36 | 1253.13 | 1 | 477 | 15.32 | 1047.27 |
| 967 | 1253.680234 | 1253.42 | 1254.00 | 1 | 319 | 10.24 | 781.16 |
| 968 | 1254.681964 | 1254.20 | 1254.97 | 1 | 243 | 7.79 | 647.89 |
| 969 | 1255.633956 | 1255.31 | 1255.85 | 1 | 286 | 9.18 | 612.77 |
| 970 | 1256.612998 | 1256.38 | 1256.92 | 1 | 271 | 8.68 | 519.38 |
| 971 | 1257.600963 | 1257.30 | 1257.89 | 1 | 188 | 6.04 | 450.06 |
| 972 | 1258.629015 | 1258.42 | 1259.05 | 1 | 197 | 6.32 | 478.49 |
| 973 | 1259.652361 | 1259.49 | 1259.98 | 1 | 261 | 8.37 | 419.30 |
| 974 | 1260.629893 | 1260.22 | 1261.05 | 1 | 205 | 6.59 | 489.95 |
| 975 | 1261.616460 | 1261.19 | 1261.92 | 1 | 169 | 5.43 | 374.46 |
| 976 | 1262.633632 | 1262.46 | 1262.89 | 1 | 172 | 5.52 | 200.12 |
| 977 | 1263.616670 | 1263.46 | 1263.87 | 1 | 223 | 7.15 | 313.03 |
| 978 | 1264.692663 | 1264.50 | 1264.89 | 1 | 162 | 5.19 | 289.53 |
| 979 | 1265.638948 | 1265.33 | 1265.91 | 0 | 208 | 6.67 | 521.09 |
| 980 | 1266.663411 | 1266.40 | 1266.94 | 1 | 168 | 5.39 | 329.72 |
| 981 | 1267.678115 | 1267.28 | 1268.01 | 1 | 418 | 13.43 | 846.68 |
| 982 | 1268.691369 | 1268.35 | 1269.03 | 1 | 341 | 10.93 | 609.24 |
| 983 | 1269.677514 | 1269.47 | 1269.91 | 1 | 247 | 7.91 | 482.20 |
| 984 | 1270.701224 | 1270.55 | 1270.94 | 1 | 171 | 5.50 | 230.35 |
| 985 | 1271.649785 | 1271.13 | 1271.86 | 1 | 192 | 6.17 | 402.04 |
| 986 | 1272.628036 | 1272.40 | 1272.99 | 1 | 210 | 6.74 | 443.83 |
| 987 | 1273.692709 | 1273.38 | 1273.87 | 1 | 209 | 6.72 | 260.12 |
| 988 | 1274.658546 | 1274.55 | 1274.85 | 1 | 179 | 5.75 | 190.37 |
| 989 | 1275.679880 | 1275.43 | 1276.02 | 1 | 176 | 5.66 | 326.49 |
| 990 | 1276.664386 | 1276.46 | 1276.85 | 1 | 200 | 6.41 | 221.56 |
| 991 | 1277.679883 | 1277.39 | 1277.83 | 1 | 211 | 6.79 | 323.16 |
| 992 | 1278.644615 | 1278.22 | 1279.15 | 1 | 273 | 8.76 | 776.89 |
| 993 | 1279.689643 | 1279.15 | 1279.94 | 1 | 233 | 7.48 | 672.62 |
| 994 | 1280.598982 | 1280.28 | 1280.67 | 1 | 232 | 7.44 | 317.36 |
| 995 | 1280.737617 | 1280.67 | 1281.01 | 0 | 211 | 6.76 | 273.24 |
| 996 | 1281.673018 | 1281.26 | 1281.95 | 1 | 266 | 8.52 | 592.84 |
| 997 | 1282.674909 | 1282.29 | 1282.98 | 1 | 237 | 7.61 | 631.58 |
| 998 | 1283.634144 | 1283.22 | 1284.01 | 1 | 203 | 6.53 | 574.44 |
| 999 | 1284.626897 | 1284.35 | 1284.89 | 1 | 202 | 6.49 | 424.57 |
| 1000 | 1285.575976 | 1285.33 | 1286.07 | 1 | 167 | 5.36 | 288.74 |
| 1001 | 1286.680126 | 1286.56 | 1286.85 | 1 | 165 | 5.28 | 175.20 |
| 1002 | 1287.672730 | 1287.54 | 1287.98 | 0 | 201 | 6.44 | 308.85 |
| 1003 | 1288.591509 | 1288.33 | 1288.72 | 1 | 186 | 5.97 | 225.55 |
| 1004 | 1289.663130 | 1289.26 | 1290.00 | 1 | 202 | 6.49 | 356.59 |
| 1005 | 1290.661014 | 1290.49 | 1290.98 | 1 | 222 | 7.13 | 341.18 |
| 1006 | 1291.660538 | 1291.46 | 1291.87 | 1 | 245 | 7.86 | 419.82 |

Figure 7U

| | | | | | | | |
|---|---|---|---|---|---|---|---|
| 1007 | 1292.664390 | 1292.36 | 1293.15 | 1 | 262 | 9.04 | 678.94 |
| 1008 | 1293.686212 | 1293.35 | 1293.89 | 1 | 243 | 7.79 | 572.58 |
| 1009 | 1294.621585 | 1294.38 | 1295.02 | 1 | 292 | 9.39 | 449.82 |
| 1010 | 1295.631612 | 1295.42 | 1295.96 | 1 | 386 | 12.38 | 723.20 |
| 1011 | 1296.652602 | 1296.26 | 1296.94 | 1 | 345 | 11.09 | 751.59 |
| 1012 | 1297.663776 | 1297.24 | 1297.98 | 1 | 277 | 8.89 | 719.07 |
| 1013 | 1298.656710 | 1298.18 | 1298.92 | 1 | 257 | 8.25 | 677.85 |
| 1014 | 1300.703443 | 1300.20 | 1300.94 | 0 | 183 | 5.86 | 592.08 |
| 1015 | 1301.607045 | 1301.49 | 1301.68 | 1 | 156 | 5.00 | 126.90 |
| 1016 | 1302.725154 | 1302.42 | 1302.92 | 1 | 168 | 5.38 | 195.03 |
| 1017 | 1303.682396 | 1303.36 | 1304.06 | 1 | 212 | 6.80 | 352.69 |
| 1018 | 1304.654249 | 1304.40 | 1304.95 | 1 | 178 | 5.70 | 341.32 |
| 1019 | 1305.662143 | 1305.19 | 1305.99 | 1 | 234 | 7.51 | 431.04 |
| 1020 | 1306.643894 | 1306.28 | 1306.97 | 1 | 236 | 7.58 | 459.90 |
| 1021 | 1307.664566 | 1307.47 | 1308.01 | 1 | 283 | 9.09 | 525.99 |
| 1022 | 1308.657320 | 1308.28 | 1308.96 | 1 | 288 | 9.26 | 745.50 |
| 1023 | 1309.639542 | 1309.45 | 1310.05 | 1 | 232 | 7.45 | 367.81 |
| 1024 | 1310.641489 | 1310.29 | 1310.89 | 1 | 171 | 5.50 | 327.06 |
| 1025 | 1311.677737 | 1311.34 | 1312.03 | 1 | 178 | 5.70 | 400.85 |
| 1026 | 1312.624441 | 1312.23 | 1312.92 | 1 | 200 | 6.43 | 528.32 |
| 1027 | 1313.691066 | 1313.52 | 1314.01 | 1 | 181 | 5.82 | 336.28 |
| 1028 | 1314.642356 | 1314.31 | 1314.76 | 1 | 231 | 7.41 | 334.76 |
| 1029 | 1315.659800 | 1315.16 | 1315.85 | 1 | 218 | 6.98 | 487.90 |
| 1030 | 1316.662877 | 1316.40 | 1316.90 | 1 | 183 | 5.88 | 283.32 |
| 1031 | 1317.704007 | 1317.29 | 1317.89 | 1 | 214 | 6.88 | 487.43 |
| 1032 | 1318.729956 | 1318.54 | 1319.16 | 1 | 224 | 7.18 | 364.66 |
| 1033 | 1319.668829 | 1319.18 | 1320.08 | 1 | 231 | 7.42 | 542.82 |
| 1034 | 1320.661406 | 1320.43 | 1320.97 | 1 | 257 | 8.25 | 564.83 |
| 1035 | 1321.686273 | 1321.37 | 1322.02 | 1 | 246 | 7.89 | 456.95 |
| 1036 | 1322.648901 | 1322.42 | 1323.26 | 1 | 174 | 5.57 | 446.64 |
| 1037 | 1323.682952 | 1323.26 | 1324.21 | 1 | 173 | 5.55 | 540.11 |
| 1038 | 1324.623321 | 1324.21 | 1324.96 | 1 | 403 | 12.92 | 775.78 |
| 1039 | 1325.643103 | 1325.41 | 1325.86 | 1 | 294 | 9.44 | 486.15 |
| 1040 | 1326.659502 | 1326.30 | 1326.95 | 1 | 250 | 8.01 | 533.98 |
| 1041 | 1327.683496 | 1327.45 | 1327.95 | 1 | 211 | 6.79 | 498.36 |
| 1042 | 1328.668697 | 1328.50 | 1329.15 | 1 | 308 | 9.87 | 631.66 |
| 1043 | 1329.672453 | 1329.15 | 1329.95 | 1 | 270 | 8.66 | 625.26 |
| 1044 | 1330.652541 | 1330.30 | 1330.95 | 1 | 192 | 6.16 | 385.07 |
| 1045 | 1331.687386 | 1331.45 | 1332.05 | 0 | 221 | 7.09 | 403.70 |
| 1046 | 1332.698744 | 1332.45 | 1332.90 | 1 | 185 | 5.94 | 285.84 |
| 1047 | 1333.687427 | 1333.30 | 1334.15 | 1 | 251 | 8.04 | 738.47 |
| 1048 | 1334.684212 | 1334.30 | 1334.75 | 1 | 207 | 6.65 | 378.65 |
| 1049 | 1334.850511 | 1334.75 | 1335.20 | 0 | 200 | 6.42 | 355.59 |
| 1050 | 1335.729457 | 1335.40 | 1336.05 | 1 | 252 | 8.09 | 560.28 |
| 1051 | 1336.652297 | 1336.40 | 1337.20 | 1 | 439 | 14.08 | 1012.28 |
| 1052 | 1337.644729 | 1337.35 | 1337.95 | 1 | 356 | 11.43 | 626.11 |
| 1053 | 1338.662001 | 1338.40 | 1339.15 | 1 | 326 | 10.46 | 529.65 |
| 1054 | 1339.650700 | 1339.30 | 1339.85 | 1 | 248 | 7.97 | 498.65 |
| 1055 | 1340.646809 | 1340.46 | 1341.21 | 1 | 213 | 6.83 | 505.02 |
| 1056 | 1341.677832 | 1341.46 | 1342.06 | 1 | 223 | 7.16 | 431.94 |
| 1057 | 1342.680303 | 1342.31 | 1343.01 | 1 | 204 | 6.54 | 478.44 |
| 1058 | 1343.721849 | 1343.62 | 1344.02 | 1 | 183 | 5.86 | 406.27 |
| 1059 | 1344.723405 | 1344.32 | 1345.02 | 1 | 276 | 8.85 | 449.25 |
| 1060 | 1345.691410 | 1345.37 | 1345.88 | 1 | 239 | 7.66 | 478.02 |
| 1061 | 1346.677032 | 1346.23 | 1347.13 | 1 | 192 | 6.16 | 478.06 |
| 1062 | 1347.719516 | 1347.59 | 1347.94 | 1 | 175 | 5.61 | 232.64 |

Figure 7V

| 1063 | 1348.659867 | 1348.44 | 1348.74 | 1 | 164 | 5.25 | 168.88 |
|------|-------------|---------|---------|---|-----|------|--------|
| 1064 | 1349.658130 | 1349.26 | 1349.95 | 0 | 184 | 5.90 | 341.32 |
| 1065 | 1350.697306 | 1350.35 | 1351.06 | 1 | 181 | 5.81 | 418.95 |
| 1066 | 1351.661420 | 1351.41 | 1352.06 | 1 | 196 | 6.30 | 479.30 |
| 1067 | 1352.708074 | 1352.47 | 1353.12 | 1 | 218 | 6.99 | 332.87 |
| 1068 | 1353.655792 | 1353.32 | 1354.18 | 1 | 280 | 9.00 | 571.87 |
| 1069 | 1354.658627 | 1354.18 | 1355.04 | 1 | 464 | 14.89 | 1069.57 |
| 1070 | 1355.663981 | 1355.39 | 1356.20 | 1 | 337 | 10.81 | 750.92 |
| 1071 | 1356.688807 | 1356.45 | 1357.00 | 1 | 242 | 7.78 | 471.07 |
| 1072 | 1357.704971 | 1357.20 | 1358.06 | 1 | 265 | 8.52 | 625.93 |
| 1073 | 1358.673653 | 1358.47 | 1358.97 | 1 | 246 | 7.91 | 397.76 |
| 1074 | 1359.659657 | 1359.37 | 1360.13 | 1 | 212 | 6.81 | 448.63 |
| 1075 | 1360.716992 | 1360.28 | 1360.99 | 1 | 182 | 5.85 | 451.25 |
| 1076 | 1361.722515 | 1361.34 | 1362.25 | 1 | 224 | 7.18 | 769.89 |
| 1077 | 1362.670347 | 1362.25 | 1362.91 | 1 | 207 | 6.64 | 560.47 |
| 1078 | 1363.659025 | 1363.42 | 1363.92 | 1 | 179 | 5.74 | 389.30 |
| 1079 | 1364.690079 | 1364.38 | 1365.14 | 1 | 234 | 7.50 | 500.60 |
| 1080 | 1365.713767 | 1365.29 | 1365.90 | 1 | 175 | 5.62 | 346.22 |
| 1081 | 1366.671860 | 1366.45 | 1367.01 | 1 | 247 | 7.94 | 498.70 |
| 1082 | 1367.727587 | 1367.41 | 1368.12 | 1 | 222 | 7.12 | 574.39 |
| 1083 | 1368.680285 | 1368.33 | 1369.19 | 1 | 197 | 6.34 | 538.83 |
| 1084 | 1369.618888 | 1369.19 | 1370.00 | 1 | 663 | 21.27 | 1439.80 |
| 1085 | 1370.633422 | 1370.40 | 1371.01 | 1 | 538 | 17.26 | 1123.20 |
| 1086 | 1371.648577 | 1371.27 | 1372.08 | 1 | 421 | 13.50 | 828.17 |
| 1087 | 1372.660947 | 1372.48 | 1373.19 | 1 | 238 | 7.65 | 553.37 |
| 1088 | 1373.675849 | 1373.30 | 1374.06 | 1 | 315 | 10.12 | 554.04 |
| 1089 | 1374.695639 | 1374.31 | 1374.92 | 1 | 271 | 8.70 | 516.71 |
| 1090 | 1375.661738 | 1375.48 | 1375.99 | 1 | 220 | 7.05 | 332.24 |
| 1091 | 1376.668227 | 1376.49 | 1377.16 | 1 | 222 | 7.14 | 420.87 |
| 1092 | 1377.721903 | 1377.51 | 1378.07 | 1 | 158 | 5.07 | 346.36 |
| 1093 | 1378.717772 | 1378.32 | 1378.93 | 1 | 182 | 5.84 | 323.11 |
| 1094 | 1379.686048 | 1379.39 | 1379.90 | 1 | 176 | 5.65 | 311.61 |
| 1095 | 1380.663346 | 1380.36 | 1380.97 | 1 | 159 | 5.09 | 196.69 |
| 1096 | 1381.627158 | 1381.33 | 1382.04 | 1 | 270 | 8.67 | 668.72 |
| 1097 | 1382.659925 | 1382.29 | 1382.95 | 1 | 209 | 6.72 | 565.93 |
| 1098 | 1383.723515 | 1383.46 | 1384.13 | 1 | 317 | 10.16 | 686.59 |
| 1099 | 1384.711208 | 1384.43 | 1384.89 | 1 | 257 | 8.26 | 432.09 |
| 1100 | 1385.663364 | 1385.45 | 1385.96 | 1 | 303 | 9.71 | 600.12 |
| 1101 | 1386.663880 | 1386.27 | 1387.08 | 1 | 282 | 9.05 | 492.18 |
| 1102 | 1387.700218 | 1387.39 | 1387.90 | 1 | 231 | 7.42 | 424.53 |
| 1103 | 1388.684550 | 1388.46 | 1389.12 | 1 | 175 | 5.63 | 324.11 |
| 1104 | 1389.711351 | 1389.53 | 1389.99 | 1 | 158 | 5.07 | 216.09 |
| 1105 | 1390.686946 | 1390.50 | 1390.96 | 1 | 172 | 5.53 | 255.78 |
| 1106 | 1391.707254 | 1391.42 | 1392.03 | 1 | 227 | 7.28 | 326.01 |
| 1107 | 1392.722695 | 1392.24 | 1392.95 | 1 | 207 | 6.64 | 396.81 |
| 1108 | 1393.689240 | 1393.41 | 1393.93 | 1 | 212 | 6.80 | 403.37 |
| 1109 | 1394.717071 | 1394.49 | 1395.05 | 1 | 224 | 7.17 | 464.61 |
| 1110 | 1395.628233 | 1395.33 | 1395.74 | 0 | 191 | 6.14 | 236.25 |
| 1111 | 1397.717236 | 1397.51 | 1398.07 | 1 | 186 | 5.98 | 375.03 |
| 1112 | 1398.720619 | 1398.33 | 1399.04 | 1 | 207 | 6.65 | 375.27 |
| 1113 | 1399.676802 | 1399.30 | 1400.07 | 1 | 1367 | 43.86 | 2564.47 |
| 1114 | 1400.675001 | 1400.27 | 1401.14 | 1 | 1074 | 34.47 | 2304.73 |
| 1115 | 1401.675568 | 1401.14 | 1402.12 | 1 | 511 | 16.39 | 1238.11 |
| 1116 | 1402.689318 | 1402.43 | 1402.89 | 1 | 237 | 7.60 | 342.18 |
| 1117 | 1403.715852 | 1403.35 | 1403.97 | 1 | 181 | 5.81 | 343.08 |
| 1118 | 1404.702844 | 1404.48 | 1405.04 | 1 | 198 | 6.37 | 311.47 |

Figure 7W

| | | | | | | | |
|---|---|---|---|---|---|---|---|
| 1119 | 1405.711725 | 1405.35 | 1405.92 | 1 | 201 | 6.44 | 418.06 |
| 1120 | 1406.756452 | 1406.43 | 1407.05 | 1 | 177 | 5.68 | 369.33 |
| 1121 | 1407.680431 | 1407.46 | 1407.82 | 1 | 167 | 5.38 | 166.69 |
| 1122 | 1408.691905 | 1408.43 | 1409.15 | 1 | 376 | 12.05 | 673.47 |
| 1123 | 1409.675798 | 1409.36 | 1410.08 | 1 | 409 | 13.11 | 764.28 |
| 1124 | 1410.722348 | 1410.28 | 1411.36 | 1 | 1323 | 42.47 | 2972.88 |
| 1125 | 1411.738560 | 1411.36 | 1412.14 | 1 | 934 | 29.97 | 2061.83 |
| 1126 | 1412.715335 | 1412.44 | 1412.96 | 1 | 454 | 14.56 | 838.88 |
| 1127 | 1413.710478 | 1413.47 | 1414.14 | 1 | 275 | 8.81 | 627.64 |
| 1128 | 1414.730876 | 1414.14 | 1415.12 | 1 | 320 | 10.26 | 866.12 |
| 1129 | 1415.737479 | 1415.43 | 1416.10 | 1 | 265 | 8.50 | 570.16 |
| 1130 | 1416.763021 | 1416.36 | 1417.03 | 1 | 175 | 5.62 | 401.85 |
| 1131 | 1417.778906 | 1417.49 | 1418.21 | 1 | 242 | 7.77 | 581.52 |
| 1132 | 1418.456584 | 1418.21 | 1418.58 | 0 | 157 | 5.04 | 241.56 |
| 1133 | 1418.792130 | 1418.58 | 1419.09 | 1 | 244 | 7.82 | 431.90 |
| 1134 | 1419.717680 | 1419.40 | 1420.07 | 1 | 209 | 6.70 | 380.98 |
| 1135 | 1420.762784 | 1420.54 | 1421.21 | 1 | 194 | 6.21 | 453.61 |
| 1136 | 1421.736257 | 1421.47 | 1421.98 | 1 | 168 | 5.40 | 282.70 |
| 1137 | 1422.731762 | 1422.45 | 1423.02 | 0 | 237 | 7.61 | 505.54 |
| 1138 | 1423.716904 | 1423.38 | 1424.20 | 1 | 214 | 6.88 | 630.26 |
| 1139 | 1424.738544 | 1424.46 | 1425.03 | 1 | 231 | 7.42 | 507.16 |
| 1140 | 1425.746704 | 1425.50 | 1426.06 | 1 | 330 | 10.58 | 621.61 |
| 1141 | 1426.734074 | 1426.43 | 1427.31 | 1 | 353 | 11.34 | 733.28 |
| 1142 | 1427.721557 | 1427.46 | 1428.24 | 1 | 261 | 8.38 | 587.70 |
| 1143 | 1428.719981 | 1428.55 | 1428.86 | 1 | 197 | 6.32 | 139.54 |
| 1144 | 1429.723874 | 1429.53 | 1430.20 | 0 | 202 | 6.47 | 331.86 |
| 1145 | 1430.662856 | 1430.46 | 1430.98 | 1 | 173 | 5.55 | 278.66 |
| 1146 | 1431.705112 | 1431.40 | 1431.91 | 1 | 188 | 6.02 | 294.97 |
| 1147 | 1432.741978 | 1432.59 | 1433.16 | 1 | 225 | 7.23 | 479.02 |
| 1148 | 1433.714149 | 1433.42 | 1433.99 | 1 | 213 | 6.85 | 423.20 |
| 1149 | 1434.756201 | 1434.45 | 1435.03 | 1 | 245 | 7.85 | 573.30 |
| 1150 | 1435.728483 | 1435.28 | 1436.01 | 1 | 222 | 7.13 | 593.79 |
| 1151 | 1436.745770 | 1436.43 | 1437.05 | 1 | 274 | 8.80 | 422.15 |
| 1152 | 1437.742554 | 1437.46 | 1437.98 | 1 | 225 | 7.23 | 408.03 |
| 1153 | 1438.670574 | 1438.50 | 1438.81 | 1 | 191 | 6.13 | 164.41 |
| 1154 | 1439.763031 | 1439.54 | 1440.06 | 1 | 190 | 6.11 | 304.66 |
| 1155 | 1440.749786 | 1440.37 | 1441.00 | 0 | 218 | 7.01 | 583.61 |
| 1156 | 1441.717089 | 1441.47 | 1442.04 | 1 | 167 | 5.35 | 342.18 |
| 1157 | 1442.699949 | 1442.40 | 1443.13 | 1 | 802 | 25.73 | 1719.31 |
| 1158 | 1443.709906 | 1443.34 | 1444.01 | 1 | 647 | 20.75 | 1376.23 |
| 1159 | 1444.704020 | 1444.27 | 1445.21 | 1 | 423 | 13.58 | 1039.76 |
| 1160 | 1445.757683 | 1445.42 | 1446.20 | 1 | 238 | 7.62 | 525.23 |
| 1161 | 1446.726779 | 1446.38 | 1447.09 | 1 | 176 | 5.65 | 521.38 |
| 1162 | 1447.766651 | 1447.56 | 1448.02 | 1 | 180 | 5.77 | 285.56 |
| 1163 | 1448.776216 | 1448.44 | 1448.86 | 1 | 199 | 6.40 | 309.04 |
| 1164 | 1448.912066 | 1448.86 | 1449.17 | 0 | 195 | 6.26 | 265.39 |
| 1165 | 1449.784744 | 1449.33 | 1450.32 | 1 | 250 | 8.01 | 896.46 |
| 1166 | 1450.718562 | 1450.32 | 1451.10 | 1 | 162 | 5.19 | 460.85 |
| 1167 | 1451.730225 | 1451.41 | 1452.04 | 1 | 236 | 7.57 | 467.56 |
| 1168 | 1452.751440 | 1452.51 | 1452.93 | 1 | 191 | 6.14 | 183.62 |
| 1169 | 1453.760189 | 1453.29 | 1454.08 | 1 | 190 | 6.11 | 454.20 |
| 1170 | 1454.736487 | 1454.49 | 1455.12 | 1 | 262 | 8.41 | 543.82 |
| 1171 | 1455.671943 | 1455.12 | 1456.11 | 1 | 201 | 6.46 | 683.31 |
| 1172 | 1456.722377 | 1456.53 | 1457.00 | 1 | 225 | 7.21 | 332.26 |
| 1173 | 1457.719192 | 1457.47 | 1458.10 | 1 | 232 | 7.45 | 517.72 |
| 1174 | 1458.699474 | 1458.52 | 1458.88 | 1 | 226 | 7.26 | 367.52 |

Figure 7X

| | | | | | | | |
|---|---|---|---|---|---|---|---|
| 1175 | 1459.748488 | 1459.46 | 1460.24 | 1 | 279 | 8.96 | 671.57 |
| 1176 | 1460.722000 | 1460.24 | 1461.13 | 1 | 251 | 8.06 | 626.45 |
| 1177 | 1461.752988 | 1461.34 | 1462.08 | 1 | 202 | 6.49 | 366.69 |
| 1178 | 1462.765632 | 1462.49 | 1463.12 | 1 | 359 | 11.54 | 635.01 |
| 1179 | 1463.752424 | 1463.54 | 1464.22 | 1 | 320 | 10.25 | 613.09 |
| 1180 | 1464.744754 | 1464.54 | 1465.17 | 1 | 291 | 9.34 | 611.00 |
| 1181 | 1465.776245 | 1465.48 | 1466.01 | 1 | 229 | 7.34 | 432.90 |
| 1182 | 1466.766819 | 1466.43 | 1467.05 | 1 | 243 | 7.80 | 433.61 |
| 1183 | 1467.764502 | 1467.53 | 1468.05 | 1 | 245 | 7.86 | 408.65 |
| 1184 | 1468.753675 | 1468.47 | 1469.21 | 1 | 207 | 6.65 | 371.47 |
| 1185 | 1469.731371 | 1469.47 | 1470.05 | 1 | 198 | 6.35 | 366.29 |
| 1186 | 1470.721935 | 1470.47 | 1471.04 | 1 | 180 | 5.78 | 323.87 |
| 1187 | 1471.754464 | 1471.20 | 1472.20 | 1 | 406 | 13.03 | 1219.95 |
| 1188 | 1472.769594 | 1472.46 | 1472.99 | 1 | 383 | 12.30 | 793.14 |
| 1189 | 1473.762930 | 1473.46 | 1474.35 | 1 | 284 | 9.13 | 719.46 |
| 1190 | 1474.796537 | 1474.62 | 1475.04 | 1 | 181 | 5.80 | 375.18 |
| 1191 | 1475.749826 | 1475.35 | 1476.83 | 1 | 177 | 5.67 | 254.60 |
| 1192 | 1475.899414 | 1475.83 | 1476.30 | 0 | 166 | 5.33 | 218.37 |
| 1193 | 1476.778995 | 1476.46 | 1477.14 | 1 | 179 | 5.75 | 376.65 |
| 1194 | 1477.771039 | 1477.46 | 1477.99 | 1 | 196 | 6.28 | 275.14 |
| 1195 | 1478.765836 | 1478.56 | 1478.99 | 1 | 243 | 7.79 | 355.83 |
| 1196 | 1479.763879 | 1479.57 | 1480.09 | 1 | 217 | 6.96 | 304.90 |
| 1197 | 1480.747623 | 1480.36 | 1480.99 | 0 | 225 | 7.21 | 399.85 |
| 1198 | 1481.790347 | 1481.51 | 1482.09 | 1 | 198 | 6.34 | 345.13 |
| 1199 | 1482.773899 | 1482.36 | 1482.99 | 1 | 285 | 9.16 | 513.77 |
| 1200 | 1483.749839 | 1483.41 | 1484.15 | 1 | 258 | 8.28 | 601.68 |
| 1201 | 1484.774031 | 1484.47 | 1485.15 | 1 | 211 | 6.76 | 450.82 |
| 1202 | 1485.753580 | 1485.37 | 1485.95 | 1 | 191 | 6.13 | 269.58 |
| 1203 | 1486.765978 | 1486.58 | 1487.05 | 1 | 181 | 5.82 | 358.68 |
| 1204 | 1487.898171 | 1487.32 | 1487.90 | 1 | 285 | 9.15 | 433.99 |
| 1205 | 1488.898372 | 1488.53 | 1489.22 | 1 | 272 | 8.72 | 569.25 |
| 1206 | 1489.691634 | 1489.48 | 1490.17 | 1 | 231 | 7.41 | 436.32 |
| 1207 | 1490.719444 | 1490.49 | 1491.18 | 1 | 282 | 9.05 | 518.24 |
| 1208 | 1491.736704 | 1491.49 | 1492.08 | 1 | 245 | 7.86 | 422.82 |
| 1209 | 1492.737087 | 1492.65 | 1492.98 | 1 | 179 | 5.73 | 228.83 |
| 1210 | 1493.743836 | 1493.35 | 1493.98 | 1 | 218 | 7.00 | 407.22 |
| 1211 | 1494.740395 | 1494.35 | 1494.99 | 1 | 166 | 5.31 | 262.11 |
| 1212 | 1495.800736 | 1495.46 | 1496.15 | 1 | 156 | 5.01 | 325.44 |
| 1213 | 1496.771918 | 1496.52 | 1497.16 | 0 | 214 | 6.88 | 363.05 |
| 1214 | 1497.774028 | 1497.58 | 1498.11 | 1 | 177 | 5.68 | 268.30 |
| 1215 | 1498.747296 | 1498.43 | 1499.07 | 1 | 241 | 7.73 | 384.54 |
| 1216 | 1499.740655 | 1499.33 | 1499.96 | 1 | 265 | 8.51 | 415.69 |
| 1217 | 1500.747413 | 1500.55 | 1501.03 | 1 | 198 | 6.34 | 433.28 |
| 1218 | 1501.774206 | 1501.45 | 1502.14 | 1 | 186 | 5.96 | 336.90 |
| 1219 | 1502.763930 | 1502.30 | 1502.99 | 1 | 231 | 7.43 | 450.91 |
| 1220 | 1503.792757 | 1503.52 | 1504.05 | 1 | 176 | 5.65 | 287.27 |
| 1221 | 1504.768069 | 1504.46 | 1505.22 | 0 | 227 | 7.28 | 486.24 |
| 1222 | 1505.768907 | 1505.22 | 1506.02 | 1 | 177 | 5.69 | 458.71 |
| 1223 | 1506.735387 | 1506.65 | 1507.03 | 1 | 236 | 7.58 | 419.68 |
| 1224 | 1507.733906 | 1507.46 | 1507.99 | 1 | 750 | 24.08 | 1178.83 |
| 1225 | 1508.747459 | 1508.20 | 1509.21 | 1 | 625 | 20.07 | 1314.23 |
| 1226 | 1509.750211 | 1509.48 | 1510.06 | 1 | 421 | 13.51 | 739.61 |
| 1227 | 1510.754796 | 1510.38 | 1511.02 | 1 | 239 | 7.67 | 504.31 |
| 1228 | 1511.771224 | 1511.39 | 1512.30 | 1 | 170 | 5.46 | 334.10 |
| 1229 | 1512.769734 | 1512.51 | 1512.99 | 0 | 178 | 5.71 | 305.76 |
| 1230 | 1513.798403 | 1513.42 | 1514.11 | 1 | 167 | 5.37 | 451.58 |

Figure 7Y

| | | | | | | | |
|---|---|---|---|---|---|---|---|
| 1231 | 1514.778532 | 1514.43 | 1515.02 | 1 | 191 | 6.13 | 307.47 |
| 1232 | 1515.730029 | 1515.60 | 1516.06 | 1 | 159 | 5.11 | 264.56 |
| 1233 | 1517.760769 | 1517.42 | 1517.95 | 1 | 187 | 5.99 | 236.25 |
| 1234 | 1518.736204 | 1518.69 | 1519.28 | 1 | 177 | 5.67 | 309.71 |
| 1235 | 1520.793844 | 1520.62 | 1521.21 | 0 | 184 | 5.91 | 358.92 |
| 1236 | 1521.772914 | 1521.42 | 1522.17 | 1 | 166 | 5.33 | 311.09 |
| 1237 | 1522.785567 | 1522.49 | 1523.18 | 1 | 318 | 10.21 | 626.65 |
| 1238 | 1523.805078 | 1523.61 | 1524.20 | 1 | 256 | 8.23 | 532.65 |
| 1239 | 1524.789876 | 1524.36 | 1525.21 | 1 | 256 | 8.21 | 515.01 |
| 1240 | 1525.787241 | 1525.43 | 1526.12 | 1 | 213 | 6.84 | 468.66 |
| 1241 | 1526.799530 | 1526.55 | 1527.19 | 1 | 209 | 6.69 | 533.74 |
| 1242 | 1527.716407 | 1527.41 | 1527.94 | 1 | 182 | 5.85 | 332.62 |
| 1243 | 1528.760323 | 1528.56 | 1529.07 | 1 | 160 | 5.12 | 236.54 |
| 1244 | 1529.708877 | 1529.39 | 1529.87 | 1 | 183 | 5.87 | 306.66 |
| 1245 | 1530.767829 | 1530.57 | 1530.94 | 1 | 198 | 6.35 | 234.25 |
| 1246 | 1531.807978 | 1531.48 | 1532.26 | 1 | 159 | 5.11 | 391.29 |
| 1247 | 1532.766708 | 1532.65 | 1532.98 | 1 | 176 | 5.64 | 219.75 |
| 1248 | 1533.780642 | 1533.51 | 1533.94 | 1 | 222 | 7.11 | 311.42 |
| 1249 | 1534.805957 | 1534.48 | 1535.12 | 1 | 260 | 8.36 | 503.88 |
| 1250 | 1535.771899 | 1535.50 | 1536.09 | 1 | 251 | 8.04 | 380.49 |
| 1251 | 1536.778836 | 1536.41 | 1536.95 | 1 | 275 | 8.84 | 507.07 |
| 1252 | 1537.791366 | 1537.54 | 1538.13 | 1 | 249 | 8.01 | 483.63 |
| 1253 | 1538.773551 | 1538.35 | 1539.04 | 1 | 245 | 7.85 | 507.40 |
| 1254 | 1539.794878 | 1539.53 | 1540.23 | 1 | 177 | 8.68 | 437.55 |
| 1255 | 1540.769263 | 1540.44 | 1541.14 | 0 | 227 | 7.27 | 467.56 |
| 1256 | 1541.805238 | 1541.68 | 1542.05 | 1 | 154 | 4.95 | 159.04 |
| 1257 | 1542.749914 | 1542.48 | 1543.13 | 1 | 174 | 5.59 | 354.54 |
| 1258 | 1543.814602 | 1543.66 | 1544.04 | 1 | 206 | 6.62 | 368.96 |
| 1259 | 1544.788108 | 1544.31 | 1545.17 | 1 | 253 | 8.11 | 584.42 |
| 1260 | 1545.747174 | 1545.44 | 1546.09 | 1 | 229 | 7.35 | 489.19 |
| 1261 | 1546.766320 | 1546.36 | 1547.11 | 1 | 221 | 7.10 | 432.90 |
| 1262 | 1547.748506 | 1547.33 | 1548.14 | 1 | 212 | 6.81 | 411.79 |
| 1263 | 1548.860174 | 1548.41 | 1549.27 | 1 | 172 | 5.51 | 555.21 |
| 1264 | 1550.778045 | 1550.58 | 1551.16 | 1 | 183 | 5.89 | 219.89 |
| 1265 | 1551.817864 | 1551.53 | 1552.18 | 1 | 206 | 6.63 | 409.22 |
| 1266 | 1552.809517 | 1552.45 | 1553.10 | 1 | 185 | 5.93 | 327.63 |
| 1267 | 1553.783008 | 1553.42 | 1554.12 | 1 | 229 | 7.36 | 560.60 |
| 1268 | 1554.772706 | 1554.39 | 1554.99 | 1 | 242 | 7.76 | 421.63 |
| 1269 | 1555.773810 | 1555.53 | 1556.34 | 1 | 289 | 9.29 | 620.27 |
| 1270 | 1556.777387 | 1556.34 | 1557.15 | 1 | 282 | 8.40 | 519.71 |
| 1271 | 1557.772879 | 1557.38 | 1558.01 | 1 | 220 | 7.07 | 340.37 |
| 1272 | 1558.805489 | 1558.50 | 1559.09 | 1 | 198 | 6.34 | 440.55 |
| 1273 | 1559.762460 | 1559.38 | 1560.12 | 1 | 170 | 5.47 | 270.34 |
| 1274 | 1560.771913 | 1560.45 | 1561.10 | 1 | 179 | 5.73 | 420.66 |
| 1275 | 1561.764332 | 1561.91 | 1562.12 | 1 | 197 | 6.31 | 454.24 |
| 1276 | 1562.754488 | 1562.39 | 1563.04 | 1 | 213 | 6.83 | 352.64 |
| 1277 | 1564.772687 | 1564.61 | 1565.05 | 1 | 155 | 4.98 | 127.37 |
| 1278 | 1565.744832 | 1565.64 | 1566.91 | 1 | 197 | 6.31 | 336.48 |
| 1279 | 1566.720834 | 1566.29 | 1567.00 | 1 | 195 | 6.26 | 386.87 |
| 1280 | 1567.743300 | 1567.60 | 1567.92 | 1 | 164 | 5.26 | 242.85 |
| 1281 | 1568.738484 | 1568.35 | 1569.22 | 1 | 223 | 7.17 | 374.64 |
| 1282 | 1569.825471 | 1569.44 | 1570.31 | 1 | 270 | 8.68 | 735.28 |
| 1283 | 1570.842138 | 1570.31 | 1571.01 | 1 | 349 | 11.21 | 646.61 |
| 1284 | 1571.780142 | 1571.45 | 1572.37 | 1 | 203 | 6.51 | 509.39 |
| 1285 | 1572.854374 | 1572.63 | 1573.35 | 1 | 205 | 6.56 | 564.17 |
| 1286 | 1573.774000 | 1573.62 | 1574.22 | 1 | 214 | 6.88 | 295.06 |

Figure 7Z

| | | | | | | | |
|---|---|---|---|---|---|---|---|
| 1287 | 1574.833802 | 1574.43 | 1575.14 | 1 | 216 | 6.93 | 600.82 |
| 1288 | 1575.779860 | 1575.41 | 1576.12 | 1 | 168 | 5.39 | 404.70 |
| 1289 | 1576.798760 | 1576.65 | 1576.99 | 0 | 187 | 6.02 | 266.25 |
| 1290 | 1577.768016 | 1577.48 | 1578.02 | 1 | 177 | 5.68 | 239.68 |
| 1291 | 1578.787576 | 1578.46 | 1579.11 | 1 | 205 | 6.58 | 437.98 |
| 1292 | 1579.795879 | 1579.49 | 1580.25 | 1 | 192 | 6.16 | 345.46 |
| 1293 | 1580.763392 | 1580.53 | 1580.98 | 1 | 188 | 6.04 | 324.21 |
| 1294 | 1581.781793 | 1581.56 | 1582.00 | 1 | 174 | 5.57 | 236.77 |
| 1295 | 1582.820758 | 1582.70 | 1583.09 | 1 | 168 | 5.39 | 227.60 |
| 1296 | 1583.778361 | 1583.47 | 1583.96 | 1 | 181 | 5.80 | 266.74 |
| 1297 | 1584.864664 | 1584.67 | 1585.21 | 1 | 184 | 5.90 | 294.06 |
| 1298 | 1586.729880 | 1586.30 | 1587.12 | 1 | 722 | 23.16 | 1673.72 |
| 1299 | 1587.732737 | 1587.28 | 1588.10 | 1 | 638 | 20.48 | 1156.10 |
| 1300 | 1588.764361 | 1588.43 | 1589.14 | 1 | 440 | 14.14 | 920.32 |
| 1301 | 1589.773956 | 1589.47 | 1590.07 | 1 | 330 | 10.60 | 677.91 |
| 1302 | 1590.809522 | 1590.34 | 1591.22 | 1 | 199 | 6.40 | 465.61 |
| 1303 | 1591.872788 | 1591.49 | 1592.09 | 1 | 264 | 8.46 | 382.31 |
| 1304 | 1592.906156 | 1592.65 | 1593.13 | 1 | 155 | 4.99 | 67.61 |
| 1305 | 1595.798961 | 1595.48 | 1596.14 | 0 | 198 | 6.35 | 358.69 |
| 1306 | 1596.803481 | 1596.62 | 1597.07 | 1 | 182 | 5.83 | 281.47 |
| 1307 | 1597.826842 | 1597.45 | 1598.00 | 1 | 191 | 6.12 | 332.86 |
| 1308 | 1598.805110 | 1598.54 | 1599.09 | 1 | 513 | 16.47 | 833.13 |
| 1309 | 1599.861311 | 1599.31 | 1600.02 | 1 | 830 | 26.63 | 1733.67 |
| 1310 | 1600.872706 | 1600.52 | 1601.28 | 1 | 736 | 23.62 | 1531.61 |
| 1311 | 1601.843200 | 1601.56 | 1602.05 | 1 | 352 | 11.30 | 763.66 |
| 1312 | 1604.711684 | 1604.46 | 1605.12 | 1 | 1535 | 49.26 | 3097.78 |
| 1313 | 1605.713919 | 1605.34 | 1606.33 | 1 | 1522 | 48.86 | 2910.41 |
| 1314 | 1606.717408 | 1606.33 | 1607.32 | 1 | 953 | 30.57 | 2148.36 |
| 1315 | 1607.739113 | 1607.32 | 1608.14 | 1 | 449 | 14.41 | 1085.49 |
| 1316 | 1608.767066 | 1608.47 | 1609.13 | 1 | 301 | 9.67 | 682.65 |
| 1317 | 1609.787848 | 1609.51 | 1610.01 | 1 | 225 | 7.22 | 391.77 |
| 1318 | 1610.765747 | 1610.50 | 1611.05 | 1 | 220 | 7.07 | 368.71 |
| 1319 | 1611.758445 | 1611.33 | 1612.15 | 1 | 241 | 7.72 | 531.96 |
| 1320 | 1612.744879 | 1612.37 | 1613.09 | 1 | 247 | 7.92 | 691.89 |
| 1321 | 1617.627374 | 1617.49 | 1618.32 | 0 | 222 | 7.13 | 546.10 |
| 1322 | 1624.838117 | 1624.49 | 1625.21 | 0 | 248 | 7.95 | 421.10 |
| 1323 | 1638.654979 | 1638.54 | 1639.15 | 0 | 241 | 7.75 | 443.02 |
| 1324 | 1642.855662 | 1642.54 | 1643.09 | 0 | 237 | 7.60 | 336.71 |
| 1325 | 1645.806169 | 1645.37 | 1646.09 | 0 | 236 | 7.69 | 453.72 |
| 1326 | 1655.819056 | 1655.60 | 1656.11 | 1 | 238 | 7.64 | 392.29 |
| 1327 | 1656.852638 | 1656.61 | 1657.33 | 1 | 250 | 8.03 | 403.32 |
| 1328 | 1674.794921 | 1674.38 | 1675.16 | 0 | 268 | 8.60 | 682.92 |
| 1329 | 1676.851910 | 1676.34 | 1677.46 | 0 | 231 | 7.42 | 652.17 |
| 1330 | 1684.836646 | 1684.37 | 1685.04 | 0 | 246 | 7.89 | 477.40 |
| 1331 | 1686.827413 | 1686.34 | 1687.07 | 1 | 231 | 7.41 | 386.21 |
| 1332 | 1687.830899 | 1687.52 | 1688.25 | 1 | 306 | 9.89 | 680.21 |
| 1333 | 1688.821624 | 1688.53 | 1689.15 | 1 | 367 | 11.77 | 605.66 |
| 1334 | 1689.834104 | 1689.66 | 1690.68 | 1 | 301 | 9.67 | 828.40 |
| 1335 | 1690.868662 | 1690.56 | 1691.40 | 1 | 283 | 9.08 | 638.00 |
| 1336 | 1691.867225 | 1691.40 | 1692.13 | 1 | 283 | 9.09 | 569.35 |
| 1337 | 1692.878161 | 1692.64 | 1693.26 | 1 | 266 | 8.55 | 476.69 |
| 1338 | 1693.895102 | 1693.71 | 1694.11 | 1 | 244 | 7.83 | 298.68 |
| 1339 | 1694.914655 | 1694.66 | 1695.35 | 1 | 221 | 7.09 | 499.98 |
| 1340 | 1697.863503 | 1697.26 | 1698.11 | 0 | 242 | 7.75 | 584.28 |
| 1341 | 1699.856786 | 1699.58 | 1700.14 | 0 | 250 | 8.03 | 410.31 |
| 1342 | 1712.841487 | 1712.48 | 1713.27 | 1 | 240 | 7.69 | 571.54 |

Figure 7AA

| | | | | | | | |
|---|---|---|---|---|---|---|---|
| 1343 | 1713.840638 | 1713.50 | 1714.12 | 1 | 246 | 7.90 | 354.07 |
| 1344 | 1714.852510 | 1714.52 | 1715.08 | 1 | 219 | 7.01 | 360.15 |
| 1345 | 1716.857828 | 1716.50 | 1717.18 | 1 | 266 | 8.53 | 507.35 |
| 1346 | 1717.877808 | 1717.64 | 1718.26 | 1 | 222 | 7.12 | 405.89 |
| 1347 | 1718.865442 | 1718.64 | 1719.51 | 0 | 231 | 7.41 | 522.80 |
| 1348 | 1728.867696 | 1728.55 | 1729.23 | 1 | 227 | 7.29 | 498.17 |
| 1349 | 1729.889507 | 1729.23 | 1730.26 | 1 | 334 | 10.72 | 879.29 |
| 1350 | 1730.899882 | 1730.60 | 1731.46 | 1 | 277 | 8.88 | 619.46 |
| 1351 | 1731.882964 | 1731.48 | 1732.37 | 1 | 235 | 7.55 | 494.42 |
| 1352 | 1746.882736 | 1746.42 | 1747.33 | 1 | 577 | 18.50 | 1257.99 |
| 1353 | 1747.898323 | 1747.62 | 1748.25 | 1 | 629 | 20.20 | 949.14 |
| 1354 | 1748.882889 | 1748.59 | 1749.11 | 1 | 382 | 12.26 | 606.01 |
| 1355 | 1749.869486 | 1749.51 | 1750.54 | 1 | 253 | 8.12 | 699.15 |
| 1356 | 1759.930609 | 1759.66 | 1760.16 | 1 | 220 | 7.06 | 392.48 |
| 1357 | 1760.901215 | 1760.58 | 1761.10 | 1 | 224 | 7.18 | 346.17 |
| 1358 | 1762.905311 | 1762.65 | 1763.34 | 0 | 229 | 7.35 | 480.82 |
| 1359 | 1768.840525 | 1768.64 | 1769.16 | 0 | 229 | 7.34 | 383.12 |
| 1360 | 1772.883341 | 1772.56 | 1773.30 | 0 | 225 | 7.21 | 479.82 |
| 1361 | 1786.638449 | 1786.61 | 1786.48 | 1 | 250 | 8.01 | 576.39 |
| 1362 | 1786.905312 | 1786.48 | 1787.40 | 1 | 219 | 7.02 | 552.57 |
| 1363 | 1794.789148 | 1794.36 | 1795.52 | 1 | 453 | 14.54 | 1230.41 |
| 1364 | 1795.817368 | 1795.52 | 1796.16 | 1 | 589 | 18.92 | 1294.07 |
| 1365 | 1796.852346 | 1796.56 | 1797.14 | 1 | 472 | 15.14 | 954.13 |
| 1366 | 1797.849565 | 1797.38 | 1798.42 | 1 | 344 | 11.05 | 920.23 |
| 1367 | 1800.942280 | 1800.40 | 1801.44 | 1 | 476 | 15.28 | 1164.28 |
| 1368 | 1801.931018 | 1801.44 | 1802.31 | 1 | 473 | 15.18 | 1192.76 |
| 1369 | 1802.960225 | 1802.55 | 1803.59 | 1 | 303 | 9.74 | 807.31 |
| 1370 | 1803.961077 | 1803.59 | 1804.47 | 1 | 220 | 7.06 | 509.87 |
| 1371 | 1830.913527 | 1830.56 | 1831.15 | 1 | 350 | 11.24 | 616.66 |
| 1372 | 1831.894125 | 1831.44 | 1832.61 | 1 | 384 | 12.32 | 914.62 |
| 1373 | 1832.925203 | 1832.61 | 1833.20 | 1 | 253 | 8.13 | 545.53 |
| 1374 | 1833.894520 | 1833.67 | 1834.26 | 1 | 227 | 7.29 | 382.21 |
| 1375 | 1837.923186 | 1837.66 | 1838.25 | 0 | 221 | 7.08 | 407.41 |
| 1376 | 1842.926569 | 1842.54 | 1843.42 | 1 | 227 | 7.27 | 528.13 |
| 1377 | 1843.940915 | 1843.59 | 1844.18 | 1 | 291 | 9.34 | 482.34 |
| 1378 | 1847.942185 | 1847.65 | 1848.12 | 0 | 241 | 7.73 | 394.10 |
| 1379 | 1862.945793 | 1862.64 | 1863.40 | 1 | 294 | 9.44 | 567.63 |
| 1380 | 1863.959609 | 1863.64 | 1864.47 | 1 | 252 | 8.10 | 586.56 |
| 1381 | 1871.928298 | 1871.63 | 1872.40 | 1 | 266 | 8.54 | 541.34 |
| 1382 | 1872.901607 | 1872.52 | 1873.17 | 1 | 293 | 9.40 | 444.35 |
| 1383 | 1873.884488 | 1873.53 | 1874.30 | 1 | 225 | 7.24 | 455.86 |
| 1384 | 1910.866194 | 1910.62 | 1911.30 | 1 | 255 | 8.18 | 544.63 |
| 1385 | 1911.902791 | 1911.60 | 1912.37 | 1 | 290 | 9.31 | 510.73 |
| 1386 | 1912.922093 | 1912.55 | 1913.27 | 1 | 220 | 7.07 | 417.44 |
| 1387 | 1917.899890 | 1917.65 | 1918.19 | 1 | 294 | 9.44 | 385.45 |
| 1388 | 1918.893569 | 1918.55 | 1919.21 | 1 | 231 | 7.41 | 437.93 |
| 1389 | 1930.962175 | 1930.44 | 1931.29 | 1 | 305 | 9.80 | 664.17 |
| 1390 | 1931.961155 | 1931.59 | 1932.25 | 1 | 254 | 8.16 | 419.35 |
| 1391 | 1932.979799 | 1932.73 | 1933.23 | 0 | 201 | 6.45 | 283.98 |
| 1392 | 1937.032003 | 1936.59 | 1937.43 | 1 | 285 | 9.14 | 570.25 |
| 1393 | 1938.024165 | 1937.61 | 1938.39 | 1 | 333 | 10.67 | 596.35 |
| 1394 | 1938.988863 | 1938.70 | 1939.42 | 1 | 252 | 8.09 | 576.91 |
| 1395 | 1941.999591 | 1941.60 | 1942.34 | 0 | 191 | 6.12 | 345.79 |
| 1396 | 1942.941670 | 1942.71 | 1943.11 | 0 | 184 | 5.91 | 152.43 |
| 1397 | 1951.044761 | 1950.81 | 1951.28 | 0 | 208 | 6.68 | 236.49 |
| 1398 | 1952.033139 | 1951.68 | 1952.47 | 1 | 263 | 8.45 | 597.59 |

Figure 7BB

| 1399 | 1953.035313 | 1952.71 | 1953.32 | 1 | 220 | 7.06 | 433.23 |
|------|-------------|---------|---------|---|-----|------|--------|
| 1400 | 1986.910214 | 1986.50 | 1987.48 | 1 | 429 | 13.77 | 1172.74 |
| 1401 | 1987.907749 | 1987.48 | 1988.27 | 1 | 471 | 15.13 | 822.24 |
| 1402 | 1988.935799 | 1988.70 | 1989.43 | 1 | 340 | 10.92 | 726.20 |
| 1403 | 1990.988547 | 1990.65 | 1991.33 | 1 | 243 | 7.81 | 407.60 |
| 1404 | 1991.981107 | 1991.57 | 1992.49 | 1 | 244 | 7.83 | 556.13 |
| 1405 | 2074.134923 | 2073.66 | 2074.37 | 1 | 277 | 8.90 | 547.43 |
| 1406 | 2075.174613 | 2074.81 | 2075.43 | 1 | 308 | 9.88 | 550.43 |
| 1407 | 2085.967212 | 2085.20 | 2086.68 | 0 | 144 | 4.63 | 421.56 |
| 1408 | 2087.057976 | 2086.68 | 2087.36 | 1 | 279 | 8.95 | 639.29 |
| 1409 | 2088.071321 | 2087.68 | 2088.62 | 1 | 267 | 8.58 | 727.20 |
| 1410 | 2089.026060 | 2088.62 | 2089.30 | 1 | 219 | 7.04 | 462.80 |
| 1411 | 2211.106558 | 2210.84 | 2211.67 | 1 | 272 | 8.72 | 751.21 |
| 1412 | 2212.109240 | 2211.67 | 2212.77 | 1 | 337 | 10.82 | 852.76 |
| 1413 | 2213.107926 | 2212.77 | 2213.41 | 1 | 230 | 7.37 | 440.93 |
| 1414 | 2691.278434 | 2690.93 | 2691.69 | 0 | 172 | 5.51 | 231.07 |
| 1415 | 2692.294465 | 2691.80 | 2692.86 | 1 | 263 | 8.45 | 577.05 |
| 1416 | 2693.302800 | 2692.86 | 2693.79 | 1 | 219 | 7.03 | 380.31 |
| 1417 | 2748.329698 | 2747.79 | 2748.75 | 0 | 106 | 3.40 | 207.58 |
| 1418 | 2749.273561 | 2748.94 | 2749.87 | 0 | 221 | 7.08 | 445.26 |

| Pepmass | Charge | Elution from | Elution to | Mass | M (H+) |
|---|---|---|---|---|---|
| 523.2579 | 2 | 29.19 | 29.23 | 1044.5168 | 1045.5168 |
| 599.2645 | 2 | 29.4 | 29.43 | 1197.5290 | 1198.5290 |
| 337.1831 | 2 | 29.46 | | 672.3662 | 673.3662 |
| 365.2001 | 2 | | | 728.4 | 729.4 |
| 591.2622 | 2 | | | 1180.5244 | 1181.5244 |
| 512.2189 | 2 | | | 1022.437 | 1023.437 |
| 563.7598 | 2 | | | 1125.5196 | 1126.5196 |
| 421.7357 | 2 | | | 841.4714 | 842.4714 |
| 412.7328 | 2 | | | 823.4656 | 824.4656 |
| 428.7442 | 1 | | | 427.7442 | 428.7442 |
| 428.7442 | 2 | | | 855.488 | 856.488 |
| 421.7345 | 2 | | | 841.469 | 842.469 |
| 412.7378 | 2 | | | 823.475 | 824.475 |
| 435.7530 | 2 | | | 869.506 | 870.506 |
| 428.7428 | 2 | | | 855.485 | 856.485 |
| 421.7357 | 2 | | | 841.471 | 842.471 |
| 577.242 | 2 | | | 1152.484 | 1153.484 |
| 435.7498 | 2 | | | 869.4996 | 870.499 |
| 428.74 | | | | 855.494 | 856.494 |
| 421.7343 | | | | 841.4687 | 842.4687 |
| 435.7548 | | | | 869.499 | 870.500 |
| 536.297 | | | | 1070.595 | 1071.595 |
| 435.7568 | | | | 869.5138 | 870.5138 |
| 434.7502 | | | | 868.500 | 869.500 |
| 434.7502 | | | | 1301.250 | 1302.250 |
| 726.8303 | | | | 1451.6608 | 1452.6608 |
| 434.7523 | | | | 867.5047 | 868.5047 |
| 681.3345 | | | | 1359.669 | 1360.669 |
| 690.9907 | | | | 2069.972 | 2070.972 |
| 460.2232 | | | | 918.446 | 919.446 |
| 702.6 | | | | 701.6 | 702.6 |
| 702.6 | | | | 1403.2 | 1404.2 |
| 702.6 | | | | 2104.8 | 2105.8 |
| 737.6767 | | | | 2210.0301 | 2211.0301 |
| 742.3500 | | | | 2224.05 | 2225.05 |
| 747.0191 | | | | 2238.0575 | 2239.0575 |
| 746.0024 | | | | 2235.007 | 2236.007 |
| 684.8425 | | | | 2735.370 | 2736.370 |
| 747.01344 | | | | 2238.0403 | 2239.0403 |
| 772.3595 | | | | 1542.719 | 1543.719 |
| 746.3916 | | | | 2236.1748 | 2237.1748 |
| 755.6879 | | | | 2264.0637 | 2265.0637 |
| 692.3 | | | | 1382.6 | 1383.6 |
| 692.3 | | | | 2073.9 | 2074.9 |
| 970.8270 | | | | 1939.854 | 1940.854 |
| 547.2877 | | | | 1092.5755 | 1093.5755 |
| 870.0806 | | | | 2607.2419 | 2608.2419 |
| 761.6939 | | | | 2282.0817 | 2283.0817 |
| 766.3613 | | | | 2296.0839 | 2297.0839 |
| 762.0313 | | | | 2283.0939 | 2284.0939 |
| 729.3529 | | | | 2913.4116 | 2914.4116 |
| 766.6986 | | | | 2297.0988 | 2298.0988 |
| 741.0014 | | | | 2220.0042 | 2221.0042 |
| 866.9423 | | | | 1731.8848 | 1732.8848 |

Figure 9A

```
SEARCH=MIS
REPTYPE=Peptide
BEGIN IONS
PEPMASS=523.257960346586
CHARGE=2+
TITLE=Elution from: 29.19 to 29.23   period: 0   experiment: 1 cycles:  2
86.1373 45
125.1085 3
139.0736 2
141.1033 8
147.0943 1
159.7486 8.5
167.0798 1
169.0993 4.5
173.7122 13.5
183.8609 23.5
186.0681 1
201.1168 6.5
206.0813 1
221.0809 1
225.1136 8.5
236.104 34
252.131 4
255.2842 6.5
262.1692 1
270.2428 39
322.1785 1
339.1747 2
358.1647 4
370.7984 19.5
378.168 13
378.843 105
382.182 1
384.8789 1
399.8512 1
405.2056 2
414.3117 45.5
423.2286 19.5
489.4542 12
590.4841 28.5
643.3382 2
661.5883 27.5
707.3831 1
768.6136 28.5
845.7813 8.5
END IONS

BEGIN IONS
PEPMASS=599.284675174475
CHARGE=2+
```

Figure 9B

```
TITLE=Elution from: 28.4 to 29.43  period: 0  experiment: 1 cycles: 2
84.0898 2.5
120.0868 8
127.0877 13
129.6026 8
138.0881 248
147.1187 13.5
155.0781 20
191.0721 3
202.0816 31.5
218.0878 42.5
228.1121 4.5
246.1796 5
262.1284 3
272.1024 2
290.2548 19.5
332.303 2.5
361.1483 2
363.1627 1.5
372.1598 1
383.24 1.5
507.3048 4
564.5121 2
567.4524 8
608.3895 6.5
723.315 2.5
837.3177 1
950.4857 1
END IONS BEGIN IONS
PEPMASS=337.183111527463
CHARGE=2+
TITLE=Elution from: 29.49 to 29.52  period: 0  experiment: 1 cycles: 2
85.6885 179
101.0706 23
107.0755 2
124.069 2
129.4773 159.5
140.87 7.5
143.116 6
147.1170 349.5
157.6893 2
168.6739 23.5
186.0933 6
197.1737 1
202.1321 1
212.8801 1
223.1109 6
235.8438 2
```

LALIGN finds the best local alignments between two sequences version 2.0u66 September 1998 Please cite: X. Huang and W. Miller (1991) Adv. Appl. Math. 12:373-381 resetting to DNA matrix
Comparison of:
(A) ./wwwtmp/lalign/.11415.1.seq E2F2          - 3203 nt
(B) ./wwwtmp/lalign/.11415.2.seq c18           -  980 nt
using matrix file: DNA, gap penalties: -14/-4

Legend
E2F2 – SEQ ID NO: 156
C18 – SEQ ID NO: 157

91.8% identity in 869 nt overlap; score: 3855 E(10,000): 1.9e-312

```
              1780      1790      1800      1810      1820      1830
E2F2   CTAGTGATTTCCTATGCTTGACTATTAGCTCCTTTTCTTTACCTATTATTATTATTTATT
       ::::::::::::::::::::::::::::::::::::::::::::::::::::::::::::
c18    CTAGTGATTTCCTATGCTTGACTATTAGCTCCTTTTCTTTACCTATTATTATTATTTATT
              100       110       120       130       140       150

1840      1850      1860      1870      1880      1890
E2F2   TTTCAGATGGAGTCTCACACTGTCGCCAGGCTGGAGTACAGTGGCGCCATCTCGGCTCAC
       ::::::::::::::::::::::::::::::::::::::::::::::::::::::::::::
c18    TTTCAGATGGAGTCTCACACTGTCGCCAGGCTGGAGTACAGTGGCGCCATCTCGGCTCAC
              160       170       180       190       200       210

1900      1910      1920      1930      1940      1950
E2F2   TGAACCCTCCACCTCACCGGGGTTCAAGTGATTCTACTGCCCGCAGTCTCCAGAGTAGCTGGG
       ::::::::::::::::::::::::::::::::::::::::::::::::::::::::::::
c18    TGAACCCTCCACCTCACCGGGGTTCAAGTGATTCTACTGCCCGCAGTCTCCAGAGTAGCTGGG
              220       230       240       250       260       270

1960      1970      1980      1990      2000      2010
E2F2   ACTACAGGCATGCACTACCACCACACCCAGCTAATTTTTTGTATTTTTAGTTGAGATGGGGTT
       ::::::::::::::::::::::::::::::::::::::::::::::::::::::::::::
c18    ACTACAGGCATGCACTACCACCACACCCAGCTAATTTTTTGTATTTTTAGTTGAGATGGGGTT
              280       290       300       310       320       330

2020      2030      2040      2050      2060      2070
E2F2   TCACCATGATGGCCAGGATGGTCTCGATCTCTTGACCTCATGATCTGCCCGCCTCAGCCT
       ::::::::::::::::::::::::::::::::::::::::::::::::::::::::::::
c18    TCACCATGATGGCCAGGATGGTCTCGATCTCTTGACCTCATGATCTGCCTGCCTCAGCCT
              340       350       360       370       380       390
```

Figure 11.1A

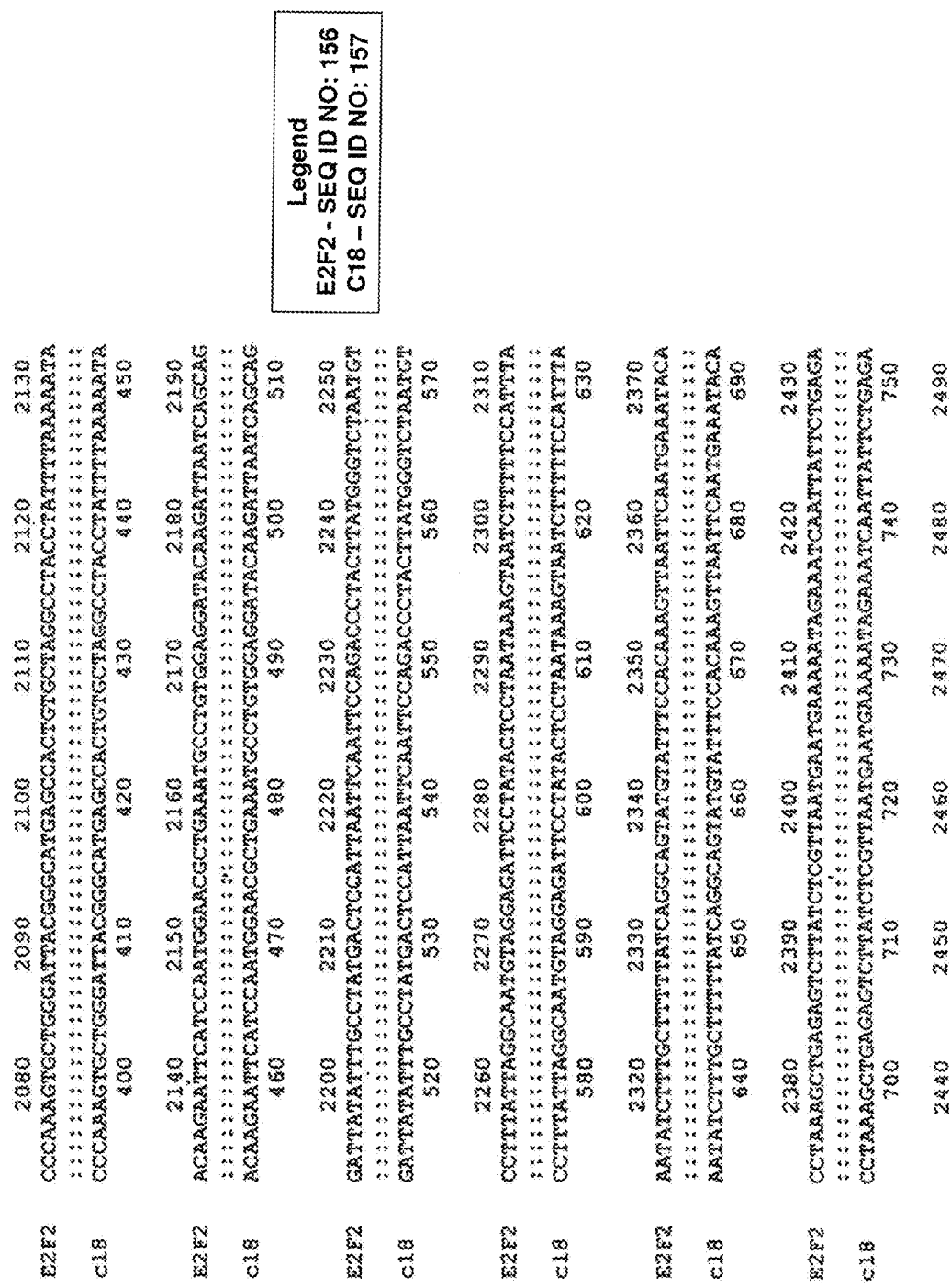
Figure 11.1B

Legend

E2F2 - SEQ ID NO: 156   c18 - SEQ ID NO: 157

```
E2F2   TGAGATTCTTCCTATAATTTTTATTAGTTGTTCTGAAATGGTACATCGGTTTGTCTTGAA
       ::::::::::::::::::::::::::::::::::::::            :::::::::::::::::
C18    TGAGATTCTTCCTATAATTTTTATTAGTTGTTCTGAAATNNN-CATGGGTTTGTCTTGAN
            760       770       780       790       800       810

2500      2510      2520      2530      2540      2550
E2F2   GATATGATGATGTATTAATTCTTAATATTGAATTAAATGCCTCTGAAGTAGAGATGACTC
       : ::::::::::::::::::::  :::::::  : :::::: ::::: :::: ::::::::::
C18    -ANATGATGATGTATTAATTCTNAATATTGNANTAAATGNCTCTGNAGTANAGATGACTC
            820       830       840       850       860

2560      2570      2580      2590      2600
E2F2   TCTTT--GTCATGGAGTTACAGTTTGTTGATTAAATTGCATTGAATTTTGAATGTTAATG
           :  ::  ::::::           :::   :     ::::::       ::  : :           :
C18    TNNTTTNNTCATGGNNNNNNACNNNNNNTTGNNNANNN-GCATTGNNNNNTGNANGNNNNNG
         870       880       890       900       910       920

2610      2620      2630
E2F2   TTATATATTAACTTAAATGAGATTTTCCA
           :         :                :::  ::
C18    TNNNNNNNNTNNNNNNNNNNNNNNNATTTNCA
         930       940       950
```

FIG. 11.2A

Legend

E2F2 - SEQ ID NO: 156    c18 - SEQ ID NO: 157

70.8% identity in 480 nt overlap; score: 970 E(10,000): 6.9e-72

```
              2650      2660      2670      2680      2690
E2F2   AATACTCT-GTGAACCTCCAGCCTTG--TGTTTCTTTCTTTTTTTT---TTTTTTTTTT
       :::  : :: ::::       : :   :::: : ::    : :::::::::: :: :: :::
C18    AATTCACTAGTGATTTCCTATGCTTGACTATTAGCTCCTTTTCTTTACCTATTATTATTA
          90       100       110       120       130       140

2700      2710      2720      2730      2740      2750
E2F2   TTTTTTTTTGATACAGAGTCTCAATCTGTCGCCCAGGCTGGAGTGCAGTGGCACGATCTC
       ::: :::::  : ::  :::::::::  ::::::::::  :::::::::::  ::::::   : :::::
C18    TTTATTTTTCAGATGGAGTCTCACACTGTCGCC-AGGCTGGAGTACAGTGGCGCCATCTC
          150       160       170       180       190       200

2760      2770      2780      2790      2800      2810
E2F2   GGCTCACTGCAACCTGTGCCTCCCAGGTTCAAGCAATTCTCCTGCCTCAGCCTCCCAAGC
       :::::::::: :  ::::   ::: :: :::::::::     ::::    ::::    :::    ::::
C18    GGCTCACTGAACCCTCCACCTACCGGGTTCAAGTGATTCTACTGCCGCAGTCTCC-----
          210       220       230       240       250

2820      2830      2840      2850      2860      2870
E2F2   AGAGTAGCTGGAACTACAAGTGGGCACCACCATGCCTGGCTATTTTTTT-TATTTTTGGT
       ::::::::::::: :::::::  ::::  ::::  :::: ::  ::::   :::::::::::::: ::
C18    AGAGTAGCTGGGACTACAGGCATGCACTACCACACCCAGCTAATTTTTTGTATTTTTAGT
          260       270       280       290       300       310
```

FIG. 11.2B

| Legend |
| --- |
| E2F2 - SEQ ID NO: 156   c18 - SEQ ID NO: 157 |

```
            2880      2890      2900      2910      2920      2930
E2F2    AGAGACGGGGTTTCACCATGTTGGCCAGGCTAGTCTCAAACTCCTGACATCGGTGATCTG
        : :: : :::::::::::::  :::::::: :   :::::  ::: : :: ::: ::::::
C18     TGAGATGGGGTTTCACCATGATGGCCAGGATGGTCTCGATCTCTTGACCTCA-TGATCTG
            320       330       340       350       360       370

2940      2950      2960      2970      2980      2990
E2F2    CCTGCCTTGGCCTCCAAAATGCTGGAATTACAAGCATCAGCCACTGCACCCGGCCTCAG
        ::::::: ::::::::::::: :::::::::::: ::: :::::::::   ::::: :
C18     CCTGCCTCAGCCTCCCAAAGTGCTGGGATTACGGGCATGAGCCACTGTGCTAGGCCT-AC
            380       390       400       410       420       430

3000      3010      3020      3030      3040      3050
E2F2    ATACCCTTTTAAGAATTCTAGGCCATACATCTCATGGAAAT-TGAATGGTAATACCTGCC
        : :   :::::::::  :      :  :: ::::  ::::::: ::::      ::  ::::
C18     CTA---TTTTAAAAATAACAAGA-ATTCATCCAATGGAACGCTGAA-----ATGCCTG--
            440       450       460       470       480

3060      3070      3080      3090      3100      3110
E2F2    TGCATTCATACTCTTGTAGAGCTAAGACCAGCATGACTTTTTCTGTCCTCTTACTTCTTT
        :: :    ::::           ::   : ::  :::::: :: : :: ::: : ::: ::
C18     TGGAGG-ATACA-------AGATTA-ATCAGCACGATTATATTTG-CCTATGACTCCATT
            490       500       510       520       530
```

FIG. 11.2C

```
ref|NT_016354.18|Hs4_16510 Homo sapiens chromosome 4 genomic contig, reference assembly
Length=92123751

Features flanking this part of subject sequence:
  74257 bp at 5' side: translocation associated membrane protein 1-like 1
  893340 bp at 3' side: N-deacetylase/N-sulfotransferase (heparan glucosaminyl) 3

Score = 1609 bits (871),  Expect = 0.0           Query - SEQ ID NO: 160
Identities = 912/929 (98%), Gaps = 14/929 (1%)   Subject - SEQ ID NO: 161
Strand=Plus/Plus Query   16        GCTTGACTATTAGCTCCtttctcttacctattattatta-ttttcagatgagtct    74
                  ||||||||||||||||||||||||||||||| ||||||||||||||| ||||||||||||
Sbjct   42628951  GCTTGACTATTAGCTCCTCCTTTCTTTACCTATTATTATTATTATTTTCAGATGGAGTCT  42629010

Query   75        -acactgtcgccaggctggagtacagtggcgcatctcggctcactgaaccctccaccta  133
                   ||||||||||||||||||||||||| ||||||||||||||||||||||||||||||||
Sbjct   42629011  CACACTGTCGCCAGGCTGGAGTACAGTGGCGCCATCTCGGCTCACTGAACCCTCCACCTA  42629070

Query   134       ccggttcaagtgattctactgcgcagtctccagagtag-tgggactacaggcatgcac   192
                  |||||||||||||||||||||||| |||||||||||||| ||||||||||||| ||||
Sbjct   42629071  CCGGGTTCAAGTGATTCTACTGCGCCAGTCTCCAGAGTAGCTGGGACTACAGGCATGCAC  42629130

Query   193       taccaccaccagctaattctttgtatttttagtgagatgggtttcaccatgatgcc     252
                  |||||||||||||||||||| |||||| ||||| ||||||||| ||||||||||||||
Sbjct   42629131  TACCACCACCAGCTAATTTTTTGTATTTTTAGTAGAGATGGGG-TTTCACCATGATGGCC  42629189

Query   253       aggatgtctcgatctcttgacctcatgatctgctgcctcagcctcccaaagtgctggg   312
                  ||||||||| ||||||||||||||||||||||||||| |||||||||||||||| |||
Sbjct   42629190  AGGATGGTCTCGATCTCTTGACCTCATGATCTGCCTGCCTCAGCCTCCCAAAGTGCTGGG  42629249

Query   313       attacggcatgagccactgtgctaggcctaCCTATTTAAAAATAACAAGAATTCATCC   372
                  |||||||||||||||||||||||||||||||||||||||||||||||||||||||||
Sbjct   42629250  ATTACGGCATGAGCCACTGTGCTAGGCCTACCTATTTAAAAATAACAAGAATTCATCC    42629309

Query   373       AATGGAACCTGAAATGCCTGTGGAGGATACAAGATTAATCAGCAGGATTATATTGCCT   432
                  |||||||||||||||||||||||||||||||||||||||||||||||||||||||||
Sbjct   42629310  AATGGAACCTGAAATGCCTGTGGAGGATACAAGATTAATCAGCAGGATTATATTGCCT    42629369
```

Figure 11.3A

```
Query  433  ATGACTCCATTAATTCAATTCCAGAGACCCTACTTATCACTTATGGGTCTAATGTCCTTTAT       492
            ||||  ||||||||||||||||||||||||  ||  |   |  ||||||||||||||||||
Sbjct 42629370 ATGATTCCATTAATTCAATTCCAGA-CC--C----T-ACTTATGGGTCTAATGTCCTTTAT 42629422

Query  493  TAGGCAATGTAGGAGAGATTCCTATACTCCTAATAAAGTAATC-TTTTCCATTAAATA-TC       550
            ||||||||||||||||||||||||||||||||||||||||||| |||||||||||||| ||
Sbjct 42629423 TAGGCAATGTAGGAGAGATTCCTATACTTCTAATAAAGTAATCTTTTTCCATTAAATAGTC 42629482

Query  551  TTTGC-TTTTATCAGGCAGTATGTATTTCCACAAAGTTAATTCAATGAAATACACCCTAAA       609
            ||| | |||||||||||||||||||||||||||||||||||||||||||||||||||||||
Sbjct 42629483 TTTGCTTTTTATCAGGCAGTATGTATTTCCACAAAGTTAATTCAATGAAATACACCCTAAA 42629542

Query  610  GCTGAGAGTCTTATCTCGTTAATGAATGAAAAATAGAAATCAATTATTCTGAGATGAGAT       669
            ||||||||||||||||||||||||||||||||||||||||||||||||||||||||||||
Sbjct 42629543 GCTGAGAGTCTTATCTCGTTAATGAATGAAAAATAGAAATCAATTATTCTGAGATGAGAT 42629602

Query  670  TCTTCCTATAATTTTTATTAGTTGTGTGTGAAATGGTACATGGGTTTGTCTTGAAGATATG       729
            ||||||||||||||  ||||||||||||||||||||||||||||||||||||||||||||
Sbjct 42629603 TCTTCCTATAATTTTTATTAGTTGTGTGTGAAATGGTACATGGGTTTGTCTTGAAGATATG 42629662

Query  730  ATGATGTATTAATTCTTAATATATTGAATTAAATGCCTCTGAAGTAGAGATGACTCTCTTG       789
            ||||||||||||||||||||||||||||||||||||||||||||||||||||||||||||
Sbjct 42629663 ATGATGTATTAATTCTTAATATATTGAATTAAATGCTTCTGAAGTAGAGATGACTCTCTTG 42629722

Query  790  TCATGGAGTTACAGTTGTTGTTTGATTAAAATTGCATTGAATTTGAATGTTAATGTTATATAT       849
            ||||||||||||||||||||||||||||||||||||||||||||||||||||||||||||
Sbjct 42629723 TCATGGAGTTACAGTTGTTGTTTGATTAAAATTGCATTGAATTTGAATGTTAATGTTATATAT 42629782

Query  850  TAACTTAAATGAGATTTTCCAATATAAATACTCTGTGAACCTCCAGCCTTGTGTTCTTT       909
            ||||||||||||||||||||||||||||||||||||||||||||||||||||||||||
Sbjct 42629783 TAACTTAAATGAGATTTTCCAATATAAATACTCTGTGAACCTCCAGCCTTGTGTTCTTT 42629842

Query  910  CTTTTTTTTTTTTTTTTTTTTTTTTT   938    Query - SEQ ID NO: 160
            ||||||||||||||||||||||||||          Subject - SEQ ID NO: 161
Sbjct 42629843 CTTTTTTTTTTTTTTTTTTTTTTTTT   42629871
```

Figure 11.3B

| clone | chr | chr p | chr q | clone p | clone q | repeat p | repeat q | size | unique | %1 | cds | cds p | cds q |
|---|---|---|---|---|---|---|---|---|---|---|---|---|---|
| 2006T7 | 1 | 31,463,479 | 31,463,809 | 533 | 198 | 198 | 498 | 336 | 36 | 83 | | | |
| C8T7 | 1 | 31,463,479 | 31,463,809 | 903 | 1,238 | 938 | 1,902 | 336 | 36 | 83 | | | |
| S55-c14 | 1 | 31,784,608 | 31,784,608 | 1 | 720 | | | 720 | 720 | 100 | c-u | 1 | 191 |
| S55-c15 | 1 | 31,785,207 | 31,785,207 | 1 | 600 | | | 600 | 600 | 100 | c-u | | |
| 2006M13 | 1 | 35,349,138 | 35,349,138 | 445 | 145 | 131 | 459 | 301 | 0 | 83 | | | |
| C8M3 | 1 | 35,349,138 | 35,349,138 | 434 | 134 | 120 | 448 | 301 | 0 | 83 | | | |
| IGNB2 | 1 | 111,106,763 | 111,106,763 | 107 | 499 | 109 | 378 | 393 | 3 | 100 | | | |
| 2006M13 | 4 | 118,300,869 | 118,300,869 | 115 | 732 | 131 | 459 | 618 | 290 | 98 | | | |
| C8T7 | 4 | 118,301,174 | 118,301,174 | 16 | 938 | 938 | 1902 | 923 | 923 | 98 | | | |
| 2006T7 | 4 | 118,301,174 | 118,301,174 | 878 | 498 | 198 | 498 | 381 | 381 | 96 | | | |
| IGNB2 | 5 | 40,195,387 | 40,195,774 | 499 | 109 | 109 | 378 | 391 | 122 | 90 | | | |
| 2006T7 | 18 | 26,801,993 | 26,802,549 | 523 | 57 | 198 | 498 | 467 | 168 | 99 | | | |
| C8T7 | 18 | 26,801,993 | 26,802,549 | 913 | 1,379 | 938 | 1,902 | 467 | 26 | 99 | | | |
| C8T7 | 18 | 26,801,993 | 26,802,549 | 1,436 | 1,902 | 938 | 1,902 | 467 | 0 | 99 | | | |

Figure 12

ALIGNMENTS HISTATIN -2-3 VARIANT / PATF / Q7TCL4

>GI : 16517085  SEQ ID NO: 169    ALIGNMENT (FASTA FORMAT)
MYIIYLKLYQAPLKKSERVLRAVPTSLHLHIHASLYPDIPTSPHPYITVSPHPCILISPH
ISLSPHPHFPAPSSCRTLLLPAVSRQQRVPSPSHYGVHMDCGLMEPPSRESIAFPDRFPA
KLMLGLLIFTEITCCERRRVYGPLTNPKPQSLSAINPKGGTENSRLFWGSNCCLEVFLSY
RCVTLSAQGRGTPKPGLSGAPCTDRRAMSFFHCYRSILHTKVGFYVKIKKKKRKKKRNNN
NKNKNNNNKYIYILKRKENKAKTCNTVFSRRNKSTNK

>SPLICING   SEQ ID NO: 171
KL----------------------------------------------------------
-----------------FVFALILALMLSMCGADS-------------------------
-----------------------------HAKR----------------------------
------------------------------------------------------------

>GI: 32401263   SEQ ID NO: 170    ALIGNMENT (FASTA FORMAT)
MTKFYCGWDRLLESLPDGWVYCDADGSQFDSSLSPYLINAVLNIRLGFMEEWDVGEIMLR
NLYTEIVYTPISTPDGTLVKKFRGNNSGQPSTVVDNTLMVILAVNYSLKKSGIPSELRDS
IIKFFVNGDDLLLSVHPEYEYILDTMADNFRELGLKYTFDSRTREKGDLWFMSHQCHKRE
GIWIPKLEPERIVSILEWDRSKEPCHRLEAICAAMIESWGYDKLTHEIRKFYAWMIEQAP
FSSLAQEGKAPYIAETALRKLYLDKEPAQEDLTHYLQAIFEIYEDGAETCVYHQAGETPD
AGLTDEQKQAEKEKKEREKAEKERERQKQLALKKGKDVAQEEGKRDREVNAGFSGTFSVP
RLKSLTSKMRVPRYEQRVALNLDHLILYTPEQTDLSNTRSTRKQFDTWFEGVMADYELTE
DKMQIILNGLMVWCIENGTSPNINGMWVMMDGDDQVEFPIKPLIDHAKPTFRQIMAHFSD
VAEAYIEKRNQDRPYMPRYGLQKNLTDMSLARYAFDFYEMTSRTPIRAREAHIQMKAAAL
RGANNNLFGLDGNVGTTVENTERHTTEDVNRNMHNLLGVKGL

>SPLICING  SEQ ID NO: 168
------------KFFVFAL-----------------------------------------
----------------------ILALMLSMCGADS-------------------------
-----------------------------HAKR---------------------------
------------------------------------------------------------

Figure 13A

Alignment of two nucleic sequences:
Sequence 1: Personal sequence: GI:16517065 transcription factor PATF
[Coturnix japonica] (query)

Sequence 2: Personal sequence: seqgallus1 (query)

Matrix: 0

/tmp/tapweb/analseq/al838740/s1 : 277 aa
ALIGN calculates a global alignment of two sequences
 version 2.0uPlease cite: Myers and Miller, CABIOS (1989) 4:11-17
GI:16517065 transcription factor PATF [Coturnix ]   277 aa vs.
seqgallus1                                           20 aa
scoring matrix: BLOSUM50, gap penalties: -10/-2
 4.7% identity;        Global alignment score: -498

```
              10        20        30        40        50        60
/tmp/t  MYIIYLHLYQAFLHRSEDVLHAVFTSLHLHIHASLYPDIPTSPHPYITVSPHPOILTSPH
                ::                                    :...
seqgal  ---------------KS-----------------------------YHSM-----------

70        80        90       100       110       120
/tmp/t  ISLSPHPHFBAPSSCRTLLLPAVSRQQNVPSPSHYGVHMDCGLMEPPSRESIAFFDEFPA
              :          :::  :.:
seqgal  -------F----------LLIMAYS---------------------------------
                         10

130       140       150       160       170       180
/tmp/t  KLMLGLLIFTEITCCERRBVYGPLTNPMPQSLSAINPKGGTENSRLFWGSNCCLEVFLSY
                                                               : :
seqgal  ---------------------------------------------------CVL-----

190       200       210       220       230       240
/tmp/t  RCVFLSAQGHGTPKPGLSGAPCTQRRAMSFFHCYRSILHTKVGFYVKIKKKKKKKKRHNH seqgal  ------------------------------------------------------------

250       260       270
/tmp/t  NHNHENRDEKYIYILKRKENKAKTCHTVFSRRHKSTNK
                                  ::
seqgal  -----------------------AKD-----------
                                  20
```

SEQ ID NO: 169

SEQ ID NO: 172

Figure 13B

Morphology of untreated MCF-7 cells or MCF-7 cells treated with TPA at 26nM

Expression of LIV 21: A: as a function of treatment time with TPA at 25 nM;
Figure B: compared with LIV 21 in protein extracts, at 12 h.

Expression, as a function of treatment time with TPA of the PKCε
and PKCζ proteins in total extracts. α-Tubulin expression serves as a control.

Compared expression of PKCε and of LIV 21 by immunocytochemistry
on cultures of untreated MCF-7 cells and of MCF-7 cells treated with TPA.

Effect of the inhibitory peptide (2 μM) on the LIV 21 expression profile in cytoplasmic (C) and nuclear (N) cell fractions.

```
Taxonomy     : Eukaryota (eukaryotes) (150050 sequences)
Timestamp    : 4 Mar 2006 at 20:47:45 GMT
Top Score    : 81 for P15516-00-01-00, (HIS3_HUMAN) Splice isoform Displ
```

Probability Based Mowse Score

Protein score is -10*Log(P), where P is the probability that the observed match is a random e
Protein scores greater than 64 are significant (p<0.05).

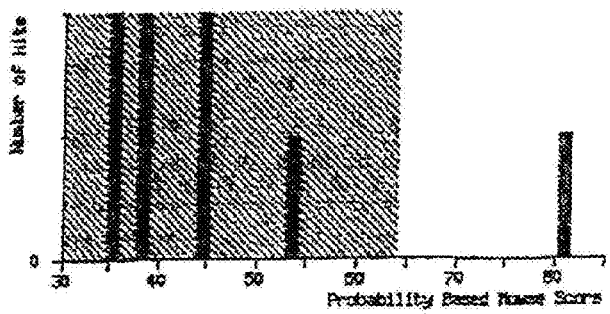

```
1.  P15516-00-01-00  Mass: 5449  Score: 81  Expect: 0.0012  Queri
    (HIS3_HUMAN) Splice isoform Displayed; Variant histatin-3-2; Conflic
    P15516-00-00-00  Mass: 6145  Score: 80  Expect: 0.0017  Queri
    (HIS3_HUMAN) Splice isoform Displayed; Variant Displayed; Conflict D:

Match to: P15516-00-01-00 Score: 81 Expect: 0.0012
(HIS3_HUMAN) Splice isoform Displayed; Variant histatin-3-2; Conflict Displayed;

Nominal mass (M_r): 5449; Calculated pI value: 10.38
NCBI BLAST search of P15516-00-01-00 against nr
Unformatted sequence string for pasting into other applications Taxonomy: Homo sapiens Cleavage by Trypsin: cuts C-term side of KR unless next residue is P
Sequence Coverage: 52%

Matched peptides shown in Bold Red

1 MKFFVFALIL ALMLSMTGAD SHAKRHHGYK RKFHEKHHSH QGYRSN      SEQ ID NO: 162
```

⊕ Residue Number  ○ Increasing Mass  ○ Decreasing Mass   SEQ ID NO: 163

| Start - End | Observed | Mr(expt) | Mr(calc) | Delta | Miss | Sequence |
|---|---|---|---|---|---|---|
| 2 - 24 | 2511.3740 | 2510.3667 | 2510.3429 | 0.0239 | 1 | M.KFFVFALILALML |
| 3 - 24 | 2383.2600 | 2382.2527 | 2382.2479 | 0.0048 | 0 | K.FFVFALILALML.S |
| 3 - 25 | 2539.3280 | 2538.3207 | 2538.3490 | -0.0283 | 1 | K.FFVFALILALMLS |

Figure 29

```
Alignment of two nucleic sequences:
Sequence 1: Personal sequence: GI:16517065 transcription factor PATF
            [Coturnix japonica] (query)

Sequence 2: Personal sequence: seqgallus1 (query)

Matrix: 0
```

```
/tmp/tmpweb/analseq/al848726/a1 :   277 aa
ALIGN calculates a global alignment of two sequences
  version 2.0uPlease cite: Myers and Miller, CABIOS (1989) 4:11-17
GI:16517065 transcription factor PATF (Coturnix j   277 aa vs.
seqgallus2                                           18 aa
scoring matrix: BLOSUM50, gap penalties: -10/-2
    4.3% identity;       Global alignment score: -475
```

SEQ ID NO: 169

```
              10        20        30        40        50        60
/tmp/t MYIIYLKLYQAPLKKSERVLRAVPTSLHLHIHASLYPDIPTSPHPYITVSPHPCILISPH
                   ::              .  ::
seqgal -----------FL--------------MIIH----------------------------
```

SEQ ID NO173

```
              70        80        90       100       110       120
/tmp/t ISLSPHPHFPAPSSCRTLLLPAVSRQQRVPSPSHYGVHMDCGLMEPPSRESIAFPDRFPA
                                         :.:                 :
seqgal ----------------------------------HLD-----------------D----
                                                                10

130       140       150       160       170       180
/tmp/t KLMLGLLIFTEITCCERRRVYGPLTNPKPQSLSAINPKGGTENSRLFWGSNCCLEVFLSY
                      :              |. ::|
seqgal -------------C----------------PHSQAL------------------------

190       200       210       220       230       240
/tmp/t RCVTLSAQGRGTFKPGLSGAPCTDRRAMSFFHCYRSILETKVGFYVKIKQKRKKRNNN seqgal ---------------------------------------------------------

250       260       270
/tmp/t NNNKNNNMKYIYILKRKENKAKTCNTVFSRRNKSTNK    SEQ ID NO: 169
                                          :
seqgal -----------------------------------K    SEQ ID NO173
```

Figure 30

```
User         : laur
Email        : laurence.lauro@wanadoo.fr
Search title : gal 6 massebande2
Database     : SwissProt 49.1 (269860 sequences; 124153853 residues)
Taxonomy     : Eukaryota (eucaryotes) (150050 sequences)
Timestamp    : 4 Mar 2006 at 20:47:45 GMT
Top Score    : 81 for P15516-00-01-00, (HIS3_HUMAN) Splice isoform Displayed;
```

Probability Based Mowse Score

Protein score is -10*Log(P), where P is the probability that the observed match is a random event.
Protein scores greater than 64 are significant (p<0.05).

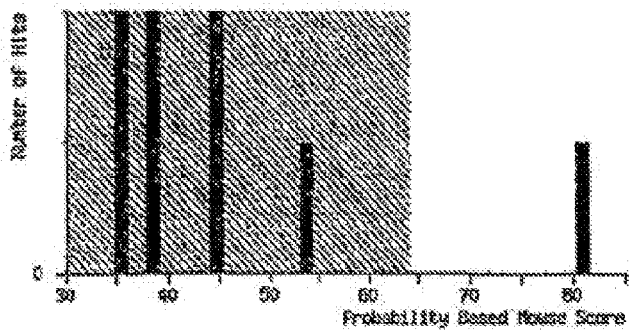

Concise Protein Summary Report

[Concise Protein Summary]  Help

Significance threshold p< 0.05    Max. number of hits 20

1.  P15516-00-01-00  Mass: 5449   Score: 81   Expect: 0.0012  Queries matc
    (HIS3_HUMAN) Splice isoform Displayed; Variant histatin-3-2; Conflict Displ
    P15516-00-00-00  Mass: 6145   Score: 80   Expect: 0.0017  Queries matc
    (HIS3_HUMAN) Splice isoform Displayed; Variant Displayed; Conflict Displaye
    Q6CLN0           Mass: 34837  Score: 57   Expect: 0.31    Queries matche
    (TSC10_KLULA) 3-ketodihydrosphingosine reductase TSC10 (EC 1.1.1.102) (3-de
    Q69FB6           Mass: 57816  Score: 48   Expect: 2.5     Queries matched
    (CP19A_IAGRC) Cytochrome P450 19A1 (EC 1.14.14.1) (Aromatase) (CYPXIX) (Est
    Q9CZU3           Mass: 117561 Score: 39   Expect: 18      Queries matched:
    (SKIV2_MOUSE) Superkiller viralicidic activity 2-like 2 (EC 3.6.1.-) (ATP-d
    Q9H478           Mass: 7380   Score: 46   Expect: 3.4     Queries matched
    (KCQ1D_HUMAN) KCNQ1 downstream neighbor protein (Beckwith-Wiedemann region
    Q06250-00-01-00  Mass: 10062  Score: 44   Expect: 5.6     Queries matched
    (WIT1_HUMAN) Splice isoform Displayed; Variant dbSNP:6508; Conflict Display
    Q4JHS0           Mass: 21556  Score: 38   Expect: 25      Queries matched:
    (BID_PIG) BH3-interacting domain death agonist BH3-interacting domain death
    P50894           Mass: 22192  Score: 38   Expect: 26      Queries matched:

Figure 31A

```
User          : laur
Email         : laurence.fauro@wanadoo.fr
Search title  :
Database      : SwissProt 49.1 (269880 sequences; 124153953 residues)
Timestamp     : 4 Mar 2006 at 20:43:12 GMT
Top Score     : 72 for P15516-00-01-00, (HIS3_HUMAN) Splice isoform Displayed;
```

Probability Based Mowse Score

Protein score is -10*Log(P), where P is the probability that the observed match is a random event.
Protein scores greater than 67 are significant (p<0.05).

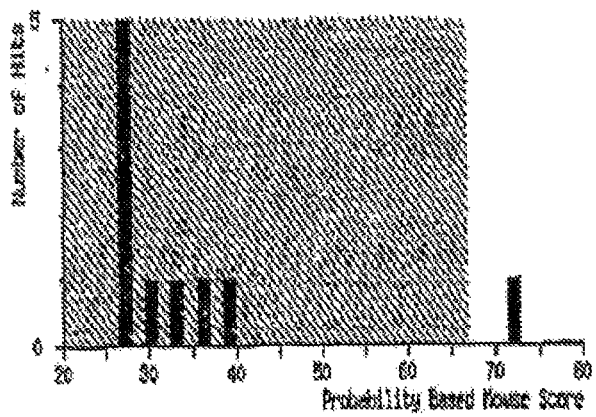

Search Parameters

```
Type of search         : Sequence Query
Enzyme                 : Trypsin
Variable modifications : Carboxymethyl (C), Oxidation (M)
Mass values            : Monoisotopic
Protein Mass           : Unrestricted
Peptide Mass Tolerance : ± 20 ppm
Fragment Mass Tolerance: ± 0.8 Da
Max Missed Cleavages   : 1
Instrument type        : Default
Query1 (2021.0030,1+)  : <no title>
Query2 (2037.0134,1+)  : <no title>
Query3 (2125.0010,1+)  : <no title>
Query4 (2383.2608,1+)  : <no title>
Query5 (2511.3749,1+)  : <no title>
Query6 (2539.3286,1+)  : <no title>
```

Figure 31B

Nested PCR performed with the reverse primers or GDBR1 Splicing PCR on A1 + od
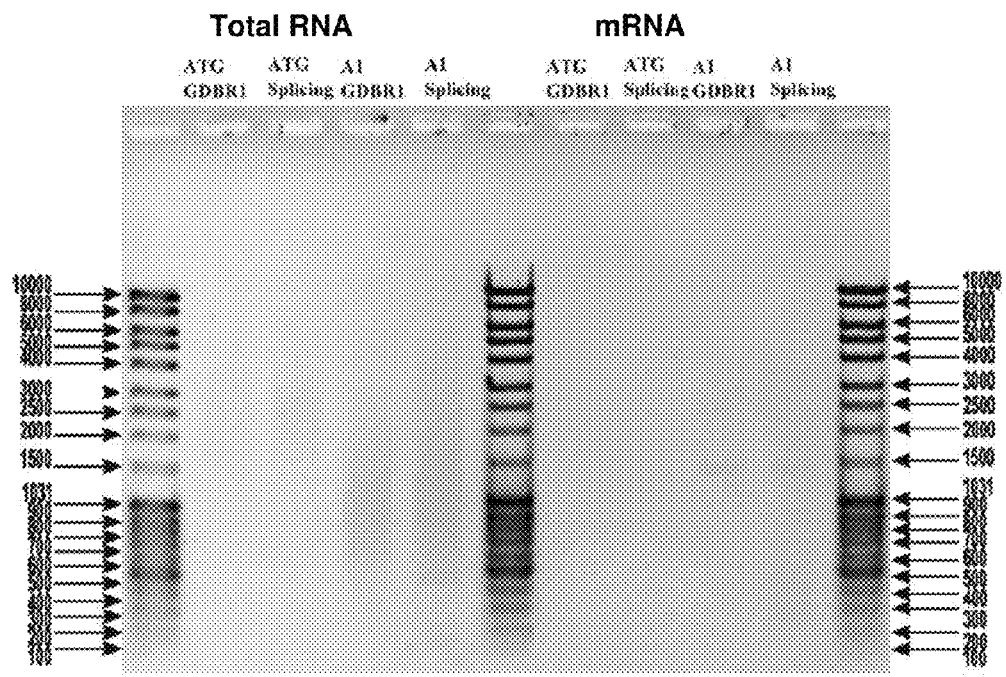
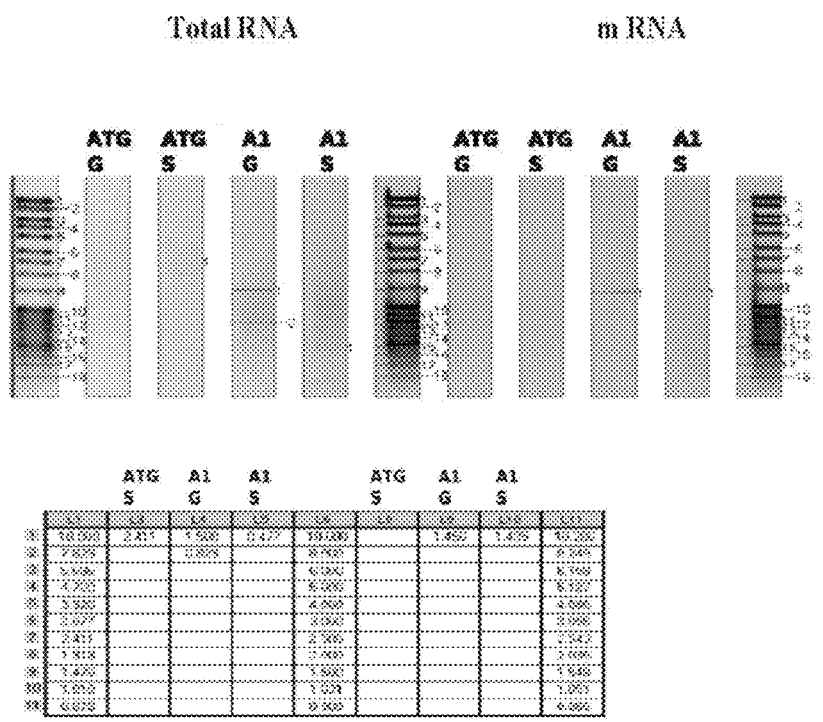
Figure 32

Gel 5: Track 2: Ligation G45T(462pb)
Track 4: Ligation S45T (1289, 783, 614, 437pb)
Track 6: Ligation G55T (11559 and 1315pb)
Track 7: Ligation S55M (412pb)
Track 8: Ligation S55T
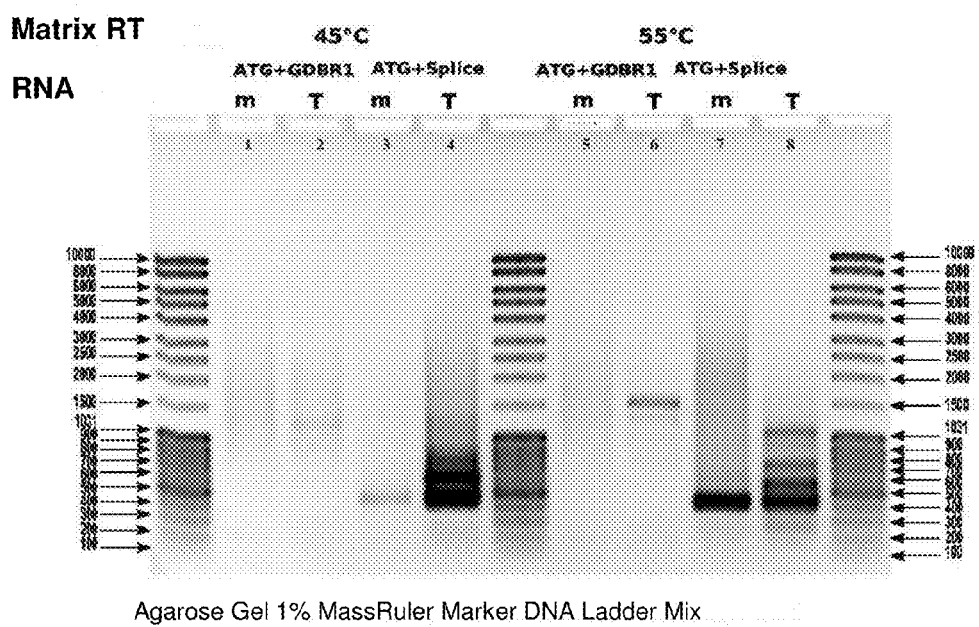
Agarose Gel 1% MassRuler Marker DNA Ladder Mix
Analysis of molecular masses :
PGEMT Easy cloning of fragments were PCR S45T (ATG splice on RT 45°C in total RNAs
and fragments G45 T (ATG GDBR1 on RT 45°C in total RNAs)
Screening minipreps by EcoR1
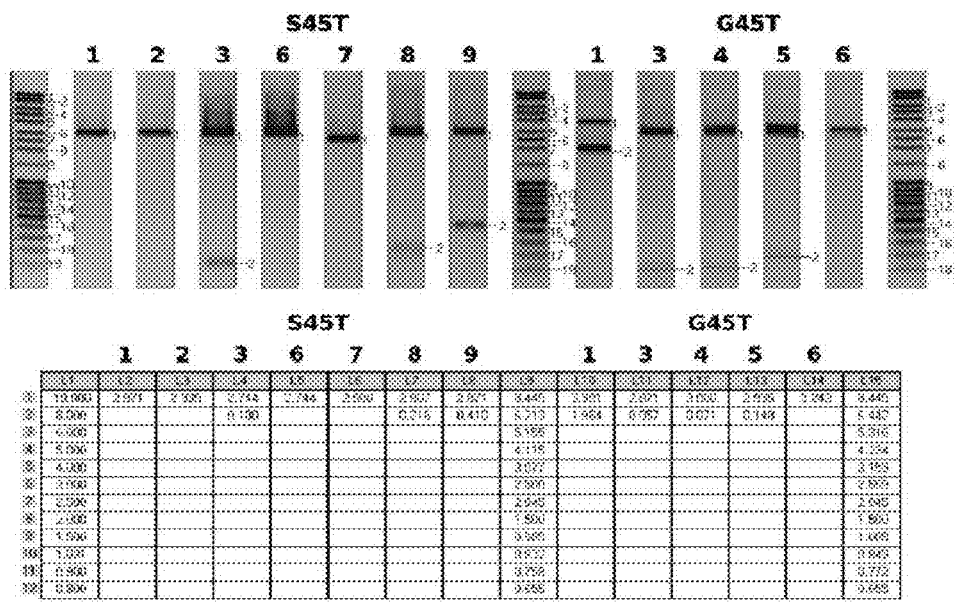
Figure 38

Gel 6: Screening of recombinant clones S55T and S55M

PGEMT Easy cloning of fragments were PCR S55T (ATG splice on RT 55°C in total RNAs
and fragments S55 M (ATG splice RT on RT 55°C mRNA)
Screening minipreps by EcoR1

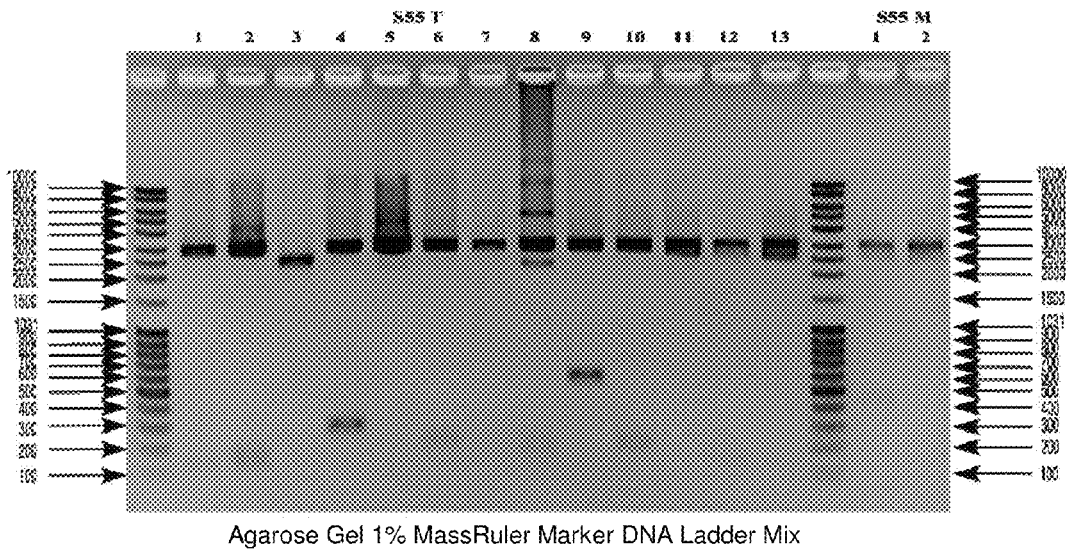

Agarose Gel 1% MassRuler Marker DNA Ladder Mix

Analysis of molecular masses:

PGEMT Easy cloning of fragments were PCR S55T (ATG splice on RT 55°C in total RNAs
and fragments S55 M (ATG splice RT on RT 55°C mRNA)
Screening minipreps by EcoR1

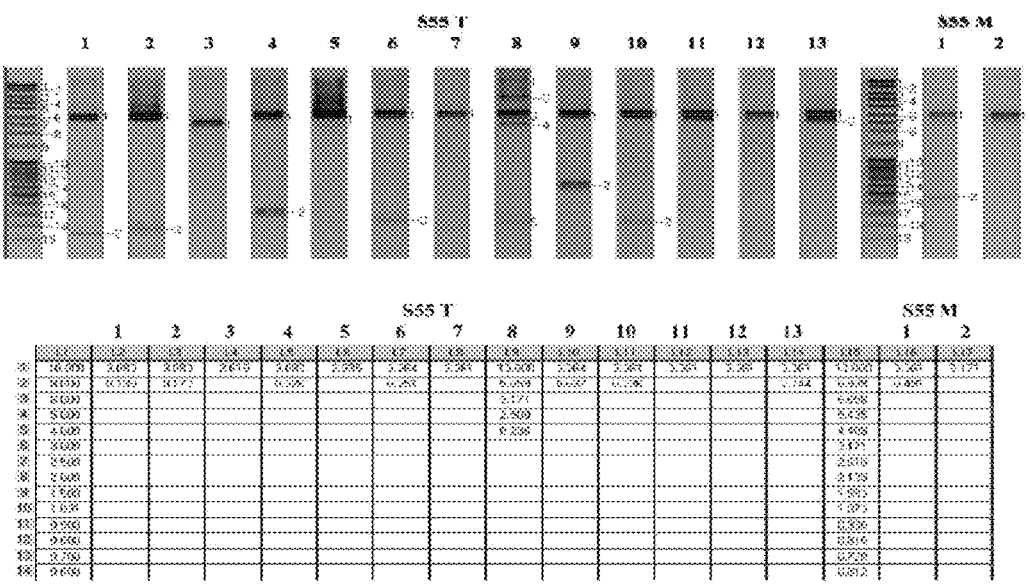

Figure 39 ref|NT_032977.8|Hs1_33153 Homo sapiens chromosome 1 genomic contig, reference assembly
Length=73835825

Features flanking this part of subject sequence:
 105575 bp at 5' side: tumor differentially expressed 2-like
 28931 bp at 3' side: PJEC3L    SEQ ID NO: 164

Score = 2148 bits (1163), Expect = 0.0
Identities = 1189/1201 (99%), Gaps = 4/1201 (0%)
Strand=Plus/Plus Query - SEQ ID NO: 148
Subject – SEQ ID NO: 164

```
Query  1        GGAGAAGGGTCCCCACTGCTCCTGTCAAGCCTTGTTGTGTCGGACTTGAACTTTATTCT   60
                ||||||||||||||||||||||||||||||||||||||||||||||||||||||||||||
Sbjct  1984539  GGAGAAGGGTCCCCACTGCTCCTGTCAAGCCTTGTTGTGTCGGACTTGAACTTTATTCT   1984598

Query  61       AAGCAGGTGAATGCGGTGCATGCAAGAGAGACAGAGAGAATGTGGCAGgaccaaggagga  120
                ||||||||||||||||||||||||||||||||||||||||||||||||||||||||||||
Sbjct  1984599  AAGCAGGTGAATGCGGTGCATGCAAGAGAGACAGAGAGAATGTGGCAGGACCAAGGAGGA  1984658

Query  121      ggctatgccacttatgtcactcctggcaaaaataaggggggcatggagtaggctgtttgtg  180
                ||||||||||||||||||||||||||||||||||||||||||||||||||||||||||||
Sbjct  1984659  GGCTATGCCACTTATGTCACTCCTGGCAAAAATAAGGGGGCATGGAGTAGGCTGTTTGTG  1984718

Query  181      gtgcagatggtgagagcagtcaggtccagcacagattttaaaggttggacccagagaatt  240
                ||||||||||||||||||||||||||||||||||||||||||||||||||||||||||||
Sbjct  1984719  GTGCAGATGGTGAGAGCAGTCAGGTCCAGCACAGATTTTAAAGGTTGGACCCAGAGAATT  1984778

Query  241      tgctgcagaatcagatgtggggtgtaaggcagagaggagtcaagggcaacttcaggattt  300
                ||||||||||||||||||||||||||||||||||||||||||||||||||||||||||||
Sbjct  1984779  TGCTGCAGAATCAGATGTGGGGTGTAAGGCAGAGAGGAGTCAAGGGCAACTTCAGGATTT  1984838

Query  301      ggggccggaactgccattagacagacagggacactggggggagaagcaggttaggtgggat  360
                ||||||||||||||||||||||||||||||| ||||||||||||||||||||||||||||
Sbjct  1984839  GGGGCCGGAACTGCCATTAGACAGACAGGGACACTGAGGGAGAAGCAGGTTAGGTGGGAT  1984898

Query  361      taaaatcaagagttcaagttaagtttgagcagcctgttagacctccaacgagggccagat  420
                |||||||||||||||||||||||||||||||||||||||||||||||| |||||||||||
Sbjct  1984899  TAAAATCAAGAGTTCAAGTTAAGTTTGAGCAGCCTGTTAGACCTCCAGCGAGGGCCAGAT  1984958

Query  421      agaagaatctggtttccagggagaggtcaggatgagagatacacacgtgggaatgattgg  480
                ||||||||||||||||||||||||||||||||||||||||||||||||||||||||||||
Sbjct  1984959  AGAAGAATCTGGTTTCCAGGGAGAGGTCAGGATGAGAGATACACACGTGGGAATGATTGG  1985018

Query  481      cattgggcggactttatattctctgggccagtgagacagctgggaagtgaccacggatag  540
                ||||||| |||||||||||||||||||| |||||||||||||||||||||||||||||||
Sbjct  1985019  CATTGGGTGGACTTTATATTCTCTGGGTCAGTGAGACAGCTGGGAAGTGACCACGGATAG  1985078
```

Figure 40A

```
Query   541     agaagagacaaagtcACAGAAACCAAGAGAGGTAATGTTGCAAGGACGGAACACTCAACT   600
                ||||||||||||||||||||||||||||||||||||||||||||||||||||||||||||
Sbjct   1985079 AGAAGAGACAAAGTCACAGAAACCAAGAGAGGTAATGTTGCAAGGACGGAACACTCAACT   1985138

Query   601     CTCAAATGCTGCTGAGACGTGGGCTGAGGGCTGAGAATGGAATTGGGAAGAACCGAGGTC   660
                ||||||||||||||||||||||||||||||||||||||||||||||||||||||||||||
Sbjct   1985139 CTCAAATGCTGCTGAGACGTGGGCTGAGGGCTGAGAATGGAATTGGGAAGAACCGAGGTC   1985198

Query   661     ACTGGTGATCCTGAGGGTTTCAGTGGCAAGGGCAGGTGGACTGCAGTGGGGCCCGGTGGG   720
                ||||||||||||||||||||||||||||||||||||||||||||||||||||||||||||
Sbjct   1985199 ACTGGTGATCCTGAGGGTTTCAGTGGCAAGGGCAGGTGGACTGCAGTGGGGCCCGGTGGG   1985258

Query   721     GATCGGTGGAGCATGGGCCCCTCTCCCGGAGAGTTGCACTGTAAACGAGGGCAGACATAT   780
                ||| ||||||||||||||||||||||||||||||||||||||||||||||||||||||||
Sbjct   1985259 GATGGGTGGAGCATGGGCCCCTCTCCCGGAGAGTTGCACTGTAAACGAGGGCAGACATAT   1985318

Query   781     GGGAGTGCAGCTAGAGGGAGGGAACGTAGGCTCAAGGGAGAGTTTATTCTGAATGAGAGA   840
                |||||||||||||||||||||||||||||||| |||||||||||||||||||||||||||
Sbjct   1985319 GGGAGTGCAGCTAGAGGGAGGGAACGTAGGGTCAAGGGAGAGTTTATTCTGAATGAGAGA   1985378

Query   841     GATCACAGCTTGTTTTTAGGCTGACGGGCATGATCCATAGAGGGAAAGTAATTAAGATG   900
                ||||||||||||||||||||||||||||||||||||||||||||||||||||||||||||
Sbjct   1985379 GATCACAGCTTGTTTTTAGGCTGACGGGCATGATCCATAGAGGGAAAGTAATTAAGATG   1985438

Query   901     CAGAAGAGAggccgggggtggtggctcacgcctgtaatctcagcactttgggaggctcga   960
                |||||||||||||||||||||||||||||||||||||||||||||||||||||||| ||
Sbjct   1985439 CAGAAGAGAGGCCGGGGGTGGTGGCTCACGCCTGTAATCTCAGCACTTTGGGAGGCT-GA   1985497

Query   961     ggtgggtggatcatttgaggacaggagttcgagaccatcctggccagcatggtgaaacct   1020
                |||||||||||||||||||||||||||||||||||||||||||||||||||||||||| ||
Sbjct   1985498 GGTGGGTGGATCATTTGAGGACAGGAGTTCGAGACCATCCTGGCCAGCATGGTGAAACT   1985557

Query   1021    cgcctctactaaaaataaaaataaaaaaaaaattagctgggtgcggtg-acgggcacctgt   1079
                ||||||||||||||||||||||||||||||||||||||| |||| | ||||||||||
Sbjct   1985558 CGCCTCTACTAAAAATAAAAATAAAAAAAAATTAGCTGGGTGTGGTGGA-GGGCACCTGT   1985616

Query   1080    agtaccagctacttgggaggctgaggtaacagaatcgcttgaaccctggaggcaggggtt   1139
                ||||||||||||||||||||||||||||||||||||||||||||||||||||||||||||
Sbjct   1985617 AGTACCAGCTACTTGGGAGGCTGAGGTAACAGAATCGCTTGAACCCTGGAGGCAGGGGTT   1985676

Query   1140    gcagtgagctgagattgtgccactgcactctagcctgggcaacaaattgagactCCA-CT   1198
                |||||||||||||||||||||||||||||||||||||||||||||||||||||||| ||
Sbjct   1985677 GCAGTGAGCTGAGATTGTGCCACTGCACTCTAGCCTGGGCAACAAATTGAGACTCCATCT   1985736

Query 1199      C 1199
                |
Sbjct 1985737 C 1985737
```

Query - SEQ ID NO: 148   Subject - SEQ ID NO: 164

Figure 40B

<u>114088 bp at 5' side: tumor differentially expressed 2-like</u>
<u>29159 bp at 3' side: P3ECSL</u>

Query - SEQ ID NO: 165

Score = 2170 bits (1175), Expect = 0.0
Identities = 1193/1201 (99%), Gaps = 4/1201 (0%)
Strand=Plus/Plus Subject - SEQ ID NO: 148

```
Query     1        GGAGAAGGGTCCCCACTGCTCCTGTCAAGCCTTGTTGTGTCGGGACTTGAACTTTATTCT    60
                   ||||||||||||||||||||||||||||||||||||||||||||||||||||||||||||
Sbjct     6142513  GGAGAAGGGTCCCCACTGCTCCTGTCAAGCCTTGTTGTGTCGGGACTTGAACTTTATTCT    6142572

Query     61       AAGCAGGTGAATGCGGTGCATGCAAGAGAGACAGAGAGAATGTGGCAGgaccaaggagga   120
                   ||||||||||||||||||||||||||||||||||||||||||||||||||||||||||||
Sbjct     6142573  AAGCAGGTGAATGCGGTGCATGCAAGAGAGACAGAGAGAATGTGGCAGGACCAAGGAGGA   6142632

Query     121      ggctatgccacttatgtcactcctggcaaaaataagggggcatggagtaggctgtttgtg   180
                   ||||||||||||||||||||||||||||||||||||||||||||||||||||||||||||
Sbjct     6142633  GGCTATGCCACTTATGTCACTCCTGGCAAAAATAAGGGGGCATGGAGTAGGCTGTTTGTG   6142692

Query     181      gtgcagatggtgagagcagtcaggtccagcacagatttaaaggttggacccagagaatt   240
                   ||||||||||||||||||||||||||||||||||||||||||||||||||||||||||||
Sbjct     6142693  GTGCAGATGGTGAGAGCAGTCAGGTCCAGCACAGATTTTAAAGGTTGGACCCAGAGAATT   6142752

Query     241      tgctgcagaatcagatgtggggtgtaaggcagagaggagtcaagggcaacttcaggattt   300
                   ||||||||||||||||||||||||||||||||||||||||||||||||||||||||||||
Sbjct     6142753  TGCTGCAGAATCAGATGTGGGGTGTAAGGCAGAGAGGAGTCAAGGGCAACTTCAGGATTT   6142812

Query     301      ggggccggaactgccattagacagacagggacactgggggagaagcaggttaggtgggat   360
                   ||||||||||||||||||||||||||||||||||||||||||||||||||||||||||||
Sbjct     6142813  GGGGCCGGAACTGCCATTAGACAGACAGGGACACTGGGGGAGAAGCAGGTTAGGTGGGAT   6142872

Query     361      taaaatcaagagttcaagttaagtttgagcagcctgttagacctccaacgagggccagat   420
                   ||||||||||||||||||||||||||||||||||||||||||||||||||||||||||||
Sbjct     6142873  TAAAATCAAGAGTTCAAGTTAAGTTTGAGCAGCCTGTTAGACCTCCAACGAGGGCCAGAT   6142932

Query     421      agaagaatctggtttccagggagaggtcaggatgagagatacacacgtgggaatgattgg   480
                   ||||||||||||||||||||||||||||||||||||||||||||||||||||||||||||
Sbjct     6142933  AGAAGAATCTGGTTTCCAGGGAGAGGTCAGGATGAGAGATACACACGTGGGAATGATTGG   6142992

Query     481      cattgggcggactttatattctctgggccagtgagacagctgggaagtgaccacggatag   540
                   ||||||||||||||||||||||||||||||||||||||||||||||||||||||||||||
Sbjct     6142993  CATTGGGCGGACTTTATATTCTCTGGGCCAGTGAGACAGCTGGGAAGTGACCACGGATAG   6143052
```

Figure 41A

```
Query    541   agaagagacaaagtcACAGAAACCAAGAGAGGTAATGTTGCAAGGACGGAACACTCAACT   600
               ||||||||||||||||||||||||||||||||||||||||||||||||||||||||||||
Sbjct    6143053  AGAAGAGACAAAGTCACAGAAACCAAGAGAGGTAATGTTGCAAGGACGGAACACTCAACT   6143112

Query    601   CTCAAATGCTGCTGAGACGTGGGCTGAGGGCTGAGAATGGAATTGGGAAGAACCGAGGTC   660
               ||||||||||||||||||||||||||||||||||||||||||||||||||||||||||||
Sbjct    6143113  CTCAAATGCTGCTGAGACGTGGGCTGAGGGCTGAGAATGGAATTGGGAAGAACCGAGGTC   6143172

Query    661   ACTGGTGATCCTGAGGGTTTCAGTGGCAAGGGCAGGTGGACTGCAGTGGGGCCCGGTGGG   720
               ||||||||||||||||||||||||||||||||||||||||||||||||||||||||||||
Sbjct    6143173  ACTGGTGATCCTGAGGGTTTCAGTGGCAAGGGCAGGTGGACTGCAGTGGGGCCCGGTGGG   6143232

Query    721   GATCGGTGGAGCATGGGCCCCTCTCCCGGAGAGTTGCACTGTAAACGAGGGCAGACATAT   780
               ||| ||||||||||||||||||||||||||||||||||||||||||||||||||||||||
Sbjct    6143233  GATGGGTGGAGCATGGGCCCCTCTCCCGGAGAGTTGCACTGTAAACGAGGGCAGACATAT   6143292

Query    781   GGGAGTGCAGCTAGAGGGAGGGAACGTAGGCTCAAGGGAGAGTTTATTCTGAATGAGAGA   840
               |||||||||||||||||||||||||||||||| |||||||||||||||||||||||||||
Sbjct    6143293  GGGAGTGCAGCTAGAGGGAGGGAACGTAGGGTCAAGGGAGAGTTTATTCTGAATGAGAGA   6143352

Query    841   GATCACAGCTTGTTTTTAGGCTGACGGGCATGATCCATAGAGGGGAAAGTAATTAAGATG   900
               ||||||||||||||||||||||||||||||||||||||||||||||||||||||||||||
Sbjct    6143353  GATCACAGCTTGTTTTTAGGCTGACGGGCATGATCCATAGAGGGGAAAGTAATTAAGATG   6143412

Query    901   CAGAAGAGAggccggggtggtggctcacgcctgtaatctcagcactttgggaggctcga   960
               ||||||||||||||||||||||||||||||||||||||||||||||||||||||||| ||
Sbjct    6143413  CAGAAGAGAGGCCGGGGTGGTGGCTCACGCCTGTAATCTCAGCACTTTGGGAGGCT-GA   6143471

Query    961   ggtgggtggatcatttgaggacaggagttcgagaccatcctggccagcatggtgaaacct   1020
               ||||||||||||||||||||||||||||||||||||||||||||||||||||||||| ||
Sbjct    6143472  GGTGGGTGGATCATTTGAGGACAGGAGTTCGAGACCATCCTGGCCAGCATGGTGAAACT   6143531

Query    1021  cgcctctactaaaaataaaaataaaaaaaattagctgggtgcggtg-acgggcacctgt   1079
               ||||||||||||||||||||||||||||||||||||||||||| ||| | ||||||||||
Sbjct    6143532  CGCCTCTACTAAAAATAAAAATAAAAAAAATTAGCTGGGTGTGGTGGA-GGGCACCTGT   6143590

Query    1080  agtaccagctacttgggaggctgaggtaacagaatcgcttgaacccctggaggcagggtt   1139
               ||||||||||||||||||||||||||||||||||||||||||||||||||||||||||||
Sbjct    6143591  AGTACCAGCTACTTGGGAGGCTGAGGTAACAGAATCGCTTGAACCCTGGAGGCAGGGTT   6143650

Query    1140  gcagtgagctgagattgtgccactgcactctagcctgggcaacaaattgagactCCA-CT   1198
               |||||||||||||||||||||||||||||||||||||||||||||||||||||||| ||
Sbjct    6143651  GCAGTGAGCTGAGATTGTGCCACTGCACTCTAGCCTGGGCAACAAATTGAGACTCCATCT   6143710
```

Query 1199    C 1199        Query - SEQ ID NO: 148    Subject - SEQ ID NO: 165
Sbjct 6143711 C 6143711

Figure 41B

SEQUENCE LISTING

<160> NUMBER OF SEQ ID NOS: 180

<210> SEQ ID NO 1
<211> LENGTH: 13
<212> TYPE: PRT
<213> ORGANISM: Homo sapiens

<400> SEQUENCE: 1

Pro Ala Ser Ala Gly Ile Thr Gly Val Ser Cys Ala Arg
1               5                   10

<210> SEQ ID NO 2
<211> LENGTH: 28
<212> TYPE: PRT
<213> ORGANISM: Homo sapiens

<400> SEQUENCE: 2

Gly Phe Thr Val Leu Ala Arg Met Val Ser Ile Ser Pro Arg Asp Pro
1               5                   10                  15

Pro Ala Ser Ala Ser Gln Ser Val Gly Ile Ala Tyr
            20                  25

<210> SEQ ID NO 3
<211> LENGTH: 13
<212> TYPE: PRT
<213> ORGANISM: Homo sapiens

<400> SEQUENCE: 3

Phe Tyr Cys Arg Ser Leu Gln Ser Ser Trp Asp Tyr Arg
1               5                   10

<210> SEQ ID NO 4
<211> LENGTH: 24
<212> TYPE: PRT
<213> ORGANISM: Homo sapiens

<400> SEQUENCE: 4

Ser Val Thr Gln Ala Gly Val Gln Trp Arg Asn Leu Gly Ser Arg Leu
1               5                   10                  15

Gln Pro Leu Pro Pro Gly Phe Lys
            20

<210> SEQ ID NO 5
<211> LENGTH: 36
<212> TYPE: PRT
<213> ORGANISM: Homo sapiens

<400> SEQUENCE: 5

Ser Val Thr Gln Ala Gly Val Gln Trp Arg Asn Leu Gly Ser Leu Gln
1               5                   10                  15

Pro Leu Pro Pro Gly Phe Lys Phe Ser Cys Arg Ser Leu Gln Ser Ser
            20                  25                  30

Trp Asp Tyr Arg
        35

<210> SEQ ID NO 6
<211> LENGTH: 19
<212> TYPE: PRT
<213> ORGANISM: Homo sapiens

<400> SEQUENCE: 6

Ser Ile Ser Pro His Asp Leu Pro Ala Ser Ala Ser Gln Ser Ala Gly
1               5                   10                  15

```
Ile Thr Gly

<210> SEQ ID NO 7
<211> LENGTH: 46
<212> TYPE: PRT
<213> ORGANISM: Homo sapiens
<220> FEATURE:
<221> NAME/KEY: misc_feature
<223> OTHER INFORMATION: Translation of clone C8T7 extracted from MCF7
      cells

<400> SEQUENCE: 7

Asp Phe Leu Cys Leu Thr Ile Ser Ser Phe Ser Leu Pro Ile Ile
1               5                   10                  15

Ile Tyr Phe Ser Asp Gly Val Ser His Cys Arg Gln Ala Gly Val Gly
                20                  25                  30

Gln Trp Arg Asn Leu Gly Ser Pro Pro Thr Gly Phe Lys
            35                  40                  45

<210> SEQ ID NO 8
<211> LENGTH: 46
<212> TYPE: PRT
<213> ORGANISM: Homo sapiens
<220> FEATURE:
<221> NAME/KEY: misc_feature
<223> OTHER INFORMATION: Translation of clone S45T9 from MCF7 cells

<400> SEQUENCE: 8

Met Glu Ser Arg Ser Val Ala Gln Ala Gly Val Gln Trp His Asn Leu
1               5                   10                  15

Gly Ser Ala Leu Pro Pro Gly Phe Met Pro Phe Ser Cys Leu Ser Leu
                20                  25                  30

Gln Ser Ser Trp Asp Tyr Arg His Ala Pro Pro Arg Pro Ala
            35                  40                  45

<210> SEQ ID NO 9
<211> LENGTH: 15
<212> TYPE: PRT
<213> ORGANISM: Homo sapiens

<400> SEQUENCE: 9

Pro Pro Arg Pro Ala Thr Phe Leu Tyr Phe Pro Arg Gln Gly Phe
1               5                   10                  15

<210> SEQ ID NO 10
<211> LENGTH: 15
<212> TYPE: PRT
<213> ORGANISM: Homo sapiens

<400> SEQUENCE: 10

Arg Arg Phe Leu Tyr Ser Ser Asn Leu Phe Pro Ser Asn Gly Thr
1               5                   10                  15

<210> SEQ ID NO 11
<211> LENGTH: 9
<212> TYPE: PRT
<213> ORGANISM: Homo sapiens

<400> SEQUENCE: 11

Arg Tyr Val Pro Ser Ser Asn Leu Pro
1               5

<210> SEQ ID NO 12
```

```
<211> LENGTH: 9
<212> TYPE: PRT
<213> ORGANISM: Homo sapiens

<400> SEQUENCE: 12

Arg Tyr Val Pro Ser Ser Asn Leu Pro
1               5

<210> SEQ ID NO 13
<211> LENGTH: 9
<212> TYPE: PRT
<213> ORGANISM: Homo sapiens
<220> FEATURE:
<221> NAME/KEY: misc_feature
<223> OTHER INFORMATION: synthesized from de novo sequencing by ESI MS
      MS

<400> SEQUENCE: 13

Arg Tyr Leu Val Thr Pro Val Asn Ala
1               5

<210> SEQ ID NO 14
<211> LENGTH: 8
<212> TYPE: PRT
<213> ORGANISM: Homo sapiens
<220> FEATURE:
<221> NAME/KEY: misc_feature
<223> OTHER INFORMATION: completely synthesized from de novo sequencing

<400> SEQUENCE: 14

Arg Tyr Val Leu Ser Pro Val Lys
1               5

<210> SEQ ID NO 15
<211> LENGTH: 9
<212> TYPE: PRT
<213> ORGANISM: Homo sapiens

<400> SEQUENCE: 15

Lys Pro Ser His Pro Lys Pro Ser Lys
1               5

<210> SEQ ID NO 16
<211> LENGTH: 6
<212> TYPE: PRT
<213> ORGANISM: Homo sapiens

<400> SEQUENCE: 16

Thr Phe Lys Asn Leu Cys
1               5

<210> SEQ ID NO 17
<211> LENGTH: 8
<212> TYPE: PRT
<213> ORGANISM: Homo sapiens

<400> SEQUENCE: 17

Lys Ala His Asn Leu Phe Lys Thr
1               5

<210> SEQ ID NO 18
<211> LENGTH: 9
<212> TYPE: PRT
<213> ORGANISM: Homo sapiens

<400> SEQUENCE: 18
```

Arg Tyr Leu Pro Ala Asn Pro Arg Tyr
1               5

<210> SEQ ID NO 19
<211> LENGTH: 13
<212> TYPE: PRT
<213> ORGANISM: Homo sapiens

<400> SEQUENCE: 19

Phe Tyr Cys Arg Ser Leu Gln Ser Ser Trp Asp Tyr Arg
1               5                   10

<210> SEQ ID NO 20
<211> LENGTH: 13
<212> TYPE: PRT
<213> ORGANISM: Homo sapiens

<400> SEQUENCE: 20

Lys Thr Leu Pro Ser Ser Ser Cys Leu Val Ala Tyr Lys
1               5                   10

<210> SEQ ID NO 21
<211> LENGTH: 14
<212> TYPE: PRT
<213> ORGANISM: Homo sapiens

<400> SEQUENCE: 21

Lys Val Ile Ile Val Ala Val Asp Trp Asp Leu Ser Lys Glu
1               5                   10

<210> SEQ ID NO 22
<211> LENGTH: 16
<212> TYPE: PRT
<213> ORGANISM: Homo sapiens

<400> SEQUENCE: 22

Lys Ile Phe Ser Pro Ala Thr Val Phe Thr Ser Ile Glu Lys His
1               5                   10                  15

<210> SEQ ID NO 23
<211> LENGTH: 18
<212> TYPE: PRT
<213> ORGANISM: Homo sapiens

<400> SEQUENCE: 23

Lys Asn Val Trp Ile Leu Thr Gly Phe Gln Gln Gly Gln Glu Phe Pro
1               5                   10                  15

Lys Phe

<210> SEQ ID NO 24
<211> LENGTH: 12
<212> TYPE: PRT
<213> ORGANISM: Homo sapiens

<400> SEQUENCE: 24

Arg Phe Asn Leu Phe Ala Gly Gly Ser Asn Lys Ala
1               5                   10

<210> SEQ ID NO 25
<211> LENGTH: 12
<212> TYPE: PRT
<213> ORGANISM: Homo sapiens

<400> SEQUENCE: 25

Arg Ala Tyr Ser Leu Leu Gly Thr Ser Glu Arg Thr
1               5                   10

<210> SEQ ID NO 26
<211> LENGTH: 12
<212> TYPE: PRT
<213> ORGANISM: Homo sapiens

<400> SEQUENCE: 26

Ala Met Ala Ala Asn Asp Thr Gly Gly Phe Val Lys
1               5                   10

<210> SEQ ID NO 27
<211> LENGTH: 11
<212> TYPE: PRT
<213> ORGANISM: Homo sapiens

<400> SEQUENCE: 27

Ala Ser Glu Glu Gly Ile Met Val Val Glu Arg
1               5                   10

<210> SEQ ID NO 28
<211> LENGTH: 18
<212> TYPE: PRT
<213> ORGANISM: Homo sapiens

<400> SEQUENCE: 28

Phe Asp Val Val Val Ile Gly Ala Gly Pro Gly Gly Tyr Val Ala Ala
1               5                   10                  15

Ile Lys

<210> SEQ ID NO 29
<211> LENGTH: 19
<212> TYPE: PRT
<213> ORGANISM: Homo sapiens

<400> SEQUENCE: 29

Arg Pro Val Thr Thr Asp Leu Leu Ala Ser Asp Ser Gly Val Thr Ile
1               5                   10                  15

Asp Glu Arg

<210> SEQ ID NO 30
<211> LENGTH: 7
<212> TYPE: PRT
<213> ORGANISM: Homo sapiens

<400> SEQUENCE: 30

Phe Tyr Cys Gly Trp Asp Arg
1               5

<210> SEQ ID NO 31
<211> LENGTH: 8
<212> TYPE: PRT
<213> ORGANISM: Homo sapiens

<400> SEQUENCE: 31

Asp Val Ala Gln Glu Glu Gly Lys
1               5

<210> SEQ ID NO 32
<211> LENGTH: 8
<212> TYPE: PRT
<213> ORGANISM: Homo sapiens

```
<400> SEQUENCE: 32

Ser Gly Ile Pro Ser Glu Leu Arg
1               5

<210> SEQ ID NO 33
<211> LENGTH: 7
<212> TYPE: PRT
<213> ORGANISM: Homo sapiens

<400> SEQUENCE: 33

Glu Ala His Ile Gln Met Lys
1               5

<210> SEQ ID NO 34
<211> LENGTH: 7
<212> TYPE: PRT
<213> ORGANISM: Homo sapiens

<400> SEQUENCE: 34

Glu Gly Ile Trp Ile Pro Lys
1               5

<210> SEQ ID NO 35
<211> LENGTH: 6
<212> TYPE: PRT
<213> ORGANISM: Homo sapiens

<400> SEQUENCE: 35

Tyr Thr Phe Asp Ser Arg
1               5

<210> SEQ ID NO 36
<211> LENGTH: 6
<212> TYPE: PRT
<213> ORGANISM: Homo sapiens

<400> SEQUENCE: 36

Leu Thr His Glu Ile Arg
1               5

<210> SEQ ID NO 37
<211> LENGTH: 5
<212> TYPE: PRT
<213> ORGANISM: Homo sapiens

<400> SEQUENCE: 37

Leu Tyr Leu Asp Lys
1               5

<210> SEQ ID NO 38
<211> LENGTH: 5
<212> TYPE: PRT
<213> ORGANISM: Homo sapiens

<400> SEQUENCE: 38

Tyr Gly Leu Gln Arg
1               5

<210> SEQ ID NO 39
<211> LENGTH: 5
<212> TYPE: PRT
<213> ORGANISM: Homo sapiens

<400> SEQUENCE: 39
```

Asp Ser Ile Ile Arg
1               5

<210> SEQ ID NO 40
<211> LENGTH: 16
<212> TYPE: PRT
<213> ORGANISM: Homo sapiens

<400> SEQUENCE: 40

Leu Glu Ala Ile Cys Ala Ala Met Ile Glu Ser Trp Gly Tyr Asp Lys
1               5                   10                  15

<210> SEQ ID NO 41
<211> LENGTH: 12
<212> TYPE: PRT
<213> ORGANISM: Homo sapiens

<400> SEQUENCE: 41

Gly Asp Leu Trp Phe Met Ser His Gln Gly His Lys
1               5                   10

<210> SEQ ID NO 42
<211> LENGTH: 11
<212> TYPE: PRT
<213> ORGANISM: Homo sapiens

<400> SEQUENCE: 42

Tyr Ala Phe Asp Phe Tyr Glu Met Thr Ser Arg
1               5                   10

<210> SEQ ID NO 43
<211> LENGTH: 14
<212> TYPE: PRT
<213> ORGANISM: Homo sapiens

<400> SEQUENCE: 43

Glu Val Asn Ala Gly Thr Ser Gly Thr Phe Ser Val Pro Arg
1               5                   10

<210> SEQ ID NO 44
<211> LENGTH: 9
<212> TYPE: PRT
<213> ORGANISM: Homo sapiens

<400> SEQUENCE: 44

Asn Gln Asp Arg Pro Tyr Met Pro Arg
1               5

<210> SEQ ID NO 45
<211> LENGTH: 9
<212> TYPE: PRT
<213> ORGANISM: Homo sapiens

<400> SEQUENCE: 45

Ile Val Ser Ile Leu Glu Trp Asp Arg
1               5

<210> SEQ ID NO 46
<211> LENGTH: 10
<212> TYPE: PRT
<213> ORGANISM: Homo sapiens

<400> SEQUENCE: 46

Ala Pro Tyr Ile Ala Glu Thr Ala Leu Arg
1               5                   10

<210> SEQ ID NO 47
<211> LENGTH: 9
<212> TYPE: PRT
<213> ORGANISM: Homo sapiens

<400> SEQUENCE: 47

Asn Met His Asn Leu Leu Gly Val Lys
1               5

<210> SEQ ID NO 48
<211> LENGTH: 9
<212> TYPE: PRT
<213> ORGANISM: Homo sapiens

<400> SEQUENCE: 48

Asn Leu Thr Asp Met Ser Leu Ala Arg
1               5

<210> SEQ ID NO 49
<211> LENGTH: 8
<212> TYPE: PRT
<213> ORGANISM: Homo sapiens

<400> SEQUENCE: 49

His Thr Thr Glu Asp Val Asn Arg
1               5

<210> SEQ ID NO 50
<211> LENGTH: 7
<212> TYPE: PRT
<213> ORGANISM: Homo sapiens

<400> SEQUENCE: 50

Lys Phe Phe Val Phe Ala Leu
1               5

<210> SEQ ID NO 51
<211> LENGTH: 15
<212> TYPE: PRT
<213> ORGANISM: Homo sapiens

<400> SEQUENCE: 51

Phe Val Phe Ala Leu Ile Leu Ala Leu Met Leu Ser Met Cys Gly
1               5                   10                  15

<210> SEQ ID NO 52
<211> LENGTH: 12
<212> TYPE: PRT
<213> ORGANISM: Homo sapiens

<400> SEQUENCE: 52

Thr Leu Gln Ile Phe Asn Ile Glu Met Lys Ser Lys
1               5                   10

<210> SEQ ID NO 53
<211> LENGTH: 17
<212> TYPE: PRT
<213> ORGANISM: Homo sapiens

<400> SEQUENCE: 53

Lys Asp Pro Glu Leu Trp Ala His Val Leu Glu Glu Thr Asn Thr Ser
1               5                   10                  15

Arg

<210> SEQ ID NO 54
<211> LENGTH: 12
<212> TYPE: PRT
<213> ORGANISM: Homo sapiens

<400> SEQUENCE: 54

Lys Ser Trp Glu Val Tyr Gln Gly Val Cys Gln Lys
1               5                   10

<210> SEQ ID NO 55
<211> LENGTH: 13
<212> TYPE: PRT
<213> ORGANISM: Homo sapiens

<400> SEQUENCE: 55

His Thr Ser Leu Val Gly Cys Gln Val Ile His Tyr Arg
1               5                   10

<210> SEQ ID NO 56
<211> LENGTH: 11
<212> TYPE: PRT
<213> ORGANISM: Homo sapiens

<400> SEQUENCE: 56

Gln Ala Gly Val Gln Trp Arg Asn Leu Gly Ser
1               5                   10

<210> SEQ ID NO 57
<211> LENGTH: 15
<212> TYPE: PRT
<213> ORGANISM: Homo sapiens

<400> SEQUENCE: 57

Ser Leu Gln Ser Ser Trp Asp Tyr Arg Arg His Pro Pro Pro Thr
1               5                   10                  15

<210> SEQ ID NO 58
<211> LENGTH: 21
<212> TYPE: PRT
<213> ORGANISM: Homo sapiens

<400> SEQUENCE: 58

Phe Leu Tyr Phe Leu Arg Trp Glu Phe Thr Gly Pro Thr Ala Ser Ala
1               5                   10                  15

Gly Ser Pro Pro Arg
            20

<210> SEQ ID NO 59
<211> LENGTH: 14
<212> TYPE: PRT
<213> ORGANISM: Homo sapiens

<400> SEQUENCE: 59

Gly Phe Thr Met Met Ala Arg Met Val Ser Ile Ser Pro His
1               5                   10

<210> SEQ ID NO 60
<211> LENGTH: 16
<212> TYPE: PRT
<213> ORGANISM: Homo sapiens

<400> SEQUENCE: 60

Met Glu Ser Arg Ser Val Ala Gln Ala Gly Val Gln Trp Arg Asn Leu

```
1               5                  10                  15
```

<210> SEQ ID NO 61
<211> LENGTH: 11
<212> TYPE: PRT
<213> ORGANISM: Homo sapiens

<400> SEQUENCE: 61

```
Pro Ala Ser Ala Ser Glu Ser Val Gly Ile Ala
1               5                  10
```

<210> SEQ ID NO 62
<211> LENGTH: 14
<212> TYPE: PRT
<213> ORGANISM: Homo sapiens

<400> SEQUENCE: 62

```
Ile Ser Arg Ala His Arg Thr Leu His Leu Pro Pro Cys Pro
1               5                  10
```

<210> SEQ ID NO 63
<211> LENGTH: 13
<212> TYPE: PRT
<213> ORGANISM: Homo sapiens

<400> SEQUENCE: 63

```
Trp Asp Tyr Arg His Ala Leu Pro His Pro Ala Asn Pro
1               5                  10
```

<210> SEQ ID NO 64
<211> LENGTH: 15
<212> TYPE: PRT
<213> ORGANISM: Homo sapiens

<400> SEQUENCE: 64

```
Gly Phe Thr Val Leu Ala Arg Met Val Ser Ile Ser Pro Arg Asp
1               5                  10                  15
```

<210> SEQ ID NO 65
<211> LENGTH: 12
<212> TYPE: PRT
<213> ORGANISM: Homo sapiens

<400> SEQUENCE: 65

```
Pro Ala Ser Ala Ser Gln Ser Ala Gly Ile Thr Gly
1               5                  10
```

<210> SEQ ID NO 66
<211> LENGTH: 10
<212> TYPE: PRT
<213> ORGANISM: Homo sapiens

<400> SEQUENCE: 66

```
Arg Asp Pro Pro Ala Ser Ala Ser Gln Ser
1               5                  10
```

<210> SEQ ID NO 67
<211> LENGTH: 16
<212> TYPE: PRT
<213> ORGANISM: Homo sapiens

<400> SEQUENCE: 67

```
Met Ser His Cys Ala Arg Pro Thr Tyr Phe Lys Asn Asn Lys Asn Ser
1               5                  10                  15
```

```
<210> SEQ ID NO 68
<211> LENGTH: 21
<212> TYPE: PRT
<213> ORGANISM: Homo sapiens

<400> SEQUENCE: 68

Leu Lys Cys Leu Trp Arg Ile Gln Asp Ser Ala Gly Leu Tyr Leu Pro
1               5                   10                  15

Met Thr Pro Leu Ile
            20

<210> SEQ ID NO 69
<211> LENGTH: 16
<212> TYPE: PRT
<213> ORGANISM: Homo sapiens

<400> SEQUENCE: 69

Gln Phe Gln Thr Leu Leu Met Gly Leu Met Ser Phe Ile Arg Gln Cys
1               5                   10                  15

<210> SEQ ID NO 70
<211> LENGTH: 14
<212> TYPE: PRT
<213> ORGANISM: Homo sapiens

<400> SEQUENCE: 70

Arg Arg Phe Leu Tyr Ser Ser Asn Leu Phe Pro Phe Lys Tyr
1               5                   10

<210> SEQ ID NO 71
<211> LENGTH: 16
<212> TYPE: PRT
<213> ORGANISM: Homo sapiens

<400> SEQUENCE: 71

Arg Thr Val Arg Pro Leu Asn Ile Glu Val Gly Val Leu Pro Lys Thr
1               5                   10                  15

<210> SEQ ID NO 72
<211> LENGTH: 24
<212> TYPE: PRT
<213> ORGANISM: Homo sapiens

<400> SEQUENCE: 72

Lys Phe Phe Val Phe Ala Leu Ile Leu Ala Leu Met Leu Ser Met Cys
1               5                   10                  15

Gly Ala Asp Ser His Ala Lys Arg
            20

<210> SEQ ID NO 73
<211> LENGTH: 20
<212> TYPE: PRT
<213> ORGANISM: Homo sapiens

<400> SEQUENCE: 73

Lys Gly Ile Thr Glu Glu Ile Met Glu Ile Ala Leu Gly Gln Ala Leu
1               5                   10                  15

Glu Ala Arg Leu
            20

<210> SEQ ID NO 74
<211> LENGTH: 10
<212> TYPE: PRT
```

<213> ORGANISM: Homo sapiens

<400> SEQUENCE: 74

Ser Gln Gln Asn Arg Trp Ala Glu Ser Lys
1               5                   10

<210> SEQ ID NO 75
<211> LENGTH: 11
<212> TYPE: PRT
<213> ORGANISM: Homo sapiens

<400> SEQUENCE: 75

Met Asn Val Glu Lys Ala Glu Phe Cys Asn Lys
1               5                   10

<210> SEQ ID NO 76
<211> LENGTH: 16
<212> TYPE: PRT
<213> ORGANISM: Homo sapiens

<400> SEQUENCE: 76

Asn Ser Gln Gly Val Ala Trp Ile Thr Leu Asn Ser Ser Ile Gln Lys
1               5                   10                  15

<210> SEQ ID NO 77
<211> LENGTH: 17
<212> TYPE: PRT
<213> ORGANISM: Homo sapiens

<400> SEQUENCE: 77

Val Cys Thr Lys Pro Val Glu Ser Thr Ile Glu Asp Lys Ile Phe Gly
1               5                   10                  15

Lys

<210> SEQ ID NO 78
<211> LENGTH: 13
<212> TYPE: PRT
<213> ORGANISM: Homo sapiens

<400> SEQUENCE: 78

Ala Gly Leu Gln Glu Glu Ala Gln Gln Leu Arg Asp Glu
1               5                   10

<210> SEQ ID NO 79
<211> LENGTH: 11
<212> TYPE: PRT
<213> ORGANISM: Homo sapiens

<400> SEQUENCE: 79

Met Ser His Lys Gln Ile Tyr Tyr Ser Asp Lys
1               5                   10

<210> SEQ ID NO 80
<211> LENGTH: 15
<212> TYPE: PRT
<213> ORGANISM: Homo sapiens

<400> SEQUENCE: 80

Tyr Asp Asp Glu Glu Phe Glu Tyr Arg His Val Met Leu Pro Lys
1               5                   10                  15

<210> SEQ ID NO 81
<211> LENGTH: 14
<212> TYPE: PRT

```
<213> ORGANISM: Homo sapiens

<400> SEQUENCE: 81

Leu Val Pro Lys Thr His Leu Met Ser Glu Ser Glu Trp Arg
1               5                   10

<210> SEQ ID NO 82
<211> LENGTH: 21
<212> TYPE: PRT
<213> ORGANISM: Homo sapiens

<400> SEQUENCE: 82

Lys Ala Tyr Glu Cys Asp Ile Thr Tyr Gly Thr Asn Asn Glu Phe Gly
1               5                   10                  15

Phe Asp Tyr Leu Arg
            20

<210> SEQ ID NO 83
<211> LENGTH: 14
<212> TYPE: PRT
<213> ORGANISM: Homo sapiens

<400> SEQUENCE: 83

Thr Ile Met Ile Thr Glu Ala Gly Ile Ser Lys Ala Glu Lys
1               5                   10

<210> SEQ ID NO 84
<211> LENGTH: 13
<212> TYPE: PRT
<213> ORGANISM: Homo sapiens

<400> SEQUENCE: 84

Glu Arg Ala Val Glu Ser Asp Cys Tyr Ala Glu Gln Val
1               5                   10

<210> SEQ ID NO 85
<211> LENGTH: 17
<212> TYPE: PRT
<213> ORGANISM: Homo sapiens

<400> SEQUENCE: 85

Cys Val Ala Val Gly Gly His Ser Gly Ser Leu Leu Ile Gln His Val
1               5                   10                  15

Met

<210> SEQ ID NO 86
<211> LENGTH: 24
<212> TYPE: PRT
<213> ORGANISM: Homo sapiens

<400> SEQUENCE: 86

Ala Arg Trp Thr Phe Gly Gly Arg Asp Leu Pro Ala Glu Gln Pro Gly
1               5                   10                  15

Ser Phe Leu Tyr Asp Ala Arg Leu
            20

<210> SEQ ID NO 87
<211> LENGTH: 16
<212> TYPE: PRT
<213> ORGANISM: Homo sapiens

<400> SEQUENCE: 87

Arg Ala Ile Cys Glu Glu Thr Lys Ala Ser Ile Asp Ile Glu Asp Asp
```

```
<210> SEQ ID NO 88
<211> LENGTH: 23
<212> TYPE: PRT
<213> ORGANISM: Homo sapiens

<400> SEQUENCE: 88

Lys Val Thr Asp Ile Leu Lys Glu Gly Gln Glu Val Glu Val Leu Val
1               5                   10                  15

Leu Asp Val Asp Asn Arg Gly
            20

<210> SEQ ID NO 89
<211> LENGTH: 15
<212> TYPE: PRT
<213> ORGANISM: Homo sapiens

<400> SEQUENCE: 89

Lys Met Leu Thr Gly Val Asn Val Leu Ala Asp Ala Val Lys Ala
1               5                   10                  15

<210> SEQ ID NO 90
<211> LENGTH: 13
<212> TYPE: PRT
<213> ORGANISM: Homo sapiens

<400> SEQUENCE: 90

Val Thr Asp Ile Leu Lys Glu Gly Gln Glu Val Glu Val
1               5                   10

<210> SEQ ID NO 91
<211> LENGTH: 11
<212> TYPE: PRT
<213> ORGANISM: Homo sapiens

<400> SEQUENCE: 91

Glu Thr Gln Ala Asp Pro Met Ala Phe Val Lys
1               5                   10

<210> SEQ ID NO 92
<211> LENGTH: 10
<212> TYPE: PRT
<213> ORGANISM: Homo sapiens

<400> SEQUENCE: 92

Lys Thr Ala Val Ala Pro Ile Glu Arg Val
1               5                   10

<210> SEQ ID NO 93
<211> LENGTH: 16
<212> TYPE: PRT
<213> ORGANISM: Homo sapiens

<400> SEQUENCE: 93

Ser Gly Gln Val Pro Arg Tyr Thr Gly Ile Val Asn Cys Phe Val Arg
1               5                   10                  15

<210> SEQ ID NO 94
<211> LENGTH: 11
<212> TYPE: PRT
<213> ORGANISM: Homo sapiens

<400> SEQUENCE: 94
```

-continued

Lys Asp Thr Ile Lys Gly Leu Phe Pro Lys Tyr
1               5                   10

<210> SEQ ID NO 95
<211> LENGTH: 21
<212> TYPE: PRT
<213> ORGANISM: Homo sapiens

<400> SEQUENCE: 95

Gly Gly Pro Met Ala Leu Tyr Gln Gly Phe Gly Val Ser Val Gln Gly
1               5                   10                  15

Ile Ile Val Tyr Arg
            20

<210> SEQ ID NO 96
<211> LENGTH: 10
<212> TYPE: PRT
<213> ORGANISM: Homo sapiens

<400> SEQUENCE: 96

Lys Gly Val Leu Phe Lys Asp Glu Arg Thr
1               5                   10

<210> SEQ ID NO 97
<211> LENGTH: 12
<212> TYPE: PRT
<213> ORGANISM: Homo sapiens

<400> SEQUENCE: 97

Val Ala Gln Gln Glu Gly Met Lys Ala Phe Phe Lys
1               5                   10

<210> SEQ ID NO 98
<211> LENGTH: 12
<212> TYPE: PRT
<213> ORGANISM: Homo sapiens

<400> SEQUENCE: 98

Phe Ile Asn Pro Asn Ala Val Ser Ser Ala Ser Glu
1               5                   10

<210> SEQ ID NO 99
<211> LENGTH: 19
<212> TYPE: PRT
<213> ORGANISM: Homo sapiens

<400> SEQUENCE: 99

Arg Ala Ala Val Glu Glu Gly Val Val Pro Gly Gly Gly Val Ala Leu
1               5                   10                  15

Ile Arg Ala

<210> SEQ ID NO 100
<211> LENGTH: 12
<212> TYPE: PRT
<213> ORGANISM: Homo sapiens

<400> SEQUENCE: 100

Phe Pro Ala Lys Leu Met Leu Gly Leu Leu Ile Phe
1               5                   10

<210> SEQ ID NO 101
<211> LENGTH: 9
<212> TYPE: PRT
<213> ORGANISM: Homo sapiens

<400> SEQUENCE: 101

Phe Leu Val Glu Thr Gly Phe His His
1               5

<210> SEQ ID NO 102
<211> LENGTH: 7
<212> TYPE: PRT
<213> ORGANISM: Homo sapiens

<400> SEQUENCE: 102

Ile Cys Asn Pro Lys Pro Gln
1               5

<210> SEQ ID NO 103
<211> LENGTH: 12
<212> TYPE: PRT
<213> ORGANISM: Homo sapiens

<400> SEQUENCE: 103

Pro Gln Ala Leu His Phe Met Leu Pro Ala Arg Met
1               5                   10

<210> SEQ ID NO 104
<211> LENGTH: 5
<212> TYPE: PRT
<213> ORGANISM: Homo sapiens

<400> SEQUENCE: 104

Pro Pro Arg Pro Pro
1               5

<210> SEQ ID NO 105
<211> LENGTH: 13
<212> TYPE: PRT
<213> ORGANISM: Homo sapiens

<400> SEQUENCE: 105

Gly Pro Thr Ser Arg His Ala Pro Gly Phe Gly Ala Pro
1               5                   10

<210> SEQ ID NO 106
<211> LENGTH: 13
<212> TYPE: PRT
<213> ORGANISM: Homo sapiens

<400> SEQUENCE: 106

Val Val Pro Ala Thr Gln Glu Ala Glu Ala Gly Glu Trp
1               5                   10

<210> SEQ ID NO 107
<211> LENGTH: 15
<212> TYPE: PRT
<213> ORGANISM: Homo sapiens

<400> SEQUENCE: 107

Pro Pro Ala Ser Arg Ala Ser Arg Gln Ser Arg Val Glu Gly Lys
1               5                   10                  15

<210> SEQ ID NO 108
<211> LENGTH: 11
<212> TYPE: PRT
<213> ORGANISM: Homo sapiens

<400> SEQUENCE: 108

Ile Thr Tyr Gly Ser Arg Asn Thr Leu Val Lys
1               5                   10

<210> SEQ ID NO 109
<211> LENGTH: 12
<212> TYPE: PRT
<213> ORGANISM: Homo sapiens

<400> SEQUENCE: 109

Tyr Arg Asn Leu Leu His Val Glu Asn Thr Glu Arg
1               5                   10

<210> SEQ ID NO 110
<211> LENGTH: 6
<212> TYPE: PRT
<213> ORGANISM: Homo sapiens

<400> SEQUENCE: 110

Phe Asn Phe His Glu Met
1               5

<210> SEQ ID NO 111
<211> LENGTH: 6
<212> TYPE: PRT
<213> ORGANISM: Homo sapiens

<400> SEQUENCE: 111

Pro Gly Tyr Phe Phe Tyr
1               5

<210> SEQ ID NO 112
<211> LENGTH: 5
<212> TYPE: PRT
<213> ORGANISM: Homo sapiens

<400> SEQUENCE: 112

Pro Pro Trp Arg Pro
1               5

<210> SEQ ID NO 113
<211> LENGTH: 6
<212> TYPE: PRT
<213> ORGANISM: Homo sapiens

<400> SEQUENCE: 113

Glu Trp Trp Arg Leu Asp
1               5

<210> SEQ ID NO 114
<211> LENGTH: 5
<212> TYPE: PRT
<213> ORGANISM: Homo sapiens

<400> SEQUENCE: 114

Lys Asn Ser Leu Asp
1               5

<210> SEQ ID NO 115
<211> LENGTH: 8
<212> TYPE: PRT
<213> ORGANISM: Homo sapiens

<400> SEQUENCE: 115

Met His Ile Glu Ser Leu Asp Ser

```
<210> SEQ ID NO 116
<211> LENGTH: 5
<212> TYPE: PRT
<213> ORGANISM: Homo sapiens

<400> SEQUENCE: 116

Leu Glu Gln Val Glu
1               5

<210> SEQ ID NO 117
<211> LENGTH: 9
<212> TYPE: PRT
<213> ORGANISM: Homo sapiens

<400> SEQUENCE: 117

Leu His Leu Glu Ser Leu Lys Asp Ser
1               5

<210> SEQ ID NO 118
<211> LENGTH: 8
<212> TYPE: PRT
<213> ORGANISM: Homo sapiens

<400> SEQUENCE: 118

Glu Ala Val Ser Leu Lys Pro Thr
1               5

<210> SEQ ID NO 119
<211> LENGTH: 30
<212> TYPE: DNA
<213> ORGANISM: Artificial Sequence
<220> FEATURE:
<223> OTHER INFORMATION: oligonucleotide

<400> SEQUENCE: 119
atgtatatta tatatctaaa gttataccaa                                        30

<210> SEQ ID NO 120
<211> LENGTH: 36
<212> TYPE: DNA
<213> ORGANISM: Artificial Sequence
<220> FEATURE:
<223> OTHER INFORMATION: oligonucleotide

<400> SEQUENCE: 120
tttcctgcta agcttatgtt gggattgctt atattt                                 36

<210> SEQ ID NO 121
<211> LENGTH: 36
<212> TYPE: DNA
<213> ORGANISM: Artificial Sequence
<220> FEATURE:
<223> OTHER INFORMATION: oligonucleotide antisense (histatine)

<400> SEQUENCE: 121
aaatataagc aatcccaaca taagcttagc aggaaa                                 36

<210> SEQ ID NO 122
<211> LENGTH: 19
<212> TYPE: RNA
<213> ORGANISM: Artificial Sequence
<220> FEATURE:
<223> OTHER INFORMATION: insert of Si RNA (PKC epsilon)
```

<400> SEQUENCE: 122
guuguagccu ggaccuuga                                                    19

<210> SEQ ID NO 123
<211> LENGTH: 420
<212> TYPE: DNA
<213> ORGANISM: Artificial Sequence
<220> FEATURE:
<223> OTHER INFORMATION: Clone S45T9T7 extracted from MCF7 cells
<220> FEATURE:
<221> NAME/KEY: misc_feature
<222> LOCATION: (420)..(420)
<223> OTHER INFORMATION: n is a, c, g, or t

<400> SEQUENCE: 123
taaatataag caatcccaac actttgggag gccgaggcgg gcggatcacg aggtcaggag        60
atggagacca tcctggctaa cacagtgaaa ccctgtctct actgaaaata caaaaaagta       120
gccgggcgtg gcggcaggcg cctgtagccc cagctactca ggaggctgag gcaggagaat       180
ggcatgaacc caggaggcag agcttgcagt gagccgagat tgtgccactg cactccagcc       240
tgggcaacag agcgagactc catctcaaaa aaaaaaaaaa aatcaccca aagcaataag        300 gagaactaga acaggacata cactccaaca ctggtgaaac taggaaaaca tatgtaaccc       360
caaaccacaa tatatacaca caaaactata cgagatgttg ggattgctta tatttaatcn       420

<210> SEQ ID NO 124
<211> LENGTH: 456
<212> TYPE: DNA
<213> ORGANISM: Artificial Sequence
<220> FEATURE:
<223> OTHER INFORMATION: antisense sequences of clone S55M1 M13
<220> FEATURE:
<221> NAME/KEY: misc_feature
<222> LOCATION: (1)..(6)
<223> OTHER INFORMATION: n is a, c, g or t
<220> FEATURE:
<221> NAME/KEY: misc_feature
<222> LOCATION: (8)..(8)
<223> OTHER INFORMATION: n is a, c, g or t

<400> SEQUENCE: 124
nnnnnngntc cggccgccat ggcggccgcg ggattcgatt aaatataagc aatcccaaca        60
ctttgggagg ccgaggcggg cggatcacga ggtcaggaga tggagaccat cctggctaac       120
acagtgaaac cctgtctcta cggaaaatac aaaaaagtag ccgggcgtgg cggcaggcgc       180
ctgtagtccc agctactcag gaggctgagg caggagaatg gcatgaaccc aggaggcaga       240
gcttgcagtg agccgagatt gtgccactgc actccagcct gggcaacaga gcgagactcc       300
atctcaaaaa aaaaaaaaa tcaccccaaa gcaataagga gaactagaac aggacataca       360
ctccaacact ggtgaaacta ggaaaacata tgtaacccca aaccacaata tatacacaca       420
aaactatacg agatgttggg attgcttata tttaat                                456

<210> SEQ ID NO 125
<211> LENGTH: 587
<212> TYPE: DNA
<213> ORGANISM: Artificial Sequence
<220> FEATURE:
<223> OTHER INFORMATION: antisense sequence of clone S55T9 M13 (MCF7
      cells)
<220> FEATURE:
<221> NAME/KEY: misc_feature
<222> LOCATION: (1)..(9)
<223> OTHER INFORMATION: n is a, c, g, or t
<220> FEATURE:

<221> NAME/KEY: misc_feature
<222> LOCATION: (11)..(15)
<223> OTHER INFORMATION: n is a, c, g, or t
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 125

```
nnnnnnnnng nnnnngnncc ntggcggccg cgggattcga ttaaatataa gcaatcccaa    60
cactttgggg gggtgaggcg acagatcac ttgaggtcag gggtttgaga ccagcatggc   120
caacgtggtg aaaactcaac tactcaaaat agaaaaatta gctggacatg gtggcacaca   180
cctgtgaagc cagctactca ggaggctgaa gcatgagaat tgcttgaacc ctggagatgg   240
aggttacagt gagcccacgt cgcgtccctg cacgcaagcc taggcaagaa agcaagaccc   300
tgtctcaaaa aaagaaaaga gatgctgata catgctacaa catagatgaa ccttgaggac   360
attattctaa gtgaaatgag cttgtcacaa aagaacaaat attgcatgat tccagttata   420
tgaggtgccc atagttgtca aattcacaaa gacaaaaagt ggcatggtcg ttaccaaggg   480
ctgggagaaa agaggaatgg tgagttagtg tttaattggt acagagtttc agttttgcaa   540
gatgaaaaga gttctggaga tgaatgttgg gattgcttat atttaat                587
```

<210> SEQ ID NO 126
<211> LENGTH: 514
<212> TYPE: DNA
<213> ORGANISM: Artificial Sequence
<220> FEATURE:
<223> OTHER INFORMATION: insert of clone extracted from MCF7 cells culture
<220> FEATURE:
<221> NAME/KEY: misc_feature
<222> LOCATION: (1)..(8)
<223> OTHER INFORMATION: n is a, c, g, or t
<220> FEATURE:
<221> NAME/KEY: misc_feature
<222> LOCATION: (10)..(11)
<223> OTHER INFORMATION: n is a, c, g, or t
<220> FEATURE:
<221> NAME/KEY: misc_feature
<222> LOCATION: (13)..(16)
<223> OTHER INFORMATION: n is a, c, g, or t
<220> FEATURE:
<221> NAME/KEY: misc_feature
<222> LOCATION: (18)..(19)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (23)..(25)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (74)..(75)
<223> OTHER INFORMATION: n is a, c, g, or t
<220> FEATURE:

```
<221> NAME/KEY: misc_feature
<222> LOCATION: (77)..(80)
<223> OTHER INFORMATION: n is a, c, g, or t

<400> SEQUENCE: 126
nnnnnnnngn ncnnnnanng nannncnact cactnnaggg cgaattgggc ccgacgtcgc        60
atgctcccgg ccgnnannnn ggccgcggga attcgattaa atataagcaa tcccaacact       120
ttgggaggcc gaggcgggcg gatcacgagg tcaggagatg agaccatcc tggctaacac        180 agtgaaaccc tgtctctact gaaaatacaa aaaagtagcc gggcgtggcg gcaggcgcct      240
gtagtcccag ctactcagga ggctgaggca ggagaatggc atgaacccag gaggcagagc      300
ttgcagtgag ccgagattgt gccactgcac tccagcctgg caacagagc gagactccat       360 ctcaaaaaaa aaaaaaaatc accccaaagc aataaggaga actagaacag gacatacact     420
ccaacactgg tgaaactagg aaaacatatg taaccccaaa ccacaatata tacacacaaa     480
actatacgag atgttgggat tgcttatatt taat                                 514

<210> SEQ ID NO 127
<211> LENGTH: 770
<212> TYPE: DNA
<213> ORGANISM: Artificial Sequence
<220> FEATURE:
<223> OTHER INFORMATION: C8 PGEMT M13 rev1605 clone (CNCM I-3940)
<220> FEATURE:
<221> NAME/KEY: misc_feature
<222> LOCATION: (711)..(711)
<223> OTHER INFORMATION: n is a, c, g, or t
<220> FEATURE:
<221> NAME/KEY: misc_feature
<222> LOCATION: (742)..(742)
<223> OTHER INFORMATION: n is a, c, g, or t
<220> FEATURE:
<221> NAME/KEY: misc_feature
<222> LOCATION: (749)..(749)
<223> OTHER INFORMATION: n is a, c, g, or t
<220> FEATURE:
<221> NAME/KEY: misc_feature
<222> LOCATION: (755)..(755)
<223> OTHER INFORMATION: n is a, c, g, or t
<220> FEATURE:
<221> NAME/KEY: misc_feature
<222> LOCATION: (760)..(760)
<223> OTHER INFORMATION: n is a, c, g, or t

<400> SEQUENCE: 127
tcctatgctt gactattagc tccttttctt tacctattat tattatttat ttttcagatg       60
gagtctcaca ctgtcgccag gctggagtac agtggcgcca tctcggctca ctgaaccctc      120
cacctaccgg gttcaagtga ttctactgcc gcagtctcca gagtagctgg gactacaggc     180
atgcactacc acacccagct aattttttgt attttttagtt gagatggggt ttcaccatga     240
tggccaggat ggtctcgatc tcttgacctc atgatctgcc tgcctcagcc tcccaaagtg     300
ctgggattac gggcatgagc cactgtgcta ggcctaccta ttttaaaaat aacaagaatt      360
catccaatgg aacgctgaaa tgcctgtgga ggatacaaga ttaatcagca ggattatatt      420
tgcctatgac tccattaatt caattccaga ccctacttat gggtctaatg tcctttatta      480
ggcaatgtag gagattccta tactcctaat aaagtaatct ttttccattt aaatatcttt     540
gctttttatc aggcagtatg tatttccaca agttaattc aatgaaatac acctaaagct      600
gagagtctta tctcgttaat gaatgaaaaa tagaaatcaa ttattctgag atgagattct    660
tcctataatt tttattagtt gttgtgaaat ggtacatggg tttgtcttga ntatgatgat    720
gtattaattc ttaatattga antaaatgnc tctgnagtan agatgactct                770
```

<210> SEQ ID NO 128
<211> LENGTH: 19
<212> TYPE: DNA
<213> ORGANISM: Artificial Sequence
<220> FEATURE:
<223> OTHER INFORMATION: Artificial Sequence

<400> SEQUENCE: 128
tcctatgctt gactattag                                                    19

<210> SEQ ID NO 129
<211> LENGTH: 23
<212> TYPE: DNA
<213> ORGANISM: Artificial Sequence
<220> FEATURE:
<223> OTHER INFORMATION: Oligonucleotide for the PCR

<400> SEQUENCE: 129
cctgacatcc ctacatcacc gca                                               23

<210> SEQ ID NO 130
<211> LENGTH: 19
<212> TYPE: DNA
<213> ORGANISM: Artificial Sequence
<220> FEATURE:
<223> OTHER INFORMATION: Oligonucleotide for the PCR

<400> SEQUENCE: 130
atgtatatta tatatctaa                                                    19

<210> SEQ ID NO 131
<211> LENGTH: 19
<212> TYPE: DNA
<213> ORGANISM: Artificial Sequence
<220> FEATURE:
<223> OTHER INFORMATION: Oligonucleotide for the PCR

<400> SEQUENCE: 131
ttagatatat aatatacat                                                    19

<210> SEQ ID NO 132
<211> LENGTH: 20
<212> TYPE: DNA
<213> ORGANISM: Artificial Sequence
<220> FEATURE:
<223> OTHER INFORMATION: Oligonucleotide for the PCR

<400> SEQUENCE: 132
aaatataagc aatcccaaca                                                   20

<210> SEQ ID NO 133
<211> LENGTH: 20
<212> TYPE: DNA
<213> ORGANISM: Artificial Sequence
<220> FEATURE:
<223> OTHER INFORMATION: Oligonucleotide for the PCR

<400> SEQUENCE: 133
tgttgggatt gcttatattt                                                   20

<210> SEQ ID NO 134
<211> LENGTH: 18
<212> TYPE: DNA
<213> ORGANISM: Artificial Sequence
<220> FEATURE:

```
<223> OTHER INFORMATION: Oligonucleotide for the PCR

<400> SEQUENCE: 134
ctttattatt ttgtaaat                                                 18

<210> SEQ ID NO 135
<211> LENGTH: 18
<212> TYPE: DNA
<213> ORGANISM: Artificial Sequence
<220> FEATURE:
<223> OTHER INFORMATION: Oligonucleotide for the PCR

<400> SEQUENCE: 135
atttacaaaa taataaag                                                 18

<210> SEQ ID NO 136
<211> LENGTH: 19
<212> TYPE: DNA
<213> ORGANISM: Artificial Sequence
<220> FEATURE:
<223> OTHER INFORMATION: Oligonucleotide for the RT-PCR

<400> SEQUENCE: 136
tcctatgctt gactattgc                                                19

<210> SEQ ID NO 137
<211> LENGTH: 23
<212> TYPE: DNA
<213> ORGANISM: Artificial Sequence
<220> FEATURE:
<223> OTHER INFORMATION: from RNAm Liv21 obtained by RT-PCR

<400> SEQUENCE: 137
cctgacatcc ctacatcacc cat                                           23

<210> SEQ ID NO 138
<211> LENGTH: 22
<212> TYPE: DNA
<213> ORGANISM: Artificial Sequence
<220> FEATURE:
<223> OTHER INFORMATION: Oligonucleotide for the PCR

<400> SEQUENCE: 138
atgttgggat tgcttatatt ta                                            22

<210> SEQ ID NO 139
<211> LENGTH: 19
<212> TYPE: DNA
<213> ORGANISM: Artificial Sequence
<220> FEATURE:
<223> OTHER INFORMATION: Oligonucleotide for the PCR

<400> SEQUENCE: 139
tatacgagat gttggattg                                                19

<210> SEQ ID NO 140
<211> LENGTH: 19
<212> TYPE: DNA
<213> ORGANISM: Artificial Sequence
<220> FEATURE:
<223> OTHER INFORMATION: Oligonucleotide for the PCR

<400> SEQUENCE: 140
tatacgagat gttggattg                                                19
```

```
<210> SEQ ID NO 141
<211> LENGTH: 19
<212> TYPE: DNA
<213> ORGANISM: Artificial Sequence
<220> FEATURE:
<223> OTHER INFORMATION: Oligonucleotide for the PCR

<400> SEQUENCE: 141
cattttgcac accaaggtt                                                   19

<210> SEQ ID NO 142
<211> LENGTH: 408
<212> TYPE: DNA
<213> ORGANISM: Artificial Sequence
<220> FEATURE:
<223> OTHER INFORMATION: ATGS1 insert of clone extracted from MCF7 cells
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t

<400> SEQUENCE: 142
taaatataag caatcccaac actttgggag gccgangngg gcggatcacg aggtcaggag      60
atggagacca tcctggctaa cacagtgaaa ccctgtctct actgaaaata caaaaaagta    120
gccgggcgtg gcggcaggcg cctgtagccc cagctactca ggaggctgag gcaggagaat    180
ggcatgaacc caggaggcag agcttgcagt gagccgagat tgtgccactg cactccagcc    240
tgggcaacag agcgagactc catctcaaaa aaaaaaaaaa tcaccccaaa gcaataagga    300
gaactagaac aggacataca ctccaacact ggtgaaacta ggaaaacata tgtaacccca    360
aaccacaata tatacacaca aaactatacg agatgttggg attgctta                408

<210> SEQ ID NO 143
<211> LENGTH: 1005
<212> TYPE: DNA
<213> ORGANISM: Artificial Sequence
<220> FEATURE:
<223> OTHER INFORMATION: T6T7 clone extracted from MCF7 cells culture
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (86)..(87)
<223> OTHER INFORMATION: n is a, c, g, or t
<220> FEATURE:
<221> NAME/KEY: misc_feature
<222> LOCATION: (90)..(92)
<223> OTHER INFORMATION: n is a, c, g, or t
<220> FEATURE:
<221> NAME/KEY: misc_feature
<222> LOCATION: (155)..(156)
<223> OTHER INFORMATION: n is a, c, g, or t
<220> FEATURE:
```

```
<221> NAME/KEY: misc_feature
<222> LOCATION: (176)..(178)
<223> OTHER INFORMATION: n is a, c, g, or t
<220> FEATURE:
<221> NAME/KEY: misc_feature
<222> LOCATION: (180)..(183)
<223> OTHER INFORMATION: n is a, c, g, or t
<220> FEATURE:
<221> NAME/KEY: misc_feature
<222> LOCATION: (185)..(185)
<223> OTHER INFORMATION: n is a, c, g, or t
<220> FEATURE:
<221> NAME/KEY: misc_feature
<222> LOCATION: (195)..(195)
<223> OTHER INFORMATION: n is a, c, g, or t
<220> FEATURE:
<221> NAME/KEY: misc_feature
<222> LOCATION: (198)..(198)
<223> OTHER INFORMATION: n is a, c, g, or t
<220> FEATURE:
<221> NAME/KEY: misc_feature
<222> LOCATION: (223)..(223)
<223> OTHER INFORMATION: n is a, c, g, or t
<220> FEATURE:
<221> NAME/KEY: misc_feature
<222> LOCATION: (238)..(238)
<223> OTHER INFORMATION: n is a, c, g, or t
<220> FEATURE:
<221> NAME/KEY: misc_feature
<222> LOCATION: (247)..(247)
<223> OTHER INFORMATION: n is a, c, g, or t
<220> FEATURE:
<221> NAME/KEY: misc_feature
<222> LOCATION: (249)..(250)
<223> OTHER INFORMATION: n is a, c, g, or t
<220> FEATURE:
<221> NAME/KEY: misc_feature
<222> LOCATION: (254)..(254)
<223> OTHER INFORMATION: n is a, c, g, or t
<220> FEATURE:
<221> NAME/KEY: misc_feature
<222> LOCATION: (261)..(262)
<223> OTHER INFORMATION: n is a, c, g, or t
<220> FEATURE:
<221> NAME/KEY: misc_feature
<222> LOCATION: (264)..(267)
<223> OTHER INFORMATION: n is a, c, g, or t
<220> FEATURE:
<221> NAME/KEY: misc_feature
<222> LOCATION: (283)..(284)
<223> OTHER INFORMATION: n is a, c, g, or t
<220> FEATURE:
<221> NAME/KEY: misc_feature
<222> LOCATION: (306)..(307)
<223> OTHER INFORMATION: n is a, c, g, or t
<220> FEATURE:
<221> NAME/KEY: misc_feature
<222> LOCATION: (309)..(309)
<223> OTHER INFORMATION: n is a, c, g, or t
<220> FEATURE:
<221> NAME/KEY: misc_feature
<222> LOCATION: (323)..(323)
<223> OTHER INFORMATION: n is a, c, g, or t
<220> FEATURE:
<221> NAME/KEY: misc_feature
<222> LOCATION: (328)..(329)
<223> OTHER INFORMATION: n is a, c, g, or t
<220> FEATURE:
<221> NAME/KEY: misc_feature
<222> LOCATION: (346)..(346)
<223> OTHER INFORMATION: n is a, c, g, or t
<220> FEATURE:
<221> NAME/KEY: misc_feature
<222> LOCATION: (365)..(365)
<223> OTHER INFORMATION: n is a, c, g, or t
<220> FEATURE:
<221> NAME/KEY: misc_feature
<222> LOCATION: (378)..(378)
<223> OTHER INFORMATION: n is a, c, g, or t
```

-continued

```
<220> FEATURE:
<221> NAME/KEY: misc_feature
<222> LOCATION: (388)..(388)
<223> OTHER INFORMATION: n is a, c, g, or t
<220> FEATURE:
<221> NAME/KEY: misc_feature
<222> LOCATION: (390)..(390)
<223> OTHER INFORMATION: n is a, c, g, or t
<220> FEATURE:
<221> NAME/KEY: misc_feature
<222> LOCATION: (400)..(402)
<223> OTHER INFORMATION: n is a, c, g, or t
<220> FEATURE:
<221> NAME/KEY: misc_feature
<222> LOCATION: (405)..(405)
<223> OTHER INFORMATION: n is a, c, g, or t
<220> FEATURE:
<221> NAME/KEY: misc_feature
<222> LOCATION: (409)..(410)
<223> OTHER INFORMATION: n is a, c, g, or t
<220> FEATURE:
<221> NAME/KEY: misc_feature
<222> LOCATION: (415)..(415)
<223> OTHER INFORMATION: n is a, c, g, or t
<220> FEATURE:
<221> NAME/KEY: misc_feature
<222> LOCATION: (421)..(421)
<223> OTHER INFORMATION: n is a, c, g, or t
<220> FEATURE:
<221> NAME/KEY: misc_feature
<222> LOCATION: (424)..(424)
<223> OTHER INFORMATION: n is a, c, g, or t
<220> FEATURE:
<221> NAME/KEY: misc_feature
<222> LOCATION: (429)..(430)
<223> OTHER INFORMATION: n is a, c, g, or t
<220> FEATURE:
<221> NAME/KEY: misc_feature
<222> LOCATION: (440)..(440)
<223> OTHER INFORMATION: n is a, c, g, or t
<220> FEATURE:
<221> NAME/KEY: misc_feature
<222> LOCATION: (442)..(444)
<223> OTHER INFORMATION: n is a, c, g, or t
<220> FEATURE:
<221> NAME/KEY: misc_feature
<222> LOCATION: (452)..(452)
<223> OTHER INFORMATION: n is a, c, g, or t
<220> FEATURE:
<221> NAME/KEY: misc_feature
<222> LOCATION: (458)..(458)
<223> OTHER INFORMATION: n is a, c, g, or t
<220> FEATURE:
<221> NAME/KEY: misc_feature
<222> LOCATION: (463)..(463)
<223> OTHER INFORMATION: n is a, c, g, or t
<220> FEATURE:
<221> NAME/KEY: misc_feature
<222> LOCATION: (469)..(469)
<223> OTHER INFORMATION: n is a, c, g, or t
<220> FEATURE:
<221> NAME/KEY: misc_feature
<222> LOCATION: (478)..(478)
<223> OTHER INFORMATION: n is a, c, g, or t
<220> FEATURE:
<221> NAME/KEY: misc_feature
<222> LOCATION: (495)..(498)
<223> OTHER INFORMATION: n is a, c, g, or t
<220> FEATURE:
<221> NAME/KEY: misc_feature
<222> LOCATION: (500)..(500)
<223> OTHER INFORMATION: n is a, c, g, or t
<220> FEATURE:
<221> NAME/KEY: misc_feature
<222> LOCATION: (508)..(509)
<223> OTHER INFORMATION: n is a, c, g, or t
<220> FEATURE:
<221> NAME/KEY: misc_feature
<222> LOCATION: (538)..(540)
```

```
<223> OTHER INFORMATION: n is a, c, g, or t
<220> FEATURE:
<221> NAME/KEY: misc_feature
<222> LOCATION: (542)..(542)
<223> OTHER INFORMATION: n is a, c, g, or t
<220> FEATURE:
<221> NAME/KEY: misc_feature
<222> LOCATION: (547)..(547)
<223> OTHER INFORMATION: n is a, c, g, or t
<220> FEATURE:
<221> NAME/KEY: misc_feature
<222> LOCATION: (556)..(557)
<223> OTHER INFORMATION: n is a, c, g, or t
<220> FEATURE:
<221> NAME/KEY: misc_feature
<222> LOCATION: (573)..(574)
<223> OTHER INFORMATION: n is a, c, g, or t
<220> FEATURE:
<221> NAME/KEY: misc_feature
<222> LOCATION: (577)..(577)
<223> OTHER INFORMATION: n is a, c, g, or t
<220> FEATURE:
<221> NAME/KEY: misc_feature
<222> LOCATION: (579)..(579)
<223> OTHER INFORMATION: n is a, c, g, or t
<220> FEATURE:
<221> NAME/KEY: misc_feature
<222> LOCATION: (581)..(581)
<223> OTHER INFORMATION: n is a, c, g, or t
<220> FEATURE:
<221> NAME/KEY: misc_feature
<222> LOCATION: (583)..(584)
<223> OTHER INFORMATION: n is a, c, g, or t
<220> FEATURE:
<221> NAME/KEY: misc_feature
<222> LOCATION: (587)..(587)
<223> OTHER INFORMATION: n is a, c, g, or t
<220> FEATURE:
<221> NAME/KEY: misc_feature
<222> LOCATION: (589)..(590)
<223> OTHER INFORMATION: n is a, c, g, or t
<220> FEATURE:
<221> NAME/KEY: misc_feature
<222> LOCATION: (602)..(602)
<223> OTHER INFORMATION: n is a, c, g, or t
<220> FEATURE:
<221> NAME/KEY: misc_feature
<222> LOCATION: (613)..(613)
<223> OTHER INFORMATION: n is a, c, g, or t
<220> FEATURE:
<221> NAME/KEY: misc_feature
<222> LOCATION: (628)..(629)
<223> OTHER INFORMATION: n is a, c, g, or t
<220> FEATURE:
<221> NAME/KEY: misc_feature
<222> LOCATION: (632)..(633)
<223> OTHER INFORMATION: n is a, c, g, or t
<220> FEATURE:
<221> NAME/KEY: misc_feature
<222> LOCATION: (644)..(644)
<223> OTHER INFORMATION: n is a, c, g, or t
<220> FEATURE:
<221> NAME/KEY: misc_feature
<222> LOCATION: (647)..(647)
<223> OTHER INFORMATION: n is a, c, g, or t
<220> FEATURE:
<221> NAME/KEY: misc_feature
<222> LOCATION: (655)..(655)
<223> OTHER INFORMATION: n is a, c, g, or t
<220> FEATURE:
<221> NAME/KEY: misc_feature
<222> LOCATION: (658)..(659)
<223> OTHER INFORMATION: n is a, c, g, or t
<220> FEATURE:
<221> NAME/KEY: misc_feature
<222> LOCATION: (669)..(670)
<223> OTHER INFORMATION: n is a, c, g, or t
<220> FEATURE:
<221> NAME/KEY: misc_feature
```

-continued

```
<222> LOCATION: (673)..(673)
<223> OTHER INFORMATION: n is a, c, g, or t
<220> FEATURE:
<221> NAME/KEY: misc_feature
<222> LOCATION: (676)..(676)
<223> OTHER INFORMATION: n is a, c, g, or t
<220> FEATURE:
<221> NAME/KEY: misc_feature
<222> LOCATION: (682)..(682)
<223> OTHER INFORMATION: n is a, c, g, or t
<220> FEATURE:
<221> NAME/KEY: misc_feature
<222> LOCATION: (684)..(684)
<223> OTHER INFORMATION: n is a, c, g, or t
<220> FEATURE:
<221> NAME/KEY: misc_feature
<222> LOCATION: (690)..(691)
<223> OTHER INFORMATION: n is a, c, g, or t
<220> FEATURE:
<221> NAME/KEY: misc_feature
<222> LOCATION: (707)..(707)
<223> OTHER INFORMATION: n is a, c, g, or t
<220> FEATURE:
<221> NAME/KEY: misc_feature
<222> LOCATION: (709)..(709)
<223> OTHER INFORMATION: n is a, c, g, or t
<220> FEATURE:
<221> NAME/KEY: misc_feature
<222> LOCATION: (711)..(711)
<223> OTHER INFORMATION: n is a, c, g, or t
<220> FEATURE:
<221> NAME/KEY: misc_feature
<222> LOCATION: (725)..(726)
<223> OTHER INFORMATION: n is a, c, g, or t
<220> FEATURE:
<221> NAME/KEY: misc_feature
<222> LOCATION: (727)..(738)
<223> OTHER INFORMATION: n is a, c, g, or t
<220> FEATURE:
<221> NAME/KEY: misc_feature
<222> LOCATION: (740)..(740)
<223> OTHER INFORMATION: n is a, c, g, or t
<220> FEATURE:
<221> NAME/KEY: misc_feature
<222> LOCATION: (742)..(743)
<223> OTHER INFORMATION: n is a, c, g, or t
<220> FEATURE:
<221> NAME/KEY: misc_feature
<222> LOCATION: (745)..(745)
<223> OTHER INFORMATION: n is a, c, g, or t
<220> FEATURE:
<221> NAME/KEY: misc_feature
<222> LOCATION: (749)..(757)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (764)..(764)
<223> OTHER INFORMATION: n is a, c, g, or t
<220> FEATURE:
<221> NAME/KEY: misc_feature
<222> LOCATION: (771)..(773)
<223> OTHER INFORMATION: n is a, c, g, or t
<220> FEATURE:
<221> NAME/KEY: misc_feature
<222> LOCATION: (776)..(776)
<223> OTHER INFORMATION: n is a, c, g, or t
<220> FEATURE:
<221> NAME/KEY: misc_feature
<222> LOCATION: (779)..(783)
<223> OTHER INFORMATION: n is a, c, g, or t
<220> FEATURE:
<221> NAME/KEY: misc_feature
<222> LOCATION: (785)..(785)
<223> OTHER INFORMATION: n is a, c, g, or t
<220> FEATURE:
```

```
<221> NAME/KEY: misc_feature
<222> LOCATION: (787)..(787)
<223> OTHER INFORMATION: n is a, c, g, or t
<220> FEATURE:
<221> NAME/KEY: misc_feature
<222> LOCATION: (789)..(789)
<223> OTHER INFORMATION: n is a, c, g, or t
<220> FEATURE:
<221> NAME/KEY: misc_feature
<222> LOCATION: (791)..(795)
<223> OTHER INFORMATION: n is a, c, g, or t
<220> FEATURE:
<221> NAME/KEY: misc_feature
<222> LOCATION: (798)..(798)
<223> OTHER INFORMATION: n is a, c, g, or t
<220> FEATURE:
<221> NAME/KEY: misc_feature
<222> LOCATION: (803)..(804)
<223> OTHER INFORMATION: n is a, c, g, or t
<220> FEATURE:
<221> NAME/KEY: misc_feature
<222> LOCATION: (806)..(807)
<223> OTHER INFORMATION: n is a, c, g, or t
<220> FEATURE:
<221> NAME/KEY: misc_feature
<222> LOCATION: (810)..(828)
<223> OTHER INFORMATION: n is a, c, g, or t
<220> FEATURE:
<221> NAME/KEY: misc_feature
<222> LOCATION: (830)..(836)
<223> OTHER INFORMATION: n is a, c, g, or t
<220> FEATURE:
<221> NAME/KEY: misc_feature
<222> LOCATION: (839)..(848)
<223> OTHER INFORMATION: n is a, c, g, or t
<220> FEATURE:
<221> NAME/KEY: misc_feature
<222> LOCATION: (850)..(850)
<223> OTHER INFORMATION: n is a, c, g, or t
<220> FEATURE:
<221> NAME/KEY: misc_feature
<222> LOCATION: (852)..(853)
<223> OTHER INFORMATION: n is a, c, g, or t
<220> FEATURE:
<221> NAME/KEY: misc_feature
<222> LOCATION: (857)..(860)
<223> OTHER INFORMATION: n is a, c, g, or t
<220> FEATURE:
<221> NAME/KEY: misc_feature
<222> LOCATION: (862)..(877)
<223> OTHER INFORMATION: n is a, c, g, or t
<220> FEATURE:
<221> NAME/KEY: misc_feature
<222> LOCATION: (879)..(880)
<223> OTHER INFORMATION: n is a, c, g, or t
<220> FEATURE:
<221> NAME/KEY: misc_feature
<222> LOCATION: (882)..(884)
<223> OTHER INFORMATION: n is a, c, g, or t
<220> FEATURE:
<221> NAME/KEY: misc_feature
<222> LOCATION: (890)..(892)
<223> OTHER INFORMATION: n is a, c, g, or t
<220> FEATURE:
<221> NAME/KEY: misc_feature
<222> LOCATION: (896)..(915)
<223> OTHER INFORMATION: n is a, c, g, or t
<220> FEATURE:
<221> NAME/KEY: misc_feature
<222> LOCATION: (917)..(920)
<223> OTHER INFORMATION: n is a, c, g, or t
<220> FEATURE:
<221> NAME/KEY: misc_feature
<222> LOCATION: (922)..(935)
<223> OTHER INFORMATION: n is a, c, g, or t
<220> FEATURE:
<221> NAME/KEY: misc_feature
<222> LOCATION: (937)..(945)
<223> OTHER INFORMATION: n is a, c, g, or t
```

```
<220> FEATURE:
<221> NAME/KEY: misc_feature
<222> LOCATION: (947)..(952)
<223> OTHER INFORMATION: n is a, c, g, or t
<220> FEATURE:
<221> NAME/KEY: misc_feature
<222> LOCATION: (954)..(964)
<223> OTHER INFORMATION: n is a, c, g, or t
<220> FEATURE:
<221> NAME/KEY: misc_feature
<222> LOCATION: (966)..(966)
<223> OTHER INFORMATION: n is a, c, g, or t
<220> FEATURE:
<221> NAME/KEY: misc_feature
<222> LOCATION: (970)..(971)
<223> OTHER INFORMATION: n is a, c, g, or t
<220> FEATURE:
<221> NAME/KEY: misc_feature
<222> LOCATION: (976)..(978)
<223> OTHER INFORMATION: n is a, c, g, or t
<220> FEATURE:
<221> NAME/KEY: misc_feature
<222> LOCATION: (980)..(983)
<223> OTHER INFORMATION: n is a, c, g, or t
<220> FEATURE:
<221> NAME/KEY: misc_feature
<222> LOCATION: (986)..(987)
<223> OTHER INFORMATION: n is a, c, g, or t
<220> FEATURE:
<221> NAME/KEY: misc_feature
<222> LOCATION: (989)..(989)
<223> OTHER INFORMATION: n is a, c, g, or t
<220> FEATURE:
<221> NAME/KEY: misc_feature
<222> LOCATION: (991)..(999)
<223> OTHER INFORMATION: n is a, c, g, or t
<220> FEATURE:
<221> NAME/KEY: misc_feature
<222> LOCATION: (1001)..(1005)
<223> OTHER INFORMATION: n is a, c, g, or t

<400> SEQUENCE: 143
tccggncgcc ntggcggccg cgggantcga ttaattgntt tttttttttt tttttttttt      60
tttttttttt tttttttttt tttttnnggn nntttttttt ccttttttttt tttttttttt    120
tttttttttt tttttttttt tttttttttt ttttnncaaa aaaccaaaaa cccagnnnan    180
nnnancccta ggggnttncc ggccccccgg ggggcccccca aangggaaaa ccccccancg    240
ggggggngnn aaanttggga nntnnnnagg ggccccaaa aanntggggg aaaccgggg       300
caaaanngnt tccgggggga aantttttnnc cccccaaaat tccccnaaaa aaaaaaaccg    360
gaaanaaaaa gggaaaancc gggggggncn aaagggggn nnaancccnn ataantgggg      420
nggncccnn ggcccctttn cnnncggaa anccggnnng gcncctggnt taaagaancc       480
ccccaccccg ggggnnnngn ggtttggnna ttggggccc ttccccttcc cccccannn       540
anccccngcc cccggnngtt cggggggggg ganngnganc ncnnccncnn agggggaaa      600
angggtatcc ccnaaaaccg gggaaaannc annaaaaaaa atgnggnaaa aaggnccnna     660
aaagggccnn aaccnaaaa angnccccggn nggggggggtt tttccanang nccccccccc    720
ccgannannn nnnnnnnan cnncncccnn nnnnnngng gggnaaaccc nnnagngann      780
nnnananan nnnnttncc ccnngnnaan nnnnnnnnnn nnnnnnnngn nnnnnccnn       840
nnnnnnnnan annaaannnn gnnnnnnnnn nnnnnnngnn annggggggn nntttnnnnn    900
nnnnnnnnnn nnnngnnn gnnnnnnnnn nnnnngnnnn nnnnntnnnn nncnnnnnnnn     960
nnnngnaaan nccccnnntn nnccnnana nnnnnnnnc nnnnn                    1005

<210> SEQ ID NO 144
```

<211> LENGTH: 805
<212> TYPE: DNA
<213> ORGANISM: Artificial Sequence
<220> FEATURE:
<223> OTHER INFORMATION: T7 sens:clone extracted from MCF7 cells
<220> FEATURE:
<221> NAME/KEY: misc_feature
<222> LOCATION: (62)..(62)
<223> OTHER INFORMATION: n is a, c, g, or t
<220> FEATURE:
<221> NAME/KEY: misc_feature
<222> LOCATION: (772)..(772)
<223> OTHER INFORMATION: n is a, c, g, or t

<400> SEQUENCE: 144

| | | | | | |
|---|---|---|---|---|---|
| ctccggccgc | catggcggcc | gcgggaattc | gatttcctat | gcttgactat | tagctgagat | 60 |
| gncggtttcc | tctccaaaga | agtaagagga | cagaaaaagt | catgctggtc | ttagctctac | 120 |
| aagagtatga | atgcaggcag | gtattaccat | tcaatttcca | tgagatgtat | ggcctacaat | 180 |
| tcttaaaagg | gtatctgagg | ccgggtgcag | tggctgatgc | ttgtaattcc | agcatttttgg | 240 |
| gaggccaagg | caggcagatc | accgatgtca | ggagtttgag | actagcctgg | ccaacatggt | 300 |
| gaaaccccgt | ctctaccaaa | aataaaaaaa | atagccaggc | atggtggtgc | gcacttgtag | 360 |
| ttccagctac | tctgcttggg | aggctgaggc | aggagaattg | cttgaacctg | ggaggcagag | 420 |
| gttgcagtga | gccgagatcg | tgccactgca | ctccagcctg | ggcgacagat | tgagactctg | 480 |
| tatcaaaaaa | aaaaaaaaaa | aaaaaaaaaa | aagaaagaaa | cacaaggctg | gaggttcaca | 540 |
| gagtatttat | attggaaaat | ctcatttaag | ttaatatata | acattaacat | tcaaaattca | 600 |
| atgcaattta | atcaaacaac | tgtaactcca | tgacaaagag | agtcatctct | acttcagagg | 660 |
| catttaattc | aatattaaga | attaatacat | catcatatct | tcaagacaaa | cccatgtacc | 720 |
| atttcacaac | aactaataaa | aattataggg | aagaatctca | tctcagaata | anttgatttc | 780 |
| tattttcat | tcattaacga | gataa | | | | 805 |

<210> SEQ ID NO 145
<211> LENGTH: 806
<212> TYPE: DNA
<213> ORGANISM: Artificial Sequence
<220> FEATURE:
<223> OTHER INFORMATION: T7 antisense sequence of clone extracted from MCF7
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (745)..(745)
<223> OTHER INFORMATION: n is a, c, g, or t

<400> SEQUENCE: 145

| | | | | | |
|---|---|---|---|---|---|
| cttatctcgt | taatgaatga | aaaatagaaa | tcaanttatt | ctgagatgag | attcttccct | 60 |
| ataatttta | ttagttgttg | tgaaatggta | catgggtttg | tcttgaagat | atgatgatgt | 120 |
| attaattctt | aatattgaat | taaatgcctc | tgaagtagag | atgactctct | ttgtcatgga | 180 |
| gttacagttg | tttgattaaa | ttgcattgaa | ttttgaatgt | taatgttata | tattaactta | 240 |
| aatgagattt | tccaatataa | atactctgtg | aacctccagc | cttgtgtttc | tttctttttt | 300 |
| tttttttt | tttttttttt | ttgatacaga | gtctcaatct | gtcgcccagg | ctggagtgca | 360 |
| gtggcacgat | ctcggctcac | tgcaacctct | gcctcccagg | ttcaagcaat | tctcctgcct | 420 |
| cagcctccca | agcagagtag | ctggaactac | aagtgcgcac | caccatgcct | ggctattttt | 480 |

```
tttattttg  gtagagacgg  ggtttcacca  tgttggccag  gctagtctca  aactcctgac    540
atcggtgatc  tgcctgcctt  ggcctcccaa  aatgctggaa  ttacaagcat  cagccactgc    600
acccggcctc  agataccctt  ttaagaattg  taggccatac  atctcatgga  aattgaatgg    660
taatacctgc  ctgcattcat  actcttgtag  agctaagacc  agcatgactt  tttctgtcct    720
cttacttctt  tggagaggaa  accgncatct  cagctaatag  tcaagcatag  gaaatcgaat    780
tcccgcggcc  gccatggcgg  ccggag                                            806
```

```
<210> SEQ ID NO 146
<211> LENGTH: 720
<212> TYPE: DNA
<213> ORGANISM: Artificial Sequence
<220> FEATURE:
<223> OTHER INFORMATION: 2006M13rev2005 clone extracted from MCF7 cells
<220> FEATURE:
<221> NAME/KEY: misc_feature
<222> LOCATION: (585)..(585)
<223> OTHER INFORMATION: n is a, c, g, or t
<220> FEATURE:
<221> NAME/KEY: misc_feature
<222> LOCATION: (610)..(610)
<223> OTHER INFORMATION: n is a, c, g, or t
<220> FEATURE:
<221> NAME/KEY: misc_feature
<222> LOCATION: (645)..(646)
<223> OTHER INFORMATION: n is a, c, g, or t
<220> FEATURE:
<221> NAME/KEY: misc_feature
<222> LOCATION: (664)..(664)
<223> OTHER INFORMATION: n is a, c, g, or t
<220> FEATURE:
<221> NAME/KEY: misc_feature
<222> LOCATION: (681)..(681)
<223> OTHER INFORMATION: n is a, c, g, or t
<220> FEATURE:
<221> NAME/KEY: misc_feature
<222> LOCATION: (707)..(708)
<223> OTHER INFORMATION: n is a, c, g, or t
<220> FEATURE:
<221> NAME/KEY: misc_feature
<222> LOCATION: (711)..(711)
<223> OTHER INFORMATION: n is a, c, g, or t
<220> FEATURE:
<221> NAME/KEY: misc_feature
<222> LOCATION: (713)..(713)
<223> OTHER INFORMATION: n is a, c, g, or t

<400> SEQUENCE: 146
tcaagctatg  catccaacgc  gttgggagct  ctcccatatg  gtcgacctgc  aggcggccgc     60
gaattcacta  gtgatttcct  atgcttgact  attagctcct  tttctttacc  tattattatt    120
atttattttt  cagatggagt  ctcacactgt  cgccaggctg  gagtacagtg  gcgccatctc    180
ggctcactga  accctccacc  taccgggttc  aagtgattct  actgccgcag  tctccagagt    240
agctgggact  acaggcatgc  actaccacac  ccagctaatt  ttttgtattt  ttagttgaga    300
tggggtttca  ccatgatggc  caggatggtc  tcgatctctt  gacctcatga  tctgcctgcc    360
tcagcctccc  aaagtgctgg  gattacgggc  atgagccact  gtgctaggcc  tacctatttt    420
aaaaataaca  agaattcatc  caatggaacg  ctgaaatgcc  tgtggaggat  acaagattaa    480
tcagcaggat  tatatttgcc  tatgactcca  ttaattcaat  tccagaccct  acttatgggt    540
ctaatgtcct  ttattaggca  atgtaggaga  ttcctatact  cctantaaag  taatcttttt    600
ccatttaaan  atctttgctt  tttatcaggc  agtatgtatt  ttccnnaaag  ttaattcaat    660
gaantacacc  ctaaagctga  nagtcttatc  ctcgttaatg  gaatggnnaa  nanaaattca    720
```

<210> SEQ ID NO 147
<211> LENGTH: 783
<212> TYPE: DNA
<213> ORGANISM: Artificial Sequence
<220> FEATURE:
<223> OTHER INFORMATION: C8sens1605 clone extracted from MCF7 cells
      culture
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (70)..(70)
<223> OTHER INFORMATION: n is a, c, g, or t

<400> SEQUENCE: 147

```
catgacaaag agagtcatct ntactncaga gncatttant tcaatattaa gaattaatac     60
atcatcatan tcaagacaaa cccatgtacc atttcacaac aactaataaa aattatagga    120
agaatctcat ctcagaataa ttgatttcta tttttcattc attaacgaga taagactctc    180
agctttaggt gtatttcatt gaattaactt tgtggaaata catactgcct gataaaaagc    240
aaagatattt aaatggaaaa agattacttt attaggagta taggaatctc ctacattgcc    300
taataaagga cattagaccc ataagtaggg tctggaattg aattaatgga gtcataggca    360
aatataatcc tgctgattaa tcttgtatcc tccacaggca tttcagcgtt ccattggatg    420
aattcttgtt atttttaaaa taggtaggcc tagcacagtg gctcatgccc gtaatcccag    480
cactttggga ggctgaggca ggcagatcat gaggtcaaga gatcgagacc atcctggcca    540
tcatggtgaa accccatctc aactaaaaat acaaaaaatt agctgggtgt ggtagtgcat    600
gcctgtagtc ccagctactc tggagactgc ggcagtagaa tcacttgaac ccggtaggtg    660
gagggttcag tgagccgaga tggcgccact gtactccagc ctggcgacag tgtgagactc    720
catctgaaaa ataaataata ataataggat aagaaaagga gctaatagtc aagcatagga    780
aat                                                                  783
```

<210> SEQ ID NO 148
<211> LENGTH: 1200
<212> TYPE: DNA
<213> ORGANISM: Artificial Sequence
<220> FEATURE:
<223> OTHER INFORMATION: clone LIV extracted from MCF7 cells culture
<220> FEATURE:
<221> NAME/KEY: misc_feature
<222> LOCATION: (1068)..(1068)
<223> OTHER INFORMATION: n is a, c, g, or t

<400> SEQUENCE: 148

```
ggagaagggt ccccactgct cctgtcaagc cttgttgtgt cgggacttga actttattct     60
aagcaggtga atgcggtgca tgcaagagag acagagagaa tgtggcagga ccaaggagga    120
ggctatgcca cttatgtcac tcctggcaaa ataagggggg catggagtag gctgtttgtg    180
gtgcagatgg tgagagcagt caggtccagc acagatttta aaggttggac ccagagaatt    240
```

-continued

```
tgctgcagaa tcagatgtgg ggtgtaaggc agagaggagt caagggcaac ttcaggattt    300
ggggccggaa ctgccattag acagacaggg acactggggg agaagcaggt taggtgggat    360
taaaatcaag agttcaagtt aagtttgagc agcctgttag acctccaacg agggccagat    420
agaagaatct ggtttccagg gagaggtcag gatgagagat acacacgtgg gaatgattgg    480
cattgggcgg actttatatt ctctgggcca gtgagacagc tgggaagtga ccacggatag    540
agaagagaca aagtcacaga aaccaagaga ggtaatgttg caaggacgga acactcaact    600
ctcaaatgct gctgagacgt gggctgaggg ctgagaatgg aattgggaag aaccgaggtc    660
actggtgatc ctgagggttt cagtggcaag ggcaggtgga ctgcagtggg gcccggtggg    720
gatcggtgga gcatgggccc ctctcccgga gagttgcact gtaaacgagg cagacatat    780 gggagtgcag ctagagggag ggaacgtagg ctcaagggag agtttattct gaatgagaga    840
gatcacagct tgttttagg ctgacgggca tgatccatag aggggaaagt aattaagatg    900
cagaagagag gccggggggtg gtggctcacg cctgtaatct cagcactttg ggaggctcga    960
ggtgggtgga tcatttgagg acaggagttc gagaccatcc tggccagcat ggtgaaacct    1020
cgcctctact aaaaataaaa ataaaaaaaa attagctggg tgcggtgnac gggcacctgt    1080
agtaccagct acttgggagg ctgaggtaac agaatcgctt gaaccctgga ggcaggggtt    1140
gcagtgagct gagattgtgc cactgcactc tagcctgggc aacaaattga gactccactc    1200
```

<210> SEQ ID NO 149
<211> LENGTH: 75
<212> TYPE: PRT
<213> ORGANISM: Homo sapiens

<400> SEQUENCE: 149

Met Glu Ser Arg Ser Val Ala Gln Ala Gly Val Gln Trp Pro Asp Leu
1               5                   10                  15

Gly Ser Leu Gln Pro Leu Pro Pro Arg Phe Lys Arg Phe Phe Cys Leu
            20                  25                  30

Ser Leu Gln Ser Ser Trp Asp Tyr Arg His Ala Pro Pro Arg Pro Ala
        35                  40                  45

Asn Phe Val Phe Leu Val Glu Thr Gly Phe Cys His Val Ser Gln Ala
    50                  55                  60

Gly Leu Glu Leu Leu Thr Ser Ser Asp Pro Pro
65                  70                  75

<210> SEQ ID NO 150
<211> LENGTH: 75
<212> TYPE: PRT
<213> ORGANISM: Homo sapiens
<220> FEATURE:
<223> OTHER INFORMATION: translation clone from C18

<400> SEQUENCE: 150

Met Glu Ser Arg Ser Val Ala Gln Ala Gly Val Gln Trp His Asn Leu
1               5                   10                  15

Gly Ser Leu Gln Ala Leu Pro Pro Gly Phe Met Pro Phe Ser Cys Leu
            20                  25                  30

Ser Leu Leu Ser Ser Trp Asp Tyr Arg Arg Leu Pro Pro Arg Pro Ala
        35                  40                  45

Thr Phe Leu Phe Leu Pro Arg Gln Gly Phe Thr Val Leu Ser Gln Ala
    50                  55                  60

Arg Met Val Ser Ile Ser Pro Arg Asp Pro Pro

<210> SEQ ID NO 151
<211> LENGTH: 136
<212> TYPE: PRT
<213> ORGANISM: Homo sapiens
<220> FEATURE:
<223> OTHER INFORMATION: translation clone from C18

<400> SEQUENCE: 151

Leu Asn Ile Ser Asn Pro Asn Ile Ser Tyr Ser Phe Val Cys Ile Tyr
1               5                   10                  15

Cys Gly Leu Gly Leu His Met Phe Ser Phe His Gln Cys Trp Ser Val
            20                  25                  30

Cys Pro Val Leu Val Leu Ile Ala Leu Gly Phe Phe Phe Phe
        35                  40                  45

Glu Met Glu Ser Arg Ser Val Ala Gln Ala Gly Val Gln Trp His Asn
    50                  55                  60

Leu Gly Ser Leu Gln Ala Leu Pro Pro Gly Phe Met Pro Phe Ser Cys
65                  70                  75                  80

Leu Ser Leu Leu Ser Ser Trp Asp Tyr Arg Arg Leu Pro Pro Arg Pro
                85                  90                  95

Ala Thr Phe Leu Tyr Phe Pro Arg Gln Gly Phe Thr Val Leu Ala Arg
            100                 105                 110

Met Val Ser Ile Ser Pro Arg Asp Pro Pro Ala Ser Ala Ser Gln Ser
        115                 120                 125

Val Gly Ile Ala Tyr Ile Ser Asn
    130                 135

<210> SEQ ID NO 152
<211> LENGTH: 133
<212> TYPE: PRT
<213> ORGANISM: Homo sapiens

<400> SEQUENCE: 152

Leu Ser Ser Ser Asp Pro Pro Ala Ser Ala Ser Gln Ser Val Gly Ile
1               5                   10                  15

Thr Gly Val Gly His His Thr Gln Leu His Gly Tyr Phe Phe His Leu
            20                  25                  30

Phe Tyr Phe Ile Leu Phe Tyr Tyr Leu Phe Phe Glu Thr Glu Ser His
            35                  40                  45

Cys Val Ala Gln Ala Gly Val Gln Trp Arg Gly Leu Gly Ser Leu Gln
        50                  55                  60

Ala Ser Pro Pro Arg Phe Thr Pro Phe Ser Cys Leu Ser Leu Pro Ser
65                  70                  75                  80

Ser Trp Asp Tyr Arg Arg Leu Pro Pro Cys Pro Ala Asn Phe Ser Tyr
                85                  90                  95

Phe Tyr Gln Asn Gly Phe Tyr His Val Gly Gln Ala Gly Leu Glu Phe
            100                 105                 110

Leu Thr Ser Gly Asp Pro Pro Ala Ser Ala Ser Gln Ser Ala Gly Ile
        115                 120                 125

Thr Gly Met Ser His
    130

<210> SEQ ID NO 153
<211> LENGTH: 93
<212> TYPE: PRT
<213> ORGANISM: Homo sapiens
<220> FEATURE:
<223> OTHER INFORMATION: translation clone from C18

<400> SEQUENCE: 153

Phe Phe Phe Phe Phe Glu Met Glu Ser Arg Ser Val Ala Gln Ala Gly
1               5                   10                  15

Val Gln Trp His Asn Leu Gly Ser Leu Gln Ala Leu Pro Pro Gly Phe
            20                  25                  30

Met Pro Phe Ser Cys Leu Ser Leu Leu Ser Ser Trp Asp Tyr Arg Arg
        35                  40                  45

Leu Pro Pro Arg Pro Ala Thr Phe Leu Tyr Phe Pro Arg Gln Gly Phe
    50                  55                  60

Thr Val Leu Ala Arg Met Val Ser Ile Ser Pro Arg Asp Pro Pro Ala
65                  70                  75                  80

Ser Ala Ser Gln Ser Val Gly Ile Ala Tyr Ile Ser Asn
                85                  90

<210> SEQ ID NO 154
<211> LENGTH: 100
<212> TYPE: PRT
<213> ORGANISM: Homo sapiens

<400> SEQUENCE: 154

Phe Phe Phe Phe Phe Glu Thr Glu Ser Arg Ser Val Ala Gln Ala Gly
1               5                   10                  15

Val Gln Trp Arg Asp Leu Gly Ser Leu Gln Ala Leu Pro Pro Gly Phe
            20                  25                  30

Thr Pro Phe Ser Cys Leu Ser Leu Pro Ser Ser Trp Asp Tyr Arg Arg
        35                  40                  45

Leu Pro Pro Leu Ala Pro Ala Asn Phe Phe Leu Ile Phe Val Phe Leu
    50                  55                  60

Val Glu Thr Gly Phe His His Val Gly Gln Ala Gly Leu Glu Leu Leu
65                  70                  75                  80

Thr Ser Gly Asp Pro Pro Ala Ser Ala Ser Gln Ser Ala Gly Ile Thr
                85                  90                  95

Gly Val Ser His
            100

<210> SEQ ID NO 155
<211> LENGTH: 149
<212> TYPE: PRT
<213> ORGANISM: Homo sapiens

<400> SEQUENCE: 155

Met Glu Ser His Ser Val Thr Gln Ala Gly Val Gln Trp Cys Gly Leu
1               5                   10                  15

Gly Ser Leu Gln Pro Leu Pro Pro Gly Phe Lys Arg Phe Phe Cys Leu
            20                  25                  30

Ser Leu Leu Ser Ser Trp Asp Tyr Arg Arg Val Pro Pro Leu Ala
        35                  40                  45

Asn Phe Cys Ile Phe Phe Ser Phe Phe Glu Lys Glu Ser Leu Ser
    50                  55                  60

Val Thr Gln Ala Gly Val Gln Trp His Asp Leu Gly Ser Leu Gln Ala
65                  70                  75                  80

Ala Pro Pro Gly Phe Thr Pro Phe Ser Cys Leu Ser Leu Pro Ser Ser
                85                  90                  95

Trp Asn Tyr Arg Arg Pro Pro Cys Pro Ala Asn Phe Phe Val Phe

```
              100                 105                 110
Leu Val Glu Met Gly Phe Cys His Ile Gly Gln Ala Gly Leu Glu Leu
            115                 120                 125

Leu Thr Ser Ser Asp Pro Pro Thr Ser Ala Ser Gln Ser Ala Gly Ile
        130                 135                 140

Thr Gly Met Ser His
145

<210> SEQ ID NO 156
<211> LENGTH: 1132
<212> TYPE: DNA
<213> ORGANISM: Homo sapiens

<400> SEQUENCE: 156
```

| | | | | | |
|---|---|---|---|---|---|
| ctagtgattt | cctatgcttg | actattagct | cctttctttt | acctattatt | attatttatt | 60 |
| tttcagatgg | agtctcacac | tgtcgccagg | ctggagtaca | gtggcgccat | ctcggctcac | 120 |
| tgaaccctcc | acctaccggg | ttcaagtgat | tctactgccg | cagtctccag | agtagctggg | 180 |
| actacaggca | tgcactacca | cacccagcta | atttttgta | tttttagttg | agatggggtt | 240 |
| tcaccatgat | ggccaggatg | gtctcgatct | cttgacctca | tgatctgcct | gcctcagcct | 300 |
| cccaaagtgc | tgggattacg | ggcatgagcc | actgtgctag | gcctacctat | tttaaaaata | 360 |
| acaagaattc | atccaatgga | acgctgaaat | gcctgtggag | gatacaagat | taatcagcag | 420 |
| gattatattt | gcctatgact | ccattaattc | aattccagac | cctacttatg | ggtctaatgt | 480 |
| cctttattag | gcaatgtagg | agattcctat | actcctaata | aagtaatctt | tttccattta | 540 |
| aatatctttg | cttttatca | ggcagtatgt | atttccacaa | agttaattca | atgaaataca | 600 |
| cctaaagctg | agagtcttat | ctcgttaatg | aatgaaaaat | agaaatcaat | tattctgaga | 660 |
| aatactctgt | gaacctccag | cctgtgtttt | ctttctttt | ttttttttt | ttttttttt | 720 |
| tttgatacag | agtctcaatc | tgtcgcccag | gctggagtgc | agtggcacga | tctcggctca | 780 |
| ctgcaacctc | tgcctcccag | gttcaagcaa | ttctcctgcc | tcagcctccc | aagcagagta | 840 |
| gctggaacta | caagtgcgca | ccaccatgcc | tggctatttt | ttttattttt | ggtagagacg | 900 |
| gggtttcacc | atgttggcca | ggctagtctc | aaactcctga | catcggtgat | ctgcctgcct | 960 |
| tggcctccca | aaatgctgga | attacaagca | tcagccactg | cacccggcct | cagatacccc | 1020 |
| tttaagaatt | ctaggccata | catctcatgg | aaattgaatg | gtaataccctg | cctgcattca | 1080 |
| tactcttgta | gagctaagac | cagcatgact | ttttctgtcc | tcttacttct | tt | 1132 |

```
<210> SEQ ID NO 157
<211> LENGTH: 1317
<212> TYPE: DNA
<213> ORGANISM: Artificial sequence
<220> FEATURE:
<223> OTHER INFORMATION: insert in PGEMT clone C18 extracted from MCF7
      cells
<220> FEATURE:
<221> NAME/KEY: misc_feature
<222> LOCATION: (700)..(702)
<223> OTHER INFORMATION: n is a, c, g, or t
<220> FEATURE:
<221> NAME/KEY: misc_feature
<222> LOCATION: (719)..(719)
<223> OTHER INFORMATION: n is a, c, g, or t
<220> FEATURE:
<221> NAME/KEY: misc_feature
<222> LOCATION: (721)..(721)
<223> OTHER INFORMATION: n is a, c, g, or t
<220> FEATURE:
<221> NAME/KEY: misc_feature
```

<222> LOCATION: (741)..(741)
<223> OTHER INFORMATION: n is a, c, g, or t
<220> FEATURE:
<221> NAME/KEY: misc_feature
<222> LOCATION: (749)..(749)
<223> OTHER INFORMATION: n is a, c, g, or t
<220> FEATURE:
<221> NAME/KEY: misc_feature
<222> LOCATION: (751)..(751)
<223> OTHER INFORMATION: n is a, c, g, or t
<220> FEATURE:
<221> NAME/KEY: misc_feature
<222> LOCATION: (758)..(758)
<223> OTHER INFORMATION: n is a, c, g, or t
<220> FEATURE:
<221> NAME/KEY: misc_feature
<222> LOCATION: (764)..(764)
<223> OTHER INFORMATION: n is a, c, g, or t
<220> FEATURE:
<221> NAME/KEY: misc_feature
<222> LOCATION: (769)..(769)
<223> OTHER INFORMATION: n is a, c, g, or t
<220> FEATURE:
<221> NAME/KEY: misc_feature
<222> LOCATION: (780)..(781)
<223> OTHER INFORMATION: n is a, c, g, or t
<220> FEATURE:
<221> NAME/KEY: misc_feature
<222> LOCATION: (785)..(786)
<223> OTHER INFORMATION: n is a, c, g, or t
<220> FEATURE:
<221> NAME/KEY: misc_feature
<222> LOCATION: (793)..(797)
<223> OTHER INFORMATION: n is a, c, g, or t
<220> FEATURE:
<221> NAME/KEY: misc_feature
<222> LOCATION: (800)..(804)
<223> OTHER INFORMATION: n is a, c, g, or t
<220> FEATURE:
<221> NAME/KEY: misc_feature
<222> LOCATION: (808)..(810)
<223> OTHER INFORMATION: n is a, c, g, or t
<220> FEATURE:
<221> NAME/KEY: misc_feature
<222> LOCATION: (812)..(814)
<223> OTHER INFORMATION: n is a, c, g, or t
<220> FEATURE:
<221> NAME/KEY: misc_feature
<222> LOCATION: (821)..(825)
<223> OTHER INFORMATION: n is a, c, g, or t
<220> FEATURE:
<221> NAME/KEY: misc_feature
<222> LOCATION: (828)..(828)
<223> OTHER INFORMATION: n is a, c, g, or t
<220> FEATURE:
<221> NAME/KEY: misc_feature
<222> LOCATION: (830)..(830)
<223> OTHER INFORMATION: n is a, c, g, or t
<220> FEATURE:
<221> NAME/KEY: misc_feature
<222> LOCATION: (832)..(836)
<223> OTHER INFORMATION: n is a, c, g, or t
<220> FEATURE:
<221> NAME/KEY: misc_feature
<222> LOCATION: (839)..(845)
<223> OTHER INFORMATION: n is a, c, g, or t
<220> FEATURE:
<221> NAME/KEY: misc_feature
<222> LOCATION: (847)..(859)
<223> OTHER INFORMATION: n is a, c, g, or t
<220> FEATURE:
<221> NAME/KEY: misc_feature
<222> LOCATION: (864)..(864)
<223> OTHER INFORMATION: n is a, c, g, or t

<400> SEQUENCE: 157
ctagtgattt cctatgcttg actattagct cctttctttt acctattatt attatttatt    60

```
tttcagatgg agtctcacac tgtcgccagg ctggagtaca gtggcgccat ctcggctcac    120
tgaaccctcc acctaccggg ttcaagtgat tctactgccg cagtctccag agtagctggg    180
actacaggca tgcactacca cacccagcta attttttgta ttttagttg agatgggtt      240
tcaccatgat ggccaggatg gtctcgatct cttgacctca tgatctgcct gcctcagcct    300
cccaaagtgc tgggattacg ggcatgagcc actgtgctag gcctacctat tttaaaaata    360
acaagaattc atccaatgga acgctgaaat gcctgtggag gatacaagat taatcagcag    420
gattatatt gcctatgact ccattaattc aattccagac cctacttatg ggtctaatgt     480
cctttattag gcaatgtagg agattcctat actcctaata aagtaatctt tttccattta    540
aatatctttg cttttatca ggcagtatgt atttccacaa agttaattca atgaaataca     600
cctaaagctg agagtcttat ctcgttaatg aatgaaaaat agaaatcaat tattctgaga    660
tgagattctt cctataattt ttattagttg ttgtgaaatn nncatgggtt tgtcttgana    720
natgatgatg tattaattct naatattgna ntaaatgnct ctgnagtana gatgactctn    780
ntttnntcat ggnnnnnacn nnnttgnnn annngcattg nnnntgnan gnnnnngtnn       840
nnnntnnnn nnnnnnnna tttncaaatt cactagtgat ttcctatgct tgactattag     900
ctccttttct ttacctatta ttattattta ttttcagat ggagtctcac actgtcgcca    960
ggctggagta cagtggcgcc atctcggctc actgaaccct ccacctaccg ggttcaagtg    1020
attctactgc cgcagtctcc agagtagctg ggactacagg catgcactac cacccagc     1080
taattttttg tatttttagt tgagatgggg tttcaccatg atggccagga tggtctcgat    1140
ctcttgacct catgatctgc ctgcctcagc ctcccaaagt gctgggatta cgggcatgag    1200
ccactgtgct aggcctacct atttaaaaa taacaagaat tcatccaatg gaacgctgaa    1260
atgcctgtgg aggatacaag attaatcagc acgattatat ttgcctatga ctccatt      1317
```

<210> SEQ ID NO 158
<211> LENGTH: 92
<212> TYPE: PRT
<213> ORGANISM: Homo sapiens
<220> FEATURE:
<223> OTHER INFORMATION: translation clone from C18

<400> SEQUENCE: 158

```
Phe Phe Phe Phe Phe Glu Met Glu Ser Arg Ser Val Ala Gln Ala Gly
1               5                   10                  15

Val Gln Trp His Leu Leu Gly Ser Leu Gln Ala Leu Pro Pro Gly Phe
            20                  25                  30

Met Pro Phe Ser Cys Leu Ser Leu Ser Ser Trp Asp Tyr Arg Arg
        35                  40                  45

Leu Pro Pro Arg Pro Ala Thr Phe Leu Tyr Phe Pro Arg Gln Gly Phe
    50                  55                  60

Thr Val Leu Ala Arg Met Val Ser Ile Ser Pro Arg Asp Pro Pro Ala
65                  70                  75                  80

Ser Ala Gln Ser Val Gly Ile Ala Tyr Ile Ser Asn
                85                  90
```

<210> SEQ ID NO 159
<211> LENGTH: 53
<212> TYPE: PRT
<213> ORGANISM: Homo sapiens
<220> FEATURE:
<223> OTHER INFORMATION: translation clone from C18

<400> SEQUENCE: 159

```
Met Glu Ser Arg Ser Val Ala Gln Ala Gly Val Gln Trp His Asn Leu
1               5                   10                  15

Gly Ser Leu Gln Ala Leu Pro Pro Gly Phe Met Pro Phe Ser Cys Leu
                20                  25                  30

Ser Leu Leu Ser Ser Trp Asp Tyr Arg Arg Leu Pro Pro Arg Pro Ala
            35                  40                  45

Thr Phe Leu Tyr Phe
    50
```

<210> SEQ ID NO 160
<211> LENGTH: 922
<212> TYPE: DNA
<213> ORGANISM: Homo sapiens

<400> SEQUENCE: 160

```
gcttgactat tagctccttt tctttaccta ttattattat ttattttcag atggagtcta      60
cactgtcgcc aggctggagt acagtggcgc catctcggct cactgaaccc tccacctacc    120
gggttcaagt gattctactg ccgcagtctc cagagtagtg ggactacagg catgcactac    180
cacacccagc taattttttg tattttttagt tgagatgggg tttcaccatg atggccagga   240
tggtctcgat ctcttgacct catgatctgc ctgcctcagc ctcccaaagt gctgggatta    300
cgggcatgag ccactgtgct aggcctacct attttaaaaa taacaagaat tcatccaatg    360
gaacgctgaa atgcctgtgg aggatacaag attaatcagc aggattatat ttgcctatga    420
ctccattaat tcaattccag accctactta tcacttatgg gtctaatgtc ctttattagg    480
caatgtagga gattcctata ctcctaataa agtaatcttt tccatttaaa tatctttgct    540
tttatcaggc agtatgtatt tccacaaagt taattcaatg aaatacacct aaagctgaga    600
gtcttatctc gttaatgaat gaaaaataga aatcaattat tctgagatga gattcttcct    660
ataattttta ttagttgttg tgaaatggta catgggtttg tcttgaagat atgatgatgt    720
attaattctt aatattgaat taaatgcctc tgaagtagag atgactctct tgtcatgga    780
gttacagttg tttgattaaa ttgcattgaa ttttgaatgt taatgttata tattaactta    840
aatgagattt tccaatataa atactctgtg aacctccagc cttgtgtttc tttctttttt    900
tttttttttt ttttttttttt tt                                             922
```

<210> SEQ ID NO 161
<211> LENGTH: 921
<212> TYPE: DNA
<213> ORGANISM: Homo sapiens

<400> SEQUENCE: 161

```
gcttgactat tagctccttt tctttaccta ttattattat ttatttttca gatggagtct     60
cacactgtcg ccaggctgga gtacagtggc gccatctcgg ctcactgaac cctccaccta   120
ccgggttcaa gtgattctac tgccgcagtc tccagagtag ctgggactac aggcatgcac    180
taccacaccc agctaatttt ttgtattttt agttgagatg gggttttcac catgatggcc    240
aggatggtct cgatctcttg acctcatgat ctgcctgcct cagcctccca aagtgctggg    300
attacgggca tgagccactg tgctaggcct acctatttta aaaataacaa gaattcatcc    360
aatgaaacgc tgaaatgcct gtggaggata caagattaat cagcaggatt atatttgcct    420
atgactccat taattcaatt ccagacccta cttagggtct aatgtccttt attaggcaat    480
gtaggagatt cctatacttc taataaagta atctttttcc atttaaatag tctttgcttt    540
```

```
ttatcaggca gtatgtattt ccacaaagtt aattcaatga atacaccta aagctgagag      600 tcttatctcg ttaatgaatg aaaaatagaa atcaattatt ctgagatgag attcttccta      660 taattttat tagttgttgt gaaatggtac atgggtttgt cttgaagata tgatgatgta       720
ttaattctta atattgaatt aaatgcctct gaagtagaga tgactctctt tgtcatggag      780
ttacagttgt ttgattaaat tgcattgaat tttgaatgtt aatgttatat attaacttaa      840
atgagatttt ccaatataaa tactctgtga acctccagcc ttgtgtttct ttctttttt       900 tttttttttt tttttttttt t                                                921
```

<210> SEQ ID NO 162
<211> LENGTH: 46
<212> TYPE: PRT
<213> ORGANISM: Homo sapiens

<400> SEQUENCE: 162

```
Met Lys Phe Phe Val Phe Ala Leu Ile Leu Ala Leu Met Leu Ser Met
1               5                   10                  15

Thr Gly Ala Asp Ser His Ala Lys Arg His His Gly Tyr Lys Arg Lys
            20                  25                  30

Phe His Glu Lys His His Ser His Gln Gly Tyr Pro Ser Asn
        35                  40                  45
```

<210> SEQ ID NO 163
<211> LENGTH: 14
<212> TYPE: PRT
<213> ORGANISM: Homo sapiens

<400> SEQUENCE: 163

```
Met Lys Phe Phe Val Phe Ala Leu Ile Leu Ala Leu Met Leu
1               5                   10
```

<210> SEQ ID NO 164
<211> LENGTH: 1199
<212> TYPE: DNA
<213> ORGANISM: Homo sapiens

<400> SEQUENCE: 164

```
ggagaagggt ccccactgct cctgtcaagc cttgttgtgt cgggacttga actttattct       60
aagcaggtga atgcggtgca tgcaagagag acagagagaa tgtggcagga ccaaggagga      120
ggctatgcca cttatgtcac tcctggcaaa ataaggggg catggagtag ctgtttgtg        180 gtgcagatgg tgagagcagt caggtccagc acagatttta aaggttggac ccagagaatt      240
tgctgcagaa tcagatgtgg ggtgtaaggc agagaggagt caagggcaac ttcaggattt      300
ggggccggaa ctgccattag acagacagag ggacactggg ggagaagcag gttaggtggg      360
attaaaatca agagttcaag ttaagtttga gcagcctgtt agacctccag cgagggccag      420
atagaagaat ctggtttcca ggagaggtca ggatgagaga tacacacgtg gaatgattg       480 gcattgggtg gactttatat tctctgggtc gtgagacagc tggaagtga ccacggatag       540 agaagagaca aagtcacaga aaccaagaga ggtaatgttg caaggacgga acactcaact      600
ctcaaatgct gctgagacgt gggctgaggg ctgagaatgg aattgggaag accgaggtc       660 actggtgatc ctgagggttt cagtggcaag ggcaggtgga ctgcagtggg gcccggtggg      720
gatcggtgga gcatgggccc ctctcccgga gagttgcact gtaaacgagg gcagacatat      780
gggagtgcag ctagagggag ggaacgtagg gtcaaggaga gtttattct gaatgagaga      840 gatcacagct tgtttttagg ctgacgggca tgatccatag agggaaagt aattaagatg       900
```

```
cagaagagag gccggggggtg gtggctcacg cctgtaatct cagcactttg ggaggctgag      960
gtgggtggat catttgagga caggagttcg agaccatcct ggccagcatg gtgaaaactc     1020
gcctctacta aaaataaaaa taaaaaaaaa ttagctgggt gtggtggagg gcacctgtag     1080
taccagctac ttgggaggct gaggtaacag aatcgcttga accctggagg cagggggttgc     1140 agtgagctga gattgtgcca ctgcactcta gcctgggcaa caaattgaga ctccatctc      1199
```

<210> SEQ ID NO 165
<211> LENGTH: 1199
<212> TYPE: DNA
<213> ORGANISM: Homo sapiens

<400> SEQUENCE: 165

```
ggagaagggt ccccactgct cctgtcaagc cttgttgtgt cgggacttga actttattct       60
aagcaggtga atgcggtgca tgcaagagag acagagagaa tgtggcacga ccaaggagga      120
ggctatgcca cttatgtcac tcctggcaaa aataaggggg catggagtag gctgtttgtg      180
gtgcagatgg tgagagcagt caggtccagc acagatttta aaggttggac ccagagaatt      240
tgctgcagaa tcagatgtgg ggtgtaaggc agagaggagt caagggcaac ttcaggattt      300
ggggccggaa ctgccattag acagacaggg acactggggg agaagcaggt taggtgggat      360
taaaatcaag agttcaagtt aagtttgagc agcctgttag acctccaacg agggccagat      420
agaagaatct ggtttccagg gagaggtcag gatgagagat acacacgtgg gaatgattgg      480
cattgggcgg actttatatt ctctgggcca gtgagacagc tgggaagtga ccacggatag      540
agaagagaca aagtcacaga aaccaagaga ggtaatgttg caaggacgga acactcaact      600
ctcaaatgct gctgagacgt gggctgaggg ctgagaatgg aattgggaag aaccgaggtc      660
actggtgatc ctgagggttt cagtggcaag ggcaggtgga ctgcagtggg gcccggtggg      720
gatgggtgga gcatgggccc ctctcccgga gagttgcact gtaaacgagg gcagacatat      780
gggagtgcag ctagagggag ggaacgtagg gtcaaggag agtttattct gaatgagaga      840
gatcacagct tgtttttagg ctgacgggca tgatccatag aggggaaagt aattaagatg      900
cagaagagag gccgggggtg gtggctcacg cctgtaatct cagcactttg ggaggctgag      960
gtgggtggat catttgagga caggagttcg agaccatcct ggccagcatg gtgaaaactc     1020
gcctctacta aaaataaaaa taaaaaaaaa ttagctgggt gcggtggagg gcacctgtag     1080
taccagctac ttgggaggct gaggtaacag aatcgcttga accctggagg cagggggttgc     1140 agtgagctga gattgtgcca ctgcactcta gcctgggcaa caaattgaga ctccatctc      1199
```

<210> SEQ ID NO 166
<211> LENGTH: 261
<212> TYPE: PRT
<213> ORGANISM: Homo sapiens
<220> FEATURE:
<223> OTHER INFORMATION: translation clone from C18-F3
<220> FEATURE:
<221> NAME/KEY: misc_feature
<222> LOCATION: (223)..(224)
<223> OTHER INFORMATION: Xaa can be any naturally occurring amino acid
<220> FEATURE:
<221> NAME/KEY: misc_feature
<222> LOCATION: (229)..(230)
<223> OTHER INFORMATION: Xaa can be any naturally occurring amino acid
<220> FEATURE:
<221> NAME/KEY: misc_feature
<222> LOCATION: (235)..(235)
<223> OTHER INFORMATION: Xaa can be any naturally occurring amino acid
<220> FEATURE:

```
<221> NAME/KEY: misc_feature
<222> LOCATION: (237)..(238)
<223> OTHER INFORMATION: Xaa can be any naturally occurring amino acid
<220> FEATURE:
<221> NAME/KEY: misc_feature
<222> LOCATION: (240)..(240)
<223> OTHER INFORMATION: Xaa can be any naturally occurring amino acid
<220> FEATURE:
<221> NAME/KEY: misc_feature
<222> LOCATION: (242)..(242)
<223> OTHER INFORMATION: Xaa can be any naturally occurring amino acid
<220> FEATURE:
<221> NAME/KEY: misc_feature
<222> LOCATION: (244)..(244)
<223> OTHER INFORMATION: Xaa can be any naturally occurring amino acid
<220> FEATURE:
<221> NAME/KEY: misc_feature
<222> LOCATION: (248)..(250)
<223> OTHER INFORMATION: Xaa can be any naturally occurring amino acid
<220> FEATURE:
<221> NAME/KEY: misc_feature
<222> LOCATION: (252)..(252)
<223> OTHER INFORMATION: Xaa can be any naturally occurring amino acid
<220> FEATURE:
<221> NAME/KEY: misc_feature
<222> LOCATION: (254)..(254)
<223> OTHER INFORMATION: Xaa can be any naturally occurring amino acid
<220> FEATURE:
<221> NAME/KEY: misc_feature
<222> LOCATION: (256)..(256)
<223> OTHER INFORMATION: Xaa can be any naturally occurring amino acid
<220> FEATURE:
<221> NAME/KEY: misc_feature
<222> LOCATION: (258)..(258)
<223> OTHER INFORMATION: Xaa can be any naturally occurring amino acid
<220> FEATURE:
<221> NAME/KEY: misc_feature
<222> LOCATION: (260)..(260)
<223> OTHER INFORMATION: Xaa can be any naturally occurring amino acid

<400> SEQUENCE: 166

Ser Asp Phe Leu Cys Leu Thr Ile Ser Ser Phe Ser Leu Pro Ile Ile
1               5                   10                  15

Ile Ile Tyr Phe Ser Asp Gly Val Ser His Cys Arg Gln Ala Gly Val
            20                  25                  30

Gln Trp Arg His Leu Gly Ser Leu Asn Pro Pro Thr Gly Phe Lys
        35                  40                  45

Phe Tyr Cys Arg Ser Leu Gln Ser Ser Trp Asp Tyr Arg His Ala Leu
    50                  55                  60

Pro His Pro Ala Asn Phe Leu Tyr Phe Leu Arg Trp Gly Phe Thr Met
65                  70                  75                  80

Met Ala Arg Met Val Ser Ile Ser Pro His Asp Leu Pro Ala Ser Ala
                85                  90                  95

Ser Gln Ser Ala Gly Ile Thr Gly Met Ser His Cys Ala Arg Pro Thr
            100                 105                 110

Tyr Phe Lys Asn Asn Lys Asn Ser Ser Asn Gly Thr Leu Lys Cys Leu
        115                 120                 125

Trp Arg Ile Gln Asp Ser Ala Gly Leu Tyr Leu Pro Met Thr Pro Leu
    130                 135                 140

Ile Gln Phe Gln Thr Leu Leu Met Gly Leu Met Ser Phe Ile Arg Gln
145                 150                 155                 160

Cys Arg Arg Phe Leu Tyr Ser Ser Asn Leu Phe Pro Phe Lys Tyr Leu
                165                 170                 175

Cys Phe Leu Ser Gly Ser Met Tyr Phe His Lys Val Asn Ser Met Lys
            180                 185                 190

Tyr Thr Ser Glu Ser Tyr Leu Val Asn Glu Lys Ile Glu Ile Asn Tyr
```

```
            195                 200                 205
Ser Glu Met Arg Phe Phe Leu Phe Leu Leu Val Val Val Lys Xaa Xaa
        210                 215                 220

Trp Val Cys Leu Xaa Xaa Cys Ile Asn Ser Xaa Tyr Xaa Xaa Lys Xaa
225                 230                 235                 240

Leu Xaa Ser Xaa Asp Asp Ser Xaa Xaa Met Xaa Thr Xaa His Xaa
                245                 250                 255

Val Xaa Phe Xaa Lys
            260

<210> SEQ ID NO 167
<211> LENGTH: 144
<212> TYPE: PRT
<213> ORGANISM: Homo sapiens
<220> FEATURE:
<221> NAME/KEY: misc_feature
<223> OTHER INFORMATION: translation clone from S55M-R2

<400> SEQUENCE: 167

Leu Asn Ile Ser Asn Pro Asn Ile Ser Tyr Ser Phe Val Cys Ile Tyr
1               5                   10                  15

Cys Gly Leu Gly Leu His Met Phe Ser Phe His Gln Cys Trp Ser Val
            20                  25                  30

Cys Pro Val Leu Val Leu Ile Ala Leu Gly Phe Phe Phe Phe
        35                  40                  45

Glu Met Glu Ser Arg Ser Val Ala Gln Ala Gly Val Gln Trp His Asn
    50                  55                  60

Leu Gly Ser Leu Gln Ala Leu Pro Pro Gly Phe Met Pro Phe Ser Cys
65                  70                  75                  80

Leu Ser Leu Leu Ser Ser Trp Asp Tyr Arg Arg Leu Pro Pro Arg Pro
                85                  90                  95

Ala Thr Phe Leu Tyr Phe Pro Arg Gln Gly Phe Thr Val Leu Ala Arg
            100                 105                 110

Met Val Ser Ile Ser Pro Arg Asp Pro Pro Ala Ser Ala Ser Gln Ser
        115                 120                 125

Val Gly Ile Ala Tyr Ile Ser Asn Pro Ala Ala Met Ala Ala Gly
            130                 135                 140

<210> SEQ ID NO 168
<211> LENGTH: 13
<212> TYPE: PRT
<213> ORGANISM: Homo sapiens

<400> SEQUENCE: 168

Ile Leu Ala Leu Met Leu Ser Met Cys Gly Ala Asp Ser
1               5                   10

<210> SEQ ID NO 169
<211> LENGTH: 277
<212> TYPE: PRT
<213> ORGANISM: Homo sapiens

<400> SEQUENCE: 169

Met Tyr Ile Ile Tyr Leu Lys Leu Tyr Gln Pro Lys Lys Ser
1               5                   10                  15

Glu Arg Val Leu Arg Ala Val Pro Thr Ser Leu His Leu His Ile His
            20                  25                  30

Ala Ser Leu Tyr Pro Asp Ile Pro Thr Ser Pro His Pro Tyr Ile Thr
            35                  40                  45
```

```
Val Ser Pro His Pro Cys Ile Leu Ile Ser Pro His Ile Ser Leu Ser
     50                  55                  60

Pro His Pro His Phe Pro Ala Pro Ser Ser Cys Arg Thr Leu Leu Leu
 65                  70                  75                  80

Pro Ala Val Ser Arg Gln Gln Arg Val Pro Ser Pro Ser His Tyr Gly
                 85                  90                  95

Val His Met Asp Cys Gly Leu Met Glu Pro Pro Ser Arg Glu Ser Ile
                100                 105                 110

Ala Phe Pro Asp Arg Phe Pro Ala Lys Leu Met Leu Gly Leu Leu Ile
            115                 120                 125

Phe Thr Glu Ile Thr Cys Cys Glu Arg Arg Val Tyr Gly Pro Leu
            130                 135                 140

Thr Asn Pro Lys Pro Gln Ser Leu Ser Ala Ile Asn Pro Lys Gly Gly
145                 150                 155                 160

Thr Glu Asn Ser Arg Leu Phe Trp Gly Ser Asn Cys Cys Leu Glu Val
                165                 170                 175

Phe Leu Ser Tyr Arg Cys Val Thr Leu Ser Ala Gln Gly Arg Gly Thr
            180                 185                 190

Pro Lys Pro Gly Leu Ser Gly Ala Pro Cys Thr Asp Arg Arg Ala Met
            195                 200                 205

Ser Phe Phe His Cys Tyr Arg Ser Ile Leu His Thr Lys Val Gly Phe
            210                 215                 220

Tyr Val Lys Ile Lys Lys Lys Arg Lys Lys Lys Arg Asn Asn Asn
225                 230                 235                 240

Asn Asn Asn Lys Asn Asn Asn Lys Tyr Ile Tyr Ile Leu Lys Arg
                245                 250                 255

Lys Glu Asn Lys Ala Lys Thr Cys Asn Thr Val Phe Ser Arg Arg Asn
            260                 265                 270

Lys Ser Thr Asn Lys
            275

<210> SEQ ID NO 170
<211> LENGTH: 582
<212> TYPE: PRT
<213> ORGANISM: Homo sapiens

<400> SEQUENCE: 170

Met Thr Lys Phe Tyr Cys Gly Trp Asp Arg Leu Leu Glu Ser Leu Pro
  1               5                  10                  15

Asp Gly Trp Val Tyr Cys Asp Ala Asp Gly Ser Gln Phe Asp Ser Ser
                 20                  25                  30

Leu Ser Pro Tyr Leu Ile Asn Ala Val Leu Asn Ile Arg Leu Gly Phe
             35                  40                  45

Met Glu Glu Trp Asp Val Gly Glu Ile Met Leu Arg Asn Leu Tyr Thr
     50                  55                  60

Glu Ile Val Tyr Thr Pro Ile Ser Thr Pro Asp Gly Thr Leu Val Lys
 65                  70                  75                  80

Lys Phe Lys Gly Asn Asn Ser Gly Gln Pro Ser Thr Val Val Asp Asn
                 85                  90                  95

Thr Leu Met Val Ile Leu Ala Val Asn Tyr Ser Leu Lys Lys Ser Gly
                100                 105                 110

Ile Pro Ser Glu Leu Arg Asp Ser Ile Arg Phe Phe Val Asn Gly
            115                 120                 125

Asp Asp Leu Leu Leu Ser Val His Pro Glu Tyr Glu Tyr Ile Leu Asp
```

```
                130                 135                 140
Thr Met Ala Asp Asn Phe Arg Glu Leu Gly Leu Lys Tyr Thr Phe Asp
145                 150                 155                 160

Ser Arg Thr Arg Glu Lys Gly Asp Leu Trp Phe Met Ser His Gln Gly
                165                 170                 175

His Lys Arg Glu Gly Ile Trp Ile Pro Lys Leu Glu Pro Glu Arg Ile
                180                 185                 190

Val Ser Ile Leu Glu Trp Asp Arg Ser Lys Glu Pro Cys His Arg Leu
                195                 200                 205

Glu Ala Ile Cys Ala Ala Met Ile Glu Ser Trp Gly Tyr Asp Lys Leu
                210                 215                 220

Thr His Glu Ile Arg Lys Phe Tyr Ala Trp Met Ile Glu Gln Ala Pro
225                 230                 235                 240

Phe Ser Ser Leu Ala Gln Glu Gly Lys Ala Pro Tyr Ile Ala Glu Thr
                245                 250                 255

Ala Leu Arg Lys Leu Tyr Leu Asp Lys Glu Pro Ala Gln Glu Asp Leu
                260                 265                 270

Thr His Tyr Leu Gln Ala Ile Phe Glu Asp Tyr Glu Asp Gly Ala Glu
                275                 280                 285

Thr Cys Val Tyr His Gln Ala Gly Glu Thr Pro Asp Ala Gly Leu Thr
                290                 295                 300

Asp Glu Gln Lys Gln Ala Glu Lys Glu Lys Glu Arg Glu Lys Ala
305                 310                 315                 320

Glu Lys Glu Arg Glu Arg Gln Lys Gln Leu Ala Leu Lys Lys Gly Lys
                325                 330                 335

Asp Val Ala Gln Glu Glu Gly Lys Arg Asp Arg Glu Val Asn Ala Gly
                340                 345                 350

Thr Ser Gly Thr Phe Ser Val Pro Arg Leu Lys Ser Leu Thr Ser Lys
                355                 360                 365

Met Arg Val Pro Arg Tyr Glu Gln Arg Val Ala Leu Asn Leu Asp His
                370                 375                 380

Leu Ile Leu Tyr Thr Pro Glu Gln Thr Asp Leu Ser Asn Thr Arg Ser
385                 390                 395                 400

Thr Arg Lys Gln Phe Asp Thr Trp Phe Glu Gly Val Met Ala Asp Tyr
                405                 410                 415

Glu Leu Thr Glu Asp Lys Met Gln Ile Ile Leu Asn Gly Leu Met Val
                420                 425                 430

Trp Cys Ile Glu Asn Gly Thr Ser Pro Asn Ile Asn Gly Met Trp Val
                435                 440                 445

Met Met Asp Gly Asp Asp Gln Val Glu Phe Pro Ile Lys Pro Leu Ile
450                 455                 460

Asp His Ala Lys Pro Thr Phe Arg Gln Ile Met Ala His Phe Ser Asp
465                 470                 475                 480

Val Ala Glu Ala Tyr Ile Glu Lys Arg Asn Gln Asp Arg Pro Tyr Met
                485                 490                 495

Pro Arg Tyr Gly Leu Gln Arg Asn Leu Thr Asp Met Ser Leu Ala Arg
                500                 505                 510

Tyr Ala Phe Asp Phe Tyr Glu Met Thr Ser Arg Thr Pro Ile Arg Ala
                515                 520                 525

Arg Glu Ala His Ile Gln Met Lys Ala Ala Leu Arg Gly Ala Asn
                530                 535                 540

Asn Asn Leu Phe Gly Leu Asp Gly Asn Val Gly Thr Thr Val Glu Asn
545                 550                 555                 560
```

-continued

Thr Glu Arg His Thr Thr Glu Asp Val Asn Arg Asn Met His Asn Leu
                565                 570                 575

Leu Gly Val Lys Gly Leu
            580

<210> SEQ ID NO 171
<211> LENGTH: 24
<212> TYPE: PRT
<213> ORGANISM: Homo sapiens

<400> SEQUENCE: 171

Lys Phe Phe Val Phe Ala Leu Ile Leu Ala Leu Met Leu Ser Met Cys
1               5                   10                  15

Gly Ala Asp Ser His Ala Lys Arg
            20

<210> SEQ ID NO 172
<211> LENGTH: 20
<212> TYPE: PRT
<213> ORGANISM: Homo sapiens

<400> SEQUENCE: 172

Lys Ser Tyr Met Ser Met Phe Leu Leu Leu Met Ala Ile Ser Cys Val
1               5                   10                  15

Leu Ala Lys Asp
            20

<210> SEQ ID NO 173
<211> LENGTH: 18
<212> TYPE: PRT
<213> ORGANISM: Homo sapiens

<400> SEQUENCE: 173

Pro Leu Met Ile Ile His His Leu Asp Asp Cys Pro His Ser Gln Ala
1               5                   10                  15

Leu Lys

<210> SEQ ID NO 174
<211> LENGTH: 19
<212> TYPE: DNA
<213> ORGANISM: Artificial Sequence
<220> FEATURE:
<223> OTHER INFORMATION: Oligonucleotide for the PCR

<400> SEQUENCE: 174
gtggtaaagc acccaggaa                                            19

<210> SEQ ID NO 175
<211> LENGTH: 20
<212> TYPE: DNA
<213> ORGANISM: Artificial Sequence
<220> FEATURE:
<223> OTHER INFORMATION: Oligonucleotide for the PCR

<400> SEQUENCE: 175
gctagctgga tgtcttttgc                                           20

<210> SEQ ID NO 176
<211> LENGTH: 19
<212> TYPE: DNA
<213> ORGANISM: Artificial Sequence
<220> FEATURE:
<223> OTHER INFORMATION: Oligonucleotide for the PCR

```
<400> SEQUENCE: 176
tgaaggtcgg agtcaacgg                                              19

<210> SEQ ID NO 177
<211> LENGTH: 18
<212> TYPE: DNA
<213> ORGANISM: Artificial Sequence
<220> FEATURE:
<223> OTHER INFORMATION: Oligonucleotide for the PCR

<400> SEQUENCE: 177
catgtgggcc atgaggtc                                               18

<210> SEQ ID NO 178
<211> LENGTH: 20
<212> TYPE: DNA
<213> ORGANISM: Artificial Sequence
<220> FEATURE:
<223> OTHER INFORMATION: Oligonucleotide for the PCR

<400> SEQUENCE: 178
ggacttcgag caagagatgg                                             20

<210> SEQ ID NO 179
<211> LENGTH: 20
<212> TYPE: DNA
<213> ORGANISM: Artificial Sequence
<220> FEATURE:
<223> OTHER INFORMATION: Oligonucleotide for the PCR

<400> SEQUENCE: 179
agcactgtgt tggcgtacag                                             20

<210> SEQ ID NO 180
<211> LENGTH: 19
<212> TYPE: DNA
<213> ORGANISM: Artificial Sequence
<220> FEATURE:
<223> OTHER INFORMATION: Oligonucleotide for the PCR

<400> SEQUENCE: 180
tttttttttt tttttttt                                               19
```

TRACEABILITY OF CELLULAR CYCLE ANOMALIES TARGETING ONCOLOGY AND NEURODEGENERATION

CROSS REFERENCE TO RELATED APPLICATIONS

This is a Divisional Application of U.S. patent application Ser. No. 12/047,173 filed on Mar. 12, 2008 now U.S. Pat. No. 8,039,439 which is a continuation in part application of U.S. patent application Ser. No. 11/908,103 filed on Sep. 7, 2007 which is a National Phase Entry of PCT Application Serial No. PCT/FR2006/000510 filed on Mar. 7, 2006 which claims priority from French Patent Application Nos. 0502258 and 0502257 filed on Mar. 7, 2005.

FIELD OF THE INVENTION

The present invention relates to the field of medicine and biology. It concerns a novel test for screening and for therapeutic follow-up in oncology. More particularly, it relates to diagnostic and/or therapeutic tests in oncology and on neurodegenerative diseases.

DESCRIPTION OF THE PRIOR ART

Age-related neurodegenerative diseases and cancers both involve a modification of the physiological process of programmed cell death or apoptosis. Neuronal death is abnormally accelerated during neurodegenerative diseases such as Alzheimer's disease, Huntington's disease, Parkinson's disease, etc. On the other hand, the cancerization process corresponds to a blocking of apoptosis which results in an uncontrolled multiplication of cells. The link between these two processes has currently become a major field of investigation in research on aging.

The control of the balance between cell division (mitosis), differentiation and programmed cell death (apoptosis) is fundamental during normal physiological processes, such as embryonic development, tissue regeneration and aging. An impairment of this balance can lead to major pathological situations such as the formation of tumors or certain neurodegenerative diseases.

Cancer is one of the principal causes of mortality throughout the world. Although, over the course of the last generation, the percentages of deaths related to cardiac and cardiovascular diseases and a large number of other diseases has decreased, the number of deaths related to the various forms of cancer is on the increase.

Despite the rapid advance in our understanding of the various forms of cancer, the low survival rates can generally be attributed to inadequate diagnosis and inadequate treatment. Most tumors can only be detected when they reach a size of approximately 1 cm. Since there is a relatively short period of time from the continuous development of a tumor to a stage which has become incompatible with survival, this leaves little time for a therapeutic intervention. Early diagnosis therefore becomes the key to success for the treatment of cancer.

For a multitude of reasons, early diagnosis remains illusory for most forms of cancer. For certain forms of cancer, disease-specific markers are not available or are only available at an advanced stage of the disease, making diagnosis difficult. In certain other forms of cancer, the markers are available but are not always specific for the disease or they may be associated with its benign form. In yet other cases, the techniques exist but the prohibitive cost for applying them to the population in general makes them unsuitable.

Skin cancer, for example, is the most widespread cancer in Canada. In 1992 alone, 50 300 new cases of skin cancer were reported, compared with 19 300 cases of lung cancer, 16 200 cases of colorectal cancer and 15 700 cases of breast cancer. In other words, skin cancer is as common as the three main types of cancer combined. Its incidence continues to increase, with 64 200 new cases thereof in 1997, that is an increase of 14 000 cases annually in 5 years. In particular, the incidence of malignant melanoma is increasing at a rate of 2% per year. Early diagnosis remains the key to an effective treatment. A malignant tumor is readily accessible and can be removed with minor surgery. In fact, recovery is 100% if skin cancer is detected early enough. The early diagnosis of skin cancer remains, however, difficult. The latter is not just one disease but an entire range of conditions related to one another, which appear similar in many cases upon visual inspection. A diagnosis on the basis of such an inspection is therefore subjective. In order to understand this subjectivity more fully, an abnormal skin growth should be considered. This growth may be pigmented or nonpigmented. If it is nonpigmented and malignant, it is then probably a basocellular epithelioma or a spinocellular epithelioma. However, the clinical development of these two forms of cancer is very different. A basocellular epithelioma spreads out laterally over the surface of the skin, without penetrating into the deeper skin layers. Thus, although it can be disfiguring, a basocellular epithelioma rarely develops metastases and is rarely fatal. However, a spinocellular epithelioma causes metastases and is often fatal. It therefore becomes important to be able to distinguish these two types of skin cancer. A definitive diagnosis of skin cancer requires a biopsy and histological analysis. However, the decision to send a biopsy for analysis (or even whether a patient should be referred to a dermatologist) becomes very subjective. There are several biopsies which are not taken although they should have been.

Colon cancer is the third most common cause of cancer-related mortality in men and women in North America (16 200 cases per year). Early detection, leading to an early intervention, has demonstrated that treatment success and survival rate can be improved. For example, the 5-year survival rate is 92% for a patient whose disease was detected at an early stage, whereas the rate drops to approximately 60% in patients with a localized cancer, and to approximately 6% in those with metastases. However, only a third of colon cancers are detected at an early stage. One of the reasons for this delay in diagnosis is the absence of a sensitive, relatively inexpensive, non-invasive screening test.

Breast cancer is one of the most common cancers in women, with colon cancer. The mortality rate is the highest of all the cancers affecting women.

There are very few diagnostic markers capable of detecting breast cancer and they only have a predictive value of 20%. There are no markers, either, which can detect or determine the invasiveness or the aggressiveness of metastatic cancer cells.

Over the last few years, considerable progress has been made in the understanding of the means used by oncogenes and tumor suppressor genes for regulating cell proliferation and apoptosis. One of the main targets of these regulators is the family of E2F-type transcription factors in the E2F and RB protein signaling pathway. These proteins play a central role in controlling cell division by coupling the regulation of the genes required for progression of the cell cycle with extracellular signals (mitogens, proliferation inhibitors). It behaves as an oncogene by stimulating tumor cell proliferation.

Among the expressed genes are found:
- overexpression of the E2F4 transcription factor and the c-myc oncogene which induce apoptosis of post-mitotic cells by accumulation of oxygenated reactants (Tanaka, 2002);
- the p53 gene, which belongs to the tumor suppressor gene family, blocks the cell cycle in the case of DNA lesion. It has now been demonstrated that this gene is also involved in the progression of apoptosis (Oren, 1994; Yonish-Rouach, 1996);
- the cyclin D1, one of the proteins constituting the regulatory subunits of the kinases of the cell cycle, essential to the progression of the cell cycle. This protein is also expressed during apoptosis in various cell types (Han et al, 1996; Pardo et al, 1996).

It would be desirable to have novel diagnostic methods which would detect the presence of cancer with greater specificity and which would make it possible to distinguish between aggressive cancer cells having a tendency to metastasize and those which are more localized which have a lower probability of metastasizing. A marker which can therefore reveal cell proliferation would be of great use.

SUMMARY OF THE INVENTION

The present invention concerns a novel test for screening for reinduction of the cell cycle targeting oncology. It is a diagnostic test and a prognostic test for various cancers (breast cancer, bladder cancer, ovarian cancer, lung cancer, skin cancer, prostate cancer, colon cancer, liver cancer, glioblastoma, sarcoma, leukaemia, etc.). More particularly, the invention concerns the use of the LIV21 protein and of derivatives thereof as diagnostic and prognostic markers for cancers. The invention therefore concerns the detection of the LIV21 protein with a kit comprising LIV21-specific antibodies.

A first objective of the present invention is to demonstrate a method for the detection and prognosis of cancer and of its metastatic potential. Preferably, the cancer is selected from breast cancer, bladder cancer, ovarian cancer, lung cancer, skin cancer, prostate cancer, colon cancer, liver cancer, a sarcoma, a leukaemia and glyoblastoma, without being limited thereto.

One aspect of the present invention consists of the use of LIV21 and isoforms of LIV21 as a prognostic indicator for cancer. In fact, when LIV21 is located in the cytoplasm, the cancer cells in the tissues are aggressive. Conversely, when the LIV21 gene expression product is preferentially located in the cell nucleus, this is a prognostic indicator that the cells of the tissue are differentiated and quiescent and therefore non-invasive. The effectiveness of a cancer treatment can also be monitored by the traceability of this protein, and of its derivatives and ratios with the associated proteins.

Moreover, detection of protein kinase C epsilon (PKCε) is also advantageous since it has been determined that PKCε phosphorylates the LIV21 protein in order to maintain it in the cytoplasm. Thus, a significant increase in PKCε is indicative of the presence of cancer cells. Moreover, the LIV21/PKCε ratio increases in the cytoplasmic fraction of cancer cells.

In addition, the detection of the E2F1 and/or E2F4 proteins is advantageous. In fact, the LIV21 protein forms a complex with E2F4 which is capable of inhibiting the expression of the E2F1 gene in the nucleus, E2F1 gene expression being a sign of cell proliferation. Thus, a decrease in the association of LIV21 with the E2F4 protein is indicative of the presence of cancer cells. Similarly, the presence of the E2F1 protein in the nucleus is indicative of the presence of cancer cells.

Consequently, the present invention concerns a method for the detection (in vitro or ex vivo) of cancer cells in a biological tissue sample (for example, breast, ovary, endometrium, bladder, melanoma, prostate, glioblastoma, etc.) from patients, this method comprising the detection of the product of expression of the LIV21 gene in the nucleus and/or the cytoplasm of the cells in the biological tissue sample from said patient, localization of said product of expression of the LIV21 gene in the cytoplasm being indicative of the presence of cancer cells, and localization of said product of expression of the LIV21 gene in the nucleus being indicative of the presence of noncancer cells. Preferably, localization of said product of expression of the LIV21 gene in the cytoplasm is indicative of the presence of invasive and/or metastatic cancer cells.

Optionally, the method according to the present invention also comprises the detection of the product of expression of at least one gene selected from the group consisting of the protein kinase C epsilon (PKCε) gene, the E2F1 gene and the E2F4 gene. The method can in particular comprise the detection of the product of expression of two of these genes or of the three genes. Moreover, at least one of the ratios LIV21/PKCε, LIV21/E2F4 and LIV21/E2F1 can be determined in the present method. This ratio can be determined in the cytoplasm and/or in the nucleus. Preferably, these ratios are determined in the nucleus. Preferably, these ratios are compared with those obtained in a normal cell.

The same is true of the detection of HDAC1, which has been shown to be involved in PML/SUMO1/Rb/HDAC-1 complexes. More generally, the HDAC family plays a key role in the regulation of gene expression. When the HDACs are overexpressed, they bring about tumor suppressor gene silencing, hence the advantage of using HDAC inhibitors in therapy, combined with other inhibitors which regulate the metabolic cascade involving the protein complex which contains LIV21. The level of expression of each enzyme or polypeptide of the SUMO/Rb/HDAC complex or, for certain cell types, of the PML/SUMO/Rb/HDAC complex is an additional indictor of the proliferative state of the cell. Thus, in a specific embodiment, the method according to the present invention also comprises the detection of the product of expression of at least one gene selected from the group consisting of SUMO1, Rb, HDAC and PML.

The methods according to the present invention also consist in using the detection of the LIV21 protein in combination with all the proliferation markers and transcription factors which play a role in the cancerization and neurodegeneration process. The method therefore also comprises the detection of the product of expression of at least five genes selected from the group consisting of RBP2, E2F4, E2F1, E2F2, SUMO1, HDAC1, cycE/cdk2, cdk1, CREB1, p300, Rb, PML, p107 and p130 of the pocket protein family. Thus, the invention lies in the fabrication and the use of diagnostic antibody arrays (FIG. 2) comprising LIV21-specific antibodies and antibodies for the various proteins of the LIV21-associated complex according to the phases of the cell cycle, that is, without restriction thereto, antibodies specific for RBP2, E2F4, E2F2, E2F1, SUMO1, SUMO3, HDAC1, cycE/cdk2, cdk1, CREB1, p300, Rb, PML, p107 and p130 of the pocket protein family (FIG. 1). In addition, the diagnostic arrays according to the present invention can comprise antibodies specific for NFkB, cdc2A, mdm2, p21, p53, p65, Ki67, erk and CAF1. Ki67 and CAF1 (Amoulzy; Institut Curie) are nuclear markers which signal the proliferative state of many cancers. The protein arrays will make it possible to study protein expression, protein interactions and post-translational modifications, more particularly phosphorylations and methylations of certain proteins, which signal a characteristic state of the diseased cell. The state of expression and of silencing of certain genes is different in diseased cells and in normal cells. Moreover, the protein interactions and the metabolism of the diseased cell are different from those of the normal cell.

The other aspect of the present invention is the use of the proteins mentioned above as markers for the invasiveness and the metastatic aggressiveness of cancer cells of the prostate, colon, bladder, melanoma, ovary, endometrium and cervix, and cancers in neurobiology, etc.

In one embodiment, the expression product of the genes is detected at the protein level. Preferably, the protein is detected using a specific antibody. For example, the protein can be detected by Western blotting analysis. In a preferred embodiment, it is detected by immunohistochemistry, immunocytochemistry or radiography, or by peroxidase labelling by microfludiic technique (sonic or light as sers or Raman effect).

In one specific embodiment of the method comprising the detection of the expression product of the PKCε gene, a significant increase in PKCε is indicative of the presence of cancer cells. Moreover, the method can also comprise the determination of the LIV21/PKCε ratio in the nucleus and/or the cytoplasm. This ratio can be compared with that observed in a normal cell. An increase in the LIV21/PKCε ratio in the cytoplasmic fraction is indicative of cancer cells.

In another specific embodiment of the method comprising the detection of the expression product of the E2F4 gene, the method comprises the detection of the association of LIV21 with the E2F4 protein, a decrease in this association in the cell nucleus being indicative of the presence of cancer cells. Moreover, the method can also comprise the determination of the LIV21/E2F4 ratio in the nucleus and/or the cytoplasm. This ratio can be compared with that observed in a normal cell. In an additional embodiment of the method comprising the detection of the expression product of the E2F1 gene, the presence of the E2F1 protein in the nucleus is indicative of the presence of cancer cells. Moreover, the method can also comprise the determination of the LIV21/E2F1 ratio in the nucleus and/or the cytoplasm. This ratio can be compared with that observed in a normal cell. The method according to the present invention allows in particular the detection of metastasized cancer, therapeutic monitoring and/or recurrences following treatment. A second aspect of the invention concerns the human LIV21 protein and also the fragments thereof. More particularly, the present invention concerns a purified or recombinant, isolated human LIV21 protein. It concerns in particular an isolated polypeptide (issue to NT032977.8, hs1 33153) having an apparent molecular weight of approximately 50-51 kD by Western blotting analysis and of approximately 60 kD when it is sumoylated and/or a polypeptide having an isoelectric point of 5.6 in its 50-51 kD form and nine polypeptides having apparent molecular weight 110 kD, 64 kD, 51 kD, 50 kD, 49 kD, 30 kD, 17 kD, 16 kD, 15 kD in hot conditions (at 100° C.) having an isoelectric point between 5.6 and 11 in its forms and a polypeptide characterized by one of the chromatograms of FIGS. 3-6 and a polypeptide comprising a peptide sequence selected from SEQ ID Nos 1-55, preferably from SEQ ID Nos 1-5, or a sequence having 70%, 80% or 90% identity to said sequences, and one of the peptide sequences obtained by MALDI (FIGS. 7 and 8) and NanoLC-ESI-MS (FIGS. 6.1, 6.2 & 9). In a preferred embodiment, the polypeptide comprises the two peptide sequences SEQ ID Nos 1 and 2. In an even more preferred embodiment, the polypeptide comprises a third peptide sequence SEQ ID No 3 and/or a fourth peptide sequence SEQ ID No 4 or a sequence having (70%), 80% or 90% identity to said sequences. Optionally, LIV21 also comprises a sequence selected from the sequences SEQ ID Nos 5-55 or a sequence having 70%, 80% or 90% identity to said sequences. Preferably, the LIV21 protein comprises a leucine zipper motif, a basic domain characteristic of DNA binding domains, a nuclearization sequence, which not only mediates DNA binding but also acts as protein protein interaction domain for E2F2, E2F4, E2F1 (by similarity with E2F proteins family (FIGS. 10.1 and 11.1&2), item for retinoblastoma protein, Bcl2, CD53 antigen) and comprises also a Hand Domain, Zinc finger Domain (PDZ domain) and helix loop helix domain like TCFL4. The similarity of the sequence with transferase domain showed also by similarity with TRAM1L1 (with transmembrane helix and NDST3 for the (antisens) sequences of C8T7 clones (FIG. 11.3) which matched also on chromosome 4q26 permits to understand the complex interactions of LIV21. Digestion of the LIV21 protein with trypsin gives more than 54 peptides corresponding to the monoisotopic peaks among all the peptides as specified, FIGS. 3-6; FIGS. 7 and 9; FIGS. 8.1 and 8.2 (SDS PAGE gels) and sequences (sens and antisens) of LIV21 gene are ID Nos 119 to 148.

A third aspect of the invention concerns an antibody which binds specifically to a polypeptide according to the present invention. More particularly, the antibody can bind specifically to a polypeptide comprising a peptide sequence selected from SEQ ID Nos 1-55, preferably from SEQ ID Nos 1-5, or a sequence having 70%, 80% or 90% identity to said sequences. The present invention concerns in particular an anti-LIV21 serum produced by immunizing an animal or a human with a polypeptide according to the present invention, in particular a polypeptide comprising a peptide sequence selected from SEQ ID Nos 1-55, preferably from SEQ ID Nos 1-5, or a sequence having 70%, 80% or 90% identity to said sequences.

A fourth aspect of the invention concerns a kit for the detection of cancer cells in a biological sample from a patient, this kit comprising one or more elements selected from the group consisting of an antibody which binds specifically to human LIV21 according to the present invention and an anti-LIV21 serum according to the present invention. In a specific embodiment of the invention, the kit also comprises means for detecting the product of expression of five genes selected from the group consisting of the protein kinase C epsilon (PKCε) gene, the E2F1 gene, E2F2 gene and the E2F4 gene. Preferably, the detection means is an antibody specific for the protein concerned. In another preferred embodiment, the kit also comprises a means for detecting the product of expression of a gene selected from the group consisting of RBP2, SUMO1, SUMO3, HDAC1, PML, cycE/cdk2, cdk1, CREB1, p300, Rb, p107, p130, NFkB, erk, Bcl2, CD53, cdc2A, mdm2, p21, p53, p65, Ki67 and CAF1. In a preferred embodiment, the kit comprises an antibody array comprising an LIV21-specific antibody. In a preferred embodiment, the array also comprises an antibody specific for a protein selected from PKCε, E2F1 and E2F4. In addition, it can comprise five antibodies specific for a protein selected from RBP2, SUMO, HDAC1, cycE/cdk2, cdk1, CREB1, p300, Rb, PML, p107 and p130 of the pocket protein family. The array can also comprise an antibody specific for a protein selected from NFkB, cdc2A, mdm2, p21, p53, p65, Ki67 and CAF1.

The invention concerns the use of an antibody specific for human LIV21 for the diagnosis of cancer, and/or of five or more antibodies specific for a protein complex containing LIV21, for example antibodies specific for RBP2, E2F4, E2F2, E2F1, SUMO1, SUMO3, BRCA1, HDAC1, cycE/cdk1, cdk1, CREB1, p300, Rb, PML, erk, Bcl2, CD53, p107 and p130 of the pocket protein family. Preferably, the diagnosis is performed ex vivo on samples from a patient.

DESCRIPTION OF THE FIGURES

FIG. 7A-7BB is a table of the monoisotopic peaks with a value M H$^+$. The masses are given with three numbers after the decimal point by the proteomic platforms since they estimate that this is the acquisition precision limit of MALDI TOF machines.

FIGS. 9A-9C describes examples of Nano LC-ESI MS characterized peptides, including the peptides of the isoforms of LIV21. The table describes a NanoLC-ESI MS experiment. NanoLC makes it possible to separate the peptides derived from the trypsin hydrolysis of the protein. The eluted peptide fragments are ionized by electrospray and the ions formed are detected by mass spectrometry (Q-TOF analyzer). Each of these ions characterizes a peptide specific for the protein. Legend illustrated by the first page (FIG. 9A) describing the ion: molecular mass 523.25 daltons. Title: elution from 29.15 to 29.23 corresponds to the peptide eluted between 29.19 and 29.23 minutes. By ionization, this molecule gives the double-charge ion (charge=2+): MH2$^+$ of molecular mass m/z: 523.25 daltons, hence the mass of the molecule M: 1044.51. The peptide sequence of this ion is determined by MSMS. The corresponding MSMS spectrum is defined by the column of numbers between Begin ions and End ions, which corresponds to an amino acid sequence (each amino acid having a specific mass, except for leucine and isoleucine, which have the same molecular mass). The first column with a 4-decimal number (daughter ion: 86.1373) corresponds to the mass of the "daughter" ions. The second column (I: 45) corresponds to the intensity of these "daughter" ions.

FIGS. 9A-9C describes the MSMS analyses giving a set of polypeptides that can be assigned to the LIV21 protein and its complex or contaminants according to the various observers of the various subcontracting proteomics platforms. Sequences common with *Gallus gallus*, the histatin variant HIS3-HUMAN, the HSP60 chaperonin, arginine deiminase, nucleotidyltransferase, dehydrogenase.

Figure 10A:
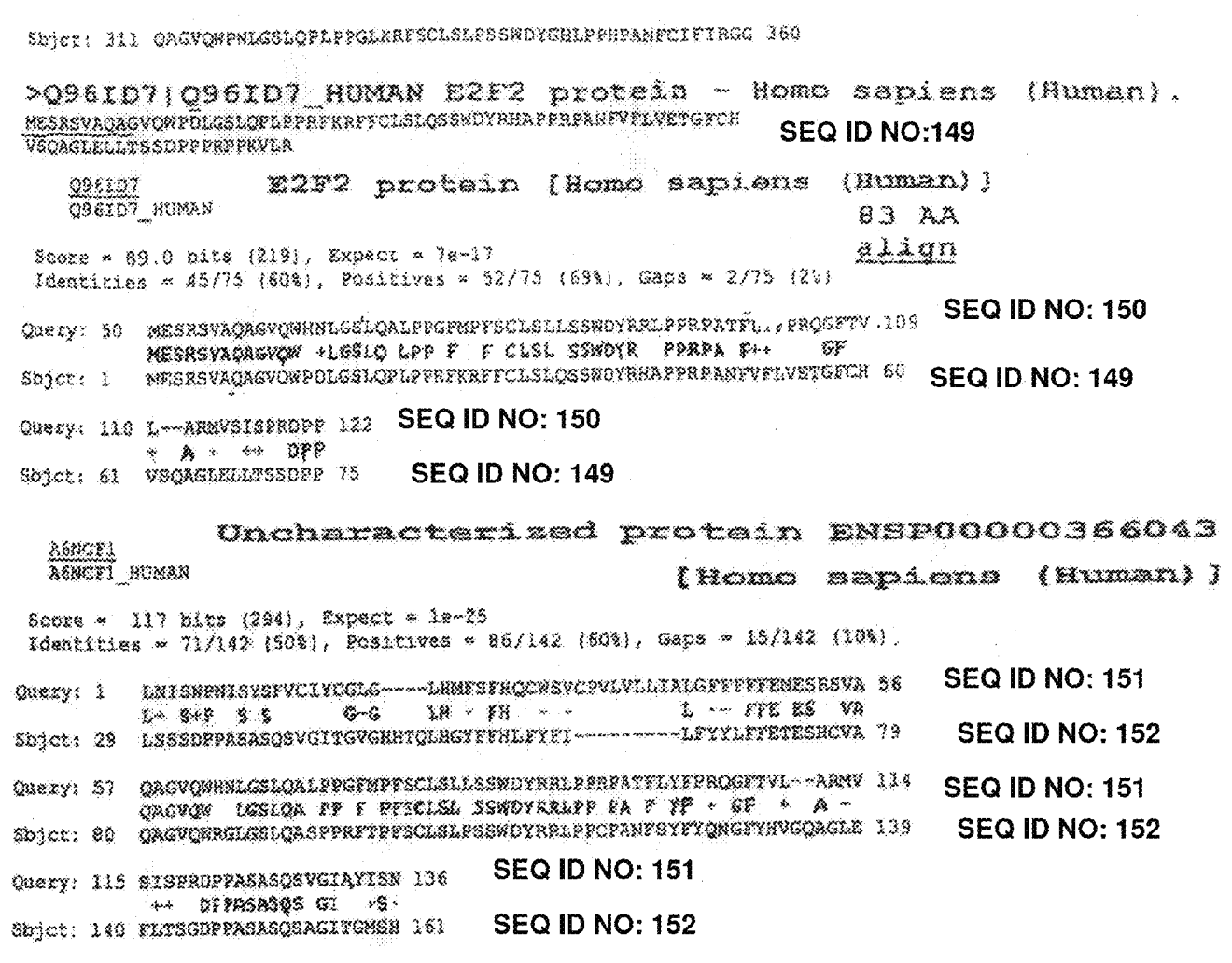
Figure 10B:
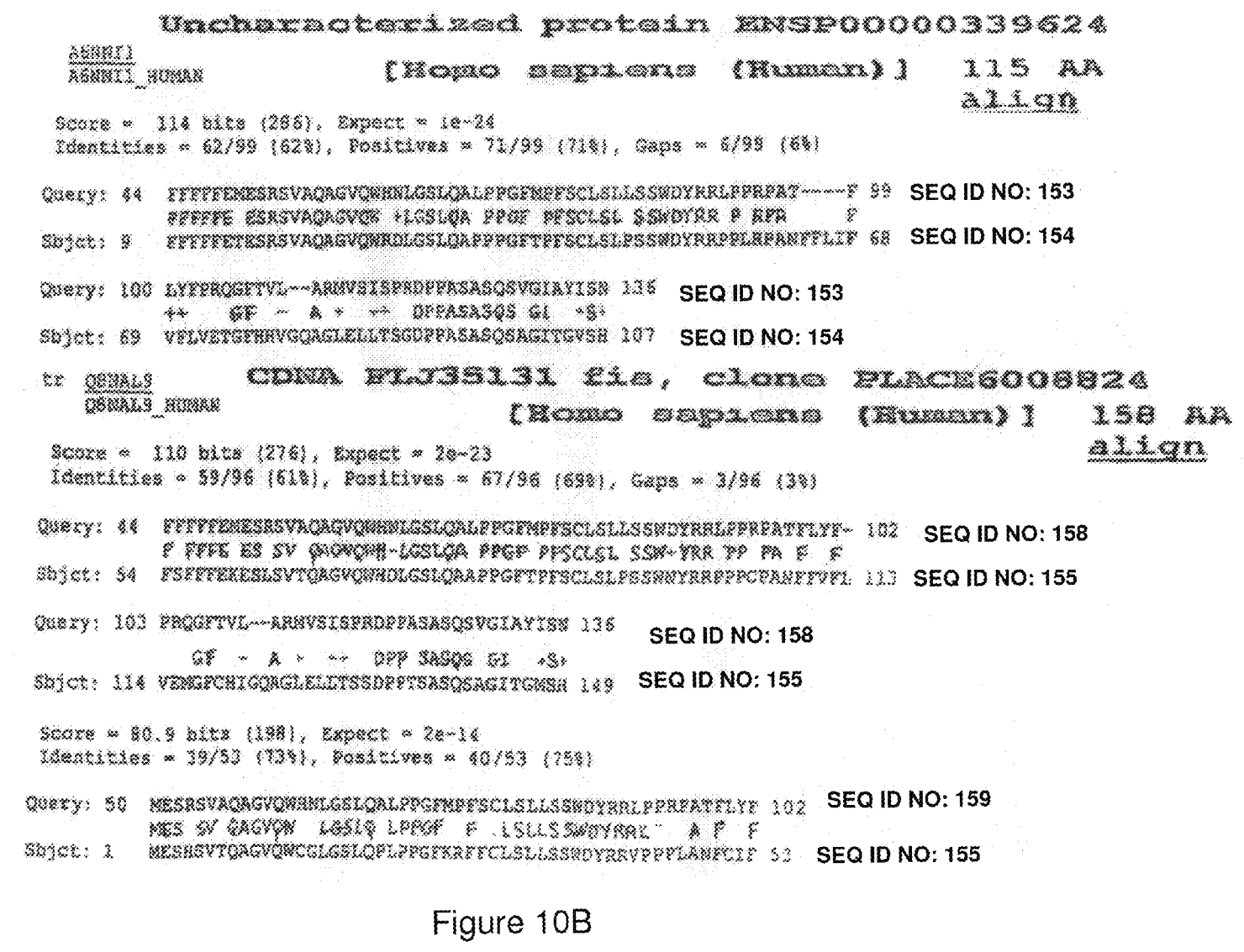

FIGS. 10A & 10B: Similarity between examples of peptides sequences LIV21 comparison to E2F2. (SEQ ID NOS: 149-152 153-155 158 & 159)

FIG. 11.1A to 11.3B: Similarity between LIV21 and other genes as E2F2 and N deacetylase/N-sulfotransferase and TRAML1.

FIGS. 12 & 12A: cartography: localization of LIV21 gene

FIG. 13A: alignments between the histatin-3-2 variant (by Brucker Maldi T of analysis), PATF and Q7TCL4 (turnip mosaic virus) AAN08045.2. (SEQ ID NOS: 168-171)

FIG. 13B: describes alignments between *Gallus gallus* (gi 50732569) and PATF and common polypeptide sequence (20 amino acids) derived from LIV21 by MALDI TOF analysis. (SEQ ID NOS: 169 & 172)

FIG. 15A. S phase, FIG. 15B. G2/M phase, FIG. 15C. G0/G1 phase. The scale along the x-axis is not proportional to the duration of treatment.

FIG. 16A. as a function of the time of treatment with TPA at 25 nM; FIG. 16B. compared with LIV21 in protein extracts, at 12 h of treatment with TPA at 25 nM.

Image 43: poorly differentiated skin cancer T2N0M0, image 58: normal tissue derived from the same individual suffering from a poorly differentiated skin cancer (the nuclei of the cells are stained yellow), image 40: 10 cm metastatic carcinoma, and image 17: metastatic carcinoma of 3.5 cm. The cell nuclei are stained red.

Figure 25:
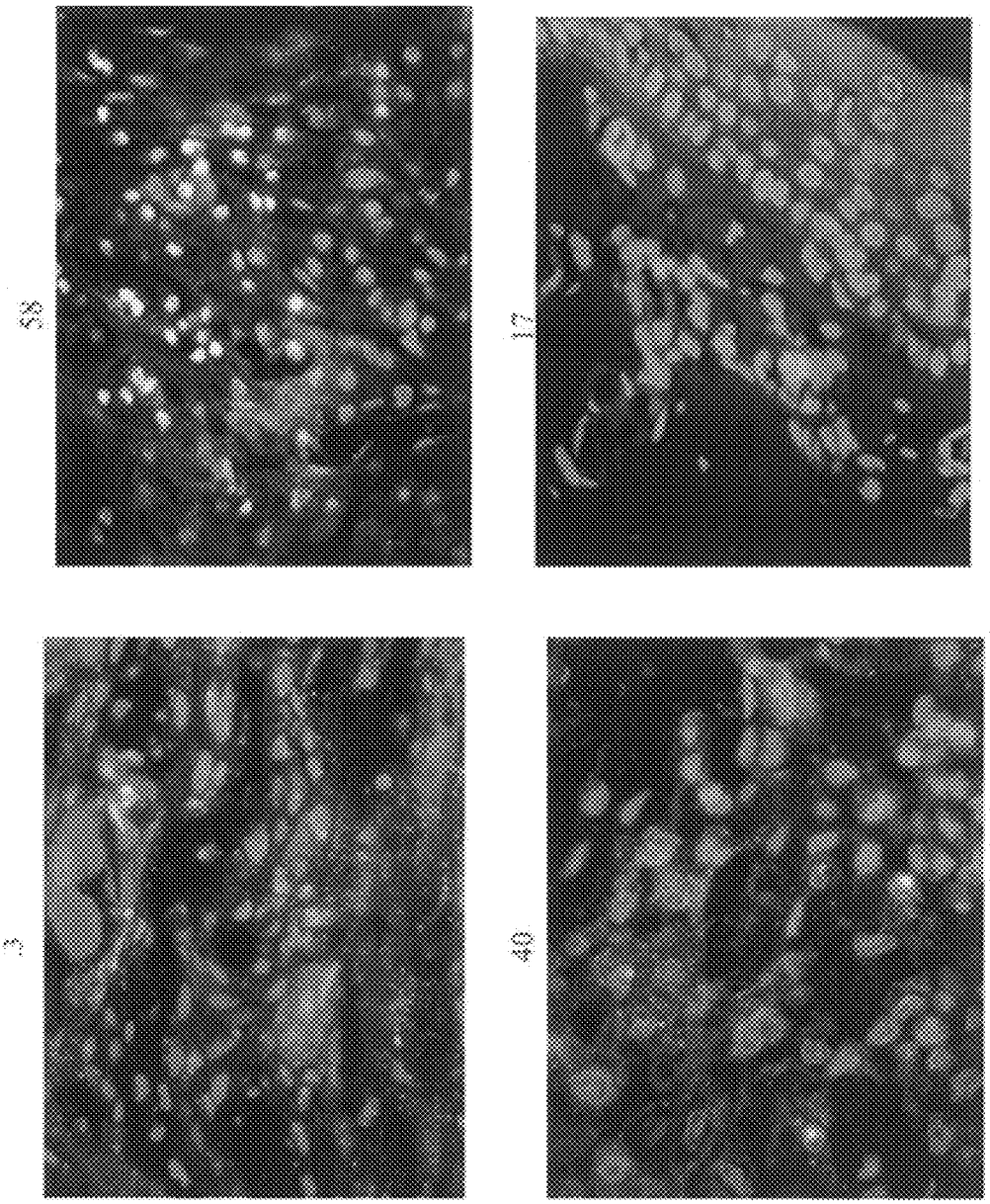
FIG. 25 shows that, using an array of 60 biopsies, including 50 of skin cancer and 9 of normal tissues and a control T; nuclear LIV21 expression is demonstrated in the biopsies of normal tissues and cytoplasmic LIV21 expression is demonstrated in the biopsies of metastatic cancers.
Figure 26:
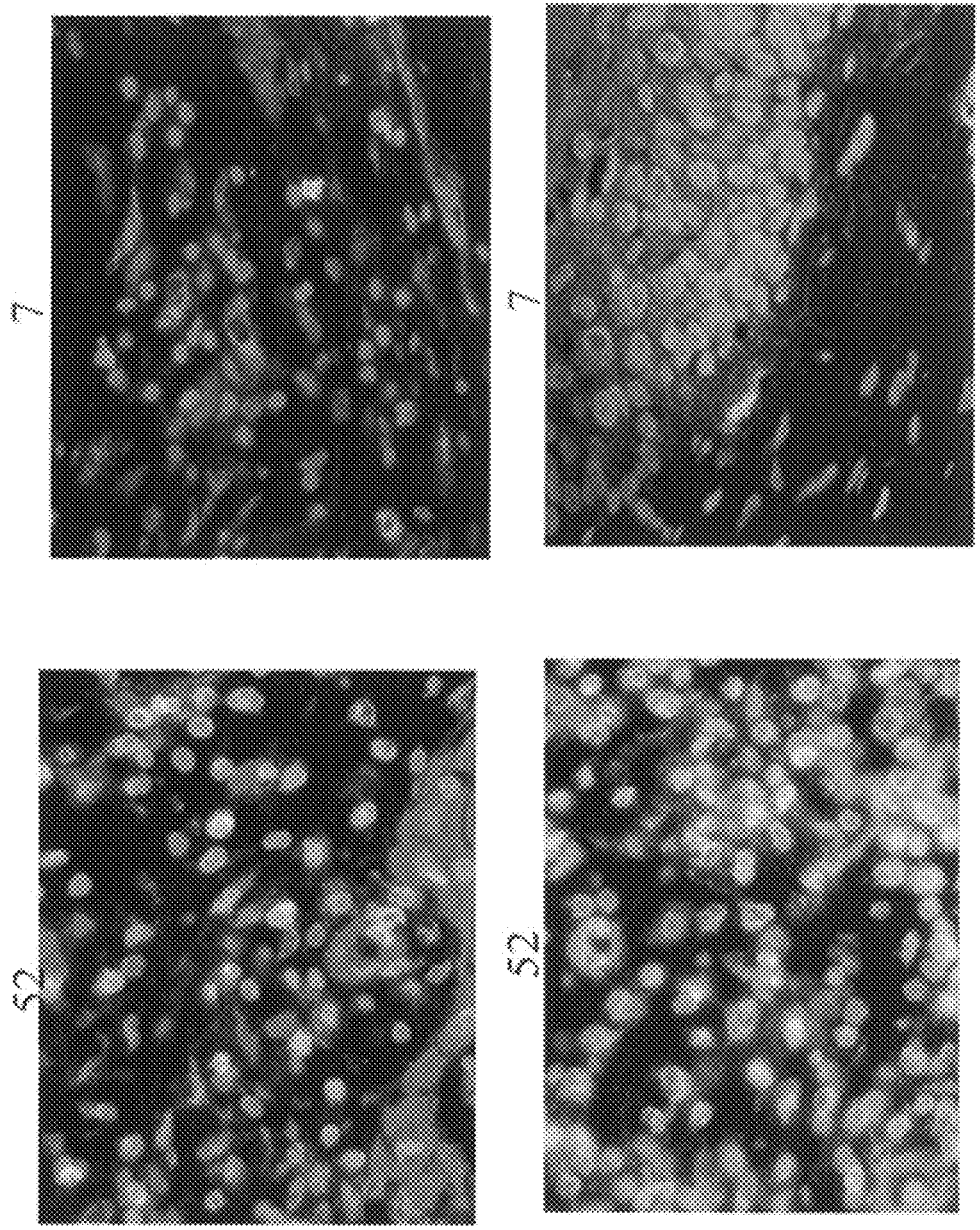

FIG. 26 is, like FIG. 25, a second example of nuclear localization of LIV21 in the control and normal tissue (No. 52) (the cell nuclei are stained yellow), of the individual No. 7 suffering from a squamous cell carcinoma of the pharynx (moderately differentiated T4N0M0). In the images No. 7 of cancerous tissue, the cell nuclei are stained red.

Figure 27:
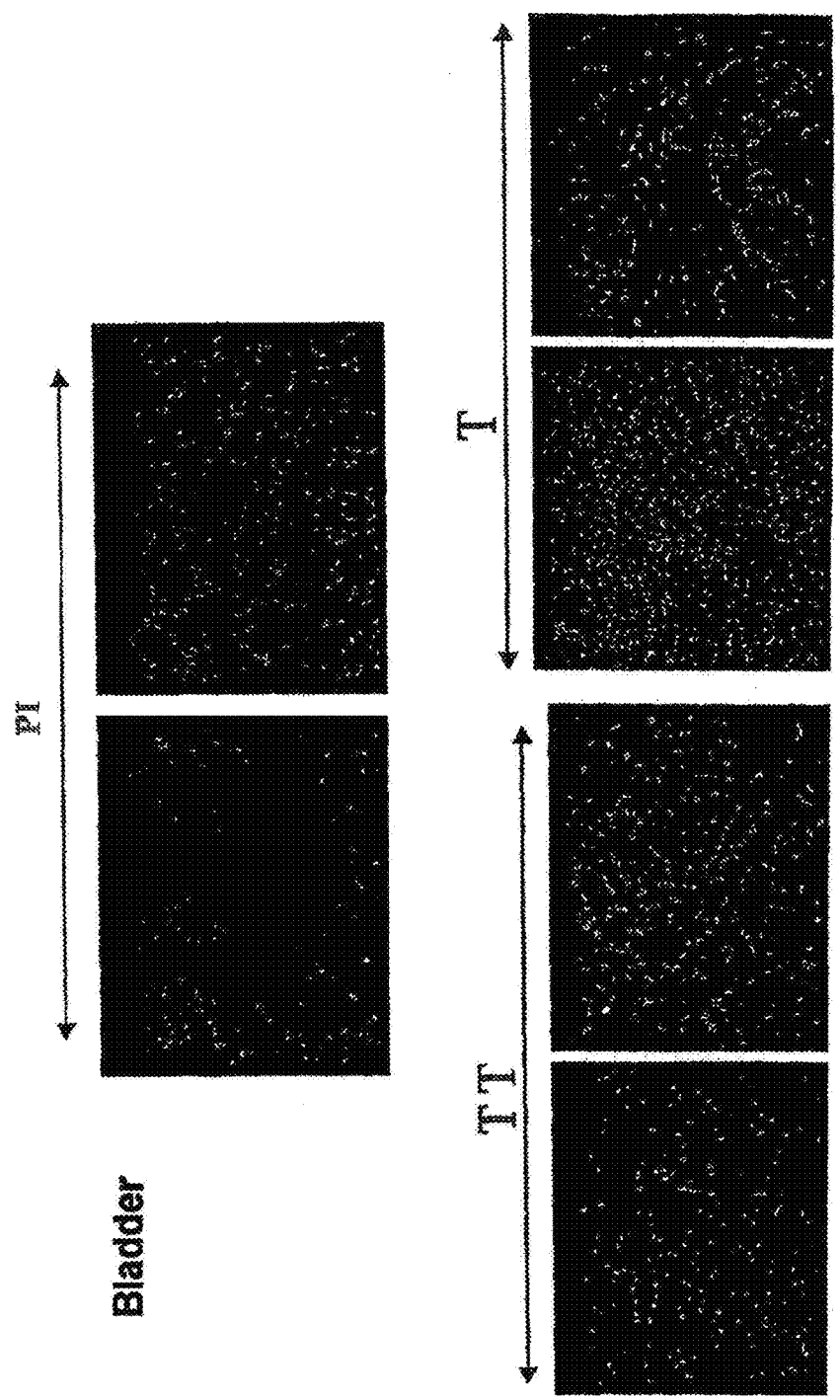

FIG. 27 is a sample of advanced bladder cancer on cystectomy (grade III urethral carcinoma infiltrating the chorion and the musculosa) versus normal bladder tissue from the same patient with an internal control (PI): preimmune serum PI before the rabbit has been immunized against LIV21, red labeling of the nuclei with propidium iodide.

Figure 28:
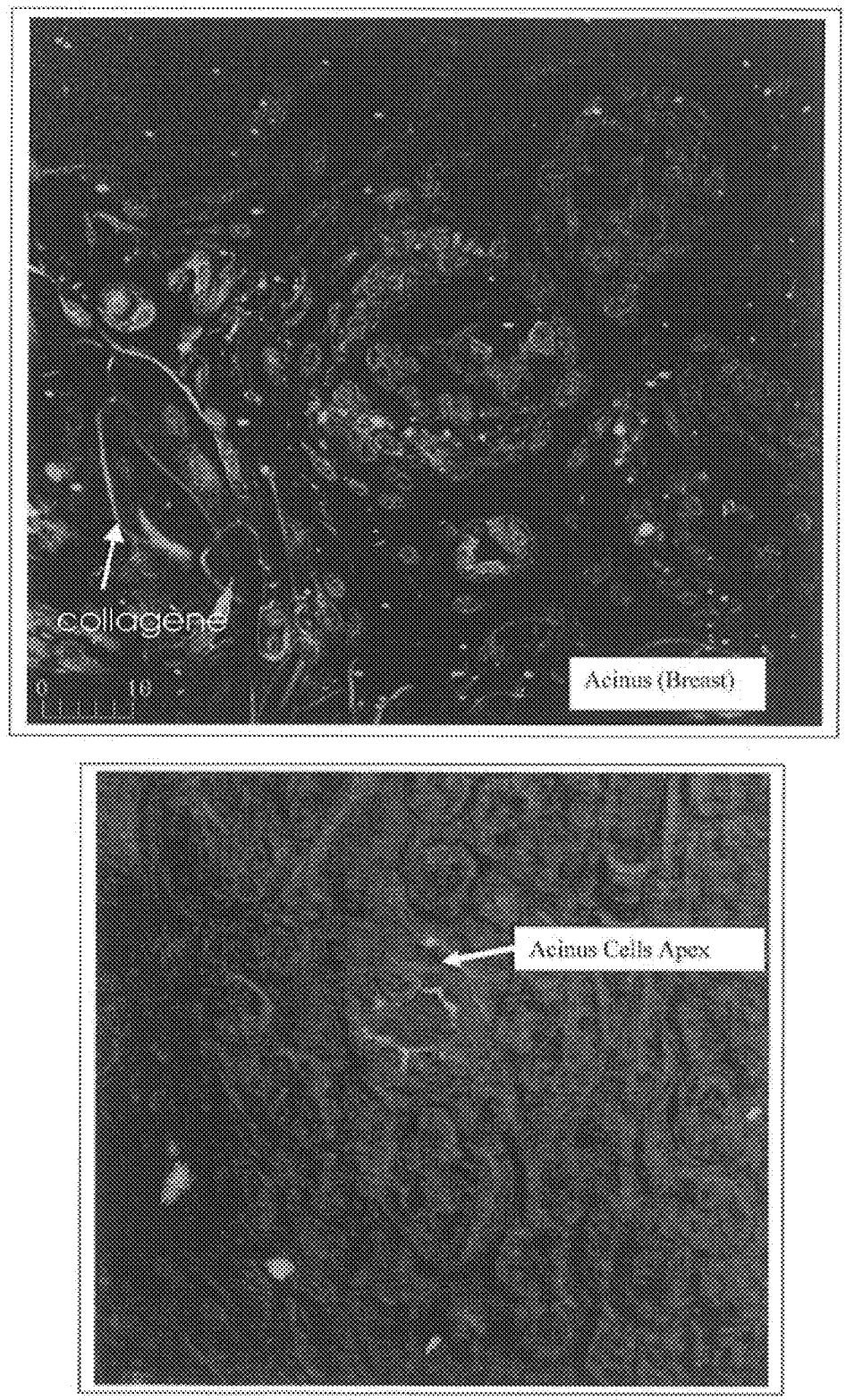

FIG. 28 is a sample of breast cancer at confocal microscopy with alexa and propidium coloration.

Figure 5:
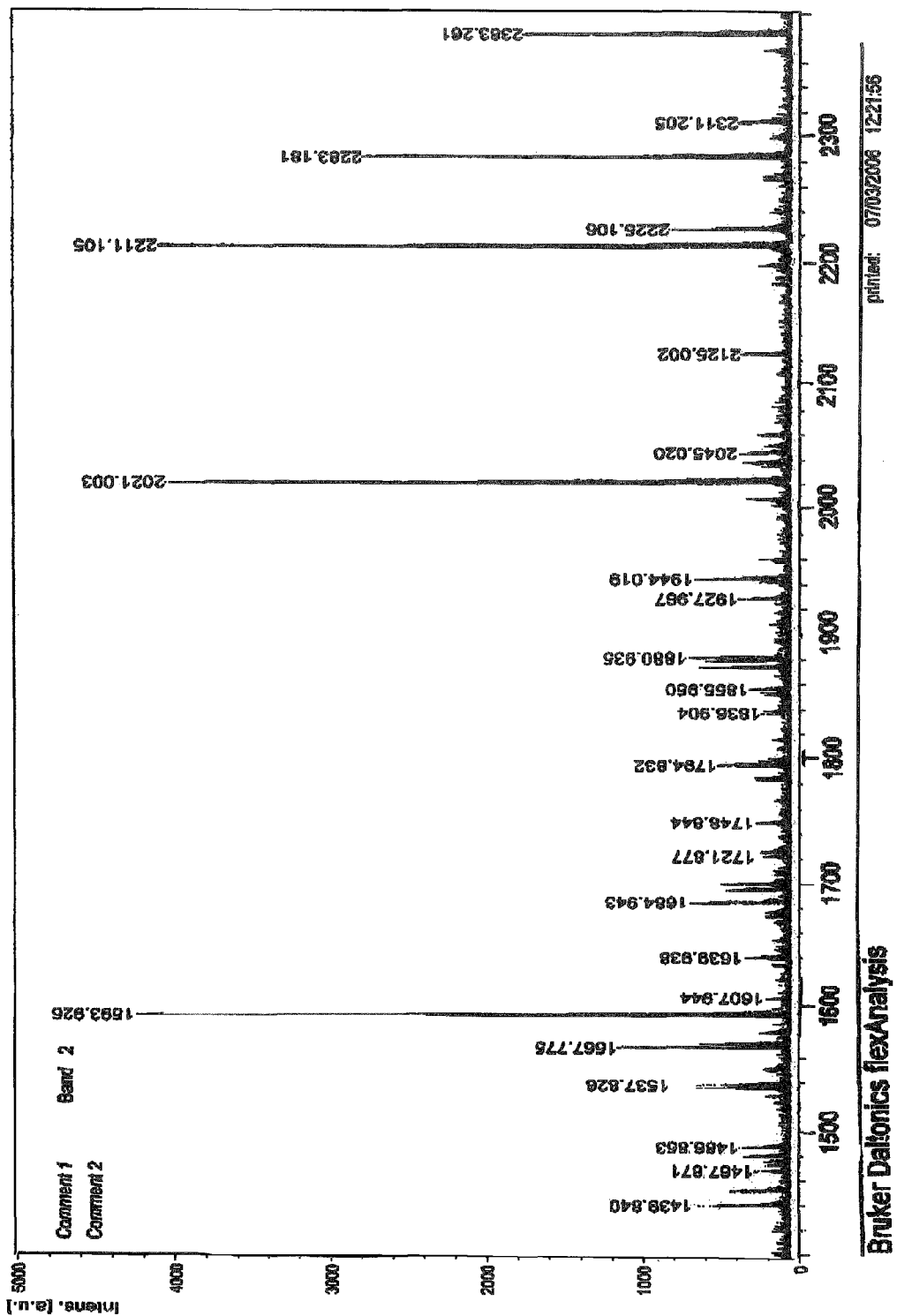
FIGS. 5 & 5A is the second chromatogram corresponding to the one-dimensional 12% acrylamide gel band migrating at 53 kD (band 2) and revealed with coomassie blue and the LIV21 antibody. The spectrum was determined on a Brucker apparatus.
Figure 5A:
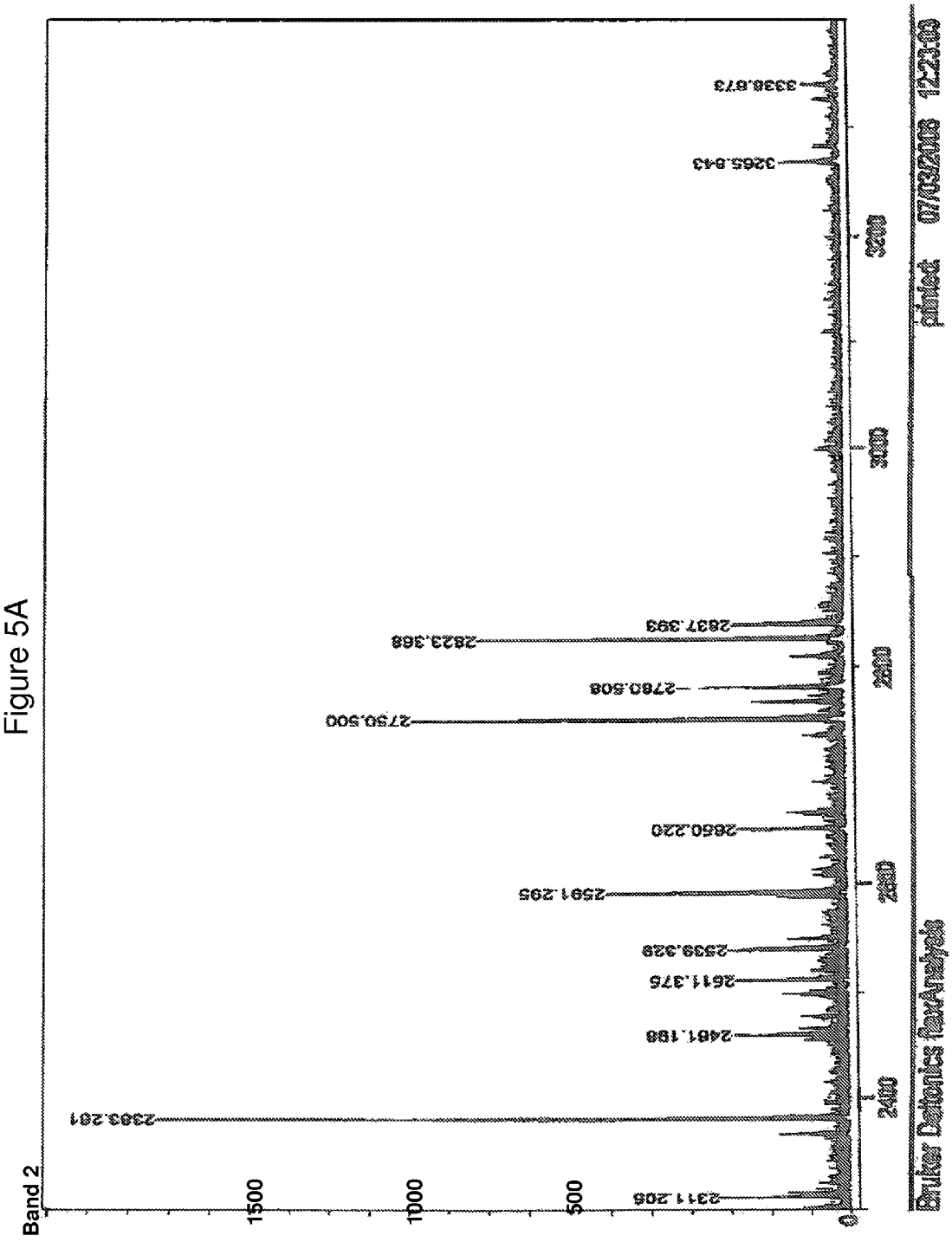
Figure 6A:
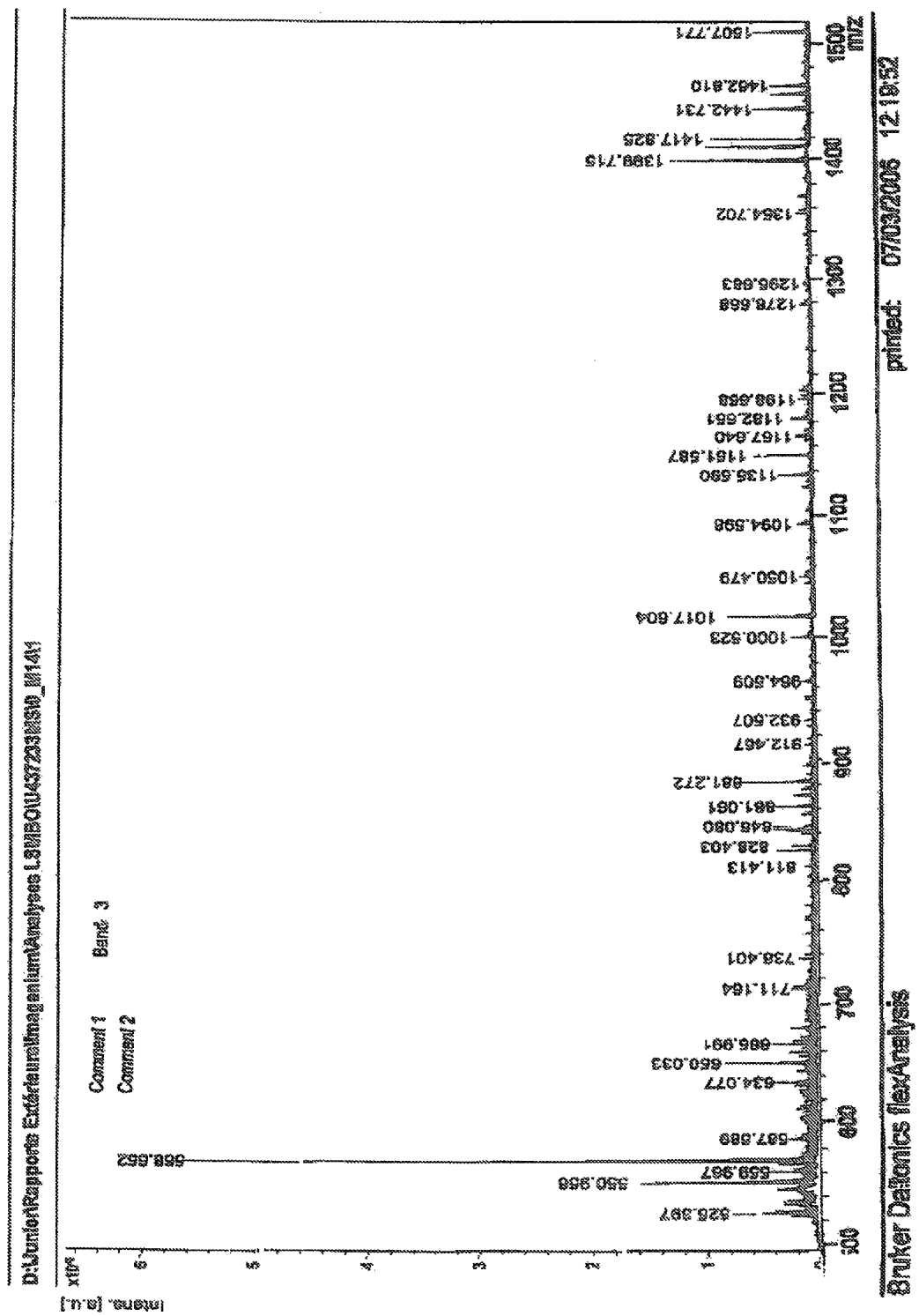
FIG. 6A is the third chromatogram corresponding to the one-dimensional acrylamide gel band migrating at 49 kD (band 3) and revealed with coomassie blue and the LIV21 antibody. The spectrum was also determined on a Brucker apparatus.
Figure 6A:
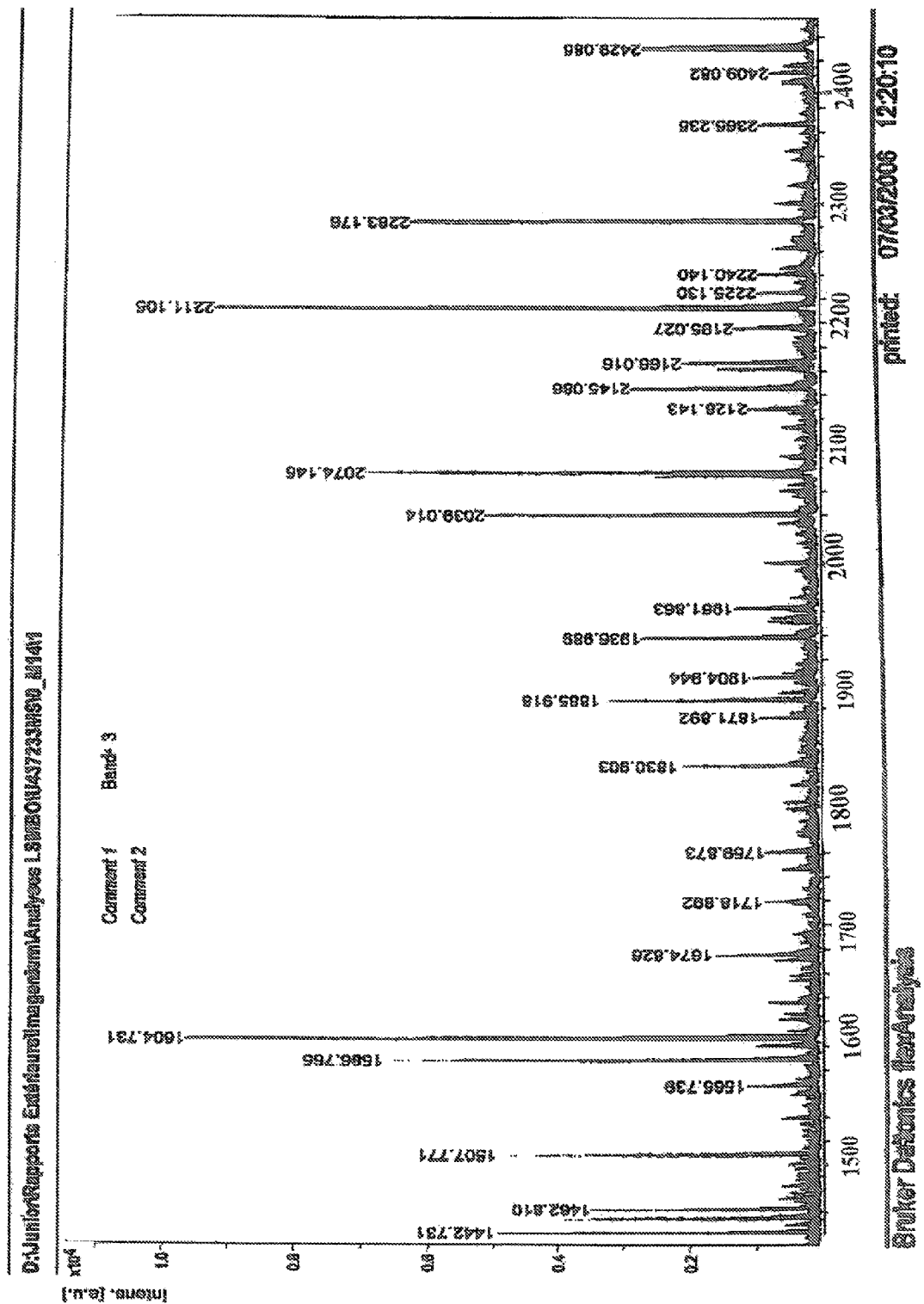
Figure 6A:
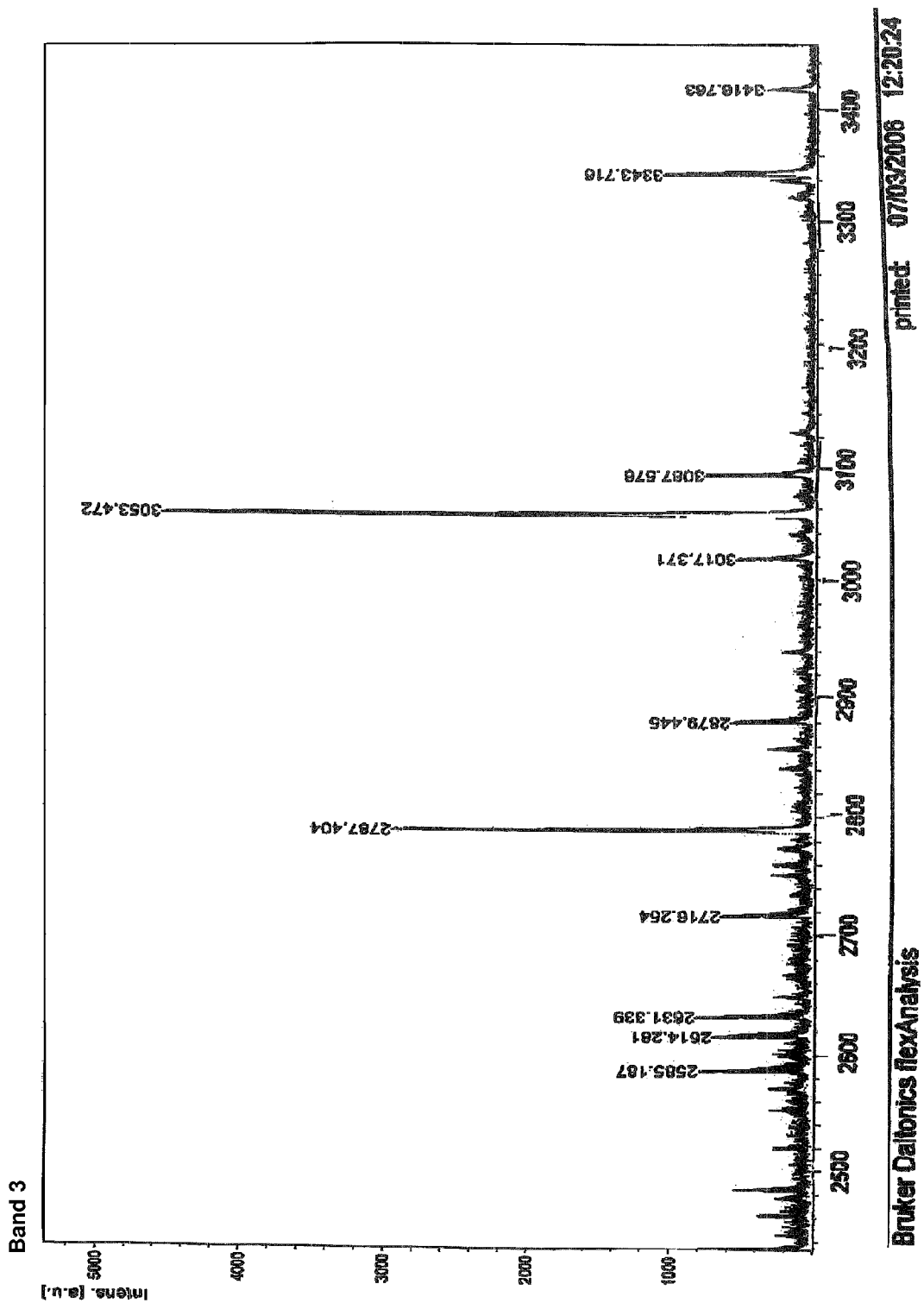
Figure 6A:
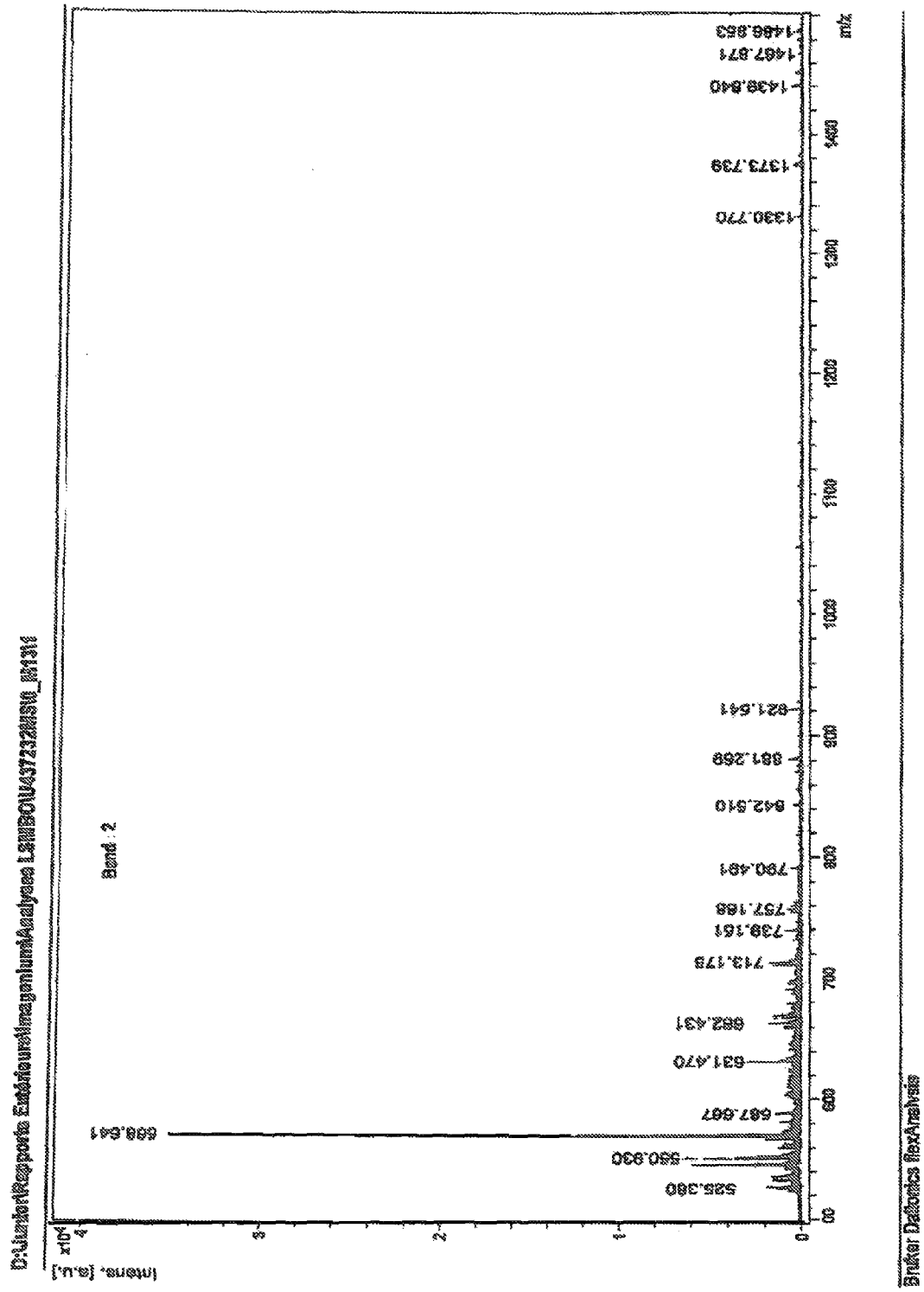
Figure 6B:
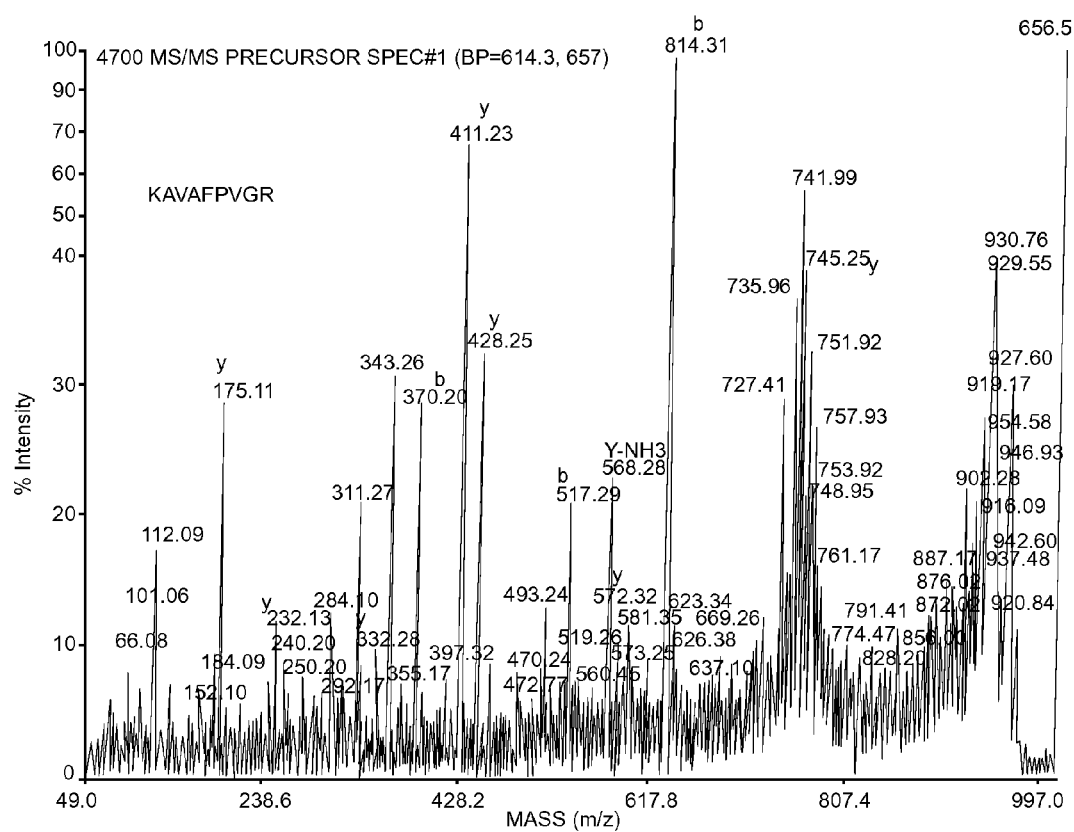
FIG. 6B is an example of a chromatogram.
Figure 6C:
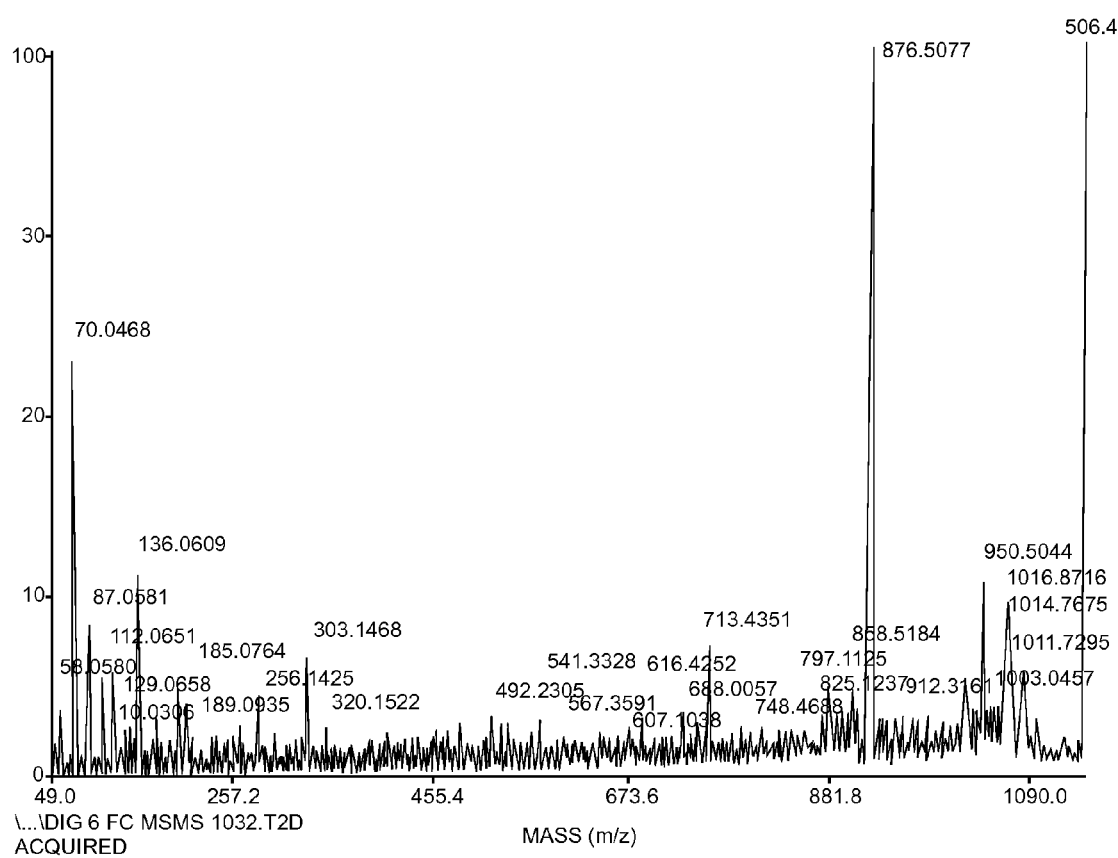
FIG. 6C is another example of a chromatogram.

FIG. 29: Describes as FIGS. 5 and 6 the MALDI TOF analyses giving a set of polypeptide (the histatin-3-2 variant) that can be assigned to LIV21 and its complex and contaminants which are sometimes different according to the observers of the various subcontracting proteomics platforms. The Mascot search parameters are: trypsin enzyme, variable modifications: carbamethylation and oxidation of methionines, without molecular mass limit, without isoelectric point restriction. Type of mass: monoisotopic. Mass error (MS): according to the observer 50 ppm or 100 ppm. Non-cleavage with trypsin: 1 The masses captured are M (H$^+$)/real masses. For chromatogram 1, the cysteins are blocked with iodoacetamide. The possibility of digestion with Promega bovine trypsin may be incomplete with cleavage oversight (SEQ ID NO: 162) and result from MS MS analysis (SEQ ID NO: 163).

Sequences common with *Gallus gallus* (gi 50732569), mouse syntaxin, the histatin-3-2 variant (P15516-00-01-00), ZN575-Human, G6 P translocase, the HSP60 chaperonin, arginine deiminase, ferredoxin-NADP(+) reductase, pseudomonas polyribonucleotidyl transferase, dehydrolipoamide dehydrogenase.

FIG. 30: alignments between *Gallus gallus* (gi 50732569) and PATF and common polypeptide sequence (18 amino acids) derived from LIV21 by MALDI TOF analysis. (SEQ ID NOS: 169 & 173)

FIGS. 31A & 31B: example of a Maldi analysis interpretation diagram for histatin 3-2, giving sequence No. 5, selecting the masses: 2383.2610 (delta at 0.005); 2539.3290 (delta: –0.02); 2511.3740 (delta at 0.02). score: 78 and expect: 0.0046.

Figure 33:
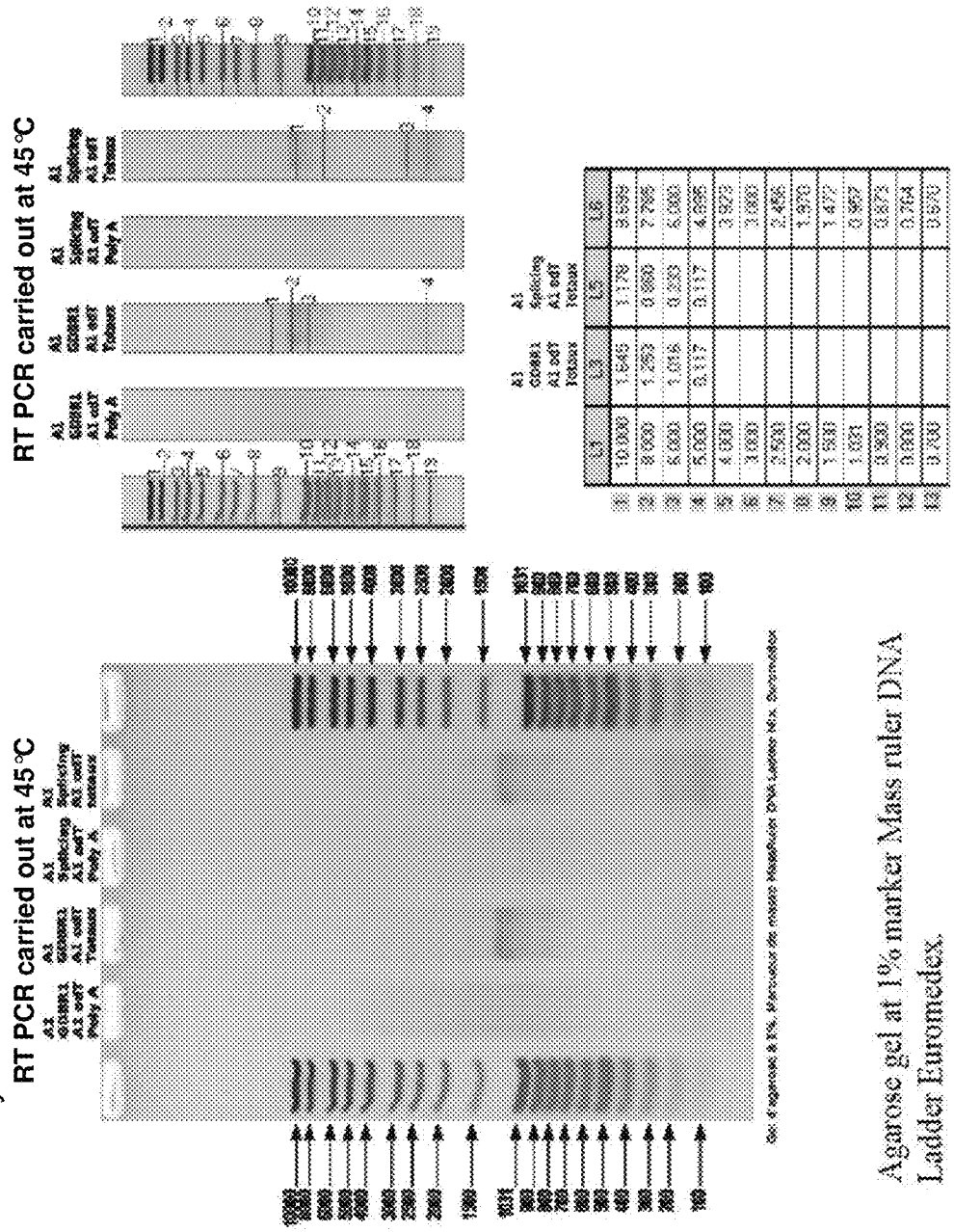
Figure 34:
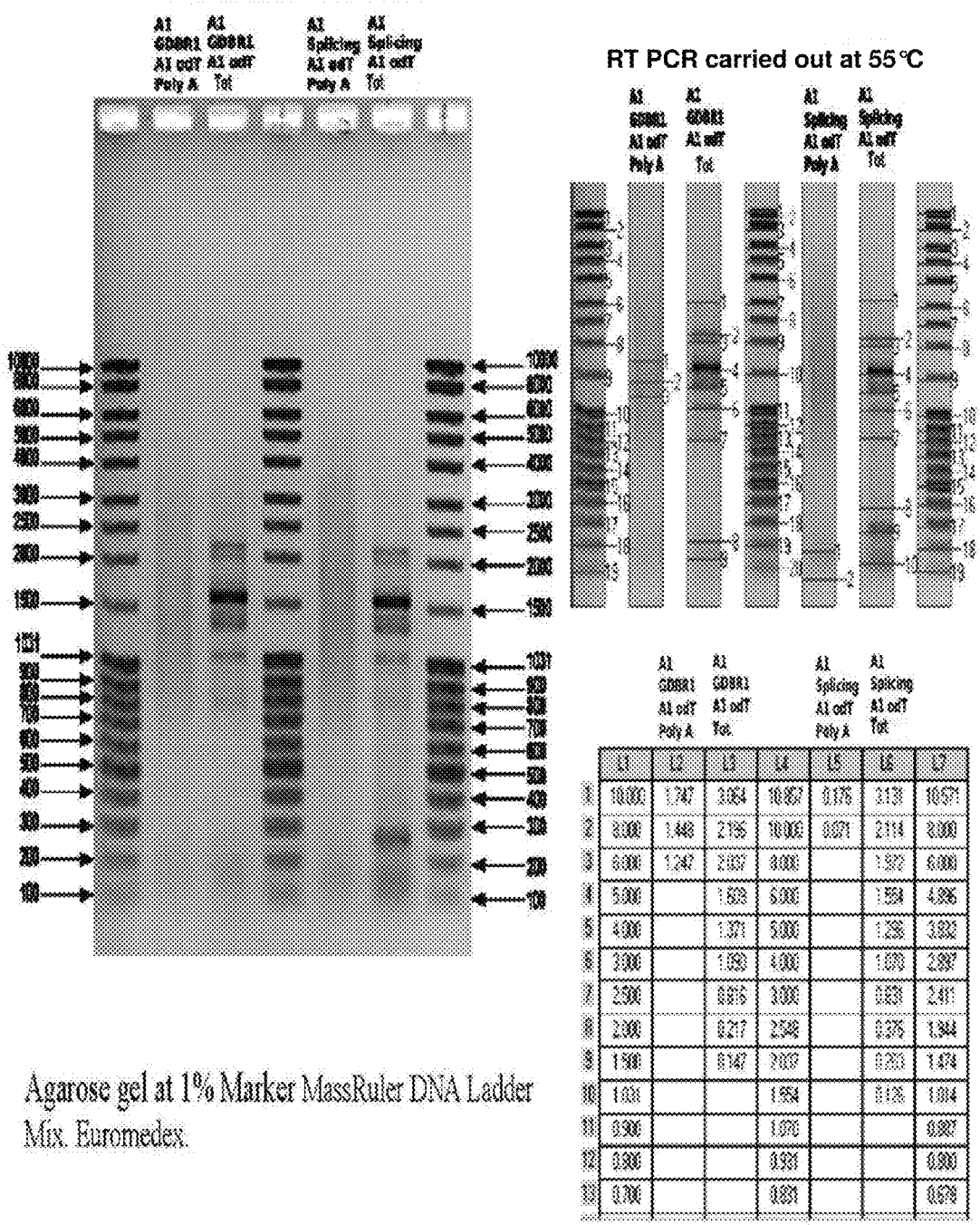
Figure 35:
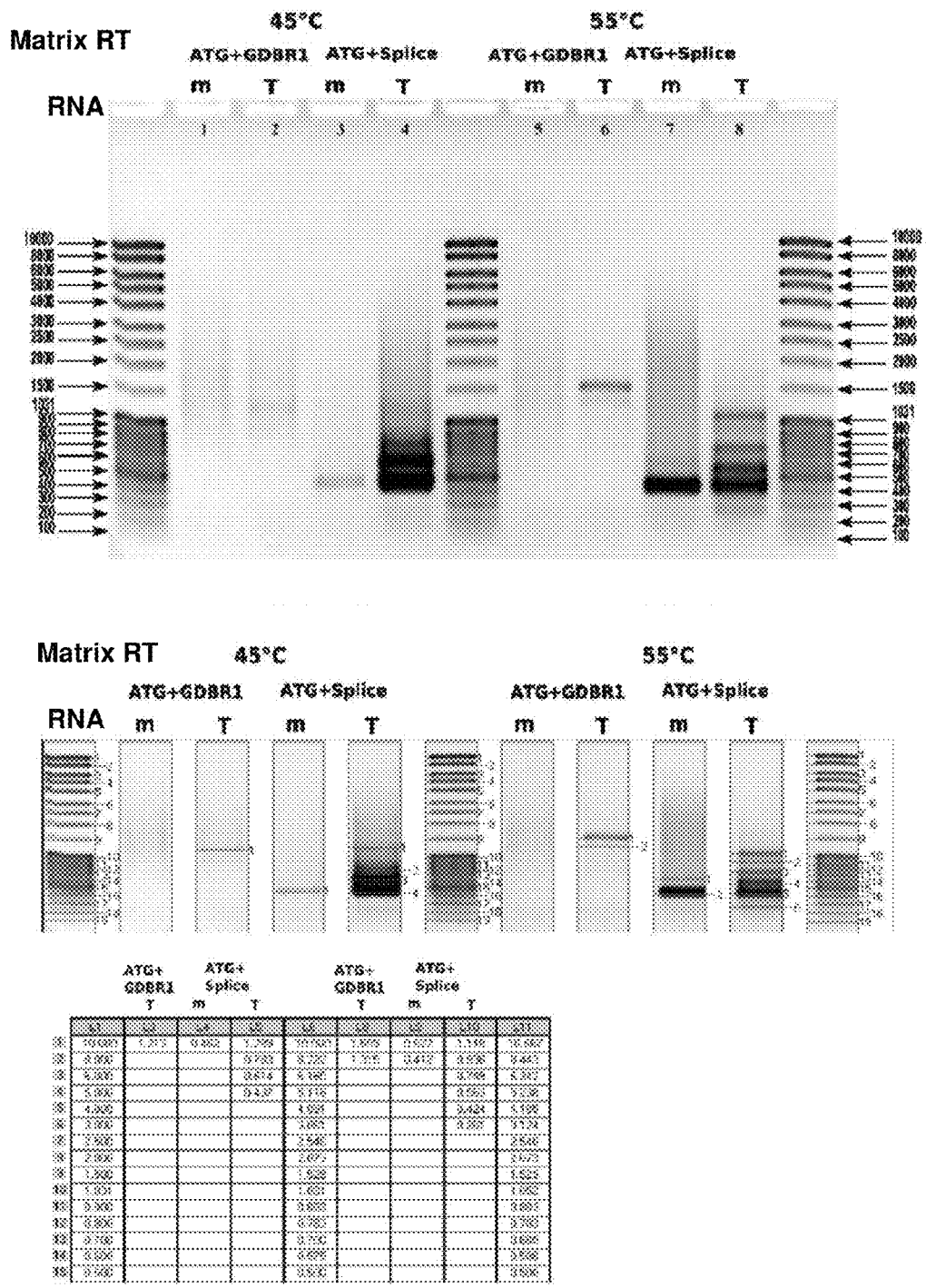
Figure 36:
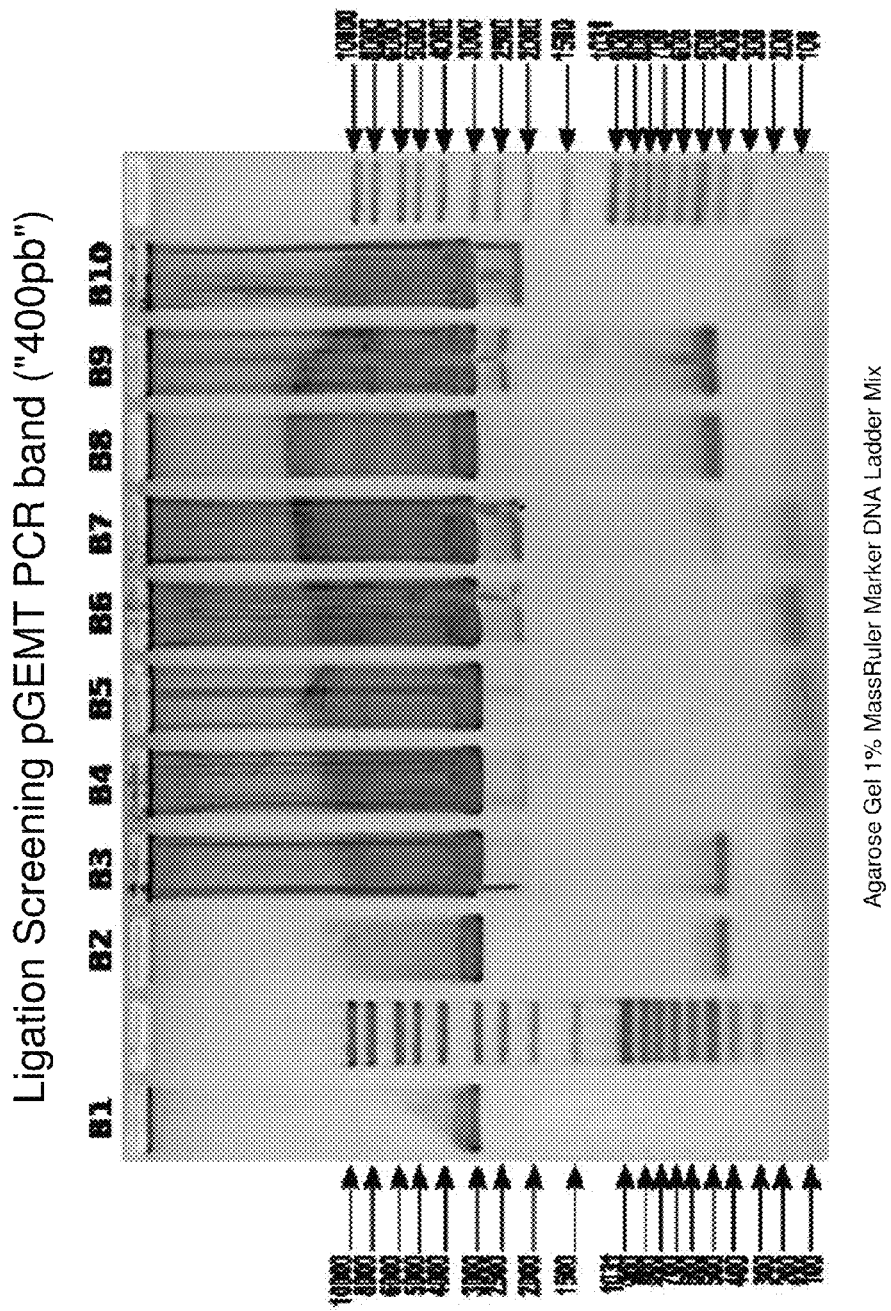
Figure 37:
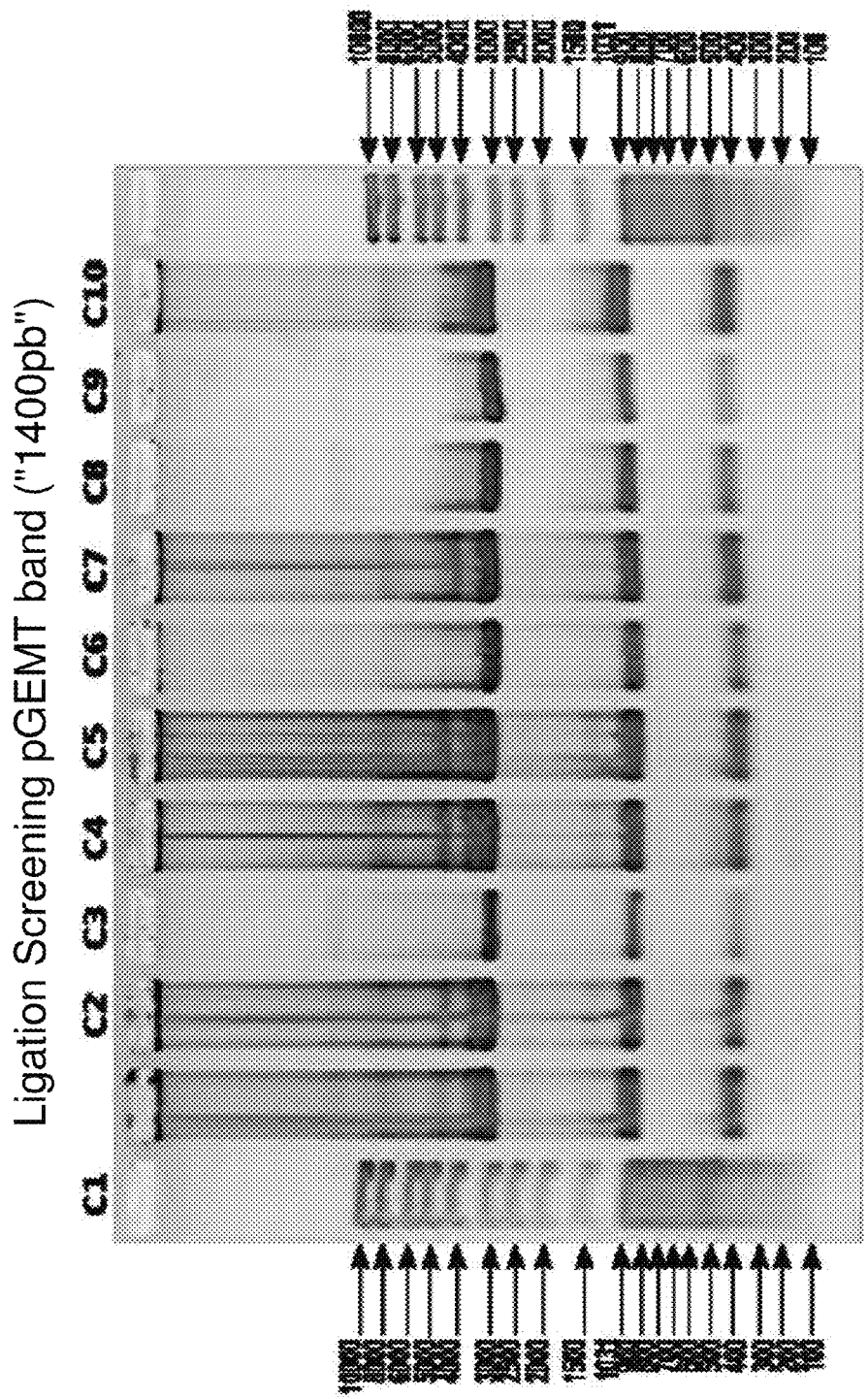
Figure 42:
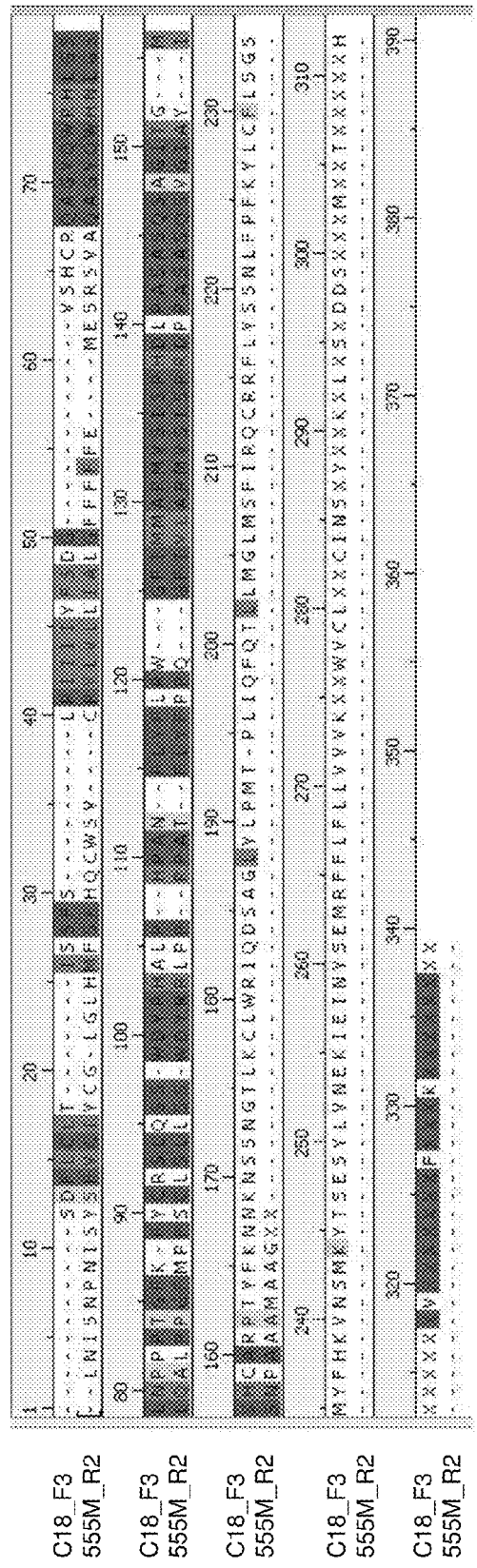

FIG. 32: PCR with the primers showing a band of 1400 bp.
FIG. 33: gel 2 with analysis of molecular masses.
FIG. 34: gel 3 at 55° and analysis of molecular masses.
FIG. 35: gel 4 at 45° and at 55° and analysis of molecular masses.
FIG. 36: screening ligation of 400 bp band, clones B1 to B10.
FIG. 37: screening ligation of 1400 bp band, clones C1 to C10.
FIG. 38: gel 5: ligation screening on the five new clones.
FIG. 39: gel 6: screening of the S55T and S55M recombinant clones and analysis of molecular masses.
FIGS. 40A-40B: examples of nucleotide sequence comparison between the sequenced Liv21 clones. (SEQ ID NOS: 148 & 164)
FIGS. 41A-41B: examples of nucleotide sequence comparison between the sequenced Liv21 clones. (SEQ ID NOS: 148 & 165)
FIG. 42: correspondence with sequences of Liv21 peptides: transduction of clones C8 and S55M1. (SEQ ID NOS: 166 & 167)

DETAILED DESCRIPTION OF THE INVENTION

The invention relates to the identification of antigens in cell lysates by immunoprecipitation. The analysis of the physical interaction of various proteins associated with E2F4 and E2F1 has been studied by coimmunoprecipitation of protein complexes. This analysis has made it possible to demonstrate a novel marker which has a diagnostic and prognostic use for cancer.

A marker for PATF proliferation associated with the E2F family had been demonstrated (Crisanti) through the characterization of exons, without the gene having ever been cloned in humans nor a corresponding protein having ever been found in humans.

The discovery of this novel molecule LIV21 could have a diagnostic value for the following reasons. By carrying out a screening of the localization of LIV21 in about ten human tumors, the inventor has been able to observe that, in all proliferating tumor cells, this protein is cytoplasmic instead of nuclear. It is not therefore in the correct cellular compartment to be active on the arrest of cell multiplication.

It has thus been possible to observe the presence of LIV21 in mammals. The panel of LIV21 expression as a function of cell state (mitotic cycles, cell in the resting state, differentiation) has been studied on tissues originating from various mammals. Protein analyses on the various tissue samples have confirmed that the expression of this transcription factor appears to be associated with a progression toward a quiescent cell state (arrest of mitoses and entry into differentiation). LIV21 is present in actively proliferating tumor cell lines and its expression is essentially cytoplasmic. The same results are obtained on human mammary adenocarcinomas.

Thus, the present invention relates to a novel test for screening for anomalies of the reinduction of the cell cycle. This diagnostic test is based on the study of the mechanism of action of the novel gene, encoding a potential novel transcription factor called LIV21, which down-regulate proliferation. LIV21 is implicated in the arrest of cell proliferation. LIV21 is cytoplasmic when the cells proliferate, whereas it becomes nuclear when the cells become quiescent. The characterization of this factor suggests a new pathway for down-regulating cell proliferation, by virtue of its association with one of the members of the EF family: E2F4. The latter is known to down-regulate the cell cycle by association with the P130 protein or pocket protein of the RB family.

The localization observed for LIV21 in tumor cells (cytoplasmic localization) and in physiological cells (nuclear localization) suggests, in any event, that its function is disturbed when cell development becomes anarchical.

The characterization of this molecule and the study of the timing and the topology of its expression also indicate that the expression and the localization of this ubiquitous transcription factor are regulated as a function of cell state: greater expression and nuclear localization for cells which have exited mitotic cycles, weak expression and cytoplasmic localization for actively proliferating cells such as human tumor cells.

LIV21 appears to be a key molecule for stabilizing another transcription factor (E2F4) in the cell nucleus and thus for inducing an arrest of cell proliferation may be to inhibiting E2F2 which active entrance of viral sequences in breast cells.

Furthermore, it has been shown that the localization of LIV21 in the cytoplasmic compartment is regulated by PKCε. In fact, when LIV21 is phosphorylated by PKCε, LIV21 is located in the cytoplasmic compartment. Conversely, when the phosphorylation of LIV21 by PKCε is inhibited, LIV21 is located in the nuclear compartment.

Figure 12:
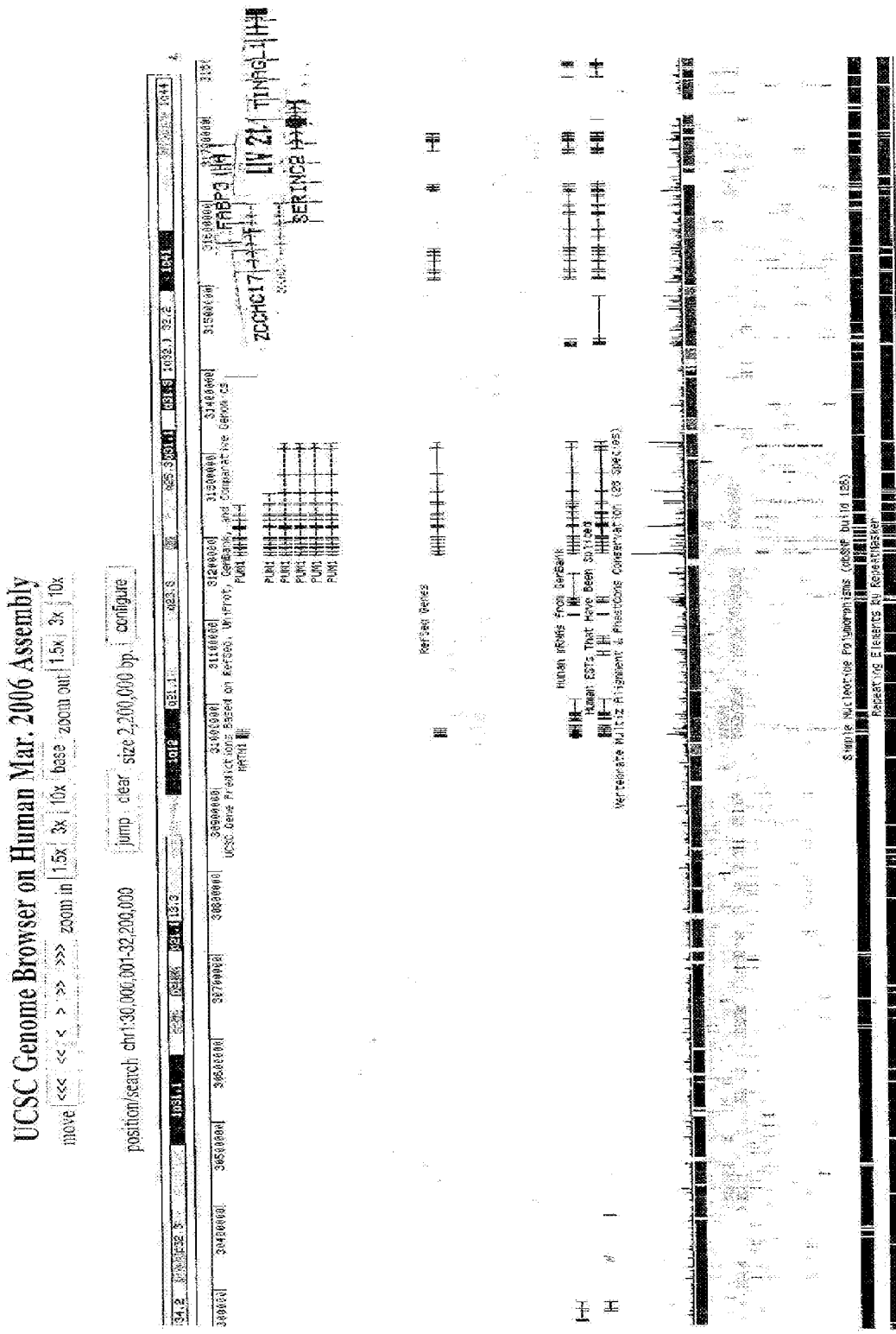

The LIV21 gene is a human gene on chromosome 1p31 near FABP3 (MDGI), SERINC2 and TINAGL (P3ESCL) between [031,783,000-031,111, 000] with the neighbours which revealed a structure function relation (means some of genes which enter in interaction with LIV21 and the complexe LIV21 are neighbours (FIG. 12). For example, E2F2, Bcl2, CD53, HDAC1 are in the same part of chromosome 1p. LIV21

The present invention therefore concerns the LIV21 gene (FIG. 40.1), the LIV21 protein and derivatives and fragments thereof (FIG. 40.3).

Figure 7A:
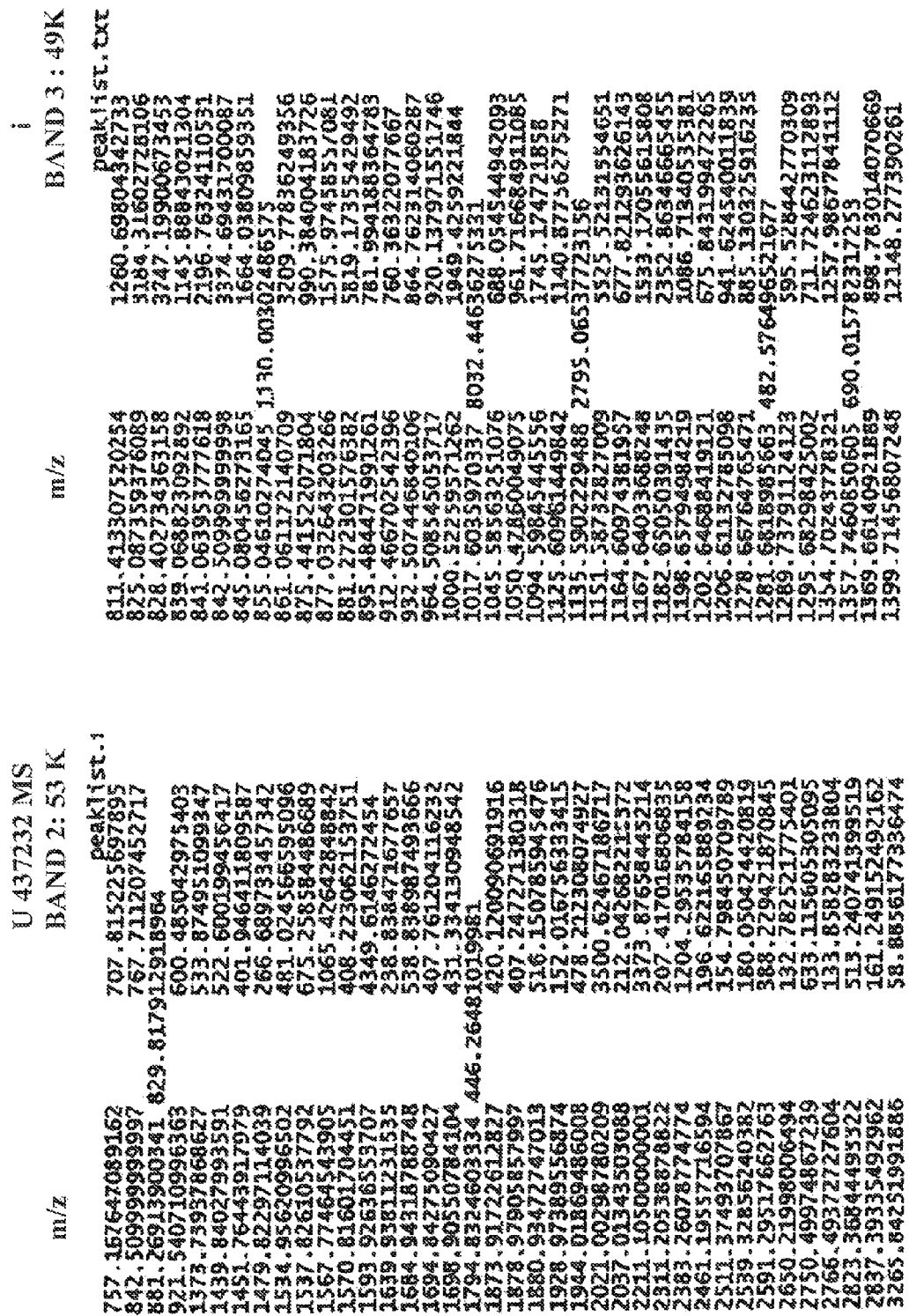
Figure 8A:
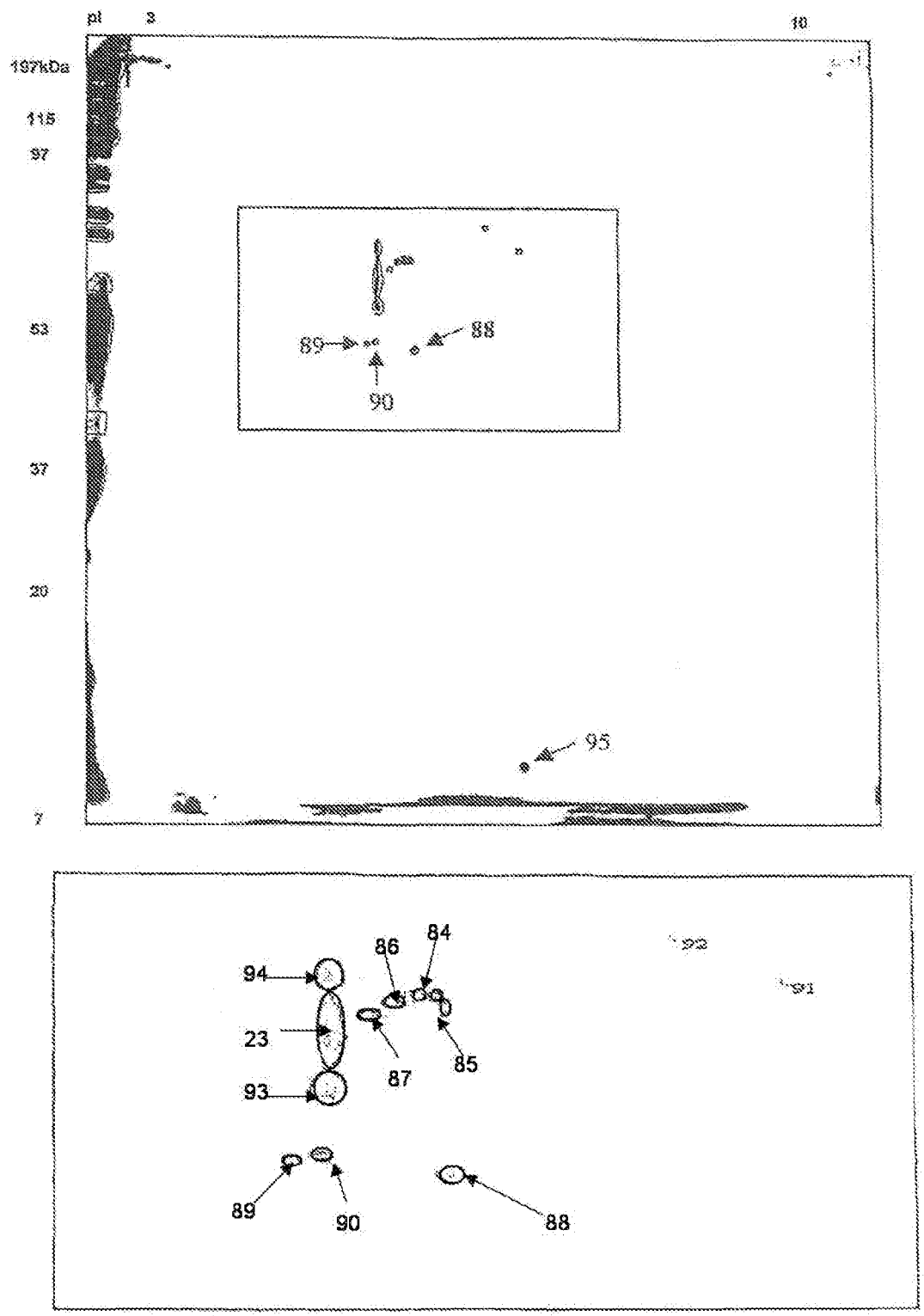
FIG. 8A represents a 2D SDS PAGE gel separating the twelve polypeptides bound by the LIV21 antibody and FIG. 8B represents the sample at 100° C. few minutes before migration.
Figure 8B:
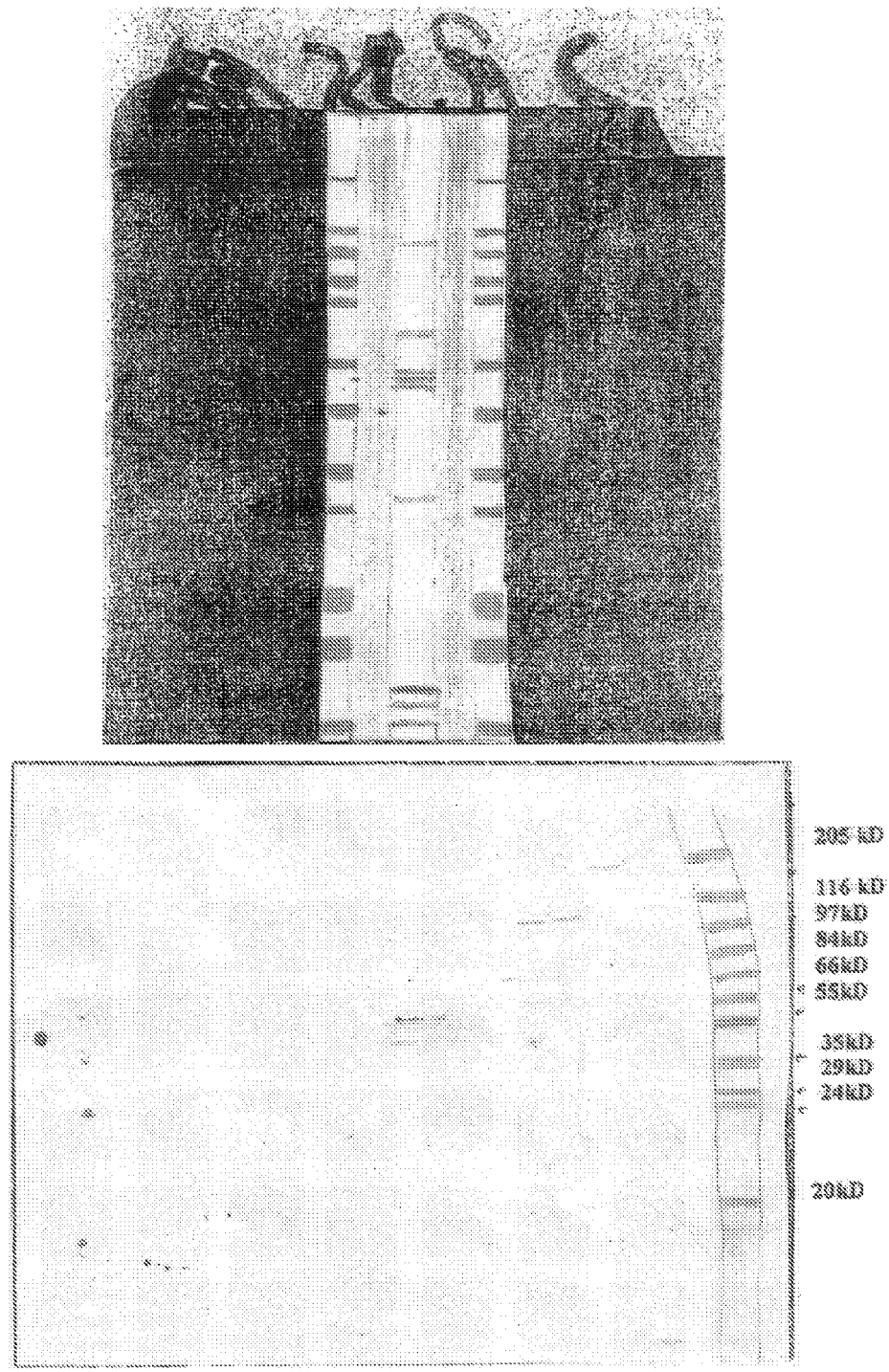

The LIV21 protein is a human protein of approximately 300 amino acids. However, depending on the alternative splicing that it undergoes, it exists as at least three forms of different sizes and nine forms in hot conditions (FIG. 8). Moreover, it can be phosphorylated or sumoylated. It has an apparent molecular weight of between 50 kD and 51 kD in Western blotting analysis. This apparent molecular weight is 60 kD when LIV21 is sumoylated and in hot temperature conditions for sample (with the most concentration of sample), the profile change and we observed apparent molecular weight for peptides (revealed helix structures) in a range of 110 kD and 15 kD (FIG. 8.2). In its 51 kD form, which may be phosphorylated or nonphosphorylated, its isoelectric point is 5.6 and its intensity is 13632 but with hot temperature and nuclear samples separated to cytoplasmic samples there are spots at basic isoelectric point (FIG. 8). This protein has been characterized by mass spectrometry (Maldi) (Example 1; FIGS. 3-13). It gives more than 54 peptides following digestion with Promega trypsin (FIG. 7). The characteristics of the LIV21 protein are also described in FIGS. 3-13. Several specific peptides of LIV21 have been characterized, and in particular the LIV21a peptide, the LIV21b peptide (SEQ ID No 2), the LIV21c peptide (SEQ ID No 3), the LIV21d peptide and the LIV21e peptide (SEQ ID No 50). The longest sequence with homology with PATF (Cortunix Japonicus Bird) is the LIV21e peptide (SEQ ID No 50 & 51) and PL MII (FIG. 30).

Other specific peptides of LIV21 (Liv21a to f) are described below in the patent in listing in ASCII form.

For the purposes of the invention, a preferred LIV21 protein comprises at least one sequence chosen from SEQ ID Nos 1-55 or a sequence having 70%, 80% or preferably 90% homology with said sequence.

The isolation of LIV21 gene by RT PCR analysis (before to choose the oligonucleotides primers for amplification) begin by using the one dimensional and two dimensional gel electrophoresis analysis (FIGS. 33 and 34), the protein samples corresponding to the putative protein and to the elements of the complex were extracted from the gels and digested with trypsin (Promega) in order to be analysed by MALDI (FIGS. 3 to 5) and ESI MS/MS mass spectrometry. The results, when put up against proteomic databanks, made it possible to reveal several peptide sequences of interest, including some given as an example (FIGS. 6 and 7), some being found in humans with very significant scores (splicing of histatin, etc., FIGS. 30 and 31), these sequences were used as primers (once reverse-transcribed to cDNA) for screening a library formed from breast cancer-specific MCF7 cells (FIGS. 32 to 39).

The cloning made it possible to bring to the fore about twenty clones out of the 150 clones obtained, of which ten clones were sequenced and characterize the new gene LIV21 (FIG. 32). Based on these sequences, siRNAs were determined in order to allow regulation of silencing type within this metabolic complex of interest so as to develop therapeutic applications (SEQ N° 122).

In post-mitotic cells, apoptosis could correspond to an aborted attempt at mitosis. It is in this context that the application of LIV21 has been developed. The inventor has identified sequences of the LIV21 gene. Using the LIV21 antibody on affinity columns it has been able to extract peptides of the LIV21 protein; it has also used a second approach by means of a coimmunoprecipitation kit (Pierce) in order to have larger amounts of proteins (Example 1). Based on peptide sequences of the LIV21 protein, obtained by mass spectrometry (Example 2), primers which make it possible to amplify a cDNA fragment were designed (Example 3). After culturing and amplification of MCF7 line cells, extraction and purification of RNAs, RT PCRs and cloning in a shuttle vector were carried out, and then screening of the resistant colonies and sequencing made it possible to reveal sequences characterizing the LIV21 gene (Examples 4 and 5). More than twenty characteristic clones out of 150 clones were studied. The cDNA of these clones was used to screen a library prepared from the total mRNA of MCF7 cells. The sequence of this new product is a new transcription factor, the nuclear translocation of which is correlated with the establishment of cell quiescence. Furthermore, it forms heterodimers with other transcription factors and it binds to DNA.

The gene of this protein is characterized by five main sequences (cf. insert of clones extracted to MCF7 cells in sequences listing) and sequences representing an alternative splicing.

Using Northern blotting, the inventor then followed the expression of this new product during development, from the embryonic stage. It was observed that the amount of the LIV21 protein increases as development progresses, i.e. as a quiescent cell state becomes established. Through the same strategy, the inventor showed that the LIV21/E2F4 complex inhibited the expression of E2F1. This complex could correspond to a new point of control in the arrest of cell proliferation.

The LIV21 protein comprises a leucine zipper motif, a basic domains characteristic of DNA binding domains, a nuclearization sequence, zinc finger domain and helix loop helix with repetitive motifs.

The present invention also concerns a purified or recombinant, isolated human polypeptide having a sequence comprising the sequence SEQ ID No 1 and/or SEQ ID No 2. Preferably, the polypeptide comprises the sequences SEQ ID Nos 1 and 2. In a preferred embodiment, the polypeptide comprises (in addition) a sequence selected from SEQ ID Nos 3-55, preferably from SEQ ID Nos 3-5, or a sequence having 70%, 80% or 90% identity to said sequences. In a specific embodiment, it comprises a sequence selected from one of the peptide sequences obtained by MALDI (FIG. 7) and NanoLC-ESI-MS (FIG. 9). The invention also concerns the two peptides LIV21a (SEQ ID No 1) and LIV21b (SEQ ID No 2). The invention also concerns a peptide having a sequence selected from SEQ ID Nos 3-55, preferably from SEQ ID Nos 3-5, or a sequence having 70%, 80% or 90% identity to said sequences. It also concerns peptides comprising at least 10 consecutive amino acids of human LIV21, preferably at least 20, 30 or 50 consecutive amino acids of LIV21.

The invention also concerns LIV21 derivatives of interest which are, for example, fusion proteins in which LIV21 is fused to labeled proteins such as GFP. Moreover, the LIV21 protein can be labeled by any means known to those skilled in the art.

The present invention also concerns an antibody which binds specifically to a polypeptide according to the present invention, preferably human LIV21, or a fragment or a derivative thereof. In a specific embodiment, the antibody binds specifically to an LIV21a or LIV21b peptide. In a preferred embodiment, the antibody binds specifically to a polypeptide comprising a sequence selected from SEQ ID Nos 1-55, preferably from SEQ ID Nos 1-5, or a sequence having 70%, 80% or 90% identity to said sequences.

The antibodies may be polyclonal or monoclonal. They may be antibody fragments and derivatives having substantially the same antigenic specificity, in particular antibody fragments (for example, Fab, Fab'2, CDRs), humanized antibodies, polyfunctional antibodies, single-chain antibodies (ScFv), etc. The antibodies of the invention can be produced using conventional methods, including the immunization of an animal and the recovery of its serum (polyclonal) or of spleen cells (so as to produce hybridomas by fusion with appropriate cell lines).

Said antibodies can be obtained directly from human serum or from serum of animals immunized with the proteins or the peptides according to the present invention. Methods for producing polyclonal antibodies from varied animal species including rodents (mice, rats, etc.), primates, horses, pigs, sheep, rabbits, poultry, etc., are described, for example, in Vaitukaitis et al. (Vaitukaitis, Robbins et al. 1971). The antigen is combined with an adjuvant (for example, Freund's adjuvant) and administered to an animal, typically by subcutaneous injection. Repeated injections can be carried out. Blood samples (immune serum) are collected and the immunoglobulins are separated.

The present invention concerns an anti-LIV21 serum produced by immunizing an animal with a polypeptide according to the present invention. In a specific embodiment, the animal was immunized with the LIV21a and/or LIV21b peptide. In a preferred embodiment, the animal is immunized with these two peptides. The present invention also concerns an anti-LIV21 serum produced by immunizing an animal or a human with a polypeptide according to the present invention, in particular a polypeptide comprising a peptide sequence selected from SEQ ID Nos 1-55, preferably from SEQ ID Nos 1-5, or a sequence having 70%, 80% or 90% identity to said sequences. For example, the peptides can be coupled to a carrier protein such as hemocyanin, and then injected into an animal, for example a rabbit, for immunization. Polyclonal antibodies were obtained using these two peptides by having immunized two rabbits and having bled one rabbit so as to have a preimmune serum.

Methods for producing monoclonal antibodies from various animal species can be found, for example, in Harlow et al. (Harlow 1988) or in Kohler et al. (Kohler and Milstein 1975). These methods include the immunization of an animal with an antigen, followed by the recovery of the spleen cells, which are subsequently fused with immortalized cells, such as myeloma cells. The resulting hybridomas produce monoclonal antibodies and can be selected by limiting dilution so as to isolate the individual clones. The antibodies can also be produced by selection from combinatorial libraries of immunoglobulins, such as those disclosed, for example, in Ward et al. (Ward, Gussow et al. 1989).

The invention also includes the use of the antibodies according to the invention for the detection and/or the purification of the human LIV21 protein. In particular, the LIV21-specific antibodies can be used for the detection of these proteins in a biological sample. They thus constitute a means of immunocytochemical or immunohistochemical analysis of LIV21 expression on tissue sections. Generally for such analyses, the antibodies used are labeled in order to be detectable. As an alternative, the antibodies can be indirectly labeled.

In a preferred embodiment, the antibodies are labeled. The labels include radiolabels, enzymes, fluorescent, luminescent or chemical labels, magnetic particles, gold labeling, biotin/avidin labeling, peroxidase labeling, etc.

The invention also includes a method for detecting the LIV21 protein in a biological sample, comprising a step of suitable treatment of the cells by any appropriate means which makes it possible to render the intracellular medium accessible, a step of bringing said intracellular medium thus obtained into contact with an antibody specific for the human LIV21 protein and a step of demonstrating the LIV21-antibody complex formed, by any appropriate means. In specific embodiments, the cytoplasmic and/or nuclear extracts are prepared, and these extracts are brought into contact with the antibody specific for the human LIV21 protein.

Diagnosis

The present invention teaches the development of the diagnostic test which also makes it possible to monitor the evolution of a cell proliferation. In particular, the present invention makes it possible to monitor the evolution of a cell proliferation on fresh cells or tissues, on frozen cells or tissues and on tissues processed, inter alia, with paraffin. The applications may be the diagnosis of cancer and also the monitoring of the evolution of a cell proliferation. Preferably, the cancer is selected from breast cancer, bladder cancer, ovarian cancer, lung cancer, skin cancer, prostate cancer, colon cancer, liver cancer, a sarcoma, a leukemia and glioblastoma, without being limited thereto.

Four of these properties can be used: its passage from the cytoplasmic cellular compartment to the nuclear compartment, the property of associating with the E2F4 transcription factor in order to form a complex which inhibits the expression of the E2F1 factor, and the ability of LIV21 to translocate in the nucleus through specific inhibition of PKCε, the sumoylation of LIV21 when the latter is nuclear and integrated into PML bodies and its interaction with HDAC.

The predominantly cytoplasmic state of this protein in cases of cancer, compared with its nuclear location in normal cells, is a geographical and structural difference which makes it possible, without the need for a fluorescent label, to differentiate spectral profiles of the functional pattern of cancerous tissue versus normal tissue, and thus to make the diagnosis.

These results show that the cytoplasmic localization of LIV21 is an indicator of the aggressiveness and of the metastatic potential of the cancer. The detection of the LIV21 expression indicates the presence of cancer cells, more particularly of invasive, aggressive and/or metastatic cancer cells. These results also show that the nuclear localization of LIV21 is an indicator of normal quiescent cells or of well-differentiated tissues.

The invention concerns, moreover, methods for the diagnosis or prognosis of cancer which implement the detection of the cytoplasmic localization of a transcription factor located in the nucleus in normal cells.

The present invention concerns a method for the detection of cancer cells in a biological sample from a patient, comprising the detection of the product of expression of the LIV21 gene in the nucleus and/or the cytoplasm of the cells in the biological sample from said patient, localization of said product of expression of the LIV21 gene in the cytoplasm being indicative of the presence of cancer cells and localization of said product of expression of the LIV21 gene in the nucleus being indicative of the presence of noncancer cells. Preferably, localization of said product of expression of the LIV21 gene in the cytoplasm is indicative of the presence of invasive and/or metastatic cancer cells. The method preferably comprises a prior step of suitable treatment of the cells contained in the sample by any appropriate means which makes it possible to render the intracellular medium accessible. The method optionally comprises a step of comparison with a biological sample which does not contain cancer cells.

Optionally, the method according to the invention also comprises the detection of the product of expression of at least one gene selected from the group consisting of the protein kinase C epsilon (PKCε) gene, the E2F1 gene and the E2F4 gene. The method can in particular comprise the detection of the product of expression of two of these genes or of the three genes. Moreover, at least one of the ratios LIV21/PKCε, LIV21/E2F4 and LIV21/E2F1 can be determined in the present method. This ratio can be determined in the cytoplasm and/or in the nucleus. Preferably, these ratios are determined in the nucleus. Preferably, these ratios are compared with those obtained in a normal cell.

The method can also comprise the detection of the product of expression of at least five genes selected from the group consisting of RBP2, E2F4, E2F1, SUMO1, SUMO3, HDAC1, cycE/cdk2, cdk1, CREB1, p300, Rb, PML, p107 and p130 of the pocket protein family. It can also comprise the detection of the product of expression of at least five genes selected from the group consisting of NFkB, cdc2A, mdm2, p21, p53, p65, Ki67, erk, CD53 and CAF1. The method can comprise the detection of an interaction between some of these proteins and/or the detection of a posttranslational modification of one of these proteins.

The method may in particular comprise the detection of the product of the expression of two of these genes or of the three genes. Moreover, at least one of the ratios LIV21/PKCε, LIV21/E2F4 and LIV21/E2F1 may be determined in the present method. This ratio can be determined in the cytoplasm and/or in the nucleus. Preferably, these ratios are determined in the nucleus. Preferably, these ratios are compared with those obtained in a normal cell.

In one embodiment, the expression product of the genes is detected at the mRNA level, it being possible for the mRNA to be detected by any means known to those skilled in the art.

Thus, the method according to the present invention also relates to the detection of a polynucleotide encoding the human LIV21 protein or a fragment thereof, for example LIV21a and/or LIV21b. The polynucleotide encoding LIV21 may be an mRNA, a cDNA or a genomic DNA. The polynucleotides may be isolated from cells of the biological sample. They may also be obtained by a polymerase chain reaction (PCR) carried out on the total DNA of the cells or else by RT PCR carried out on the total RNA of the cells or polyA RNAs.

The mRNA may be detected by an RT PCR analysis. For this, the method uses a pair of primers specific for the expression product to be detected, in particular LIV21, PKCε, E2F1 or E2F4. The term "specific pair of primers" is intended to mean that at least one of the primers is specific for the expression product to be detected, i.e. that this pair of primers makes it possible to specifically amplify a fragment of the desired mRNA. Preferably, the RT PCR analysis is carried out on nuclear and/or cytoplasmic extracts of the cells contained in the sample from the patient. Optionally, the RT PCR analysis may be a quantitative analysis. A pair of primers specific for LIV21 can be prepared on the basis of the teachings of the present application. For example, the pair of primers may comprise the primers described in the sequences listing.

The pairs of primers specific for PKCε, E2F1 and E2F4 are well known by those skilled in the art (Caroll J S 2000; Mundle S D 2003; Stevaux O 2002; Cheng T 2002; Opalka B 2002).

The mRNA may also be detected by Northern blotting analysis. For this, the method uses a probe specific for the expression product to be detected, in particular LIV21, PKCε, E2F1 or E2F4. A probe specific for LIV21 can be prepared on the basis of the teachings of the present application. An example of a specific probe comprises the sequence SEQ ID No 50. Preferably, the Northern blotting analysis is carried out on nuclear and/or cytoplasmic extracts of the cells contained in the sample from the patient. The nucleic probe is labelled. The oligonucleotide labelling technique is well known to those skilled in the art. The labelling of the probes according to the invention can be carried out with radioactive elements or with non radioactive molecules. Among the radioactive isotopes used, mention may be made of $^{32}$P, $^{33}$P or $^{3}$H. The non radioactive entities are selected from ligands such as biotin, avidin, streptavidin or digoxigenin, haptens, dyes and luminescent agents such as radioluminescent, chemoluminescent, bioluminescent, fluorescent or phosphorescent agents. The probes specific for PKCε, E2F1 and E2F4 are well known to those skilled in the art.

In a preferred embodiment, the expression product of the genes is detected at the protein level. Preferably, the protein is detected using a specific antibody. Thus, the method comprises a step of bringing the cells of the biological sample into contact with an anti-human LIV21 antibody. The antibodies may be monoclonal or polyclonal. The anti-LIV21 antibody can, for example, be an anti-LIV21 serum.

When the product of expression of one of the genes PKCε, E2F1 and E2F4 must be detected, the method can use antibodies specific for the PKCε, E2F1 and E2F4 proteins, respectively. Polyclonal and monoclonal antibodies directed against PKCε, E2F1 and E2F4 are commercially available. By way of example, mention may be made of, for PKCε, a rabbit polyclonal antibody (Santa Cruz Technology, sc-214), for E2F1, a rabbit polyclonal antibody (Santa Cruz Technology, sc-860), and for E2F4, a rabbit polyclonal antibody (Santa Cruz Technology, sc-866). Preferably, the antibodies are labeled, directly or by means of a secondary antibody. The antibody labeling techniques are well known to those skilled in the art.

In a specific embodiment, the protein can be detected by Western blotting analysis. The Western blotting analysis can be carried out on nuclear and/or cytoplasmic extracts of the cells contained in the sample from the patient. Briefly, the proteins are migrated in a gel and then blotted onto a membrane. This membrane is then incubated in the presence of the antibodies and the binding of the antibodies is optionally revealed using labeled secondary antibodies.

In another embodiment, the protein is detected by immunohistochemistry, immunocytochemistry or immunoradiography. These techniques are well known to those skilled in the art. The immunocytochemical analysis can be carried out on whole cells originating from the sample or which are derived therefrom, for example by cell culture. It can also be carried out on isolated nuclei. The immunohistochemical analysis can be carried out on mammary tissue sections.

By way of illustration, an immunocytochemical analysis can include the following steps. However, it is understood that other preparatory methods can be carried out. Cells originating from the biological sample are cultured, preferably on slides (Lab Tek, Nunc, Germany), and then washed with buffer and fixed with paraformaldehyde (for example, 4%). A saturation step is preferably carried out by incubating the cells with buffer S (PBS-0.1% Triton X100-10% FCS). The cells are then incubated with a primary antibody and are then washed and incubated with a fluorescent secondary antibody, if necessary. The nuclei can be labeled with propidium iodide (Sigma). The slides are mounted in moviol for observation by fluorescence microscopy. Moreover, isolated nuclei sampled during a nuclear extraction can be fixed with paraformaldehyde (for example, 4%). The suspensions of nuclei are deposited between a slide and cover slip and the observation is carried out by fluorescence microscopy and by confocal microscopy. The primary antibodies are, for example, rabbit antibodies and the secondary antibodies are labeled antibodies directed against rabbit IgGs.

The present invention also concerns the use of a protein array for detecting the expression of one or more of these proteins, and/or an interaction between two or more of these proteins, and/or the posttranslational modification of one or more of these proteins.

In a preferred embodiment, the detection of the product of expression of one or more genes or of the interaction between several proteins is carried out by means of a protein array. Thus, a polypeptide according to the present invention, in particular LIV21 or a fragment thereof, or an antibody specific thereto, or a fragment or a derivative thereof which conserves the binding specificity, can advantageously be immobilized on a support, preferably a protein array. Such a protein array is included in the invention. This array can also contain at least one polypeptide selected from the group consisting of protein kinase C epsilon (PKCε), RBP2, E2F4, E2F1, SUMO, HDAC1, cycE/cdk2, cdk1, CREB1, p300, Rb, PML, p107 and p130 of the pocket protein family or at least one antibody specific for one of these polypeptides, or a fragment or a derivative thereof which conserves the binding specificity. The array can also comprise other polypeptides well known to those skilled in the art to be advantageous for the detection and/or the prognosis of a cancer, or antibodies specific for said polypeptides. These polypeptides can, for example, be selected from the following list: NFkB, cdc2A, mdm2, p21, p53, p65, Ki67 and CAF1.

The protein arrays according to the present invention can be prepared according to the techniques well known to those skilled in the art. In practice, it is possible to synthesize the attached polypeptides directly on the protein array, or it is possible to perform an ex situ synthesis followed by a step of attachment of the synthesized polypeptide to said array. Moreover, the polypeptides or antibodies to be attached can be purified from a cell. The supports include smooth supports (for example, metal, glass, plastic, silicon, and ceramic surfaces) and also texturized and porous materials. Such supports also include, but are not limited to, gels, rubbers, polymers and other flexible materials. The supports do not need to be flat. The proteins or antibodies of the array can be attached directly to the support or can be attached by means of a spacer or a linker.

In a specific embodiment, an LIV21-specific antibody or a fragment or derivative thereof which conserves the binding specificity is immobilized on the solid support. Thus, this array provides a practical means for measuring the LIV21 expression product. Preferably, the array comprises at least one antibody specific for a polypeptide selected from the group consisting of PKCε, RBP2, E2F4, E2F1, SUMO, HDAC1, cycE/cdk2, cdk1, CREB1, p300, Rb, PML, p107 and p130 of the pocket protein family, preferably PKCε, E2F1 and E2F4. The array also comprises at least one antibody specific for a polypeptide known to those skilled in the art to be advantageous for the detection and/or the prognosis of a cancer, for example NFkB, cdc2A, mdm2, p21, p53, p65, Ki67 and CAF1. The array can comprise an antibody or a fragment or derivative thereof which has the same specificity.

The protein arrays according to the invention are also extremely useful for experiments in proteomics, which studies the interactions between the various proteins. In a simplified manner, peptides representative of the various proteins are attached to a support. Said support is then brought into contact with labeled proteins and, after an optional rinsing step, interactions between said labeled proteins and the peptides attached to the protein array are detected.

"Protein array" is intended to denote a support to which are attached polypeptides or antibodies, it being possible for each of them to be pinpointed by its geographical location. These arrays differ mainly in terms of their size, the material of the support and, optionally, the number of polypeptides which are attached thereto.

The protein arrays can also be useful for the screening of test compounds.

The present invention also relates to a method for the detection of cancer cells in a biological sample from a patient, comprising the detection of the product of expression of the LIV21 gene in the nucleus and/or the cytoplasm of the cells in a sample of cells in the biological sample from said patient, which method is characterized in that it comprises at least: (a) bringing said biological sample into contact with a protein array as defined above, and (b) revealing, by any appropriate means, antigen-antibody complexes formed in (a), for example by EIA, ELISA or RIA or by immunofluorescence. Other detection methods are described in detail in the following document: US2004152212.

Methods applicable for the synthesis of protein arrays are described, for example, in the following patents: WO2004/063719, WO2005/016515, US2005019828, WO03018773, US2002187464, U.S. Pat. No. 5,143,854, U.S. Pat. No. 5,242,974, U.S. Pat. No. 5,252,743, U.S. Pat. No. 5,324,633, U.S. Pat. No. 5,384,261, US2006035387, US2005100947, US2005233473, WO0198458, WO0172458, WO0004382, WO0004389, WO9015070, WO9210092, WO9310161, WO9512808 and WO9601836, the content of these patents being incorporated into the present application by way of reference. For example, these protein arrays can be fabricated according to conventional methods described (Lubman David M, QIAO TIECHENG Alex, Mathew ABY J etc.) or novel tools for the automation of hybridization and of reading, US2004152212 and Yu Xinglong US 2005019828 and novel supports which attach polypeptides, Claus Peter Klages et al. (example FIG. 2).

The biological samples originate from a patient potentially suffering from cancer or for whom it has been established that said patient is suffering from cancer. "Biological sample" is intended in particular to mean a sample of the biological fluid, living tissue, tissue fragment, mucosity, organ or organ fragment type, or any culture supernatant obtained by means of taking a sample. The method according to the present invention can comprise a step of taking a biological sample from the patient. The detection step can be carried out directly on a tissue section of the sample, or on a culture of cells originating from the sample, or on total cell extracts, nuclear extracts and/or cytoplasmic extracts. The sample from the patient can come from a puncture, a biopsy, ground cellular material, a bronchial aspiration, a blood sample or a urine sample.

In a specific embodiment of the method comprising the detection of the product of expression of the PKCε gene, a significant increase in PKCε is indicative of the presence of cancer cells. More specifically, the amount of PKCε in normal cells is compared with the amount of PKCε in the cells of the sample, and the significant increase is determined by means of this comparison. The method according to the present invention can optionally comprise the measurement of the LIV21/PKCε content. This LIV21/PKCε ratio increases in the cytoplasmic fraction of cancer cells compared with normal cells.

In another specific embodiment of the method comprising the detection of the product of expression of the E2F4 gene, the method comprises the detection of the association of LIV21 with the E2F4 protein, and a decrease in this association is indicative of the presence of cancer cells. The detection of the association of LIV21 with the E2F4 protein can be carried out by concurrent detection of LIV21 and of E2F4 and/or by the concurrent measurement of HDAC1. The method according to the present invention can optionally comprise the measurement of the E2F4/LIV21 content. This E2F4/LIV21 ratio decreases in the nucleus of cancer cells compared with normal cells.

In an additional embodiment of the method comprising the detection of the product of expression of the E2F1 gene, the presence of the E2F1 protein in the nucleus is indicative of the presence of cancer cells. The method according to the present invention can optionally comprise the measurement of the E2F1/LIV21 content. This E2F1/LIV21 ratio increases in the nuclear fraction of cancer cells compared with normal cells.

The method according to the present invention allows in particular the detection of metastasized cancer, therapeutic monitoring and/or recurrences following treatment and makes it possible to determine the degree of invasiveness of a cancer. The specificity of the detection can be related to the crossing over of information obtained through the existence and the topography of LIV21 by all imaging and spectroscopy means and obtained by combination with other known cancerological indicators via protein arrays or microarrays. Thus, the detection based on LIV21 can be combined with the detection of other cancer markers, in particular breast cancer markers, known to those skilled in the art.

In fact, the present invention concerns a method for the therapeutic monitoring of an anticancer treatment in a patient suffering from cancer, comprising the administration of the anticancer treatment to said patient and the detection of cancer cells in a biological sample from the patient, according to the method of the present invention. A decrease in cancer cells will be indicative of the effectiveness of the treatment. The detection of cancer cells in a biological sample from the patient, according to the method of the present invention, can be carried out once or several times over the course of the anticancer treatment or after the anticancer treatment. Preferably, the biological sample originates from the tissue affected by the cancer treated.

Moreover, the present invention also concerns a method for the detection of recurrences subsequent to an anticancer treatment of a cancer in a patient, comprising the detection of cancer cells in a biological sample from the patient, according to the method of the present invention. The detection of cancer cells in a biological sample from the patient, according to the method of the present invention, can be carried out once or several times after the anticancer treatment. The detection of cancer cells is indicative of recurrences. Preferably, the biological sample originates from the tissue affected by the cancer treated.

The present invention also describes a kit for carrying out a method according to the invention. More particularly, the invention concerns a kit for the detection of cancer cells in a biological sample from a patient, comprising one or more elements selected from the group consisting of an antibody which binds specifically to human LIV21 according to the present invention and an anti-LIV21 serum according to the present invention, an oligonucleotide probe specific for the LIV21 mRNA and a pair of primers specific for the LIV21 mRNA. In a preferred embodiment, the kit comprises antibodies which bind specifically to human LIV21. In another preferred embodiment, the kit comprises an oligonucleotide probe specific for the LIV21 mRNA. It may also comprise a probe specific for a "housekeeping" gene. The kit according to the present invention can comprise reagents for the detection of an LIV21-antibody complex produced during an immunoreaction. Optionally, the kit according to the present invention also comprises means for detecting the product of expression of at least one gene selected from the group consisting of the protein kinase C epsilon (PKCε) gene, the E2F1 gene and the E2F4 gene. This detection means can be antibodies specific for the protein, oligonucleotide probes specific for the mRNA concerned and/or a pair of primers specific for the mRNA.

The present invention also relates to a diagnostic composition comprising one or more elements selected from the group consisting of an antibody according to the present invention and a serum according to the present invention, an oligonucleotide probe specific for the LIV21 mRNA and a pair of primers specific for the LIV21 mRNA.

The present invention also concerns a diagnostic composition comprising one or more elements selected from the group consisting of an antibody according to the present invention and a serum according to the present invention.

Anticancer Therapy

In the context of an anticancer therapy, it is possible to envision increasing the amount of LIV21 present in the nucleus. For this, the nuclear localization of LIV21 could be promoted, for example by decreasing the activity of PKCε in the cancer cells and by using HDAC inhibitors.

In another specific embodiment of anticancer therapy, it is possible to envision decreasing the activity of PKCε in the cancer cells. This decrease in activity can be produced by decreasing the activity of the PKCε protein or by decreasing its expression. A decrease in the activity of the PKCε protein can be obtained by administering PKCε-protein inhibitors to the cancer cells. The PKCε-protein inhibitors are well known to those skilled in the art. A decrease in the expression of the PKCε protein can be obtained by using antisenses or siRNA specific for the PKCε gene. Kits are commercially available. Moreover, the techniques concerning inhibition by means of antisense or siRNA are well known to those skilled in the art (Arya R 2004, Lee W 2004, Sen A 2004, Platet N 1998, Hughes 1987).

The present invention therefore concerns a pharmaceutical composition comprising a PKCε-protein inhibitor. It also concerns the use of a pharmaceutical composition comprising a PKCε-protein inhibitor as a medicament, in particular for the preparation of a medicament for use in treating cancer. Finally, it concerns a method for treating cancer in a patient, comprising the administration to the cancer cells of a PKCε-protein inhibitor, the pKCε-protein inhibitor making it possible to reduce or abolish the cancerous phenotype of the treated cells. In a first embodiment, the PKCε-protein inhibitor decreases the activity of the PKCε protein. In a second embodiment, the PKCε-protein inhibitor decreases the expression of the PKCε protein. Preferably, cancer is selected from breast cancer, bladder cancer, ovarian cancer, lung cancer, skin cancer, prostate cancer, colon cancer, liver cancer, a sarcoma, a leukaemia and glioblastoma, without being limited thereto.

In the context of a therapy for a neurodegenerative disease, it is possible to envision decreasing the amount of LIV21 present in the nucleus of the cells affected by the neurodegenerative disease. The cells affected by the neurodegenerative disease are generally neurons, motor neurons, etc. In a preferred embodiment, the neurodegenerative disease is chosen from Alzheimer's disease, Huntington's disease, Parkinson's disease and amyotrophic lateral sclerosis (ALS). For this, the nuclear localization of LIV21 could also be hindered, for example by increasing the activity of PKCε in the cells affected by the neurodegenerative disease.

The inhibition or the blocking of LIV21 expression can be carried out by any means known to those skilled in the art. In particular, by way of illustration, mention may be made of the antisense strategy, siRNA and ribozymes. Thus, an antisense oligonucleotide or an expression vector encoding this antisense oligonucleotide could be prepared and used to block the translation of the mRNA encoding LIV21 n-vivo. Moreover, a ribozyme can be prepared for cleaving and destroying, in vivo, the mRNA encoding LIV21. It is also possible to envisage a triple-helix strategy in which an oligonucleotide is designed so as to hybridize with the gene encoding LIV21 and to thus block the transcription of this gene.

Moreover, the nuclear localization of LIV21 could also be made unfavourable, for example by increasing the activity of PKCε in the cells affected by the neurodegenerative disease. We observed a strong similarity of LIV21 with ADC7 neuronal thread protein (O60448 HUMAN) which is knew to be implicated in Alzheimer disease and find in the cerebrospinal fluid. So regulate an interaction between these two proteins with therapeutic peptides or siRNA is interesting for the treatment of Alzheimer disease.

In another specific method of therapy against a neurodegenerative disease, it is possible to envisage increasing the activity of PKCε in the cells affected by the neurodegenerative disease and permits apoptosis. The cells affected by the neurodegenerative disease are generally neurons, motorneurons, etc. In a preferred embodiment, the neurodegenerative disease is chosen from Alzheimer's disease, hungtington's disease, parkinson's disease and amyotrophic lateral sclerosis (ALS). For this, the nuclear localization of Liv21 could also be hindered, for example by increasing the activity of PKCε in the cells affected by the neurodegenerative disease.

This increase in activity can be produced by increasing the activity of the PKCε protein or by increasing its expression. An increase in the activity of the PKCε protein can be obtained by administering PKCε-protein activators to the cells affected by the neurodegenerative disease. The PKCε-protein activators are well known to those skilled in the art (Toma O (2004), Activation of PKCs by DAG, AGPI: oleic acid, linoleic acid, arachidonic acid, etc. Activation and proteolysis of PKCs in gonadotropic cells: Communication 2004 by Macciano H, Junoy B, Mas J L, Drouva S V, UMR6544 Marseille). An increase in the expression of the PKCε protein can be obtained by using expression vectors encoding the PKCε protein and which make it possible to overexpress it in the cells affected by the neurodegenerative disease.

Thus, the present invention concerns a pharmaceutical composition comprising a PKCε-protein activator or an expression vector encoding the PKCε protein. It also concerns the use of a PKCε-protein activator or of an expression vector encoding the PKCε protein, for the preparation of a medicament for use in the treatment of a neurodegenerative disease.

Screening Method

The invention concerns methods for the selection, identification, characterization or optimization of active compounds which decrease cell proliferation, based on the measurement of the nuclear versus cytoplasmic localization of LIV21, or of the binding of the LIV21 protein to the E2F4 protein.

In a first embodiment, the selection, the identification, the characterization or the optimization of active compounds of therapeutic interest comprises bringing a candidate compound into contact with a cell and determining the nuclear versus cytoplasmic localization of the LIV21 expression product. An increase in the nuclear localization of LIV21 indicates that the candidate compound is active in terms of decreasing or abolishing cell proliferation. A decrease in the nuclear localization of LIV21 indicates that the candidate compound is active in terms of treating or preventing a neurodegenerative disease.

In a second embodiment, the selection, the identification, the characterization or the optimization of active compounds of therapeutic interest comprises bringing a candidate compound into contact with a cell and determining the level of expression of the gene encoding the PKCε protein. A decrease in the expression of PKCε indicates that the candidate compound is active in terms of decreasing or abolishing cell proliferation. An increase in the expression of PKCε indicates that the candidate compound is active in terms of treating or preventing a neurodegenerative disease.

In a third embodiment, the selection, the identification, the characterization or the optimization of active compounds of therapeutic interest comprises bringing a candidate compound into contact with a cell and determining the level of LIV21/E2F4 complex. An increase in the level of LIV21/E2F4 complex indicates that the candidate compound is active in terms of decreasing or abolishing cell proliferation.

A decrease in the level of LIV21/E2F4 complex indicates that the candidate compound is active in terms of treating or preventing a neurodegenerative disease.

In a fourth embodiment, the selection, the identification, the characterization or the optimization of active compounds of therapeutic interest comprises bringing a candidate compound into contact with a cell and determining the level of expression of the gene encoding the E2F1 protein. A decrease in the expression of E2F1 indicates that the candidate compound is active in terms of decreasing or abolishing cell proliferation. An increase in the expression of E2F1 indicates that the candidate compound is active in terms of treating or preventing a neurodegenerative disease.

The invention also relates to a method of screening for a compound capable of interacting in vitro, directly or indirectly, with LIV21, characterized in that: in a first step, the candidate compound and LIV21 are brought into contact and, in a second step, the complex formed between said candidate compound and LIV21 is detected by any appropriate means.

The present invention also relates to a method of screening for a compound capable of modulating (activating or inhibiting) the activity of the LIV21 protein, characterized in that: in a first step, cells of a biological sample expressing the LIV21 protein are brought into contact with a candidate compound, in a second step, the effect of said candidate compound on the activity of said LIV21 protein is measured by any appropriate means, and in a third step, candidate compounds capable of modulating said activity are selected. The activity of LIV21 can, for example, be estimated by means of evaluating the ability of the cell to divide, by measuring the expression of the E2F1 gene or by the cytoplasmic and/or nuclear localization of LIV21.

The candidate compound can be a protein, a peptide, a nucleic acid (DNA or RNA), a lipid, or an organic or inorganic compound. In particular, the candidate compound could be an antibody, an antisense, a ribozyme or an siRNA.

Other advantages and characteristics of the invention will appear in the examples and the figures which follow, and which are given in a nonlimiting manner.

EXAMPLES

Example 1

The inventor performed mass spectrometry (MALDI) for the LIV21 protein based on a one-dimensional acrylamide gel. The LIV21 protein was digested with trypsin. The peptides derived from the digestion are solubilized in a solvent: acetonitrile/water (1/1) containing 0.1% of TFA (trifluoroacetic acid). A saturated solution of the alpha-cyano-4-hydroxycinnamic matrix was prepared in the same solvent. The same volume of the two solutions was taken and mixed together and 1 µl was deposited onto the MALDI plate for analysis. The mass spectrometry showed that the LIV21 protein digested with trypsin reveals 54 peptides (cf. FIGS. 3-4). The LIV21 protein was characterized by a molecular weight of 50 kD, revealed by Western blotting. Since the first MALDI results were not probative, the inventor produced a two-dimensional SDS PAGE gel (FIG. 8). More than ten proteins were revealed by silver nitrate staining, but the very small amount of material did not make it possible to test samples derived from this gel by MALDI or MSMS.

When it changes cell compartment and when it is sumoylated, the LIV21 protein has a molecular weight of approximately 60 kD. When it is phosphorylated in the cytoplasm, it exhibits two forms which differ by a few kilobases. A doublet is then observed.

The inventor performed a third MALDI analysis, which gave interesting results, especially with regard to the 49 kD gel band, on *Gallus gallus* and a histatin variant (FIG. 13), the inventor then examined the sequence alignments, which made it possible to confirm homologies between *Gallus gallus*, PATF, Q7TCL4 and the polypeptides of histatin and of *Gallus gallus* (FIGS. 29 to 31.2).

Only two peptides characterize in common PATF and LIV21:
The LIV21a peptide is located between a site of interaction with the Rb/p107/p130 protein (ITCCE) and a site of sumoylation by SUMO1. The sequence of this peptide is the following:
PeptideLIV21a peptide is SEQ ID No 1
The LIV21b peptide is located between a sumoylation site (PKPG) and a phospholipase C site (YVKI) followed by (KKKRK) NLS. The sequence of this peptide is SEQ ID No 2
The LIV21c peptide is SEQ ID No 3
The LIV21d peptide SEQ ID No 4 are specific of LIV21.
Other peptides are provided in the sequences SEQ ID Nos 5-55.

Example 2

Study of the Nuclear Translocation of LIV21 in MCF-7 Cells

The study of the subcellular distribution of LIV21 in different tumor lines of various origins showed an exclusively cytoplasmic localization of this protein. The mechanism(s) by which LIV21 could be translocated into the nucleus in order to act on the cell cycle was (were) shown.

The presence of putative sites for phosphorylation by protein kinases C (PKCs), based on the possible homology that PATF is thought to have with the LIV21 sequence, directed the inventor's study toward a possible involvement of these proteins with respect to its nuclear translocation. The inventor therefore chose to study the MCF-7 line treated with TPA, which is known to modulate PKCs.

In parallel to this work, the inventor also studied the expression and the localization of cell cycle proteins implicated in the signaling pathway in which LIV21 could act.

The MCF-7 Cell Line

The MCF-7 line is a nonclonal human line of breast adenocarcinoma cells. During their differentiation induced by exogenous factors, these cells develop a hypertrophy, membrane protrusions and a tendency to dissociate from one another. They acquire a secretory phenotype which is characterized by the appearance of numerous granules and of secretory canaliculi.

In vivo, these cells are relatively nonmetastatic and this low invasiveness is thought to be due to a low constitutive activity of the protein kinases C (PKCs) and to a relatively low level of expression of protein kinase C alpha.

This line is used in many studies on proliferation, differentiation and apoptosis. These studies use appropriate drugs, such as TNF for the induction of apoptosis, or TPA (12-O-tetradecanoyl phorbol-13-SUMOate) for the induction of differentiation and therefore for the study of departure from the cell cycle.

The Effect of TPA on the MCF-7 Line

TPA is a known activator of PKCs. It activates the growth of normal breast cells, does not modify the proliferation of the cells of benign tumors from this same tissue, but drastically inhibits the proliferation of the cells of human mammary tumor lines such as the MCF-7 line. It reduces the cell growth of this line by positively controlling the c-erb-2 receptor and negatively controlling the retinoic acid receptor α, which are both expressed in particularly large amount in these cells. TPA greatly and rapidly inhibits the expression and the function of estrogen receptors (ERs) and it induces the time- and dose-dependent translocation of protein kinases C (PKCs) from the cytosol to the membranes.

Furthermore, TPA increases the migratory capacity of MCF-7 cells in vitro and a short period of treatment of these cells with TPA induces cellular expansion and microtubule organization characteristic of their differentiation.

Expression of LIV21 in MCF-7 Cells

Firstly, the inventor verified the expression of LIV21 in these cells at the protein level.

The inventor tackled the study of the expression of the LIV21 protein through the Western blotting technique, with an anti-LIV21 antibody, in MCF-7 cells compared with mammary tissues. The anti-LIV21 antibodies were obtained by the method described below. In this line, LIV21 is expressed, both in the mammary tissues and in the MCF-7 cells, in the form of a doublet which migrates at an apparent molecular weight of 50 kDa.

Production of Purified Anti-LIV21 Serum

The specific peptide sequences are the sequences No. 1 and No. 2.

These peptides were injected into rabbits (NZ W ESD 75 female, 2.3 kg at day 0), in agreement with standard immunization procedures, such as:

| Day | STEPS OF THE PROCEDURE |
|---|---|
| Day 0 | Collection of a control serum (20 ml)<br>First intradermal injection (1 ml/rabbit)<br>1 tube for two rabbits with 1 ml of antigen + 1 ml Freund's Complete |
| Day 14 | Second intramuscular injection (1 ml per rabbit)<br>1 tube for two rabbits with 1 ml of antigen + 1 ml Freund's Incomplete |
| Day 28 | Third intramuscular injection (idem D14) |
| Day 39 | The test serum is collected (5 ml) and conserved at 4° C. (serum D39) |
| Day 49 | Four subcutaneous injections (1 ml)<br>1 tube for two rabbits with 1 ml of ag + 1 ml Freund's Incomplete |
| Day 60 | Test serum collected (25-30 ml) and storage at 4° (serum D60) |
| Day 77 | Fifth intradermal injection (1 ml/rabbit) idem D49 |
| Day 88 | Test serum collected (5 ml) and storage at 4° (serum D88) |
| Day 99 | Test serum collected (25 ml) and storage at 4° (serum D98) |
| Day 102 | Test serum collected (25 ml) and storage at 4° (serum D102) |
| Day 104 | Test serum collected (25 ml) and storage at 4° (serum D104) |
| Day 106 | Test serum collected (25 ml) and storage at 4° (serum D106) |
| Day 109 | Total collected by total collection of blood and storage at 4° C. (serum D109) |

The reactivity of the serum obtained was tested with respect to binding of the peptide sequences No. 1 and 2.

At D60, the serum shows a good reactivity with each sequence. The serum produced did not bind to any member of the E2F family.

The Effect of TPA in MCF-7 Cells

Figure 14:
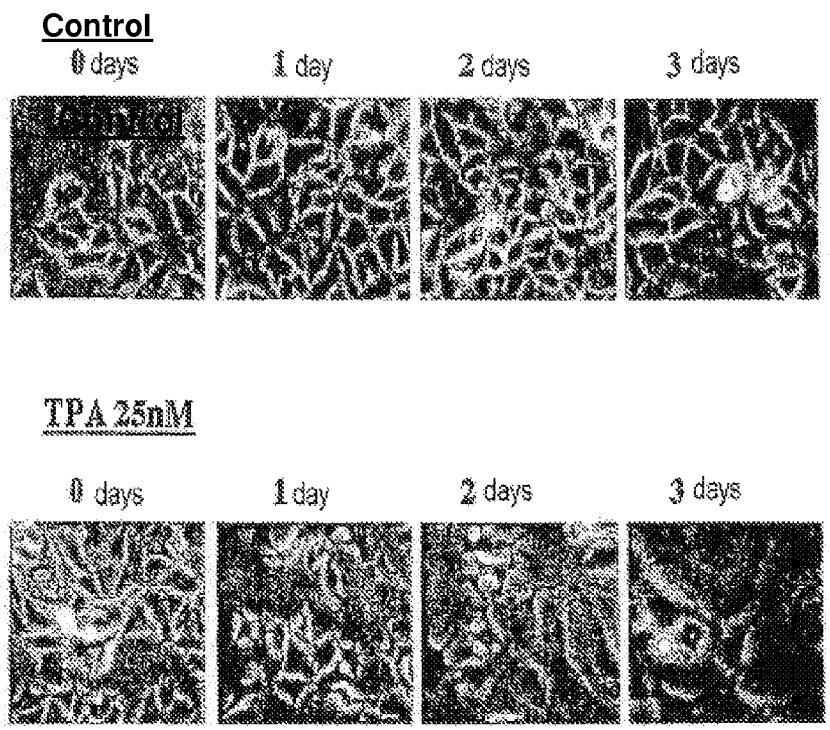
FIG. 14 is the morphology of MCF7 cells treated or not treated with TPA at 25 nM.

It has been described in the literature that TPA induces the arrest of proliferation and the differentiation of tumor cells of the MCF-7 line. In order to validate the culture conditions, the cell growth was monitored (by counting) beforehand over three days of culture in the presence or absence of TPA at a concentration of 25 nM (FIG. 14).

The cell counts demonstrate a variation in the growth kinetics between the nontreated cultures and the TPA-treated cultures. In fact, from the second day of culture onward, the number of cells is significantly different between the two treatment conditions, TPA already inducing the arrest of cell proliferation. After 3 days of treatment, the control cultures have twice as many cells as the treated cultures. TPA at the concentration of 25 nM therefore clearly inhibits proliferation under our culture conditions.

In parallel, the inventor was able to observe that the TPA-treated cells rapidly acquire characteristics of differentiated mammary gland cells (FIG. 14): hypertrophy, membrane protrusions and tendency to dissociate from one another. However, in the period of time over which the cells were studied, the secretory phenotype (appearance of granules and of secretory canaliculi) was not observed.

FACS Analysis of the Effect of TPA

Figure 15:
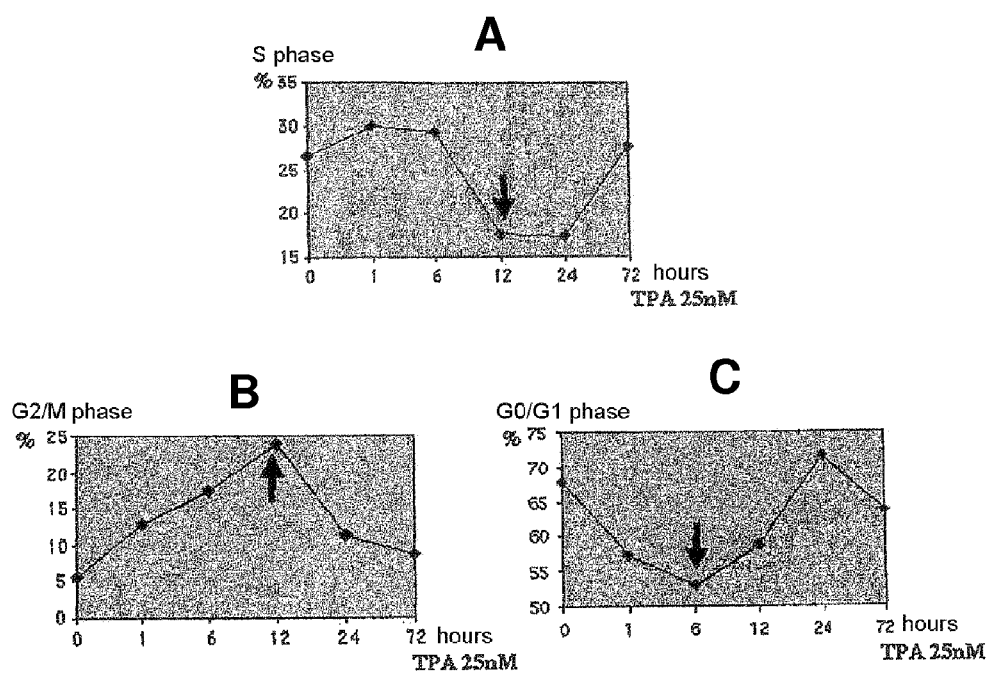
FIG. 15 is an analysis by FACS; representation, for each phase of the cell cycle, of the percentage of cells as a function of treatment time.

These preliminary studies of the effect of TPA showed in:

S phase: The FACS study shows that the number of cells in the S phase decreases and reaches a limiting value between 12 h and 24 h of TPA treatment (FIG. 15A). However, without any further addition of TPA, the number of cells in the S phase increases again so as to return to the initial state at 72 h of treatment.

G2/M phase: The number of cells in the G2/M phase increases from the beginning of the treatment, with a maximum observed at 12 hours (FIG. 15B).

G0/G1 phase: The number of cells in the G0/G1 phase is at a minimum at 6 hours and at a maximum at 24 hours (FIG. 15C).

A maximum of cells in the S phase are therefore observed in the early periods of the kinetics (0 h to 6 h), a maximum of cells in the G2/M phase is observed at 12 h and, finally, a maximum of cells in the G0/G1 phase is observed at 24 h. Finally, without any further addition of TPA, the cells return to the S phase at 72 h.

In conclusion, these results therefore show that TPA acts rapidly on the arrest of cell proliferation and its effect on the reduction of the number of cells in the S phase is optimal at 12 h. 72 h after the single addition of TPA, the cells reinitiate the cell cycle.

The Effect of TPA on the Nuclear Localization of LIV21

Figure 16:
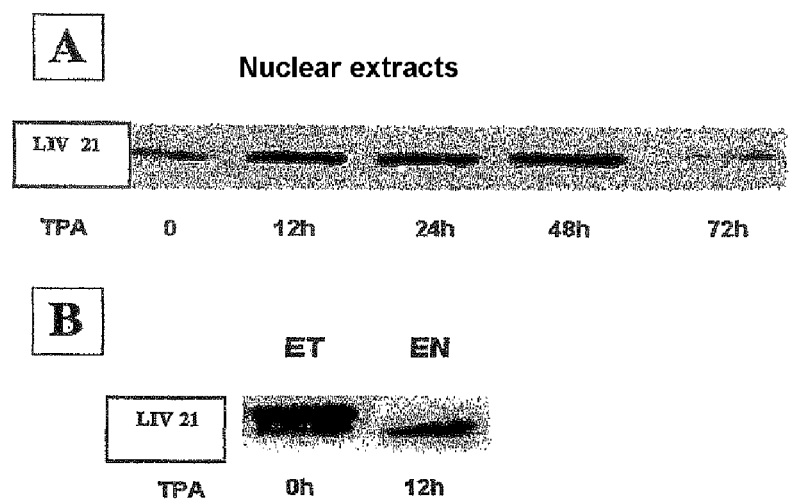
FIG. 16 is a Western blot comparing total extracts (ET) and nuclear extracts (EN) and showing the inhibition, with TPA, of the expression of LIV21 phosphorylation.

The results obtained by flow cytometry led the inventor to study, in parallel, the expression of LIV21 in nuclear extracts prepared after 12 h, 24 h, 48 h and 72 h of TPA treatment (FIG. 16A). During these kinetics, maximum anti-LIV21 immunoreactivity was observed from 12 h, was maintained up to 48 h and returned to its initial intensity after 72 h of treatment. These data are to be compared with those obtained by FACS. The immunoreactivity of LIV21 significantly increases at 12 h, at which time the number of cells in the S phase is minimal. It lasts until the reinitiation of the cell cycle observed at 72 h.

Furthermore, it can be noted that this immunoreactivity is detected in the form of a single band at an apparent molecular weight of 50 kDa, whereas it was expressed predominantly in the form of a doublet in the total extracts. In order to determine the form of LIV21 to which this single band corresponds, it was compared on the same Western blot with a total extract and a nuclear extract at 12 h of treatment (FIG. 16B). The results obtained show that the nuclear form of LIV21 corresponds to the lower band of the doublet. These data suggest that the LIV21 protein might be in a different phosphorylation state according to the cell compartment.

Figure 17:
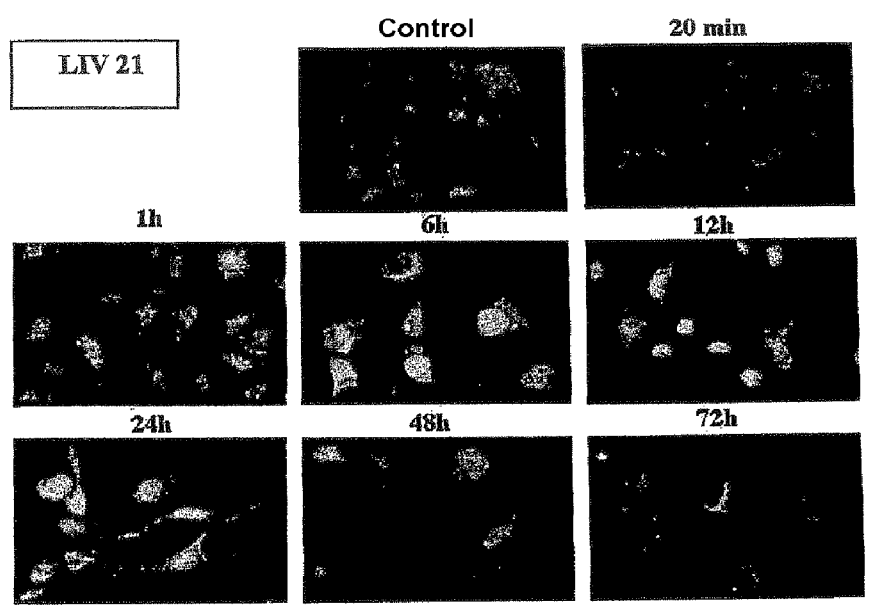
FIG. 17 is a study of the nuclear translocation of LIV21 by immunocytochemistry with an anti-LIV21 primary antibody (in green) in cultures treated or not treated with TPA at 25 nM. The nuclei are stained red with propidium iodide. The nuclei are predominantly stained yellow at 12 H until 24 H since the anti-LIV21 primary antibody (in green) is nuclear, whereas it is predominantly cytoplasmic at 72 H (red nuclei and green cytoplasms).

The results of the immunocytochemical study carried out using an anti-LIV21 antibody show that the nuclear translocation of LIV21 is at a maximum at 12 h (FIG. 17) and the localization of LIV21 is predominantly cytoplasmic at 72 h, which is in agreement with the Western blotting observations.

However, it is interesting to note that the expression of LIV21 already begins from 1 h of treatment in certain cells, since they are not synchronous.

All these observations show that the nuclear translocation of LIV21 is concurrent with the decrease in the number of cells in the S phase.

Example 3

Study of the Influence of PKCs on the Nuclear Translocation of LIV21

Effect of TPA on PKCε Expression

Figure 18:
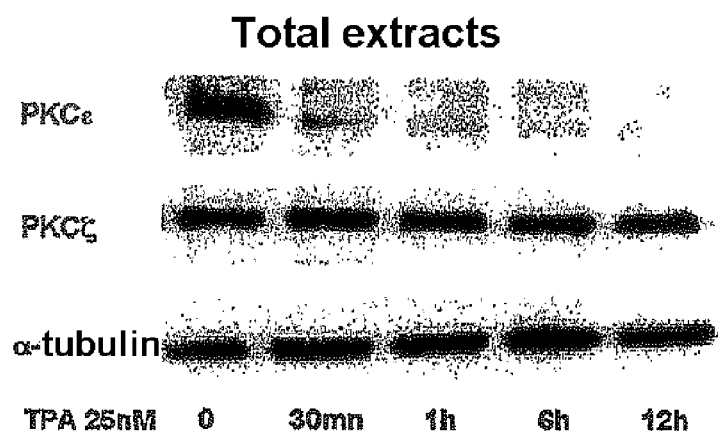
FIG. 18 shows the expression, as a function of time of treatment with TPA at 25 nM, of PKCε and PKCζ proteins in total extracts. α-Tubulin expression serves as a control for the amount of total proteins loaded in the wells.

Western blotting study: Given that the protein sequence of LIV21 has putative PKC phosphorylation sites, including two specific for PKCε, the inventor tested the variation in the expression of this PKC as a function of the duration of TPA treatment. It was observed that TPA acts very rapidly on PKCε expression, which decreases from 30 min (FIG. 18). The expression of PKCzeta (PKCζ) is used as an internal control since it is not sensitive to TPA.

Figure 19:
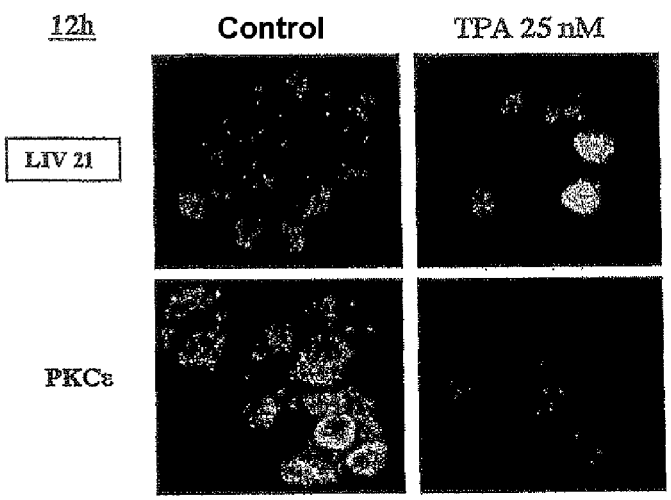
FIG. 19 shows the compared expression of PKCε and of LIV21 by immunocytochemistry on MCF-7 cell cultures treated or not treated with TPA at 25 nM for 12 h, carried out with anti-LIV21 and anti-PKCε antibodies in green, and propidium iodide staining the DNA red. The LIV21 is translocated into the nucleus by specific inhibition of PKCε. The PKCε is weakly expressed at 12 h in the presence of TPA. In fact, red nuclei and little green staining in the cytoplasms are observed. On the other hand, the expression of LIV21 is strong in the nuclei, which are stained yellow (merge) both with the anti-LIV21 antibody (green) and with the nucleus-specific propidium iodide.

Immunocytochemistry: In parallel, immunofluorescence experiments on treated or nontreated cultures made it possible to demonstrate this decrease in PKCε concurrent with the nuclear translocation of LIV21 (FIG. 19). It can be observed that PKCε disappears from the cytoplasm when the cells are treated with TPA and that LIV21 is detected in the nucleus.

To conclude, it is interesting to note that PKCε is weakly expressed at 12 h, at which time the fewest number of cells in the S phase and the maximum nuclear translocation of LIV21 are observed.

Example 4

Study of the Specific Role of PKCε on the Nuclear Translocation of LIV21 Using a Peptide which Inhibits PKCε Function and Translocation In order to determine the specific action of PKCε on the translocation of LIV21, the cultures were treated with a peptide which is a selective antagonist of the function and the translocation of this PKCε (EAVSLKPT (SEQ ID No 118)), and the results were compared with those obtained with TPA treatment. This peptide is recognized by the enzyme and binds as a modified substrate at the level of its catalytic site. It cannot be phosphorylated and acts as a specific inhibitor of the activity of PKCε.

Figure 20:
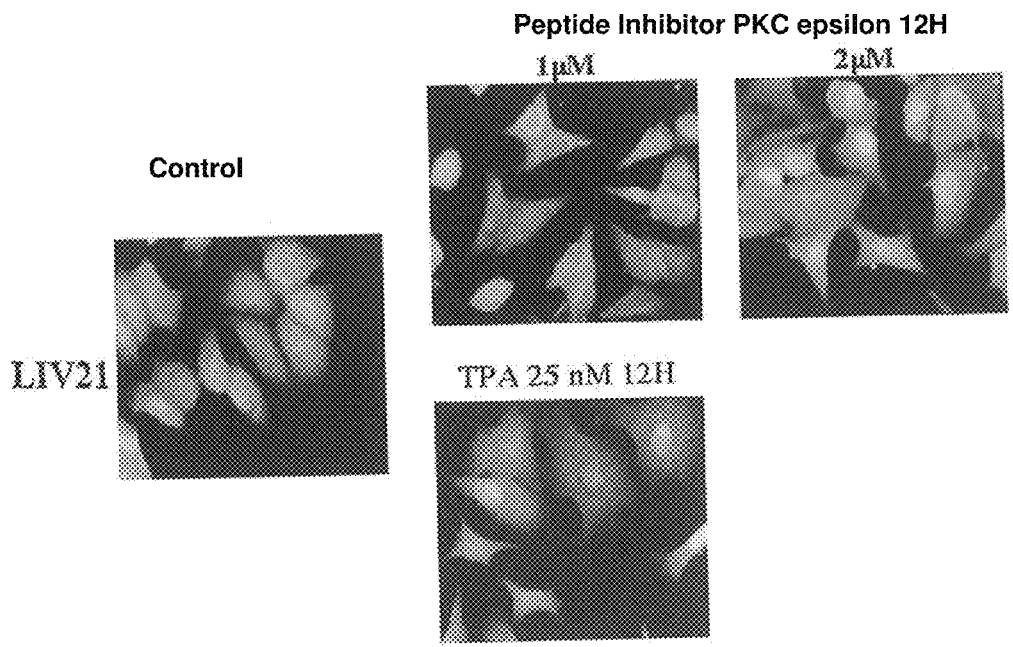
FIG. 20 shows the effect of the PKCε-inhibiting peptide on the LIV21 expression profile by immunocytochemistry on cultures: control or treated with 1 μM of peptide, 2 μM of peptide, or 25 nM of TPA. The treatments last 12 hours. The cells are labeled with anti-LIV21 (in green), and with propidium iodide (in red). It is observed that 2 μM of peptide (image referred to as 2 μM) have the same effectiveness as "25 nM of TPA 12 H": the nuclei (yellow) are predominantly labeled both with propidium iodide and with the anti-LIV21 antibody (in green) on these two images, whereas the control and the cells treated with only 1 μM of PKC-inhibiting peptide show red staining of the nuclei, reflecting the absence of nuclear translocation of LIV21 through its anti-LIV21 antibody (in green).

The effect of the selective inhibition of the activity of PKCε on the nuclear translocation of LIV21 was studied by immunocytochemistry. These experiments were carried out on non-treated cultures or cultures treated for 12 h with TPA at 25 nM or with the peptide at two different concentrations, 1 and 2 µM (FIG. 20). The peptide used at the concentration of 2 µM has an effect identical to that of TPA on the nuclear translocation of LIV21.

Figure 21:
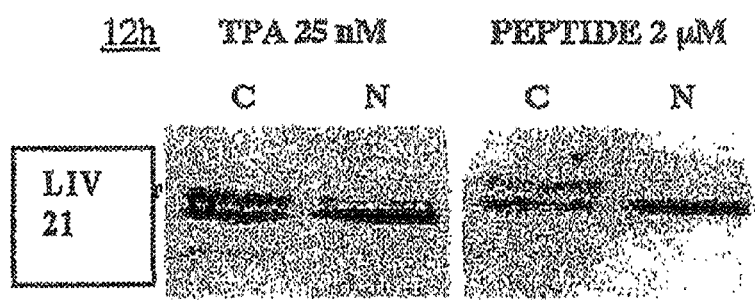
FIG. 21 shows the effect of the PKCε-inhibiting peptide on the LIV21 expression profile in cytoplasmic (C) and nuclear (N) cellular fractions, after treatment for 12 h with TPA (25 nM) or with peptide (2 μM).

These results were supported by cell fractionation experiments on cultures treated with the PKCε-inhibiting peptide at 2 µM, compared with TPA-treated cultures (FIG. 21). The same LIV21 expression profile was observed in the form of a doublet in the cytoplasm and of a single band in the nuclear fraction.

The specific inhibition of PKCε induces nuclear translocation of LIV21, thereby suggesting that LIV21 could be the target for PKCε, which would maintain it in the cytoplasm in a phosphorylated form.

Example 5

Western Blotting Analysis

This example describes the conditions used for a Western blotting analysis of cancerous breast cells.

The protein extracts are heated at 80° C. for 5 minutes in a Laemmli buffer (pH 7.4, 0.06 M Tris, 3% SDS, 10% glycerol, 1 mM PMSF, β-mercaptoethanol). The migration is carried out by SDS-PAGE (sodium dodecyl sulfate-polyacrylamide gel electrophoresis). 10 to 20 µg of proteins migrate in a 12% polyacrylamide gel for 1 h under denaturing conditions (migration buffer: 25 mM Tris base, 192 mM glycine, 1% SDS, pH 8.3). The proteins are then transferred onto a nitrocellulose membrane (Schleicher & Schuell) for one hour by liquid transfer, in a transfer membrane (25 mM Tris, 192 mM glycine, 20% methanol, pH 8.3). The membranes, saturated in PBS-0.1% Tween-0.1% Triton X100-5% skimmed milk for one hour, are brought into contact with the primary antibody diluted in PBS-0.1% Tween-0.1% Triton X100-1% milk at ambient temperature with gentle agitation for one hour to two hours. After washing, the peroxidase-coupled secondary antibody is incubated with the membranes for 1 h. Revelation is carried out by means of a chemiluminescence reaction using the ECL kit according to the supplier's protocol (Amersham).

The Primary Antibodies Used are:

The anti-LIV21 serum which was produced using two synthetic peptides based on the sequence of LIV21: peptide LIV21a (SEQ ID No 1) and peptide LIV21b (SEQ ID No 2). The peptides were coupled to hemocyanin before being injected into rabbits for the immunization. The polyclonal antibody was obtained from these two peptides by having immunized two rabbits and having bled one rabbit so as to have a preimmune serum (in order to be sure that this antibody did not already exist in this rabbit).

The rabbit anti-CDK2 polyclonal antibody (Santa-Cruz technology sc-163) diluted to 1/200.

The mouse anti-p21 monoclonal antibody (Dako, M7202) diluted to 1/150.

The mouse anti-p27 monoclonal antibody (Santa-Cruz technology sc-1641) diluted to 1/100.

The rabbit anti-PKCε polyclonal antibody (Santa-Cruz technology sc-214) diluted to 1/200.

The rabbit anti-PKCδ polyclonal antibody (Santa-Cruz technology sc-216) diluted to 1/200.

The rat anti-α tubulin polyclonal antibody (Serotec, MCAP77) diluted to 1/500.

The Peroxidase-Coupled Secondary Antibodies Used (Caltag) are:

The goat anti-rabbit IgG(H+L) F(ab')2 antibody diluted to 1/2000.

The goat anti-mouse IgG(H+L) F(ab')2 antibody diluted to 1/2000.

Example 6

Figure 22:
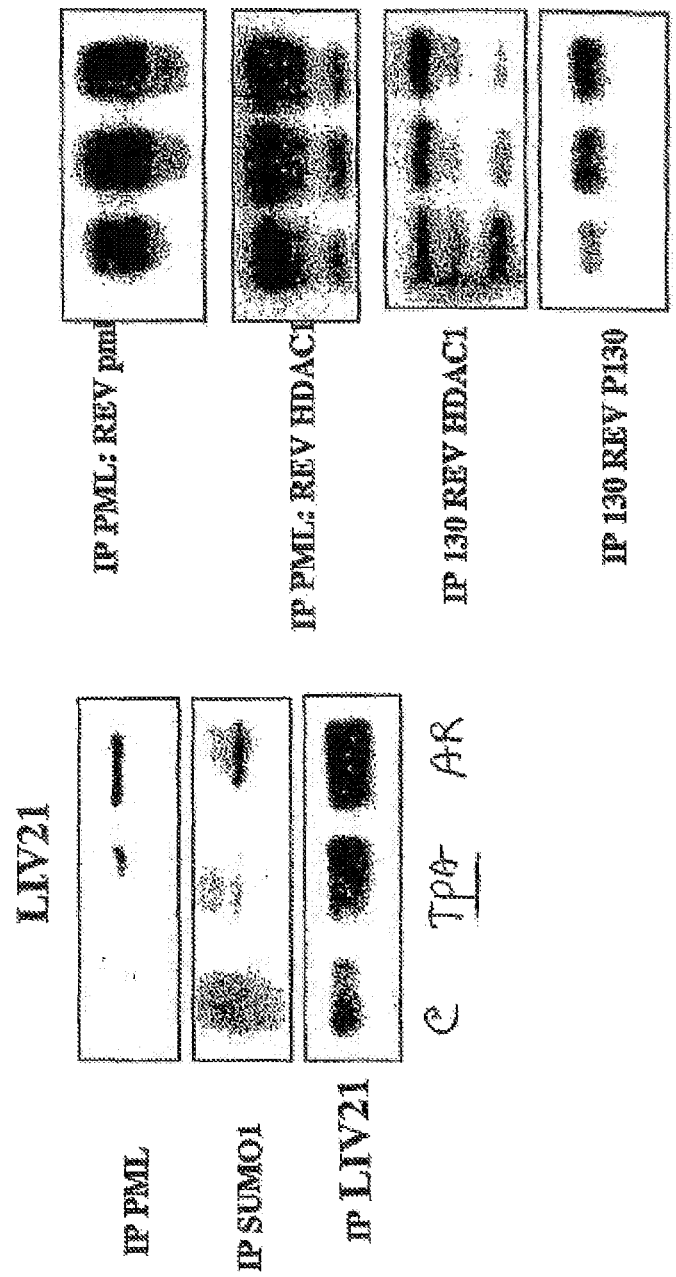
FIG. 22 shows, by immunoprecipitation (IP), the coexistence between PML/SUMO and LIV21: nuclear yellow fluorescence (merge) corresponding to the colocalization of PML/SUMO and LIV21 is observed in the cell nuclei.

It was demonstrated that the LIV21 protein is associated with PML bodies and that, during sumoylation, LIV21 goes from a molecular weight of 50 kd to 60 kd. Colocalization of LIV21 with SUMO in the PML-SUMO/LIV21 complex was shown by immunoprecipitation (FIG. 22).

Figure 1:
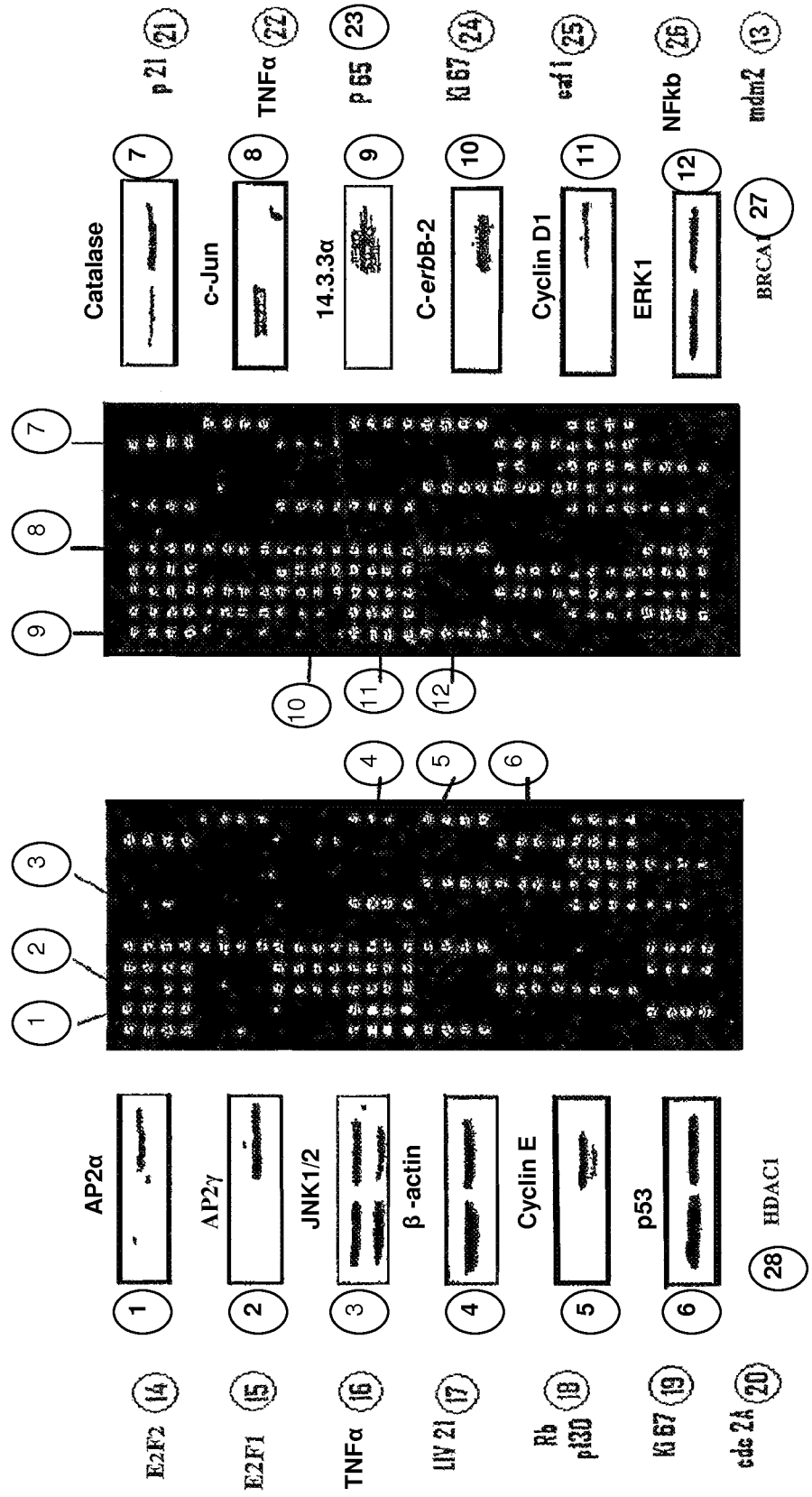
FIG. 1: antibody array.
Figure 2:
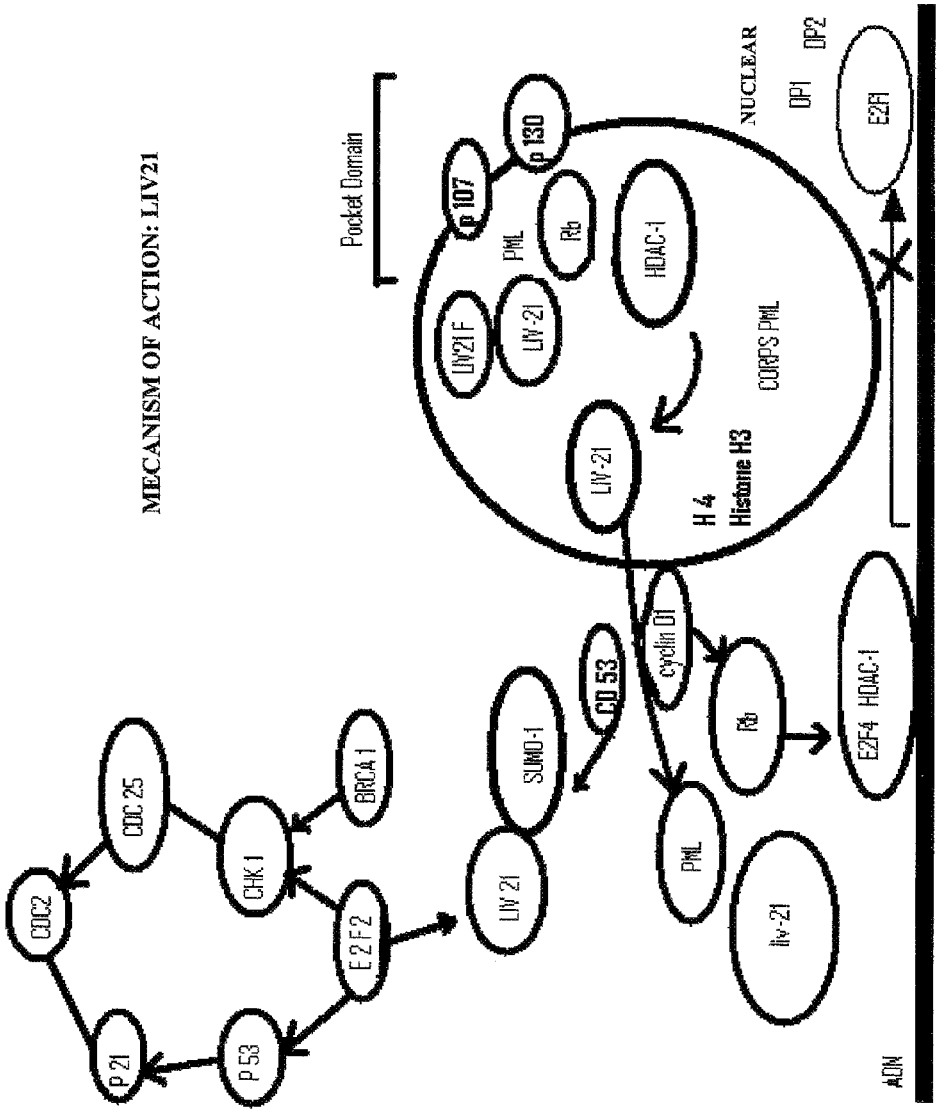
FIG. 2: scheme of nuclear protein interactions and consequences on the study of therapeutics.
Figure 3:
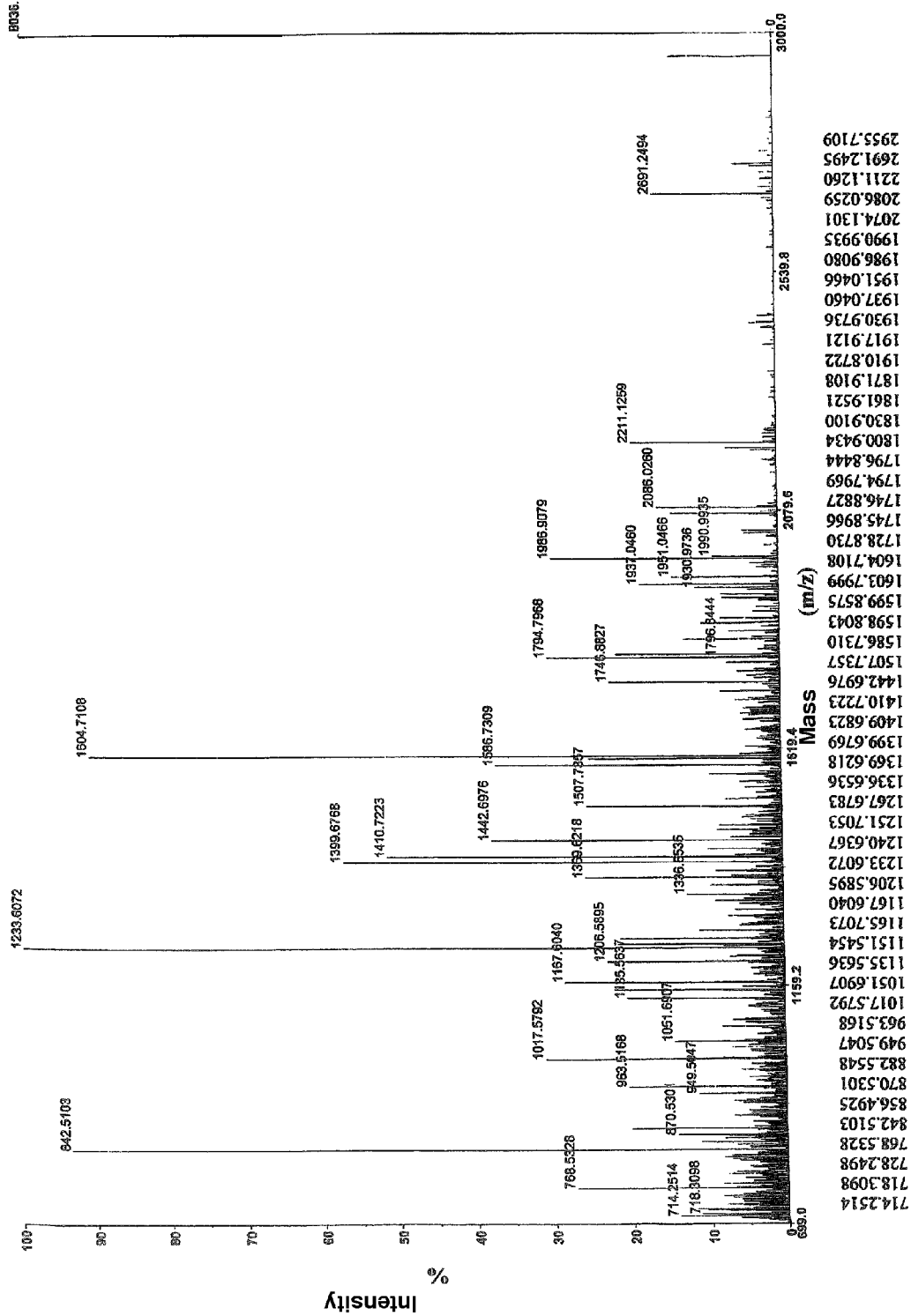
FIG. 3: LIV21 protein profile by mass spectrometry (Maldi) M (H$^+$) for the one-dimensional gel band corresponding to the protein doublet migrating at 50 kD. The peptides derived from the digestion are solubilized in a solvent: acetonitrile/water (1/1) containing 0.1% of TFA (trifluoroacetic acid). A saturated solution of the alpha-cyano-4-hydroxycinnamic acid matrix is prepared in the same solvent. The same volume of the two solutions is taken and mixed together, and 1 microliter is deposited onto the Maldi plate for analysis. The spectrum was determined on a Voyager with Waters software. The calibration with respect to the autolysis and trypsin digestion peaks is not excellent and needs to be looked at again.
Figure 4:
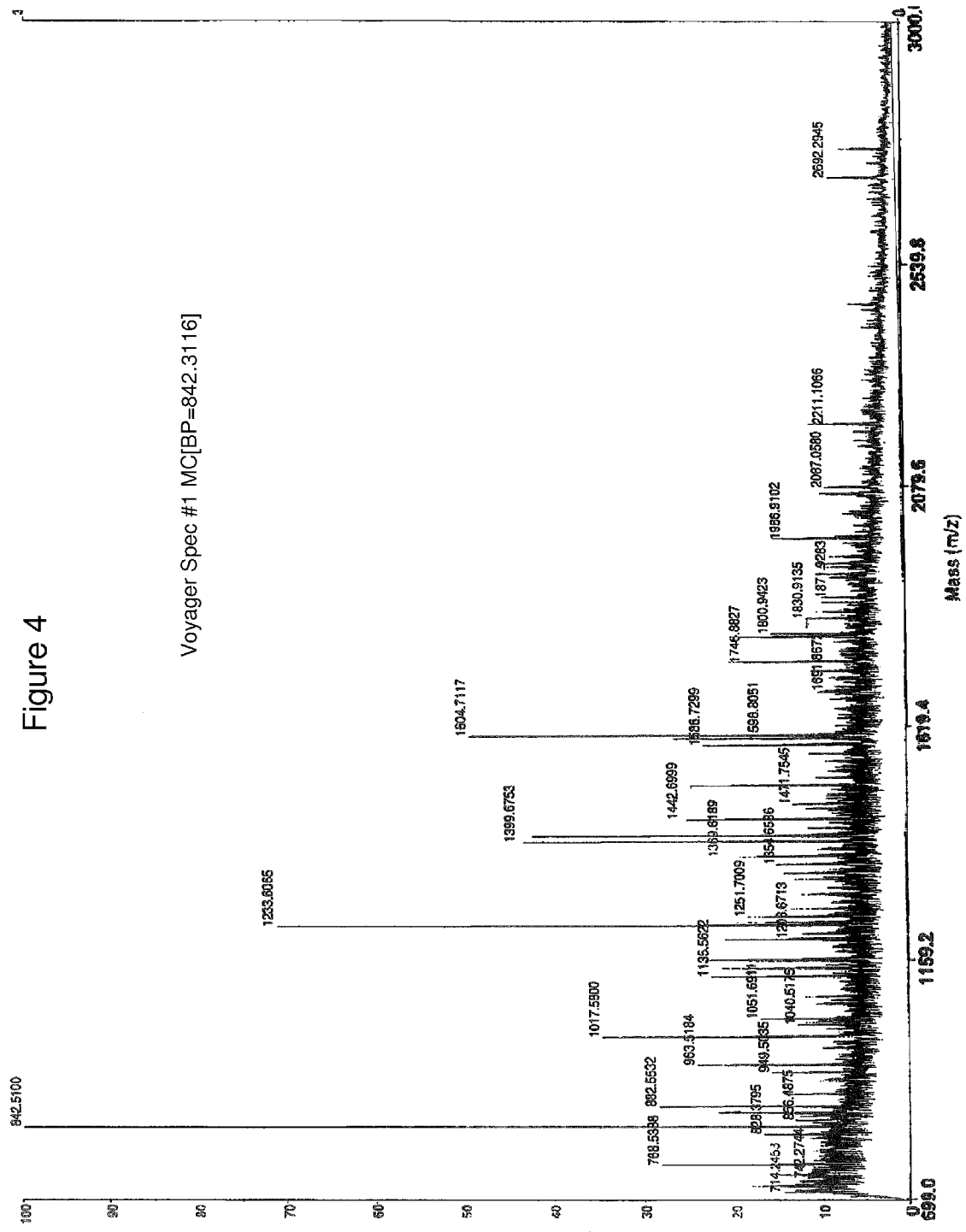
FIG. 4 is a zoomed-in profile of the chromatogram of the 49 kD band without smoothing.

Antitumor role of PML bodies: At the proliferation stage, there are visualized modifications in the PML bodies since these PML bodies dissociate and degrade: (speckles), proteins then become available in the nucleus for ensuring transcription, proliferation, immune reactions and everything that is required for gene transcription. It has been shown that PML associates with SUMO and with HDAC-1 (histone deacetylase 1) and that its complex acts on the expression of E2F1 and PML thus acts on the arrest of proliferation by blocking E2F1. Thus, the PML/HDAC-1 complex down-regulates E2F1 expression. PML associated with Rb (p130) binds to the deacetylated histones and blocks E2F1 by binding to the chromatin (FIG. 2).

In acute promyelocytic leukemias, PML is truncated and becomes a fusion protein with the retinoic acid receptor. This fusion protein (PMLRARalpha) is due to a 15/17 chromosomal translocation. A new treatment for this disease by combining arsenic and retinoic acid in order to induce cancer cells into apoptosis has been reported in the literature. The PML protein is thought to regulate proliferation in cancers and lymphomas. The inventor has shown, by immunoprecipitation, the association SUMO-PML in which LIV21 is located.

In the above examples, it was shown that LIV21 is phosphorylated by PKCε and that TPA is an inhibitor of PKCs. The TPA-treated MCF-7 lines show an inhibition of cancerous proliferation and a cell differentiation, and LIV21 is translocated into the nucleus. If a PKCε-specific inhibitory peptide was used, it was the activity and not the expression of PKCε which was inhibited.

Figure 23:
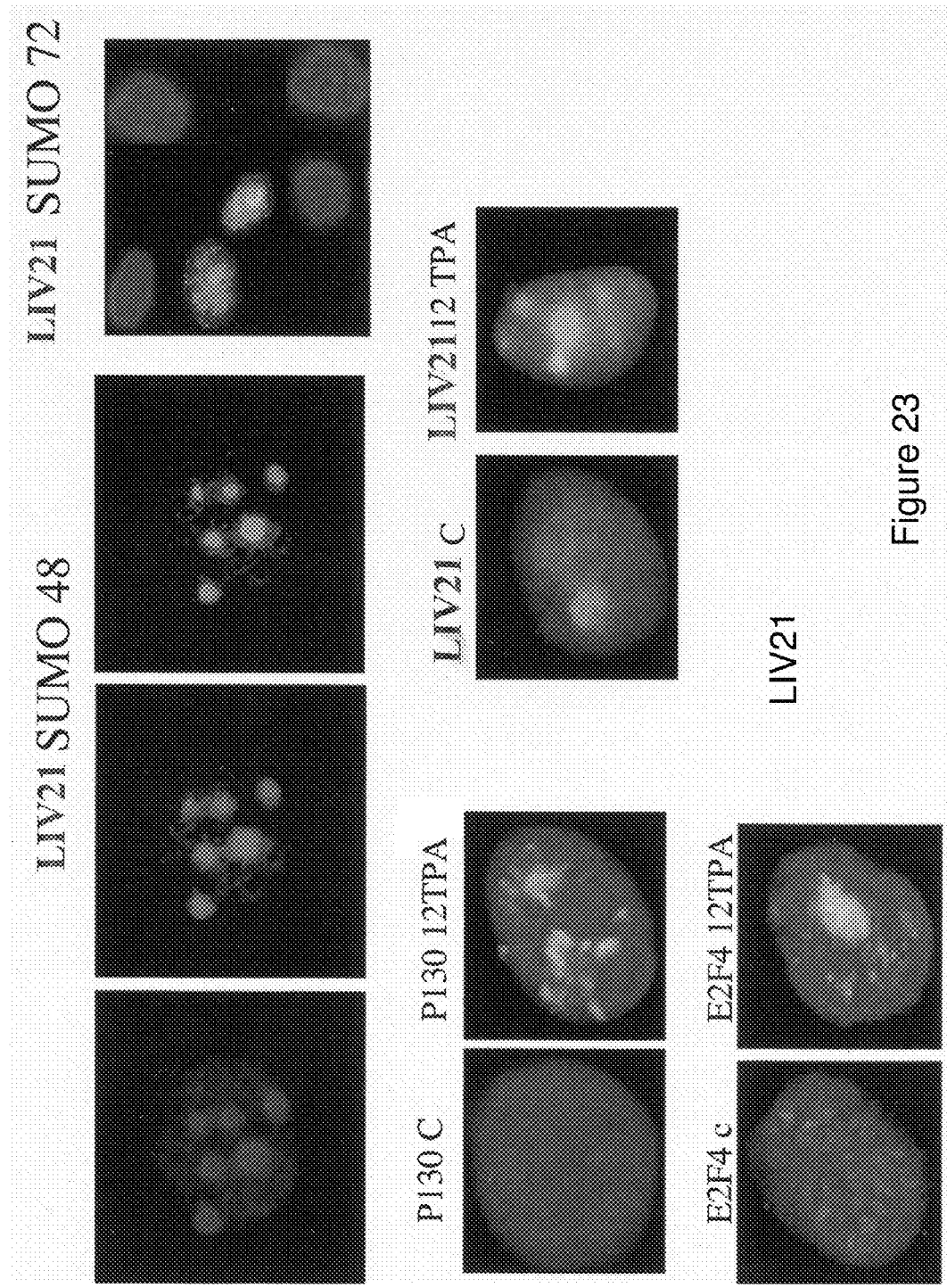
FIGS. 23 and 24 show, by immunocytochemistry, the coexistence between PML/SUMO and LIV21. The colabeling (by fluorescent immunolabeling) of LIV21 (green) and of SUMO-1 (red) in the nuclei of the cells treated or not treated with TPA for 24 h and 72 h show that, at 24 h, LIV21 is translocated into the nucleus where SUMO and PML coexist (merge: yellow nuclei), whereas, at 72 h, LIV21 (green) is cytoplasmic. The nuclear bodies containing the SUMO1 protein are called PML bodies.
Figure 24:
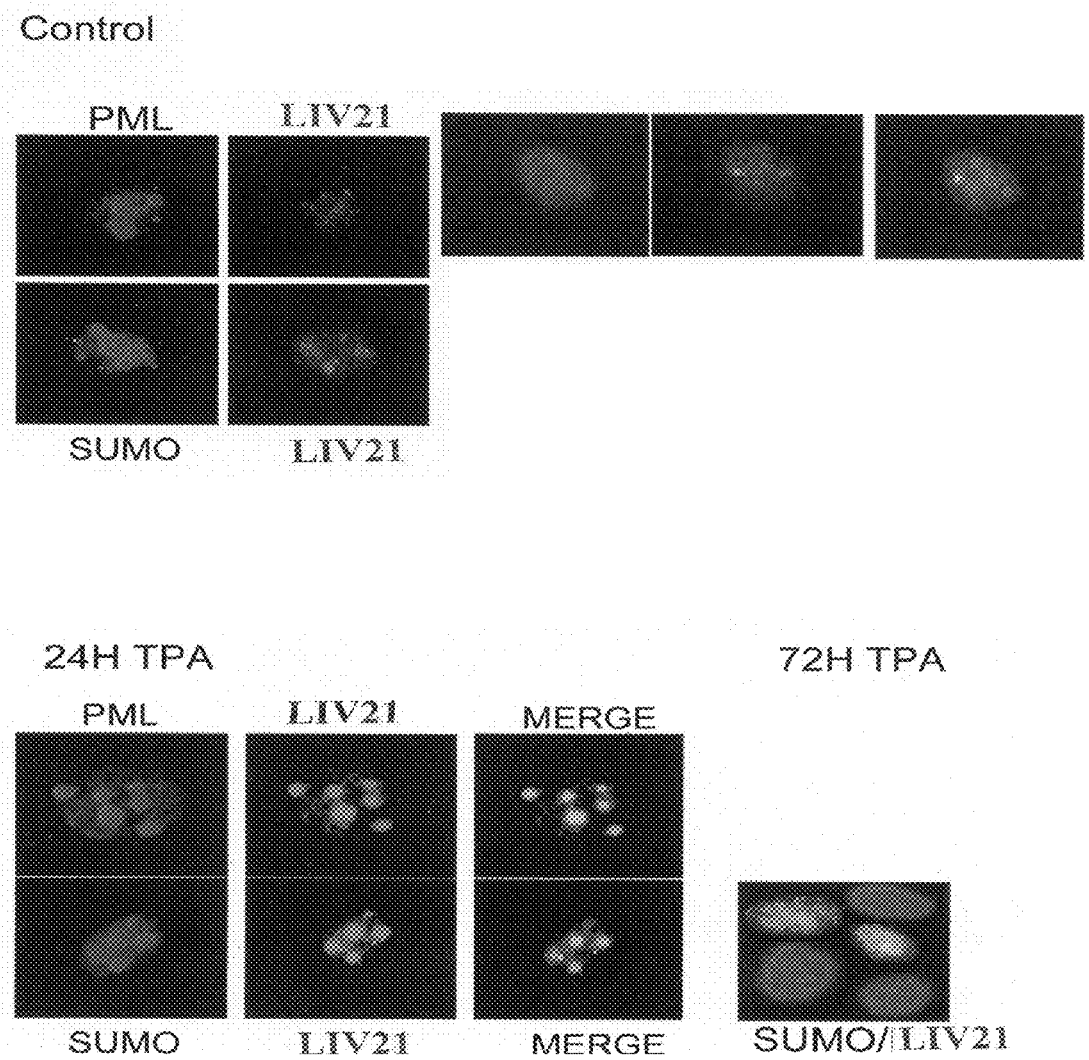

During this TPA treatment (25 nM), when E2F4, p130 and LIV21 were studied (green fluorescence) in the nuclei labeled (DNA) with propidium iodide (red fluorescence) (FIGS. 23 and 24), the following were observed:
after 12 h, intranuclear green fluorescence signals with the same pattern for E2F4, p130 and LIV21;
after 48 h, when the proliferation begins, E2F4 has a comparable localization; but at 72 h, it disappears from the nucleus (to the benefit of E2F1).

By observing, by double labeling, the colocalization of PML and of LIV21 at 24 h of TPA treatment (cf. merge: yellow fluorescence), it was observed that they are colocalized in the nuclei. At 48 h, the colocalization between LIV21 and SUMO is also observed (cf. FIG. 23). The hypothesis is that SUMO, which binds to LIV21, in fact targets LIV21 into the PML bodies and that LIV21 is involved in the PML/SUMO/Rb/HDAC-1 complexes. Two different approaches were carried out in order to demonstrate that LIV21 is physically associated with PML and SUMO in the nuclear bodies, by immunoprecipitation (FIG. 22) and by colocalization by immunocytochemistry (FIGS. 23 and 24) (Rb, p130 and p107 are pocket proteins which have the same binding site). The Rb proteins repress cell growth (Fabbro, Regazzi R, Bioch Biophys Res Comm 1986 Feb. 2; 135 (1): 65-73).

When TPA is added only once, its action is exhausted after 72 h, proliferation begins again and, at this time, the PML bodies dissociate, break up and become speckles, thus leaving the proteins to ensure transcription, proliferation, etc. LIV21 is no longer located in the nucleus since it is then rephosphorylated by PKCε and thus remains located in the cytoplasm.

Example 7

Study of the Expression of LIV21 in Breast Cancer Biopsies and Skin Cancer Biopsies In order to determine whether the observations obtained above are applicable to human tissues, a large number of skin cancer biopsies obtained from patients were studied by immunohistochemical reaction with LIV21-specific antibodies. The immunohistochemical determination of LIV21 protein expression was carried out on 60 biopsies from patients (9 patients having a biopsy of normal tissue versus a biopsy of cancerous tissue), the other biopsies corresponding to cancers which were more or less advanced and, for some, metastatic (cf. Lame superbiochips Laboratories, Seoul, Korea). Moreover, some paraffin slides from patients suffering from bladder cancer and from breast cancer were also studied.

Immunocytochemical Analysis Protocol:
Deparaffinize the slides.
Rehydrate the tissues.
Saturate the nonspecific sites and permeabilize the membranes.
Add the antibody in a humid chamber.
Reveal the antibody.
Deparaffinize the slides under a hood.
Two successive baths of toluene (rectapur Prolabo) 2×30 min or 2×20 min; then dehydrate the tissues with rectapur alcohol at 100% for 15 min; then rectapur ethanol at 95% for 10 min; then rectapur 70% for a further 10 min
Thaw the antibody at the same time.
Rehydrate the tissues gently in PBS supplemented with 10% fetal calf serum and 0.1% Triton.
Saturate the nonspecific sites (for example, with ovalbumin) and permeabilize the membranes.
Rehydrate for one hour.
Deposit one ml of this "PBS" per section in order to cover the slide without it drying out at any moment (when it is a slide with cells and not tissues, half an hour is sufficient).
Place the pane and the stainless steel cover and water below so as to create a humid chamber.
Add the antibody in the humid chamber.
Dilute the rabbit serum to $1/200$ in 4 ml of PBS triton, so as to continue to permeabilize the membranes, and FCS.
Place 1 ml on each slide and keep away from the light and avoid evaporation.
Leave overnight or for a minimum of three hours.
Then rinse with 1× normal PBS pH 7, carry out two washes of 5 to 10 min so that no trace of the first antibody remains.
While preparing the Alexa 488 green probe (in the cold at 4° and in the dark) diluted to $1/250$, therefore 10 μliter in 2.5 ml of PBS, still with 10% FCS and 0.1% Triton, rest the slides on the plate. Cover the section again with 2.5 ml in order to maintain a humid chamber for one hour, and then wash with 1×PBS, pH 7.
Wash with propidium iodide at 0.5 microgram per microliter to be diluted to 20 microgram per ml and then again to $1/50$, but this time, diluted in 1×PBS alone (50 microliters per 2.5 ml of PBS). Drain while taking them out of the PBS and then dispense 2.5 ml of propidium iodide over the four slides for one minute, followed by two rinses with simple PBS. Mount the slides in Moviol before reading.

All the results are summarized in Table 1 below.

TABLE 1

Expression of the LIV21 protein determined by immunohistochemistry in 50 skin cancer biopsies and 9 normal tissue biopsies

| TUMOR TYPE | NUCLEAR LIV21 NEGATIVE | "MIXED" LIV21 WEAKLY POSITIVE | CYTOPLASMIC LIV21 POSITIVE |
|---|---|---|---|
| NORMAL TISSUES FROM THE SAME PATIENTS | 6/9 | 3/9 | 0 |
| WELL-DIFFERENTIATED CARCINOMAS | 18/21 | 2/21 | 1/21 |

TABLE 1-continued

Expression of the LIV21 protein determined by immunohistochemistry in 50 skin cancer biopsies and 9 normal tissue biopsies

| TUMOR TYPE | NUCLEAR LIV21 NEGATIVE | "MIXED" LIV21 WEAKLY POSITIVE | CYTOPLASMIC LIV21 POSITIVE |
|---|---|---|---|
| MODERATELY DIFFERENTIATED CARCINOMAS | 1/7 | 5/7 | 1/7 |
| POORLY DIFFERENTIATED CARCINOMAS | 2/11 | 3/11 | 6/11 |
| CARCINOMA METASTASES | 0 | 2/9 | 7/9 |

For Example:

FIG. 25: Results: image 43: poorly differentiated cancer; image 58: normal tissue derived from the same individual suffering from a cancer; image 40: metastatic carcinoma 10 cm and image 17: metastatic carcinoma of 3.5 cm.

FIG. 26 is, like FIG. 25, a second example of nuclear localization of LIV21 in the control and normal tissue (No. 52) of individual No. 7 suffering from a squamous cell carcinoma of the pharynx (moderately differentiated T4N0M0).

FIG. 27 is a sample of advanced bladder cancer on cystectomy (grade III urothelial carcinoma infiltrating the chorion and the musculosa) versus normal bladder tissue from the same patient with an internal control (PI): preimmune serum PI before the rabbit has been immunized against LIV21, labeling of the nuclei with propidium iodide.

FIG. 28 is a sample of breast cancer which makes it possible to demonstrate the cytoplasmic labeling of the LIV21 antibody in the cancer cells.

These results show that the cytoplasmic localization of LIV21 is an indicator of the aggressiveness and of the metastatic potential of the cancer. The detection of LIV21 expression indicates the presence of invasive, aggressive and metastatic cancer cells. These results also show that the nuclear localization of LIV21 is an indicator of normal quiescent cells, that is of well-differentiated tissues.

Example 8

Physical Interaction of LIV21 with the Proteins of the E2F Family

Communoprecipitation experiments carried out using anti-LIV21, anti-E2F1 and anti-E2F4 antibodies made it possible to demonstrate that LIV21 associates with E2F4.

The members of the E2F family are transcription factors whose role has been widely described in the literature as being key molecules in the positive or negative control of the cell cycle (Slansky J E and Farnham P J 1996; Helin K 1998 and Yamasaki L, 1998), by virtue of their association with the pRb protein (Wu C L, Zukerberg L R, Lees J A 1995) or pocket proteins. E2F1 positively controls the cell cycle by transactivating the promoter of the genes responsible for cell proliferation (DNA polymerase alpha, thymidine kinase, DHFR, etc.), whereas E2F4 is described as one of the members of the EF family which negatively controls the cycle. Furthermore, a high expression of E2F1 in embryonic mammary tissues has been shown (Espanel X, Gillet G 1998), whereas it is no longer expressed in post-mitotic mammary tissues, to the benefit of a large increase in E2F4 expression (Kastner A Brun G 1998).

The identification of antigens has been carried out in cell lysates by immunoprecipitation. The analysis of the physical interaction of various proteins associated with E2F4 and E2F1 was demonstrated by coimmunoprecipitation of protein complexes. The complex was studied using µ MACS PROTEIN with MICROBEADS (MILTENYIBIOTEC). When lysates of S aureus are added, the proteins A interact with the Fc portion of the specific antibodies and the immunocomplexes become insoluble and are therefore recovered by centrifugation. After breaking of the bonds (heating) between AG/AB and protein A-rich membranes, Western blotting was carried out. These results suggest that the LIV21/E2F4 complex appears to play an important role in establishing cell quiescence.

Example 9

Functional Interaction of LIV21 with the Proteins of the E2F Family

It was demonstrated that blocking the expression of the LIV21 protein was correlated with a decrease in the expression of E2F4 and with an increase in the expression of E2F1. In parallel, the functional aspect of the increase in E2F1 was verified by studying the transcription of two of its target genes, DHFR and DNA polymerase α.

Example 10

Reverse Transcriptions

After MCF7 cells (ATCC passage 15) had been thawed and cultured up to 200 million, they were trypsinized and frozen at 80° C. The RNA was extracted from two pools of 50 million cells with the Nucleospin RNA L kit (Macherey Nagel) ref. 740.962.20, resulting in a pool 1 of 318 µg and a second of 182 µg. The poly A+ RNA was extracted from 313 µg of total RNA of pool 1 using the oligo Tex mRNA Midi kit (Qiagen) ref. 70042.

I Reverse Transcription:

The RNA was reverse transcribed with the Fermentas Revert Aid H minus M MuLV Reverse Transcriptase, ref. EP0451 batch 1124, with 3.64 µg of total RNA and 0.45 µg of mRNA, according to the supplier's conditions, with an oligo dT primer. Reactions were carried out at 2 different temperatures at 45° C. and 55° C. so as to eliminate the RNA structures that may hinder reverse transcription.

II PCR

The PCRs were carried out with the reverse transcriptions as templates, initially with the primers A1+oligo dT. Nested PCRs were subsequently carried out on these first PCRs, with the primers A1+Splicing, A1+GDBR1, or ATG+Splicing, ATG+GDBR1.

PCR amplification was then carried out with the primers specific for the genes to be detected, using the cDNAs obtained after oligo dT RT.

Enzyme: Fermentas Taq DNA polymerase. Thermocycler: Bio Rad iCycler.

The quality of the cDNAs was tested by amplification of GAPDH, b actin and Histone H3.3 housekeeping genes.

TABLE 1

Primers

| Reference | 5'-3' sequence | Amplified fragment size |
|---|---|---|
| Histone N | 5'-GTG GTa aag cac cca gga a-3' SEQ ID NO: 174 | 347 bp |
| Histone I (reverse) | 5'-gct agc tgg atg tct ttt gc-3' SEQ ID NO: 175 | |
| Hum GAPDH sense | 5'-TGA AGG TCG GAG TCA ACG G-3' SEQ ID NO: 176 | 983 bp |
| Hum GAPDH antisense | 5'-CAT GTG GGC CAT GAG GTC-3' SEQ ID NO: 177 | |
| Hum b-actin sense | 5'-GGA CTT CGA GCA AGA GATGG-3' SEQ ID NO: 178 | 234 bp |
| Hum b-actin antisense | 5'-AGC ACT GTG TTG GCG TAC AG-3' SEQ ID NO: 179 | |
| LIV21 (A1) | 5'- -3' | |
| LIV21 (A2) | 5'- -3' | |
| odT | 5'-TTTTTTTTTTTTTTTTTTTT-3' SEQ ID NO: 180 | |
| ATG galgal | 5'- -3' | |
| Splicing sense | 5'- -3' | |
| Splicing reverse | 5'- -3' | |
| G reverse | 5'- -3' | |

TABLE 2

PCR mix

| $H_2O$ | 10X buffer | 25 mM $Mg^{++}$ (1.5 mM final concentration) | 10 mM dNTP (µl) | Forward primer 10 µM (µl) | Reverse primer 10 µM (µl) | Taq (µl) 5 U/µl | cDNA (µl) |
|---|---|---|---|---|---|---|---|
| 18.3 | 2.5 | 1.5 | 0.5 | 0.5 | 0.5 | 0.2 | 1 |

PCR Cycles
Denaturation: 94° C. 2 minutes
Denaturation: 94° C. 30 seconds
Annealing: 52-55° C. 1 minute 35 cycles
Elongation: 72° C. 1 minute 30
Final elongation: 72° C. 7 minutes
Conservation: 4° C.

III Controls

The PCR Products were Subsequently Controlled on Agarose Gels and Analysed with the Biocapt 11.01 Software from Vilber Lourmat.

FIG. 32: Analysis molecular masses gel 1
FIG. 33: Gel 2 with analysis of molecular masses
FIG. 34: Gel 3 at 55° and analysis of molecular masses
FIG. 35: Gel 4 at 45° and 55° and analysis of molecular masses
FIG. 36: Screening ligation of 400 bp band, clones B1 to B10
FIG. 37: PCR with the primers showing a band at 1400 bp, clones C1 to C10
FIG. 38: Gel 5: ligation, screening on the five new clones
FIG. 49: Gel 6: screening of the S55T and S55M recombinant clones and analysis of molecular masses.

Gel 2:

PCRs carried out using templates from PCRs performed with the primers A1+oligo dT on the RTs carried out at 45° C. on the total RNA and the poly A+RNA (messenger RNA). The primers used for these PCRs are A1+G or A1+Splicing reverse.

On the RTs carried out using the total RNA, a band of 1178 1253 bp is amplified with the primers A1+G and A1+Splicing reverse. The poly A RNA was used to carry out the RT and is weakly observed at the size (FIG. 33) of 1400 bp for amplification with the primers A1+G, and of 415 bp with the primers A1+Splicing reverse. In the A1+splicing PCR product, there are other bands, of 860 and 233 bp (FIGS. 38 & 39).

Gel 3:

PCRs carried out using templates from PCRs performed with the primers A1+oligo dT on the RTs carried out at 45° C. on the total RNA and the poly A+RNA (messenger RNA). The primers used for these PCRs are A1+GDBR1 or A1+Splicing reverse (FIG. 34).

For the PCRs carried out on RTs performed at 55° C., the same overall pattern of bands as that obtained on the RTs performed at 45° C. is found.

No specific amplification is observed when the poly A RNA was used to carry out the RT. On the RTs carried out on the total RNA, a major band of 1554 1609 bp is found with the primers A1+GDBR1 and A1+Splicing reverse. A band at the theoretical size of 1455 bp is expected for an amplification with the primers A1+GDBR1 and a band with the theoretical size of 415 bp is expected with the primers A1+Splicing reverse. In the 2 profiles, very clear bands of 1900-2100 bp and of 1000-1300 bp are found, but with a weaker intensity than that of the band of 1500-1600 bp.

In the A1+splicing reverse PCR product, there is another major band, of 263 bp.

Gel 4:

Nested PCRs carried out using templates from PCRs performed with the primers A1+GDBR1 or A1+Splicing reverse on the RTs carried out at 45° C. on the total RNA and the poly A+RNA (messenger RNA). The primers used for these PCRs are ATG+GDBR1 or ATG+Splicing reverse (FIG. 35).

The nested PCRs carried out with the primers ATG+GDBR1 give bands at 1213 bp (RT 45° C.) and 1559+1315 bp (RT at 55° C.); the expected theoretical size is 1455 bp. The PCRs carried with the primers ATG+Splice reverse give more varied band profiles.

These PCRs carried out on other PCRs performed with the primers A1+GDBR1 or A1+Splicing reverse.

The presence of a band of 400 bp is noted in the profiles obtained from messenger RNA (the band obtained from the reverse transcription carried out at 55° C. is of greater intensity).

The profiles of the ATG+Splice reverse PCRs carried with total RNA at the start give a band of 424 437 bp of very strong intensity. Bands of 614 and 783 bp of very strong intensity are also found in the profile of the RT 45 and a greater number of bands, but of weaker intensity, is found in the profile of the RT 55, bands at 1118, 936 and 749 bp. The products of these various PCRs were cloned and sequenced.

Example 12

The PCR products of lanes 2, 4, 6, 7 and 8 were ligated with the plasmid pGEMT Easy, Promega, T7 vector and the recombinant clones were screened (FIG. 38).

Lane 2: G45T ligations

Lane 4: S45T ligations

Lane 6: G55T ligations

Lane 7: S55M ligations

Lane 8: S55T ligations

The recombinant clones obtained were screened (after extraction of the plasmid DNA) by restriction with the Eco RI enzyme, the sites of which border the site of insertion of the PCR products into the pGEMT Easy vector.

Screening of the Recombinant Clones:

The first experiments had been carried out using the ten clones B and the ten clones C, FIGS. 36 and 37, and the results of the sequences of clones B2 and C8 are given in the following example, and exhibit, by sequence comparison between clones, great homology with the clones of the second series of experiments.

Gel 5: Screening of the S45T and G45T Recombinant Clones

Analysis of Molecular Masses

The screening of the clones with Eco RI shows that, out of the 9 S45T clones, 3 have inserts of 100 bp, 216 bp and 410 bp.

On the G45T clones, out of the 6 clones tested, 3 have inserts of 57, 71 and 148 bp (FIG. 38).

FIG. 39: Screening of the S55T and S55M recombinant clones

Analysis of Molecular Masses

The screening with Eco RI shows that, out of the 13 clones screened, 7 have inserts of sizes between 239 and 637 bp.

The clones G45T5 (148 bp), S45T9 (410 bp), S45T3 (100 bp), S55M1 (491 bp), S55T6 (251 bp) and S55T9 (637 bp) were extracted so as to be sequenced.

Primers Used for Determining the Sequences of the Various Clones:

```
ATG galgal 5'-atgtatattatata-3'

INV COMP ttagatatataata

Splicing reverse 5'-aaatat-3'

Splicing reverse 5'-t-3' inv comp

G reverse 5'-TG-3'

G reverse 5'-AT . . . -3' inv comp
```

Results:

Clone B2, the band which is approximately 400 bp is the same fragment as S55M1, which itself is the same fragment as S45T9. These fragments are approximately between 400 and 450 bp. This is not surprising since they were obtained after a nested PCR carried out with the splicing reverse primer and the A1 primer (for the B2 fragment) and the ATG galgal primer for the S45T9 and S55M1 fragments. These fragments were obtained with RTs carried out at various temperatures. On the other hand, the S55T9 fragment is nevertheless approximately 600 bp, and a part (300 bp) exhibits quite strong identity with the other fragments cloned (clone FLJ)

The inventor approached the study of the expression of the LIV21 protein by the Western blotting technique, with an anti LIV21 antibody, in MCF 7 cells compared with breast tissues. The anti LIV21 antibodies were obtained by the method described. In this line, LIV21 was expressed, both in breast tissues and in the MCF 7 cells, in the form of a doublet that migrates at an apparent molecular weight of 50 kDa.

In conclusion, these results suggest that the LIV21/E2F4 complex acts as a complex which inhibits the expression of the E2F1 gene. This complex could correspond to a new point of control in the arrest of cell proliferation.

REFERENCES

Arya R, Kedar V, Hwang J R, McDonough H, Li H H, Taylor J, Patterson C. Muscle ring finger protein-1 inhibits PKC{epsilon} activation and prevents cardiomyocyte hypertrophy. J. Cell Biol. 2004 Dec. 20; 167(6):1147-59. Epub 2004 Dec. 13.

Caroll J S, Prall O W J, Musgrove E A, Sutherland R L. A pure Estrogen Antagonist Inhibits Cyclin E-Cdk2 Activity in MCF-7 Breast Cancer Cells and Induces Accumulation of p130-E2F4 Complexes Characteristic of Quiescence. (2000) *J. Biol. Chem.*, 275 (49):38221-38559.

Chau B N, Wang J Y. Coordinated regulation of life and death by RB. (2003) *Nat Rev Cancer,* 3 (2): 130-8.

Cheng T, Scadden D T. Cell cycle entry of hematopoietic stem and progenitor cells controlled by distinct cyclin-dependent kinase inhibitors. (2002) *Int J Hematol,* 75 (5):460-5.

Classon M, Harlow E. The retinoblastoma tumour suppressor in development and cancer. (2002) *Nat Rev Cancer,* 2 (12): 910-7.

Coqueret O. Linking cyclins to transcriptional control. (2002) *Gene,* 299 (1-2): 35-55.

Crisanti P, Raguenez G, Blancher C, Neron B, Mamoune A, Omri B. Cloning and characterization of a novel transcription factor involved in cellular proliferation arrest: PATF. (2001) *Oncogene* 20: 5475-5483.

Durocher D, Taylor I A, Sarbassova D, Haire L F, Westcott S L, Jackson S P, Smerdon S J, Yaffe M B. The molecular basis of FHA domain:phosphopeptide binding specificity and implications for phospho-dependant signaling mechanisms. (2000) *Mol Cell*, 6 (5):1169-82.

Durocher D, Jackson S P. The FHA domain. (2002) *FEBS Lett*, 513 (1): 58-66.

Espanel X; Le Cam L, North S, Sardet C, Brun G, Gillet G. Regulation of E2F-1 gene expression in avian cells. (1998) *Oncogene*, 17 (5): 585-94.

Fraering, Wenjuan Ye, Michael S Wolfe. Purification and characterization of the Human J Secretase Complex (2004) *Biochemistry* 43: 9774-9789.

Han E K, Begemann M, Sgambato A, Soh J W, Doki Y, Xing W Q, Liu W, Weinstein I B. Increased expression of cyclin D1 in a murine mammary epithelial cell line induces p27kip1, inhibits growth, and enhances apoptosis. Cell Growth Differ. 1996 June; 7(6):699-710.

Harlow et al Antibodies: A laboratory Manual, CSH Press, 1988

He L Z, Merghoub T, Pandolfi P P. In vivo analysis of the molecular pathogenesis of acute promyelocytic leukemia in the mouse and its therapeutic implications. (1999) *Oncogene*, 18: 5278-5292.

Helin K. Regulation of cell proliferation by the E2F transcription factors. (1998) *Curr Opin Genet Dev*, 8 (1): 28-35.

Horman S, Galand P, Mosselmans R, Legros N, Leclereq G, Mairesse N. Changes in the phosphorylation status of the 27 kDa heat shock protein (HSP27) associated with the modulation of growth and/or differentiation in MCF-7 cells. (1997) *Cell Prolif*, 30 (1):21-35.

Hughes et al. Adaptor plasmids simplify the insertion of foreign DNA into helper-independent retroviral vector. (1987) *J. Virol* 61: 3004-3012

Kastner A, Espanel X, Brun G. Transient accumulation of retinoblastoma/E2F-1 protein complexes correlates with the onset of neuronal differentiation in the developing quail neural retina. (1998) *Cell Growth Differ*, 9 (10): 857-67.

Katalin F. Medzihradszky, Characterization of Protein N-Glycosylation, (2005) *Methods in Enzymology*, vol 405: 116-438.

Kohler G, Milstein C. Continuous cultures of fused cells secreting antibody of predefined specificity. Nature. 1975 Aug. 7; 256(5517):495-7.

Lee W, Boo J E, Jung M W, Park S D; Kim Y E, Kim S U, Mook-Jung I. Amyloid beta peptide directly inhibits PKC activation. Mol Cell Neurosci. 2004 June; 26(2):222-31

Mairesse N, Horman S, Mosselmans R, Galand P. Antisense inhibition of the 27 kDa heat shock protein production affects growth rate and cytoskeletal organization in MCF-7 cells. (1996) *Cell Biol Int*, 20 (3): 205-1.2.

Matunis M J. On the road to repair: PCNA encounters SUMO and ubiquitin modifications. (2002) *Mol Cell*, 10 (3): 441-2.

Melchior F, Hengst L. SUMO-1 and p53. (2002) *Cell Cycle*, 1 (4): 245-9.

Mundle S D, Saberwal G. Evolving intricacies and implications of E2F1 regulation. (2003) *FASEB J*, 17 (6): 569-74.

Opalka B, Dickopp A, Kirch H C. Apoptotic genes in cancer therapy. (2002) *Cells Tissues Organs*, 172 (2): 126-32.

Pardo F S, Su M, Borek C. Cyclin D1 induced apoptosis maintains the integrity of the G1/S checkpoint following ionizing radiation irradiation. Somat Cell Mel Genet. 1996 March; 22(2):135-44.

Pawson T, Gish G D; Nash P. SH2 domains, interaction modules and cellular wiring. (2001) *Trends Cell Biol*, 11 (12): 504-11.

Platet N, Prevostel C, Derocq D, Joubert D, Rochefort H, Garcia M. Breast cancer cell invasiveness: correlation with protein kinase C activity and differential regulation by phorbol ester in estrogen receptor-positive and -negative cells. (1998) *Int Cancer*, 75 (5): 750-6.

Ree A H, Bjornland K, Brunner N, Johansen H T, Pedersen K B, Aasen A O, Fodstad O. Regulation of tissue-degrading factors and in vitro invasiveness in progression of breast cancer cells. (1998) *Clin Exp Metastasis*, 16 (3) 205-15.

Regazzi R, Fabbro D, Costa S D, Brunner C, Eppenberger U. Effects of tumor promoters on growth and on cellular redistribution of phospholipid/$Ca^{2+}$-dependant protein kinase in human breast cancer cells. (1986) *Int J Cancer*, 37 (3); 731-737, Schneider S M, Offterdinger M, Huber H, Grunt T W. Involvement of nuclear steroid/thyroid/retinoid receptors and of protein kinases in the regulation of growth and of c-erbB and retinoic acid receptor expression in MCF-7 breast cancer cells. (1999) *Breast Cancer Res and Treat*, 58: 171-181.

Senderowicz A M, Cyclin-dependent kinases as targets for cancer therapy. (2002) *Cancer Chemother Biol Response Modif*, 20: 169-96.

Slansky J E and Farnham P J. Introduction to the E2F family; protein structure and gene regulation. (1996) *Curr Top Microbial Immunol*, 53: 347-360.

Songyang Z, Shoelson S E, Chaudhuri M, Gish G, Pawson T, Haser W G, King F, Roberts T, Ratnofsky S, Lechleider R J, SH2 domains recognize specific phosphopeptide sequences. (1993) *Cell*, 72 (5): 767-78.

Starzec A B., Spanakis E, Nehme A, Salle V, Veber N, Mainguene C, Planchon P, Valette A, Prevost G, Israel L. Proliferative responses of epithelial cells to 8-bromo-cyclic AMP and to a phorbol ester change during breast pathogenesis. (1994) *J Cell Physiol*, 161 (1): 31-8.

Stevaux O, Dyson N J. A revised picture of the E2F transcriptional network and RB function. (2002) *Curr Opin Cell Biol*, 14 (6): 684-91.

Stiegler P, Giordano A. The family of retinoblastoma proteins. (2001) *Crit Rev Eukaryot Gene Expr*, 11 (1-3): 59-76

Toma O, Weber N C, Wolter J I, Obal D, Preckel B, Schlack W. Desflurane preconditioning induces time-dependent activation of protein kinase C epsilon and extracellular signal-regulated kinase 1 and 2 in the rat heart in vivo. Anesthesiology. 2004 December; 101(6):1372-80.

Vaitukaitis J, Robbins J B, Nieschlag E, Ross G T. A method for producing specific antisera with small doses of immunogen. J Clin Endocrinol Metab. 1971 December; 33(6): 988-91.

Ward E S, Gussow D, Griffiths A D, Jones P T, Winter G. Binding activities of a repertoire of single immunoglobulin variable domains secreted from *Escherichia coli*. Nature. 1989 Oct. 12; 341(6242):544-6.

Wu C L, Zukerberg L R, Ngwu C, Harlow E, Lees J A. In vivo association of E2F and DP family proteins. (1995) *Mol Cell Biol*, 15 (5): 2536-46.

Yaffe M B. Phosphotyrosine-binding domains in signal transduction. (2002) *Nat Rev Mol Cell Biol*, 3 (3): 177-86.

Yamasaki L. Growth regulation by the E2F and DP transcription factor families. (1998) *Results Probl Cell Differ*, 22: 199-227.

Zee-Yong Park and David H. Russell. Identification of Individual Proteins in Complex Protein. Mixtures by High-Resolution, High-Mass-Accurancy MALDI TOF-Mass Spectrometry Analysis of In-Solution Thermal denaturation/Enzymatic Digestion. (2001) *Anal Chem*, 73 (11): 2558-2564.

What is claimed is:

1. A pharmaceutical composition comprising a PKCε-protein inhibitor and a carrier, wherein said PKCε-protein inhibitor includes a siRNA nucleotide sequence specific for the PKCε gene and comprises SEQ ID NO: 122.

2. The pharmaceutical composition as claimed in claim 1, further comprising an HDAC inhibitor.

3. The pharmaceutical composition as claimed in claim 1, wherein said composition is formed as a medicament for treating at least one type of cancer.

4. The pharmaceutical composition as claimed in claim 3, wherein said at least one type of cancer comprises any of breast cancer, bladder cancer, ovarian cancer, lung cancer, skin cancer, prostate cancer, colon cancer, liver cancer, a sarcoma, a leukaemia and glioblastoma.

5. A method for treating cancer comprising the activity of administering a therapeutically effective amount of a composition comprising a PKCε-protein inhibitor and a carrier, wherein said PKCε-protein inhibitor includes a siRNA nucleotide sequence specific for the PKCε gene, wherein the siRNA nucleotide is as SEQ ID NO: 122.

6. The method as claimed in claim 5, wherein the cancer treated by said activity of administering includes at least one of breast cancer, bladder cancer, ovarian cancer, lung cancer, skin cancer, prostate cancer, colon cancer, liver cancer, a sarcoma, a leukaemia and glioblastoma.

7. The method as claimed in claim 5, further comprising administering a therapeutically effective amount of an HDAC inhibitor.

* * * * *